United States Patent
Jennewein et al.

(10) Patent No.: US 11,920,173 B2
(45) Date of Patent: Mar. 5, 2024

(54) FERMENTATIVE PRODUCTION OF N-ACETYLNEURAMINIC ACID

(71) Applicant: Chr. Hansen HMO GmbH, Rheinbreitbach (DE)

(72) Inventors: Stefan Jennewein, Bad Honnef (DE); Dirk Wartenberg, Bonn (DE)

(73) Assignee: Chr Hansen HMO GmbH, Rheinbreitbach (DE)

( * ) Notice: Subject to any disclaimer, the term of this patent is extended or adjusted under 35 U.S.C. 154(b) by 681 days.

(21) Appl. No.: 16/756,279

(22) PCT Filed: Oct. 17, 2018

(86) PCT No.: PCT/EP2018/078318
§ 371 (c)(1),
(2) Date: Apr. 15, 2020

(87) PCT Pub. No.: WO2019/076941
PCT Pub. Date: Apr. 25, 2019

(65) Prior Publication Data
US 2020/0332331 A1    Oct. 22, 2020

(30) Foreign Application Priority Data
Oct. 17, 2017  (EP) ..................... 17196925

(51) Int. Cl.
*C12P 19/28*  (2006.01)
*A23L 33/135*  (2016.01)
*C12N 15/52*  (2006.01)
*A23L 33/00*  (2016.01)

(52) U.S. Cl.
CPC ............. *C12P 19/28* (2013.01); *A23L 33/135* (2016.08); *A23L 33/40* (2016.08)

(58) Field of Classification Search
CPC ........ C12P 19/28; A23L 33/135; C12N 15/52; C12N 15/70
See application file for complete search history.

(56) References Cited

U.S. PATENT DOCUMENTS

| 6,846,656 B1 | 1/2005 | Koizumi et al. |
| 7,579,175 B2 | 8/2009 | Koizumi et al. |
| 9,675,649 B2 | 6/2017 | Bode |
| 2004/0202765 A1 | 10/2004 | McMahon et al. |
| 2005/0255572 A1 | 11/2005 | Eiteman et al. |
| 2012/0009627 A1 | 1/2012 | Deng et al. |

FOREIGN PATENT DOCUMENTS

| CN | 103361283 A | 10/2013 |
| CN | 106929461 A | 7/2017 |
| EP | 0578825 A1 | 1/1994 |
| EP | 1484406 A1 | 12/2004 |
| JP | H07267866 A | 10/1995 |
| JP | 2001136982 A | 5/2001 |
| JP | 2002520067 A | 7/2002 |
| JP | 2006508643 A | 3/2006 |
| JP | 2010517509 A | 5/2010 |
| KR | 1020140087201 A | 7/2014 |
| RU | 2396879 C2 | 8/2010 |
| WO | 9429476 A1 | 12/1994 |
| WO | 0004182 A1 | 1/2000 |
| WO | 2004003175 A2 | 1/2004 |
| WO | 2006044188 A1 | 4/2006 |
| WO | 2008040717 A2 | 4/2008 |
| WO | 2008097366 A2 | 8/2008 |
| WO | 2012083329 A1 | 6/2012 |
| WO | 2014153253 A1 | 9/2014 |
| WO | 2018122225 A1 | 7/2018 |
| WO | 2019043029 A1 | 3/2019 |

OTHER PUBLICATIONS

Machine translation of JPH07267866, Oct. 17, 1995, Yakabe et al., 6 pages.
Machine Translation of KR 10-2014-0087201, Jul. 9, 2014, Daesang Corp, 9 pages.
Wang et al., "Sialic Acid is an Essential Nutrient for Brain Development and Cognition," Annu. Rev. Nutr., 2009, 29:177-222.
International Search Report for PCT/EP2018/078318 dated Nov. 28, 2018.
Deqiang Zhu, et al., "Phosphoenolpyruvate-supply module in *Escherichia coli* improves N-acetyl-D-neuraminic acid biocatalysis," Biotechnology Letters, (2017), vol. 39, No. 2, 227-234.
Deqiang Zhu, et al., "Efficient whole-cell biocatalyst for Neu5Ac production by manipulating synthetic, degradation and transmembrane pathways," Biotechnology letters, (2017), vol. 39, No. 1:55-63.
Machine translation of CN103361283, Oct. 23, 2013, Yan et al., 8 pages.
Jeff Abramson, et al., "Structure and mechanism of the lactose permease of *Escherichia coli*", Science, 301(5633): 610-615, Aug. 1, 2003., New York, US.
Jiangong Lu, et al. "Model-based dynamic engineering of *Escherichia coli* for N-acetylglucosamine overproduction", Biotechnology Notes, 3:15-24, Feb. 2022 (10 pages).
Sang-Woo Lee, et al. "A synthetic suicide riboswitch for the high-throughput screening of metabolite production in Saccharomyces cerevisiae", Metabolic Engineering, 28:143-150, 2015.
Communication Pursuant to Rule 114(2) EPC—Third Party Observation in EP3697805, dated Oct. 30, 2023 (6 pages).

*Primary Examiner* — Lynn Y Fan

(74) *Attorney, Agent, or Firm* — McNeill Baur PLLC

(57) ABSTRACT

Disclosed are non-naturally-occurring microorganisms for the production of N-acetylneuraminic acid, a method for the production of N-acetylneuraminic acid by fermentation of the non-naturally-occurring microorganisms, and nutritional compositions containing N-acetylneuraminic acid which has been produced by fermentation of the non-naturally-occurring microorganisms.

14 Claims, 3 Drawing Sheets

Specification includes a Sequence Listing.

FERMENTATIVE PRODUCTION OF N-ACETYLNEURAMINIC ACID

CROSS-REFERENCE TO RELATED APPLICATIONS

This application is the National Stage entry of International Application No. PCT/EP2018/078318, filed 17 Oct. 2018, which claims priority to European Patent Application No. 17196925.6, filed 17 Oct. 2017.

REFERENCE TO SEQUENCE LISTING SUBMITTED AS A COMPLIANT ASCII TEXT FILE (.TXT)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_3000045-012000_ST25.txt" created on 14 Apr. 2020, and 320,181 bytes in size) is submitted concurrently with the instant application, and the entire contents of the Sequence Listing are incorporated herein by reference.

BACKGROUND

Field

The present invention relates to non-naturally-occurring microorganisms that are capable of producing N-acetylneuraminic acid, to methods for the production of N-acetylneuraminic acid by fermentation using said non-naturally-occurring microorganisms, to the use of N-acetylneuraminic acid produced by means of fermentation as well as to products containing N-acetylneuraminic acid produced in this manner.

Description of Related Art

Sialic acids (Sia) are a family of negatively charged monosaccharides with a nine-carbon backbone. More than 50 forms of these α-keto acids have been found in nature. The most abundant sialic acid appears to be N-acetylneuraminic acid (NANA, NeuNAc, Neu5Ac).

Sialic acids are present as the terminal saccharides of the glycans present in glyco-conjugates (glycoproteins and glycolipids) on the surface of cells of vertebrates and higher invertebrates. Sialic acids are components of the lipopolysaccharides and capsular polysaccharides of pathogenic bacteria including *Escherichia coli* K1, *Haemophilus influenzae*, *Haemophilus ducreyi*, *Pateurella multocida*, *Neisseria gonorrhoeae*, *Neisseria meningitidis*, *Campylobacter jejuni* and *Streptococcus agalactiae*.

Sialic acids play important roles in many physiological and pathophysiological processes including the development of the embryonic nervous system, metastasis, the regulation of immune responses and infections with bacteria or viruses. Sialic acids are an essential component of brain gangliosides and of the polysialic acid chains that modify neural cell adhesion molecules (NCAMs) that facilitate cell-to-cell interactions, neuronal outgrowth, the modification of synaptic connectivity and memory formation. In piglets, a diet rich in sialic acids increases the level of brain sialic acids and the expression of two learning-related genes. Accordingly, the diet also enhances learning and memory.

Infants, in particular preterm infants, have a high demand for nutrients including sialic acids due to the rapid brain growth and development of their immune system at this developmental stage. Levels of sialic acids, particularly N-acetylneuraminic acid, are high in human breast milk (approx. 0.5 g·L$^{-1}$). In contrast, infant formulas contain a low or even insignificant amount of N-acetylneuraminic acid.

It is therefore necessary to provide sialic acids, in particular Neu5Ac, of a sufficient quality and quantity sufficient for the supplementation of infant formulas and other nutritional compositions. In this regard, various approaches have been published in the past.

Document EP 1 484 406 A1 describes a process for producing N-acetylneuraminic acid using a microorganism which has the ability to produce Neu5Ac but has limited or no ability to decompose Neu5Ac compared with a wild-type strain, such that Neu5Ac accumulates in the culture medium and can be recovered therefrom. To enable the production of Neu5Ac, the microorganism possesses strong N-acetylneuraminic acid synthase activity and/or N-acetylglucosamine 2-epimerase activity. More specifically, *E. coli* cells were subjected to random mutagenesis and a cell line that grew favorably on medium containing glucose but showed limited or no growth on medium containing N-acetylneuraminic acid was transformed with an expression plasmid encoding N-acetylneuraminic acid synthase and N-acetylglucosamine 2-epimerase. After a period of cultivation, the cells were pelleted by centrifugation, stored at −20° C. as so-called "wet cells" and used as needed after thawing. For the production of N-acetylneuraminic acid, a reaction mixture (30 mL) was provided comprising 90 g·L$^{-1}$ N-acetylglucosamine, 50 g·L$^{-1}$ glucose, 10 mL·L$^{-1}$ xylene and 200 g·L$^{-1}$ of said wet cells being permeabilized by the presence of 4 g·L$^{-1}$ detergent. After completion of the in-vitro reaction, the formation of Neu5Ac was evaluated by HPLC.

Document WO 94/29476 A1 discloses an in vitro method for the preparation of N-acetyl-D-neuraminic acid from N-acetyl-D-glucosamine (NAG, GlcNAc). In the preparation, NAG is converted to N-acetyl-D-mannosamine (NAM, ManNAc) by base-catalyzed epimerization. Subsequently, NAM reacts with pyruvate in a reaction catalyzed Neu5Ac-aldolase to yield Neu5Ac. The Neu5Ac-aldolase was prepared from recombinant *E. coli* cells expressing the said Neu5Ac-aldolase. The aldolase enzyme was immobilized by mixing Eupergit-C® beads with a crude extract of said recombinant *E. coli* cells. The conversion of NAM to Neu5Ac was initiated by adding the said immobilized enzyme beads to a mixture of NAM and pyruvate. At the end of the reaction, Neu5Ac was isolated from the reaction mixture.

In an alternative to the previous process, EP 0 578 825 A1 discloses an in vitro process for the production of N-acetylneuraminic acid by treating a mixture of N-acetylglucosamine and pyruvic acid with an N-acetylneuraminic acid lyase under alkaline conditions.

U.S. Pat. No. 7,579,175 discloses a process for the production of N-acetylneuraminic acid utilizing permeabilized microorganisms. The method comprises the preparation of a mixture containing (i) a culture of a microorganism having N-acetylneuraminic acid aldolase activity or N-acetylneuraminic acid synthetase activity, or a treated matter of the culture, (ii) a culture of a microorganism capable of producing pyruvic acid or a treated matter of the culture, or a culture of a microorganism capable of producing phosphoenolpyruvic acid or a treated matter of the culture, (iii) N-acetylmannosamine, and (iv) an energy source which is necessary for the formation of pyruvic acid or phosphoenolpyruvic acid. The mixture is prepared in an aqueous medium comprising a chelating agent or surfactant allowing the formation and accumulation of N-acetylneuraminic acid in the aqueous medium, followed by the recovery of N-acetylneuraminic acid from the aqueous medium.

The drawbacks of the aforementioned processes are (i) that only small-scale production is possible and (ii) an excess of pyruvate is required to drive the reaction equilibrium towards Neu5Ac. In addition, N-acetylglucosamine, N-acetylmannosamine and phosphoenolpyruvate are expensive substrates for these reactions.

International publication WO 2008/040717 A2 discloses a method for the production of sialic acid comprising the cultivation of a microorganism in a medium, wherein said microorganism carries heterologous genes encoding a sialic acid synthase (NeuB) and a UDP-GlcNAc epimerase (NeuC), wherein said microorganism is devoid of a gene encoding CMP-Neu5Ac synthase (NeuA) or wherein any genes encoding CMP-Neu5Ac synthase (NeuA) have been inactivated or deleted, and wherein endogenous genes coding for sialic acid aldolase (NanA), for the sialic acid transporter (NanT) and, optionally, for ManNAc kinase (NanK) have been deleted or inactivated. Neu5Ac has been purified from the supernatant (2 liters) of a culture by precipitation using glacial acetic acid.

International Publication No. WO 2008/097366 A2 concerns metabolically engineered *E. coli* cells that produce sialic acid. In said cells, the nanT (sialic acid transporter) and nanA (sialic acid aldolase) genes are inactivated, and the neuC and neuB genes that facilitate sialic acid biosynthesis in *Neisseria meningitidis* group B are introduced and over-expressed using expression plasmids in said nanT⁻ nanA⁻ *E. coli* cells. In addition, the *E. coli* glucosamine synthase gene (glmS) is co-overexpressed with neuB and neuC.

International Publication No. WO 2012/083329 A1 discloses methods and agents for the production of Neu5Ac in fungal cells of the genus *Trichoderma*, which constitutively express N-acetylglucosamine 2-epimerase and N-acetylneuraminic acid synthase. Such *Trichoderma* cells were cultivated in the presence of GlcNAc, and mycelia were analyzed for the presence of Neu5Ac by HPLC-MS.

Chinese Patent Application No. CN 106 929 461 A discloses a process for the production of N-acetylneuraminic acid using *Bacillus subtilis* cells which expresses genes encoding for a glucosamine-fructose-6-phosphate transaminase, a glucosamine-6-phosphate N-acetyltransferase, a N-acetylglucosamine isomerase and a N-acetylneuraminic acid synthase. The cells further have the ptsG gene deleted, which encodes a glucose-specific component of the phosphotransferase system EIICBA. A yield of 0.66 g·L$^{-1}$ Neu5Ac was obtained by cultivating these cells in a glucose-containing medium.

Zhu, D. and colleagues (Zhu, D. et al. (2017) Biotechnol. Lett. 39: 227-234) report that using a high copy number co-expression vector for overexpression of PEP synthesis-related genes, pck and ppsA in *E. coli* enhance Neu5Ac production.

It was therefore an objective to provide microbial organisms that are capable of producing sialic acid more efficiently on an industrial scale, and with the use of an inexpensive carbon source as a sole carbon source.

The objective is achieved by providing a non-naturally-occurring microorganism carrying a sialic acid synthesis pathway comprising at least one heterologous enzyme, having the naturally-occurring sialic acid catabolic pathway disabled, being improved with respect to the availability of phosphoenolpyruvic acid for Neu5Ac biosynthesis, and capable of utilizing a single inexpensive exogenous carbon source present in the fermentation broth without using a phosphoenolpyruvic acid:phosphotransferase system for the acquisition of said exogenous carbon source.

SUMMARY

In a first aspect, provided is a non-naturally-occurring microorganism for the production of Neu5Ac, wherein the non-naturally-occurring microorganism possesses a sialic acid synthesis pathway comprising at least one heterologous enzyme, wherein the naturally-occurring sialic acid catabolic pathway has been disabled, wherein at least one phosphotransferase system for the import of a saccharide that is not used as a carbon source during the fermentative production of Neu5Ac has been disabled, and wherein said non-naturally-occurring microorganism can utilize an exogenous carbon source present in the fermentation broth without using a phosphotransferase system for the acquisition of said exogenous carbon source.

In a second aspect, provided is the use of the non-naturally-occurring microorganisms according to the first aspect for the production of Neu5Ac.

In a third aspect, provided is a method for the production of Neu5Ac by fermentation using a non-naturally-occurring microorganism according to the first aspect.

In a fourth aspect, provided is Neu5Ac produced by a method according to the second aspect.

In a fifth aspect, provided is the use of Neu5Ac according to the fourth aspect for the manufacture of a nutritional composition.

In a sixth aspect, provided is a nutritional composition comprising Neu5Ac which has been produced by the method of the third aspect.

DETAILED DESCRIPTION

Figure 1:
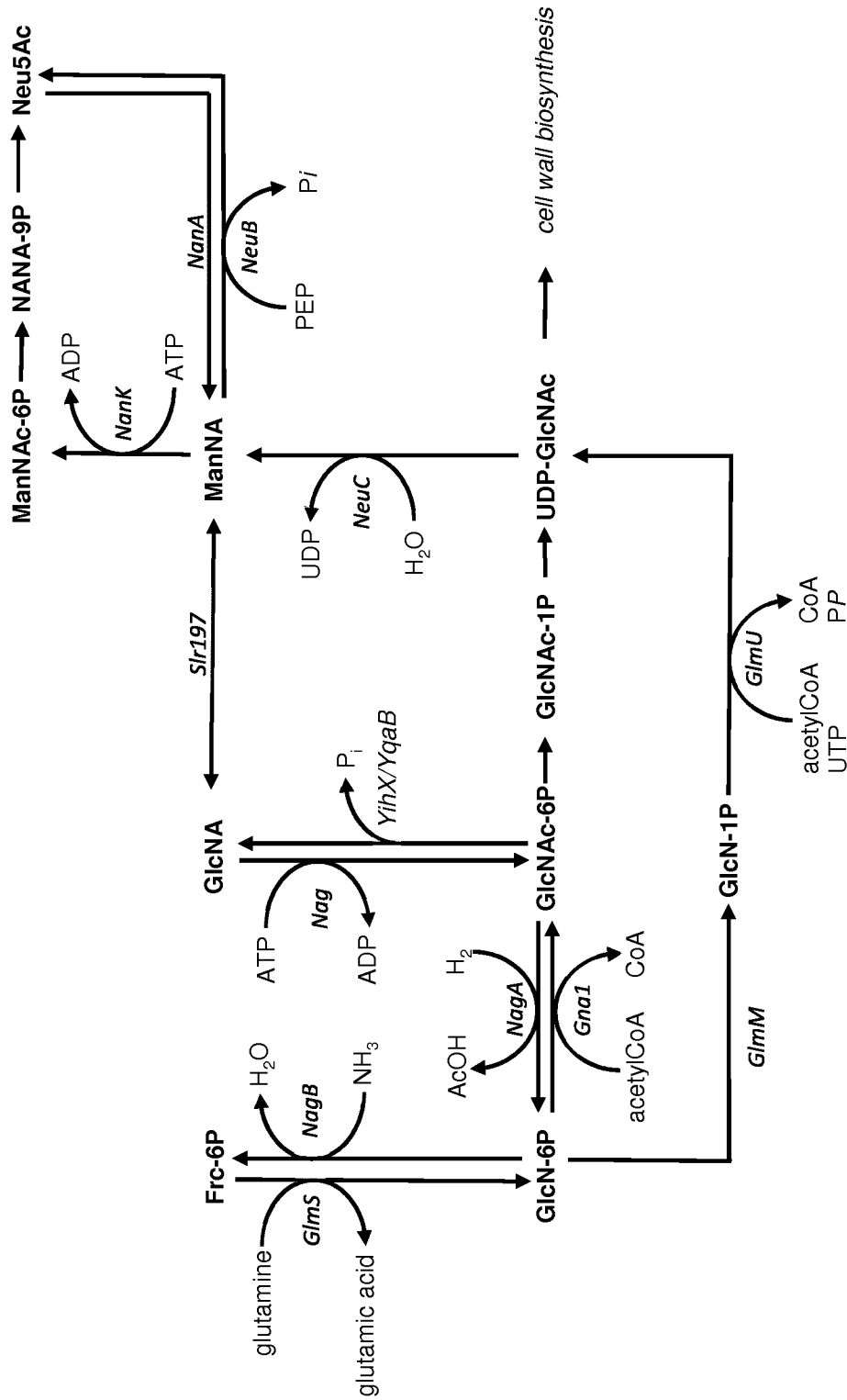
FIG. 1 shows a schematic representation illustrating metabolic pathways for the production of Neu5Ac.

According to the first aspect, provided is a non-naturally-occurring microorganism which is able to produce Neu5Ac. Said non-naturally-occurring microorganism possesses a sialic acid biosynthesis pathway comprising at least one heterologous enzyme which is expressed from a heterologous nucleotide sequence in a manner sufficient to produce sialic acid. The naturally-occurring sialic acid catabolic pathway of said microorganisms has been disabled. At least one phosphoenolpyruvate:sugar phosphotransferase system has also been disabled. The non-naturally-occurring microorganism can utilize an exogenously supplied carbon source as a sole carbon source without requiring a phosphoenolpyruvate: sugar phosphotransferase system for the acquisition of said carbon source.

The term "non-naturally-occurring microorganism" as used herein refers to a microorganism that has been genetically engineered to introduce at least one heterologous nucleotide sequence and/or in that a nucleotide sequence which occurs naturally in the microorganism has been modified, i.e. altered, substituted, inserted or deleted.

The term "heterologous" as used herein refers to a compound, a polypeptide, protein, enzyme, nucleic acid molecule or nucleotide sequence—as part of a nucleic acid molecule—in a host organism which does not naturally have this compound, polypeptide, protein, enzyme, or nucleotide sequence. A "heterologous nucleotide sequence" may be a gene or gene fragment. The term "heterologous expression" refers to the expression of a heterologous gene or gene fragment in a host organism which does not naturally have this gene or gene fragment. Heterologous gene expression leads to the presence of a heterologous polypeptide, protein or enzyme in the host organism.

The non-naturally-occurring microorganism is capable of producing Neu5Ac. The term "producing" as used herein refers to the production of Neu5Ac by microbial fermentation. "Microbial fermentation" is to be understood as a—generally large-scale —industrial process, wherein the desired product, e.g. Neu5Ac, is produced by cultivating a microorganism in a fermentation broth containing nutrients, such that the microorganism can convert compounds to other compounds. The terms "large-scale" and "industrial" indicate that the production can occur by microbial fermentation in a volume of fermentation broth exceeding 100 L, 500 L, 1000 L, 5000 L, 10,000 L 50,000 L 100,000 L or even 200,000 L.

The term "capable of producing" or "able to produce" as used herein refers to the ability of the microorganism to produce Neu5Ac provided that it is cultivated in a medium or broth and under conditions that are permissive for the microorganism to synthesize Neu5Ac.

Sialic Acid Biosynthesis Pathway

The non-naturally-occurring microorganism is a microorganism for the production of Neu5Ac. Therefore, said non-naturally-occurring microorganism is able to produce Neu5Ac. The non-naturally-occurring microorganism is a microorganism that has been genetically engineered to possess a sialic acid biosynthesis pathway.

In an embodiment, the sialic acid biosynthesis pathway of the non-naturally-occurring microorganism comprises at least one heterologous enzyme selected from the group consisting of glutamine-fructose-6-phosphate aminotransferase, glucosamine-6-phosphate N-acetyltransferase, N-acetylglucosamine 2-epimerase, N-acetylneuraminic acid synthase, and a sugar phosphatase of the haloacid dehydrogenase (HAD)-like superfamily. Preferably, the non-naturally-occurring microorganism is a microorganism that has been genetically engineered to contain one or more of the genes encoding said enzymes. It is to be understood that a host microorganism already carrying one or more genes encoding said enzymes, and expressing said genes in a manner sufficient to produce Neu5Ac, does not need to be genetically engineered to complete sialic acid biosynthesis pathway but may nevertheless be genetically engineered to alter the expression level of one or more of said genes to increase the quantity of glutamine-fructose-6-phosphate aminotransferase, glucosamine-6-phosphate N-acetyltransferase, N-acetylglucosamine 2-epimerase, N-acetylneuraminic acid synthase and/or sugar phosphatase of the HAD-like superfamily, thus increasing the rate of Neu5Ac biosynthesis in the non-naturally-occurring microorganism.

The enzyme glutamine-fructose-6-phosphate aminotransferase (EC 2.6.1.16) catalyzes the conversion of fructose 6-phosphate to glucosamine-6-phosphate using glutamine. This enzymatic reaction is typically considered to be the first step in the hexosamine biosynthesis pathway. Alternative names of the glutamine-fructose-6-phosphate aminotransferase are D-fructose-6-phosphate amidotransferase, GFAT, glucosamine-6-phosphate synthase, hexosephosphate aminotransferase, and L-glutamine-D-fructose-6-phosphate amidotransferase.

In an additional and/or alternative embodiment, the non-naturally-occurring microorganism possesses a glutamine-fructose-6-phosphate aminotransferase (GlmS), preferably a heterologous glutamine-fructose-6-phosphate aminotransferase, more preferably a glutamine-fructose-6-phosphate aminotransferase which is derived from *E. coli*, or a functional variant of the *E. coli* GlmS. Most preferably, the functional variant is a version of the *E. coli* GlmS which shows significantly reduced sensitivity to glucosamine-6-phosphate inhibition as the wild-type enzyme does, for example as encoded by the mutant glmS gene (glmS*54 or glmS* (see SEQ ID NO: 6).

The term "functional variant" as used herein, with respect to an enzyme, refers to polypeptide variants of the designated enzymes without loss of activity, and which share at least 70%, preferably at least 80%, more preferably at least 90% and even more preferably at least 95% identity with the amino acid sequence of the designated enzyme. This takes into account the possibility of some variability in the genomic sequence data from which these polypeptides are derived, and also the possibility that some of the amino acids present in these polypeptides can be substituted without significantly affecting the enzyme's catalytic activity.

The Term "Functional Variants" Also Includes Polypeptide Variants of the Designated enzymes which represent truncated variants of the enzyme without significant loss of the catalytic activity. Thus, the amino acid sequence of the truncated variants may differ from the amino acid sequences of the designated enzyme in that one, two or a stretch of more than two consecutive amino acids are absent. The truncation may be at the amino terminus (N-terminus), at the carboxyl terminus (C-terminus) and/or within the amino acid sequence of the designated enzyme.

In an additional and/or alternative embodiment, the non-naturally-occurring microorganism contains a nucleic acid molecule comprising a nucleotide sequence encoding a glutamine-fructose-6-phosphate aminotransferase. In an additional and/or alternative embodiment, the nucleotide sequence encoding the glutamine-fructose-6-phosphate aminotransferase is a heterologous nucleotide sequence. In an additional and/or alternative embodiment, the nucleotide sequence encoding the glutamine-fructose-6-phosphate aminotransferase encodes the *E. coli* glutamine-fructose-6-phosphate aminotransferase or a functional variant thereof. In an additional and/or alternative embodiment, the non-naturally-occurring microorganism has been genetically engineered to contain a nucleic acid molecule comprising the nucleotide sequence encoding a glutamine-fructose-6-phosphate aminotransferase or functional variant thereof and/or to comprise the glutamine-fructose-6-phosphate aminotransferase or functional variant thereof.

The *E. coli* glutamine-fructose-6-phosphate aminotransferase (UniProtKB-P17169; SEQ ID NO: 11) is encoded by the *E. coli* glmS gene (SEQ ID NO: 10). In an additional and/or alternative embodiment, the non-naturally-occurring microorganism contains a nucleic acid molecule comprising and expressing a nucleotide sequence encoding *E. coli* GlmS or a functional variant thereof, preferably the nucleotide sequence encoding GlmS* (SEQ ID NO: 12 and SEQ ID NO: 13).

In an additional and/or alternative embodiment, the nucleotide sequence encoding the *E. coli* GlmS or one of the functional variants of the *E. coli* GlmS has a sequence identity to *E. coli* glmS of at least 80%, at least 85%, at least 90%, at least 95%, at least 98% or at least 99%.

The enzyme glucosamine-6-phosphate N-acetyltransferase (Gna1, EC 2.3.1.4) converts glucosamine-6-phosphate to N-acetylglucosamine-6-phosphate using acetyl-CoA. This enzymatic reaction is considered to be the first step of the subpathway that synthesizes N-acetyl-alpha-D-glucosamine 1-phosphate from alpha-D-glucosamine 6-phosphate in *Saccharomyces cerevisiae*. Gna1 is also known as phosphoglucosamine acetylase or phosphoglucosamine transacetylase.

In an additional and/or alternative embodiment, the non-naturally-occurring microorganism comprises a glucosamine-6-phosphate N-acetyltransferase (Gna1), preferably a heterologous glucosamine-6-phosphate N-acetyltransferase, more preferably a glucosamine-6-phosphate N-acetyltransferase which is derived from *S. cerevisiae* (UniProtKB-P43577, SEQ ID NO: 15), or a functional variant of the *S. cerevisiae* Gna1.

In an additional and/or alternative embodiment, the non-naturally-occurring microorganism contains a nucleic acid molecule which comprises a nucleotide sequence encoding a glucosamine-6-phosphate N-acetyltransferase. In an additional and/or alternative embodiment, the nucleotide sequence encoding the glucosamine-6-phosphate N-acetyltransferase is a heterologous nucleotide sequence. In an additional and/or alternative embodiment, the nucleotide sequence encoding the glucosamine-6-phosphate N-acetyltransferase encodes the *S. cerevisiae* glucosamine-6-phosphate N-acetyltransferase or a functional fragment thereof. However, glucosamine-6-phosphate N-acetyltransferases, their deduced amino acid sequences and the nucleotides sequences encoding these glucosamine-6-phosphate N-acetyltransferases are known from a variety of different species, and may also be used as suitable glucosamine-6-phosphate N-acetyltransferases.

In an additional and/or alternative embodiment, the non-naturally-occurring microorganism has been genetically engineered to contain a nucleic acid molecule comprising a nucleotide sequence encoding a glucosamine-6-phosphate N-acetyltransferase or functional variant thereof and/or to comprise a glucosamine-6-phosphate N-acetyltransferase or functional variant thereof.

The *S. cerevisiae* glucosamine-6-phosphate N-acetyltransferase (UniProtKB-P43577; SEQ ID NO: 15) is encoded by the *S. cerevisiae* gna1 gene (SEQ ID NO: 14). In an additional and/or alternative embodiment, the non-naturally-occurring microorganism comprises nucleic acid molecule comprising and expressing a nucleotide sequence encoding *S. cerevisiae* Gna1 or a functional variant thereof, preferably the nucleotide sequence encoding *S. cerevisiae* Gna1 (SEQ ID NO: 14).

In an additional and/or alternative embodiment, the nucleotide sequence encoding the *S. cerevisiae* Gna1 or one of the functional variants of the *S. cerevisiae* Gna1 has a sequence identity to *S. cerevisiae* gna1 of at least 80%, at least 85%, at least 90%, at least 95%, at least 98% or at least 99%.

In an additional and/or alternative embodiment, the non-naturally-occurring microorganism expresses a sugar phosphatase of the HAD-like superfamily which catalyzes the conversion of N-acetylglucosamine-6-phosphate (GlcNAc6P) to N-acetylglucosamine (GlcNAc). The HAD-like superfamily is named after the bacterial enzyme haloacid dehydrogenase and includes phosphatases. A suitable phosphatase of the HAD-like superfamily catalyzing the conversion of GlcNAc6P to GlcNAc may be selected from the group consisting of fructose-1-phosphate phosphatase (YqaB, UniProtKB-P77475) and alpha-D-glucose 1-phosphate phosphatase (YihX, UniProtKB-P0A8Y3). The *E. coli* YqaB and *E. coli* YihX enzymes are considered to also act on GlcNAc6P (Lee, S.-W. and Oh, M.-K. (2015) Metabolic Engineering 28: 143-150). In an embodiment, the sugar phosphatase of the HAD-like superfamily catalyzing the conversion of GlcNAc-6-phosphate to GlcNAc is a heterologous enzyme in the non-naturally-occurring microorganism. In an additional and/or alternative embodiment, the sugar phosphatase of the HAD-like superfamily catalyzing the conversion of GlcNAc6P to GlcNAc is selected from the group consisting of *E. coli* YqaB, *E. coli* YihX, and functional variants thereof.

In an additional and/or alternative embodiment, the non-naturally-occurring microorganism contains a nucleic acid molecule which comprises a nucleotide sequence encoding a sugar phosphatase of the HAD-like superfamily catalyzing the conversion of GlcNAc6P to GlcNAc. In an additional and/or alternative embodiment, the nucleotide sequence encoding the sugar phosphatase of the HAD-like superfamily catalyzing the conversion of GlcNAc6P to GlcNAc is a heterologous nucleotide sequence. In an additional and/or alternative embodiment, the nucleotide sequence encoding the sugar phosphatase of the HAD-like superfamily catalyzing the conversion of GlcNAc6P to GlcNAc encodes The *E. coli* fructose-1-phosphate phosphatase or the *E. coli* alpha-D-glucose 1-phosphate phosphatase or a functional fragment of one of these two enzymes.

In an additional and/or alternative embodiment, the non-naturally-occurring microorganism has been genetically engineered to contain a nucleic acid molecule comprising a nucleotide sequence encoding a sugar phosphatase of the HAD-like superfamily catalyzing the conversion of GlcNAc6P to GlcNAc or a functional fragment of said HAD phosphatase and/or to comprise a sugar phosphatase of the HAD-like superfamily catalyzing the conversion of GlcNAc6P to GlcNAc or functional variant thereof.

Nucleotide sequences encoding a suitable sugar phosphatase of the HAD-like superfamily catalyzing the conversion of GlcNAc6P to GlcNAc may be selected from the group of nucleotide sequences encoding *E. coli* YqaB, *E. coli* YihX and functional variants thereof.

*E. coli* YqaB (SEQ ID NO: 17) and *E. coli* YihX (SEQ ID NO: 19) are encoded by *E. coli* genes yqaB (SEQ ID NO: 16) and yihX (SEQ ID NO: 18) respectively. Thus, in an additional and/or alternative embodiment, the non-naturally-occurring microorganism contains a nucleic acid molecule comprising a nucleotide sequence encoding *E. coli* YqaB, *E. coli* YihX, or a functional fragment of one of these two enzymes.

In an additional and/or alternative embodiment, the nucleotide sequence encoding *E. coli* YqaB or functional variant thereof has a sequence identity to *E. coli* yqaB of at least 80%, at least 85%, at least 90%, at least 95%, at least 98% or at least 99%.

In an additional and/or alternative embodiment, the nucleotide sequence encoding *E. coli* YihX or functional variant thereof has a sequence identity to *E. coli* yihX of at least 80%, at least 85%, at least 90%, at least 95%, at least 98% or at least 99%. N-acetylglucosamine 2-epimerase (EC 5.1.3.8) is an enzyme that catalyzes the conversion of N-acetylglucosamine (GlcNAc) to N-acetylmannosamine (ManNAc). The enzyme is a racemase acting on carbohydrates and their derivatives. The systematic name of this enzyme class is N-acyl-D-glucosamine 2-epimerase. This enzyme participates in amino-sugar metabolism and nucleotide-sugar metabolism.

In an additional and/or alternative embodiment, the non-naturally-occurring microorganism possesses a N-acetylglucosamine 2-epimerase, preferably a heterologous N-acetylglucosamine 2-epimerase.

In an additional and/or alternative embodiment, the N-acetylglucosamine 2-epimerase is derived from *Anabena variabilis, Acaryochloris* sp., *Nostoc* sp., *Nostoc punctiforme, Bacteroides ovatus* or *Synechocystis* sp. or is a functional variant thereof. The N-acetylglucosamine 2-epimerase of *B. ovatus* ATCC 8483 (UniProtKB-A7LVG6, SEQ ID NO: 21) is encoded by gene BACOVA_01816 (SEQ ID NO: 20). The *Synechocystis* sp. (strain PCC 6803) N-acetylglucosamine 2-epimerase (UniProtKB-P74124; SEQ ID NO: 23) is also known as renin-binding protein and is encoded by the slr1975 gene (SEQ ID NO: 22).

In an additional and/or alternative embodiment, the non-naturally-occurring microorganism contains a nucleic acid molecule comprising a nucleotide sequence encoding the N-acetylglucosamine 2-epimerase or functional variant thereof. In an additional and/or alternative embodiment, the nucleotide sequence encoding the N-acetylglucosamine 2-epimerase is selected from the group consisting of nucleotide sequences encoding the N-acetylglucosamine 2-epimerase of *Anabena variabilis, Acaryochloris* sp., *Nostoc* sp., *Nostoc punctiforme, Bacteroides ovatus* or *Synechocystis* sp., and functional variants thereof. In an additional and/or alternative embodiment, the nucleotide sequence encoding the N-acetylglucosamine 2-epimerase is a heterologous nucleotide sequence.

In an additional and/or alternative embodiment, the non-naturally-occurring microorganism has been genetically engineered to contain a nucleic acid molecule comprising the nucleotide sequence encoding an N-acetylglucosamine 2-epimerase or functional variant thereof and/or to comprise the N-acetylglucosamine 2-epimerase or functional variant thereof.

In an additional and/or alternative embodiment, the nucleotide sequence encoding one of the functional variants of the N-acetylglucosamine 2-epimerase has a sequence identity of at least 80%, at least 85%, at least 90%, at least 95%, at least 98% or at least 99% to the *Synechocystis* sp. slr1975 gene.

In an additional and/or alternative embodiment, the non-naturally-occurring microorganism possesses GlcNAc-6-phosphate epimerase activity and ManNAc-6-phosphate phosphatase activity.

Figure 2:
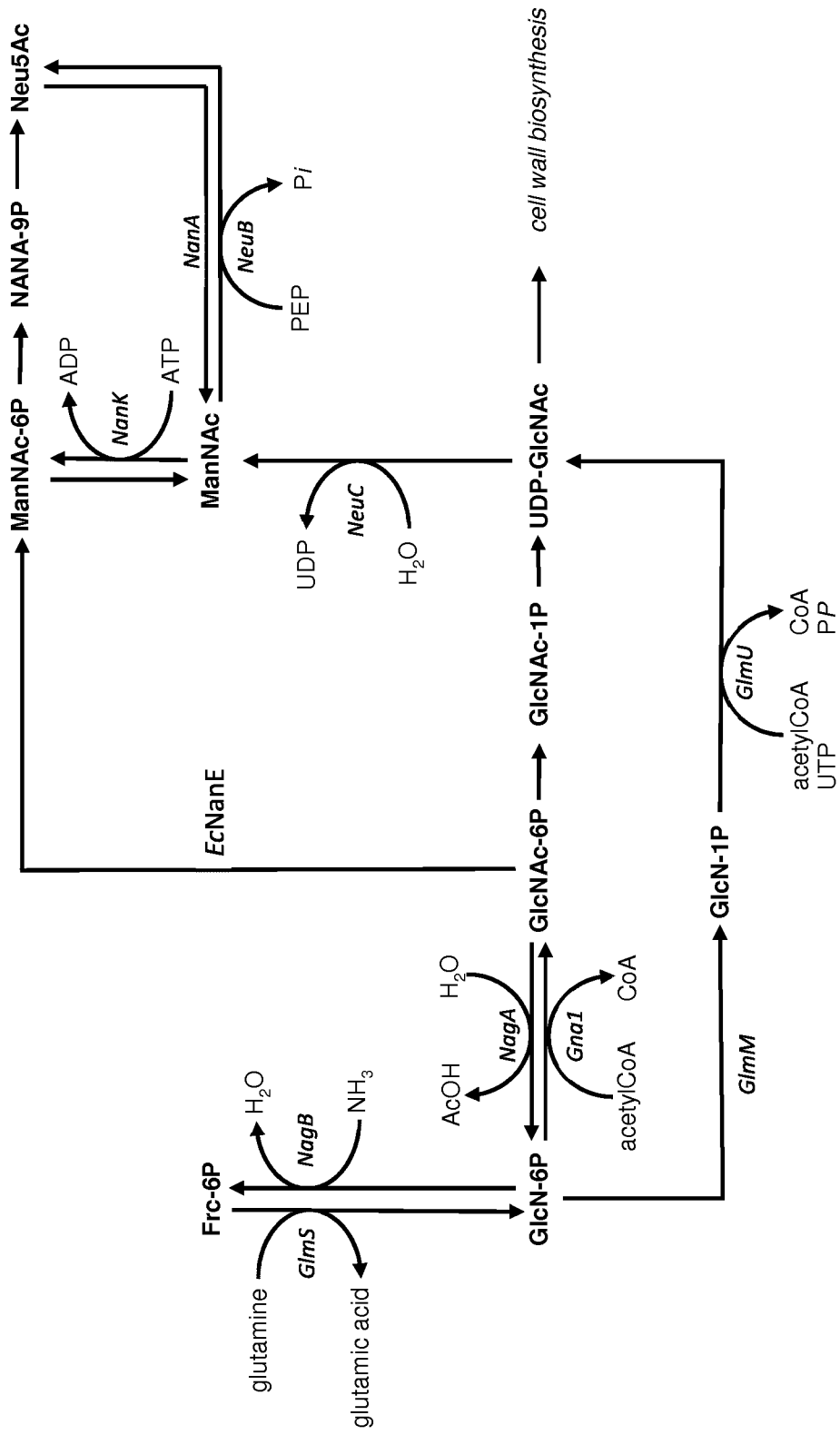
FIG. 2 shows a schematic representation illustrating additional and/or alternative metabolic pathways for the production of Neu5Ac.

GlcNAc-6-phosphatase epimerase converts GlcNAc-6-phosphate to ManNAc-6-phosphate, whereas ManNAc-6-phosphate phosphatase dephosphorylates ManNAc-6-phosphate to give ManNAc. Possessing GlcNAc-6-phosphate epimerase activity and ManNAc-6-phosphate phosphatase activity provides an additional or alternative way in the production of Neu5Ac to convert GlcNAc-6-phosphate to ManNAc as shown in FIG. 2.

In an additional and/or alternative embodiment, the non-naturally-occurring microorganism has been genetically engineered to possess a gene encoding GlcNAc-6-phosphate epimerase or functional variant thereof. Preferably, the non-naturally-occurring microorganism has been genetically engineered to contain a nucleic acid molecule comprising and expressing a nucleotide sequence encoding GlcNAc-6-phosphate epimerase.

Preferably the GlcNAc-6-phosphate epimerase is derived from *Enterobacter cloacae* subsp. *cloacae* (SEQ ID NO: 25) or a functional variant thereof. The nucleotide sequence encoding GlcNAc-6-phosphate epimerase of *E. cloacae* subsp. *cloacae* is the protein-coding region of the nanE gene of *Enterobacter cloacae* subsp. *cloacae* ATCC 13047 (SEQ ID NO: 24).

In an additional and/or alternative embodiment, the nucleotide sequence encoding one of the functional variants of GlcNAc-6-phosphate epimerase has a sequence identity of at least 80%, at least 85%, at least 90%, at least 95%, at least 98% or at least 99% to the *E. cloacae* subsp. *cloacae* nanE gene.

In an additional and/or alternative embodiment, the non-naturally-occurring microorganism has been genetically engineered to possess a gene encoding ManNAc-6-phosphate phosphatase or a functional variant thereof.

N-acetylneuraminic acid synthase (EC 2.5.1.56) is an enzyme that catalyzes the conversion of N-acetylmannosamine (ManNAc) to Neu5Ac using phosphoenolpyruvate (PEP). The N-acetylneuraminic acid synthase (NeuB) is encoded by the neuB gene.

In an additional and/or alternative embodiment, the non-naturally-occurring microorganism comprises an N-acetylneuraminic acid synthase or a functional variant thereof, preferably a heterologous N-acetylneuraminic acid synthase. In an additional embodiment, the N-acetylneuraminic acid synthase is derived from *Campylobacter jejuni* SEQ ID NO: 29), *Streptococcus agalactiae, Butyrivibrio proteoclasticus, Methanobrevibacter ruminatium, Acetobacterium woodii, Desulfobacula toluolica, Escherichia coli, Prevotella nigescens, Halorhabdus tiamatea, Desulfotignum phosphitoxidans,* or *Candidatus Scalindua* sp., *Idomarina loihiensis, Fusobacterium nucleatum* or *Neisseria meningitidis*.

In an additional and/or alternative embodiment, the non-naturally-occurring microorganism contains a nucleic acid molecule comprising a nucleotide sequence encoding an N-acetylneuraminic acid synthase or a functional variant thereof. In an additional and/or alternative embodiment, the nucleotide sequence encoding the N-acetylneuraminic acid synthase is a heterologous nucleotide sequence. In an additional and/or alternative embodiment, the nucleotide sequence encoding the N-acetylneuraminic acid synthase is selected from the group consisting of nucleotide sequences encoding *C. jejuni* NeuB (SEQ ID NO: 28), *S. agalactiae* NeuB, *B. proteoclasticus* NeuB, *M. ruminatium* NeuB, *A. woodii* NeuB, *D. toluolica* NeuB, *E. coli* NeuB, *P. nigescens* NeuB, *H. tiamatea* NeuB, *D. phosphitoxidans* NeuB, *Ca. scalindua* sp. NeuB, *I. loihiensis* NeuB, *F. nucleatum* NeuB, *N. meningitidis* NeuB and functional variants thereof.

In an additional and/or alternative embodiment, the nucleotide sequence encoding the N-acetylneuraminic acid synthase or one of the functional variants of the N-acetylneuraminic acid synthase has a sequence identity of at least 80%, at least 85%, at least 90%, at least 95%, at least 98% or at least 99% to one of the nucleotide sequences encoding *C. jejuni* NeuB, *S. agalactiae* NeuB, *B. proteoclasticus* NeuB, *M. ruminatium* NeuB, *A. woodii* NeuB, *D. toluolica* NeuB, *E. coli* NeuB, *P. nigescens* NeuB, *H. tiamatea* NeuB, *D. phosphitoxidans* NeuB, *Ca. Scalindua* sp. NeuB, *I. loihiensis* NeuB, *F. nucleatum* NeuB, *N. meningitidis* NeuB

Sialic Acid Catabolic Pathway

The non-naturally-occurring microorganism for the production of Neu5Ac can not utilize Neu5Ac. In an additional embodiment, the non-naturally-occurring microorganism has been genetically engineered such that it does not utilize sialic acid. Thereby, the Neu5Ac that has been synthesized by the non-naturally-occurring microorganism is neither degraded in naturally occurring catabolic pathways, nor incorporated into lipopolysaccharides and/or into polysialic acids. Instead, the non-naturally-occurring microorganism is capable of secreting the Neu5Ac it has synthesized into the culture medium or fermentation broth.

The non-naturally-occurring microorganism is able to produce Neu5Ac. For being able to produce Neu5Ac, the naturally-occurring sialic acid catabolic pathway has been disabled. Disruption of the sialic acid catabolic pathway in the microorganism prevents any sialic acid synthesized by that microorganism from being metabolized further, and thus increases the yield of sialic acid that can be produced by the non-naturally-occurring microorganism.

In an additional and/or alternative embodiment, the naturally-occurring sialic acid catabolic pathway is disabled by genetically engineering the microorganism.

In an additional and/or alternative embodiment, the naturally occurring sialic acid catabolic pathway has been disrupted by deleting or otherwise mutating one or more of the genes encoding enzymes required for sialic acid catabolism. The enzyme(s) required for sialic acid catabolism are therefore no longer produced, or are produced at much lower level than normal, e.g. in the wild type microorganism. For example, one or more genes encoding enzymes required for sialic acid catabolism can be deleted from the genome, such that the corresponding enzymes are not produced at all. Alternatively, the regulatory sequences controlling gene expression can be replaced or mutated so that the gene can not be transcribed or translated. This impairment of transcription or translation includes permanent impairment of transcription or translation as well as transient impairment of transcription or translation. I.e. transcription or translation of the respective gene can be regulated by inducing or repressing transcription or translation. Thus, expression of a respective gene can be induced at any desired point of time during cultivation of the microorganism, preferably by adding a compound inducing expression of the respective gene (inducer) to the culture medium. In another embodiment, expression of a respective gene can be repressed at any desired point of time during cultivation of the microorganism, preferably by adding a compound which represses expression of the respective gene (repressor) to the culture medium or by depleting the culture medium of any compound acting as an inducer. In a different approach, the nucleotide sequence encoding an enzyme required for sialic acid catabolism can be altered in such a way that the activity of the enzyme is abolished. This may be achieved by altering the nucleotide sequence to replace a sense codon (specifying an amino acid) in the original nucleotide sequence with a stop codon such that a truncated polypeptide is generated which lacks the activity of the enzyme required for sialic acid catabolism, or by replacing a sense codon with another codon specifying a different amino acid, which produces a non-functional variant of the enzyme required for sialic acid catabolism.

In an additional and/or alternative embodiment, the genes targeted for disruption or alteration to abolish sialic acid catabolism in the non-naturally-occurring microorganism encode one or more enzymes selected from the group consisting of N-acetylmannosamine kinase, N-acetylmannosamine-6-phosphate epimerase, N-acetylneuraminic acid aldolase and sialic acid permease.

N-acetylmannosamine kinase (EC 2.7.1.60) is an enzyme that phosphorylates N-acetylmannosamine to yield N-acetylmannosamine-6-phosphate. The N-acetylmannosamine kinase is encoded by the nanK gene. The nucleotide sequence of the protein-coding region of E. coli nanK is represented by SEQ ID NO: 30.

N-acetylmannosamine-6-phosphate epimerase is an enzyme that converts N-acetylmannosamine-6-phosphate (ManNAc-6-P) to N-acetylglucosamine-6-phosphate (GlcNAc-6-P). This enzymatic reaction is a step of the subpathway that synthesizes D-fructose 6-phosphate from N-acetylneuraminate. The N-acetylmannosamine-6-phosphate epimerase is encoded by the nanE gene. The nucleotide sequence of the protein-coding region of E. coli nanE is represented by SEQ ID NO: 32.

N-acetylneuraminic acid aldolase, also called N-acetylneuraminate lyase, catalyzes the reversible aldol cleavage of N-acetylneuraminic acid to form pyruvate and N-acetylmannosamine (ManNAc). N-acetylneuraminic acid aldolase is encoded by the nanA gene. The nucleotide sequence of the protein-coding region of E. coli nanA is represented by SEQ ID NO: 34.

Sialic acid permease catalyzes the proton-dependent transport of sialic acid across the cell membrane. Sialic acid permease can transport N-acetylneuraminic acid. Variants of sialic acid permease can also transport the related sialic acids N-glycolylneuraminic acid (Neu5Gc) and 3-keto-3-deoxy-D-glycero-D-galactononic acid (KDN). Although sialic acid permease is known to function as a bidirectional transproter in vitro, it accounts for the cellular import of extracellular Neu5Ac in vivo. The sialic acid permease is encoded by the nanT gene. The nucleotide sequence of the protein-coding region of E. coli nanT is represented by SEQ ID NO: 36. Disruption of nanT prevents reimport of Neu5Ac that has been produced and secreted into the culture medium by the non-naturally-occurring microorganism.

In an additional and/or alternative embodiment, the non-naturally-occurring microorganism has reduced or abolished activity of at least one of the enzymes selected from the group consisting of N-acetylmannosamine kinase, N-acetylmanno-samine-6-phosphate epimerase, N-acetylneuraminic acid aldolase and sialic acid permease, as compared to the wildtype microorganism. In an additional and/or alternative embodiment, the microorganism has been genetically engineered to have reduced or abolished activity of at least one of these enzymes. In an additional and/or alternative embodiment, the non-naturally-occurring microorganism has been genetically engineered to completely delete one or more of the genes encoding N-acetylmannosamine kinase, N-acetylmannosamine-6-phosphate epimerase, N-acetylneuraminic acid aldolase and sialic acid permease, to impair the expression of one or more of those genes, or to abolish the activity of one or more of the corresponding enzymes by introducing mutations into the protein-coding region of the gene(s) such that the polypeptide encoded by the altered nucleotide sequence does not possess the enzymatic activity of the enzyme encoded by the non-amended nucleotide sequence.

In an additional and/or alternative embodiment, the non-naturally-occurring microorganism does not possess an enzymatic activity provided by at least one of the enzymes N-acetylglucosamine-6-phosphate deacetylase and N-acetyl-glucosamine-6-phosphate deaminase.

In an additional and/or alternative embodiment, at least one of the enzymes N-acetylglucosamine-6-phosphate deacetylase and N-acetylglucosamine-6-phosphate deaminase has been disabled in the non-naturally-occurring microorganism.

N-acetylglucosamine-6-phosphate deacetylase (EC 3.5.1.25) is the enzyme involved in the first step in the biosynthesis of amino-sugar-nucleotides. It catalyzes the hydrolysis of the N-acetyl group of N-acetylglucosamine-6-phosphate (GlcNAc-6-P) to yield glucosamine 6-phosphate and acetate. The N-acetylglucosamine-6-phosphate deacetylase is encoded by the nagA gene. The nucleotide sequence of the protein coding region of E. coli nagA is represented by SEQ ID NO: 38.

Glucosamine-6-phosphate deaminase (EC 3.5.99.6) catalyzes the reversible isomerization-deamination of glucosamine 6-phosphate (GlcN6P) to form fructose 6-phosphate (Fru6P). Glucosamine-6-phosphate deaminase is encoded by the nagB gene. The nucleotide sequence of the protein coding region of E. coli nagB is represented by SEQ ID NO: 40.

In an additional and/or alternative embodiment, the non-naturally-occurring microorganism has been genetically engineered to disable N-acetylglucosamine-6-phosphate deacetylase and/or Glucosamine-6-phosphate deaminase. In an additional and/or alternative embodiment, the non-naturally-occurring microorganism has been genetically engineered to completely delete one or more of the genes encoding N-acetylglucosamine-6-phosphate deacetylase and Glucosamine-6-phosphate deaminase, to impair the expression of one or more of those genes, or to abolish the activity of one or more of the corresponding enzymes by introducing mutations into the protein-coding region of at least one of those genes such that the polypeptide encoded the altered nucleotide sequence does not possess the enzymatic activity of the enzyme encoded by the non-amended nucleotide sequence.

Phosphotransferase Carbohydrate Transport System

The intracellular production of sialic acid requires phosphoenolpyruvate (PEP). PEP is a very important metabolic intermediate because it is involved in glycolysis and gluconeogenesis. To improve the production of Neu5Ac, the non-naturally-occurring microorganism has been genetically engineered to provide a better supply of PEP for sialic acid biosynthesis. To this end, the non-naturally-occurring microorganism has been genetically engineered in that at least one PEP-dependent, sugar-transporting phosphotransferase system (PTS) has been disabled, i.e. the corresponding gene has been deleted or disrupted, or the expression of the gene has been impaired.

A PEP-dependent, sugar-transporting phosphotransferase system suitable for disruption is GlcNAc permease, also known as protein-Npi-phospho-L-histidine:N-acetyl-D-glucosamine Npi-phosphotransferase (EC 2.7.1.193), which is encoded by the nagE gene. NagE (known as enzyme II) is a component of a PEP-dependent, sugar transporting phosphotransferase system. The system simultaneously transports its substrate from the periplasm or extracellular space into the cytoplasm and phosphorylates it. The deletion or disruption of nagE or the impairment of its expression is advantageous, because this prevents the import of GlcNAc at the expense of PEP, which would otherwise reduce the amount of PEP available for sialic acid production. Hence, the deletion or disruption of nagE or the impairment of its expression increases the intracellular pool of PEP that can be utilized by the non-naturally-occurring microorganism to produce Neu5Ac, thereby increasing the Neu5Ac yield in the non-naturally-occurring microorganism as compared to a non-naturally-occurring microorganism that can produce sialic acid, but which carries an intact and functional nagE gene. The nucleotide sequence of the protein coding region of E. coli nagE is represented by SEQ ID NO: 42.

In an additional and/or alternative embodiment, the non-naturally-occurring microorganism has been genetically engineered to abolish protein-Npi-phospho-L-histidine:N-acetyl-D-glucosamine Npi-phosphotransferase activity.

In an additional and/or alternative embodiment, the non-naturally-occurring microorganism has been genetically engineered to completely delete the nagE gene, to impair its expression, or to abolish the activity of the NagE enzyme by introducing mutations into the protein-coding region of the nagE gene such that the polypeptide encoded the altered nucleotide sequence does not possess the enzymatic activity of the enzyme encoded by the non-amended nucleotide sequence.

Another or additional PEP-dependent, sugar-transporting phosphotransferase system for import of a carbohydrate that is suitable for disruption is the mannose permease.

ManXYZ, the Enzyme II$^{Man}$ complex (mannose PTS permease, protein-Npi-phosphohistidine-D-mannose phosphotransferase) imports exogenous hexoses (mannose, glucose, glucosamine, fructose, 2-deoxyglucose, mannosamine, N-acetylglucosamine, etc.) and releases the phosphate esters into the cell cytoplasm. This enzyme is also a component of a PEP-dependent, sugar-transporting phosphotransferase system. ManXYZ possesses four domains in three polypeptide chains, ManX=IIAB$^{Man}$, ManY=IIC$^{Man}$ and ManZ=IID$^{Man}$. They are members of the mannose PTS permease family, the splinter group, which is not homologous to most other PTS permeases. The nucleotide sequences of the protein-coding regions of E. coli manX, manY and manZ are represented by SEQ ID NO: 44, SEQ ID NO: 46 and SEQ ID NO: 48 respectively.

In an additional and/or alternative embodiment, the non-naturally-occurring microorganism has been genetically engineered to abolis protein-Npi-phospho-L-histidine:mannose Npi-phosphotransferase activity.

In an additional and/or alternative embodiment, the non-naturally-occurring microorganism has been genetically engineered to completely delete one or more of the genes encoding ManX, ManY and ManZ, to impair the expression of one or more of those genes, or to abolish the activity of one or more of the corresponding enzymes by introducing mutations by introducing mutations into the protein-coding region(s) of the gene(s) such that the polypeptide encoded the altered nucleotide sequence does not possess the enzymatic activity of the enzyme encoded by the non-amended nucleotide sequence.

Another or additional PEP-dependent, sugar-transporting phosphotransferase system suitable for disruption is the glucose transporter.

The glucose-specific PTS transporter (PtsG/Crr) takes up exogenous glucose, releasing the phosphate ester into the cytoplasm. The enzyme II$^{Glc}$ complex possesses two domains in a single polypeptide chain with the domain order IIC-IIB (PtsG), and it functions with an additional polypeptide chain, the Crr or IIA$^{Glc}$ protein.

The deletion or disruption of ptsG and/or crr or the impairment of its expression is advantageous, because this prevents the import of glucose at the expense of PEP, which would otherwise reduce the amount of PEP available for sialic acid production. Hence, the deletion or disruption of the ptsG gene and/or the crr gene or impairment of its expression increases the intracellular pool of PEP that can be utilized by the non-naturally-occurring microorganism to produce Neu5Ac, thereby increasing the Neu5Ac yield in the non-naturally-occurring microorganism that can produce Neu5Ac as compared to a non-naturally occurring microorganism that can produce sialic acid, but which carries an intact and functional ptsG and/or crr gene.

The nucleotide sequences of the protein-coding regions of E. coli ptsG and crr are represented by SEQ ID NO: 50 and SEQ ID NO: 52 respectively.

In an additional and/or alternative embodiment, the non-naturally-occurring microorganism has been genetically engineered to abolish PtsG/Crr activity.

In an additional and/or alternative embodiment, the non-naturally-occurring microorganism has been genetically engineered to completely delete the ptsG gene and/or the crr gene, to impair the expression of the ptsG gene and/or the crr, or to abolish the activity of PtsG/Crr by introducing mutations into the protein-coding region of the ptsG gene and/or the crr gene such that the polypeptide encoded by the altered nucleotide sequence(s) does not possess the enzymatic activity of the enzyme(s) encoded by the non-amended nucleotide sequence.

Acquisition of Carbon Source

The non-naturally-occurring microorganism requires a carbon source for growth, proliferation and production of Neu5Ac. In an additional and/or alternative embodiment, the non-naturally-occurring microorganism may grow on an inexpensive sole carbon source, such as—for example—glucose or sucrose. Said sole carbon source provides an educt for sialic acid biosynthesis in the non-naturally-occurring microorganism. Hence, for the production of Neu5Ac it is not necessary to cultivate the non-naturally-occurring microorganism in the presence of ManNAc, GlcNAc or glucosamine (GlcN). In addition, the non-naturally-occurring microorganism does not require a PEP-dependent, sugar-transporting phosphotransferase system for import of the sole carbon source, and hence does not need to utilize PEP for the acquisition of the sole carbon source.

In an additional and/or alternative embodiment, the non-naturally-occurring microorganism has been genetically engineered to utilize sucrose as the sole carbon source.

In an additional and/or alternative embodiment, the non-naturally-occurring microorganism possesses a functional sucrose utilization system. Said functional sucrose utilization system enables cellular import of exogenously supplied sucrose and its hydrolysis such that the resulting monosaccharides glucose and fructose can be metabolically utilized by the non-naturally-occurring microorganism's metabolism and for the desired Neu5Ac production.

In an additional and/or alternative embodiment, the non-naturally-occurring microorganism has been genetically modified to possess a functional sucrose utilization system. In an additional and/or alternative embodiment the sucrose utilization system of the non-naturally-occurring microorganism comprises a sucrose proton symport transport system, a fructokinase, an invertase and a sucrose operon repressor.

A suitable a sucrose proton symport transport system is CscB, encoded by the cscB gene, for example CscB of E. coli (SEQ ID NO: 55) as encoded by the cscB gene of E. coli (SEQ ID NO: 54).

A suitable fructokinase (EC 2.7.1.4) is CscK, encoded by the cscK gene, for example CscK of E. coli (SEQ ID NO: 57) as encoded by the cscK gene of E. coli (SEQ ID NO: 56).

A suitable invertase (EC 3.2.1.26) which hydrolysis terminal non-reducing beta-D-fructofuranoside residues in beta-D-fructofuranosides is CscA, for example cscA of E. coli (SEQ ID NO: 59) as encoded by the cscA gene of E. coli (SEQ ID NO: 58).

A suitable sucrose operon repressor is CscR as encoded by the cscR gene, for example the CscR of E. coli (SEQ ID NO: 61) as encoded by the cscR gene of E. coli (SEQ ID NO: 60).

In an additional and/or alternative embodiment, the non-naturally-occurring microorganism has been genetically engineered to possess a sucrose proton symport transport system, a fructokinase, an invertase and a sucrose operon repressor or functional variants of any one of these proteins.

In an additional and/or alternative embodiment, the non-naturally-occurring microorganism has been genetically engineered to possess a nucleic acid molecule comprising nucleotide sequences encoding a sucrose proton symport transport system, a fructokinase, an invertase and a sucrose operon repressor for the expression of said sucrose proton symport transport system, fructokinase, invertase and sucrose operon repressor. In an additional and/or alternative embodiment, the non-naturally-occurring microorganism has been genetically engineered to express the genes cscB, cscK, cscA, preferably the E. coli genes cscB, cscK, cscA and cscR.

In an additional and/or alternative embodiment, the nucleotide sequence encoding a functional variant of CscB, CscK, CscA or CscR has a sequence identity or at least 80%, at least 85%, at least 90%, at least 95%, at least 98% or at least 99% to E. coli cscB, cscK, cscA or cscR, respectively.

The non-naturally-occurring microorganism that can produce Neu5Ac and carries a functional sucrose utilization system can be cultivated in the presence of sucrose as a sole carbon source for the microorganism's metabolism as well as Neu5Ac biosynthesis. Sucrose is an inexpensive sugar and its utilization as sole carbon source for the production of Neu5Ac by fermentation is more cost efficient than other sialic acid precursors, such as GlcNAc.

Another suitable saccharide utilization system allows the non-naturally-occurring microorganism to grow on a sole carbon source without a PEP-dependent, sugar-transporting phosphotransferase system is LacY, encoded by the lacY gene of the lac operon. LacY is a β-galactoside permease which imports lactose across cell membranes using a proton gradient in the same direction. Intracellular lactose may be hydrolyzed by a β-galactosidase (LacZ) to provide glucose and galactose within the cell. The lacZ gene is also part of the lac operon.

In an additional and/or alternative embodiment, the non-naturally-occurring microorganism expresses a β-galactoside permease and a β-galactosidase.

In an additional and/or alternative embodiment, the non-naturally-occurring microorganism has been genetically engineered to express β-galactoside permease, preferably the E. coli lactose permease LacY (SEQ ID NO: 63) or a functional variant thereof and β-galactosidase, preferably E. coli LacZ (SEQ ID NO: 65) or a functional variant thereof. In an additional and/or alternative embodiment, the non-naturally-occurring microorganism has been genetically engineered to carry a nucleic acid molecule comprising a nucleotide sequence encoding a β-galactoside permease, preferably a nucleotide sequence encoding the E. coli LacY (SEQ ID NO: 62) or a functional variant thereof, and/or a nucleotide sequence encoding a β-galactosidase, preferably a nucleotide sequence encoding E. coli LacZ (SEQ ID NO: 64) or a functional variant thereof.

In an additional and/or alternative embodiment, the nucleotide sequence encoding E. coli LacY or a functional variant thereof has a sequence identity to *E. coli* lacY of at least 80%, at least 85%, at least 90%, at least 95%, at least 98% or at least 99%.

In an additional and/or alternative embodiment, the nucleotide sequence encoding *E. coli* LacZ or a functional variant thereof has a sequence identity to *E. coli* lacZ of at least 80%, at least 85%, at least 90%, at least 95%, at least 98% or at least 99%.

A non-naturally-occurring microorganism that can produce Neu5Ac, and which expresses a functional β-galactoside permease and a functional β-galactosidase allows the cultivation of said non-naturally-occurring microorganism on lactose as a sole carbon source.

In an additional and/or alternative embodiment, the non-naturally-occurring microorganism expresses a glucose/$H^+$-symporter. Preferably, the non-naturally-occurring microorganism has been genetically engineered to carry a nucleic acid molecule comprising a nucleotide sequence encoding and allowing the expression of a glucose/$H^+$-symporter in said non-naturally-occurring microorganism.

A suitable glucose/$H^+$-symporter is selected from the group consisting of the *Staphylococcus epidermis* glucose/$H^+$-symporter (UniProtKB-A0A0U5QDM9; SEQ ID NO: 67), the *Lactobacillus brevis* glucose/$H^+$-symporter (UniProtKB-A0A0C1PU75, SEQ ID NO: 69) and functional variants thereof.

In an additional and/or alternative embodiment, the non-naturally-occurring microorganism has been genetically engineered to carry a nucleic acid molecule encoding the *S. epidermis* glucose/$H^+$-symporter or the *L. brevis* glucose/$H^+$-symporter. Preferably, the non-naturally-occurring microorganism carries a nucleic acid molecule comprising a nucleotide sequence selected from the group consisting of SEQ ID NO: 66, SEQ ID NO: 68, and nucleotide sequences having a sequence identity of at least 80%, at least 85%, at least 90%, at least 95%, at least 98% or at least 99% to SEQ ID NO: 66 or SEQ ID NO: 68.

The non-naturally occurring microorganism that can produce Neu5Ac, and that expresses either the *S. epidermis* glucose/$H^+$-symporter or the *L. brevis* glucose/$H^+$-symporter, can be cultivated in the presence of glucose as a sole carbon source without needing PEP for the acquisition of the exogenously supplied glucose.

Additional Genetic Modifications

The non-naturally-occurring microorganism that can produce Neu5Ac may—optionally —include additional features, and may be genetically engineered to possess these additional features. These additional features are considered to improve the productivity of the non-naturally-occurring microorganism leading to higher Neu5Ac yields.

In an additional and/or alternative embodiment, the non-naturally-occurring microorganism synthesizes more PEP than the wildtype of the microorganism. In an additional and/or alternative embodiment, the non-naturally-occurring microorganism has been genetically engineered to possesses an enhanced PEP biosynthesis pathway. Preferably, the non-naturally-occurring microorganism has been genetically engineered to possess an increased phosphoenolpyruvate synthase activity, for example in that the ppsA gene encoding phosphoenolpyruvate synthase gene is overexpressed and/or in that the non-naturally-occurring microorganisms contains at least one additional copy of a nucleotide sequence allowing the expression of a phosphoenolpyruvate synthase or a functional variant thereof. Overexpression of ppsA enhances intracellular PEP synthesis such that more PEP is available for the production of sialic acid. For example, a suitable phosphoenolpyruvate synthase is PpsA of *E. coli* (SEQ ID NO: 71).

In an additional and/or alternative embodiment, the non-naturally occurring microorganism contains a nucleic acid molecule comprising a nucleotide sequence encoding *E. coli* PpsA or a functional variant thereof. Said nucleotide sequence encoding *E. coli* PpsA or a functional variant thereof has a sequence identity of at least 80%, at least 85%, at least 90%, at least 95%, at least 98% or at least 99% to the *E. coli* ppsA gene (SEQ ID NO: 70).

In an additional and/or alternative embodiment, the non-naturally-occurring microorganism has been genetically engineered to overexpress phosphoenolpyruvate carboxykinase. A suitable phosphoenolpyruvate carboxykinase is *E. coli* Pck (SEQ ID NO: 73).

The enzyme phosphoenolpyruvate carboxykinase (EC 4.1.1.49) is encoded by the pck gene and catalyzes the following reaction: oxaloacetate+ATP→phosphoenolpyruvate+ADP+$CO_2$. Phosphoenolpyruvate carboxykinase is involved in gluconeogenesis.

In an additional and/or alternative embodiment, the non-naturally-occurring microorganism has been genetically engineered to overexpress a phosphoenolpyruvate carboxykinase and/or to contain at least one additional nucleotide sequence allowing the expression of a phosphoenolpyruvate carboxykinase or a functional variant thereof. The overexpression of a phosphoenolpyruvate carboxykinase increases the intracellular level of PEP such that more PEP is available for the production of sialic acid.

The nucleotide sequence encoding the additional nucleotide sequence encoding phosphoenolpyruvate kinase or a functional variant thereof may be SEQ ID NO: 72 or a nucleotide sequence having a sequence identity of at least 80%, at least 85%, at least 90%, at least 95%, at least 98% or at least 99% to the *E. coli* pck gene (SEQ ID NO: 72).

In an additional and/or alternative embodiment, the non-naturally-occurring microorganism does not possess a functional phosphoenolpyruvate carboxylase (EC 4.1.1.31). The phosphoenolpyruvate carboxylase forms oxaloacetate, a four-carbon dicarboxylic acid source for the tricarboxylic acid cycle. The phosphoenolpyruvate carboxylase in encoded by the ppc gene. In *E. coli* the phosphoenolpyruvate carboxylase (SEQ ID NO: 27) is encoded by the pepC gene (SEQ ID NO: 26).

In an additional and/or alternative embodiment, the non-naturally-occurring microorganism has been genetically engineered to abolish PEP carboxylase activity.

In an additional and/or alternative embodiment, the non-naturally-occurring microorganism has been genetically engineered to delete the ppc gene or the pepC gene, to impair its expression, or to abolish PEP carboxylase activity by introducing mutations into the protein-coding region of the ppc/pepC gene such that the polypeptide encoded by the altered nucleotide sequence does not possess PEP carboxylase activity.

In an additional and/or alternative embodiment, the non-naturally occurring microorganism has been genetically engineered to have pyruvate kinase activity diminished or abolished.

The enzyme pyruvate kinase generates adenosine triphosphate (ATP) from adenosine diphosphate (ADP) and PEP. The generation of ATP from ADP and PEP is the last step in glycolysis, a step that is irreversible under physiological conditions. Many Enterobacteriaceae, including *E. coli*, have two isoforms of pyruvate kinase, PykA (SEQ ID NO: 75) and PykF (SEQ IC NO: 77), which are 37% identical in *E. coli*.

In an additional and/or alternative embodiment, the non-naturally-occurring microorganism has been genetically engineered to delete one or more genes encoding pyruvate kinase, preferably the pykA gene (SEQ ID NO: 74) and/or the pykF gene (SEQ ID NO: 76), to impair expression of one or more of those genes encoding pyruvate kinase, or to abolish the activity of at least one pyruvate kinase by introducing one or more mutations into the nucleotide sequence of the protein-coding region of one or more of those genes encoding pyruvate kinase such that the polypeptid encoded by the altered nucleotide sequence does not possess pyruvate kinase activity.

In an additional and/or alternative embodiment, the non-naturally-occurring microorganism synthesizes more glutamine as compared to the wild-type. In an additional and/or alternative embodiment, the non-naturally-occurring microorganism has been genetically engineered to possess an enhanced glutamine biosynthesis pathway.

Glutamine synthetase (GlnA) converts glutamate to glutamine by the following reaction: ATP+L-glutamate+$NH_3$=ADP+phosphate+L-glutamine. In *E. coli*, glutamine synthetase (SEQ ID NO: 79) is encoded by the glnA gene (SEQ ID NO: 78).

In an additional and/or alternative embodiment, the non-naturally-occurring microorganism has been genetically engineered to overexpress a glutamine synthase and/or to contain at least one additional nucleotide sequence allowing the expression of a glutamine synthase or a functional variant thereof. The overexpression of a glutamine synthase increases the intracellular level of glutamine, which in turn improves the intracellular conversion of fructose-6-phosphate (Frc-6P) to glucosamine-6-phosphate (GlcN-6P). Preferably, the nucleotide sequence encoding the additional nucleotide sequence encoding a glutamine synthase or functional variant thereof may be SEQ ID NO: 78 or a nucleotide sequence having a sequence identity of at least 80%, at least 85%, at least 90%, at least 95%, at least 98% or at least 99% to the *E. coli* glnA gene (SEQ ID NO: 78).

Metabolic modelling in *E. coli* has confirmed that enhancing glutamine synthesis boosts the production of Neu5Ac. In addition, transcriptome analysis in a Neu5Ac-producing *E. coli* strain (#NANA1) which was not genetically engineered to enhance glutamine synthesis revealed that glutamine synthase was expressed at a higher level compared to a related *E. coli* strain that is not able to produce Neu5Ac.

In an additional and/or alternative embodiment, the non-naturally-occurring microorganism does not carry a functional glutamate synthase or has less glutamate synthase activity as compared to a wild-type microorganism. The *E. coli* glutamate synthase consists of two subunits, GltB (SEQ ID NO: 81) and GltD (SEQ ID NO: 83), and synthesizes glutamate at the expense of glutamine. GltB is encoded by the gltB gene (SEQ ID NO: 80), and GltD is encoded by the gltD gene (SEQ ID NO: 82).

In an additional and/or alternative embodiment, the non-naturally-occurring microorganism has been genetically engineered to delete the gltB gene and/or the gltD gene, to impair the expression of at least one of those genes, or to reduce or abolish glutamate synthase activity by introducing one or more mutations into the protein-coding region of the gltB gene and/or the gltD gene such that the polypeptide(s) encoded by the altered nucleotide sequence(s) provide a non-functional variant of the glutamate synthase.

In an additional and/or alternative embodiment, the non-naturally-occurring microorganism does not possess glutaminase activity.

In an additional and/or alternative embodiment, the non-naturally-occurring microorganism has been genetically engineered to delete at least one of the glutaminase genes asnB, ybaS and yneH, to impair expression of at least one of those genes, or to abolish glutaminase activity by introducing one or more mutations into the protein-coding region of asnB, ybaS and/or yneH such that the polypeptide encoded by one of the altered nucleotide sequences does not possess glutaminase activity.

AsnB is an asparagine synthetase and catalyzes the ATP-dependent conversion of of aspartate into asparagine, using glutamine. The *E. coli* asparagine synthetase AsnB (SEQ ID NO: 85) is encoded by the *E. coli* asnB gene (SEQ ID NO: 84).

YbaS, also known as GlsA1 or Gls1, is glutaminase 1, a glutaminase that is highly selective for L-glutamine. YbaS converts L-glutamine to L-glutamate. The *E. coli* glutaminase YbaS (SEQ ID NO: 87) is encoded by the *E. coli* ybaS gene (SEQ ID NO: 86).

YneH, also known as GlsA2, GlsB or glutaminase 2, catalyzes the following reaction: L-glutamine+$H_2O$=L-glutamate+$NH_3$. The *E. coli* glutaminase YneH (SEQ ID NO: 89) is encoded by the *E. coli* yneH gene (SEQ ID NO: 88).

In an additional and/or alternative embodiment, the non-naturally-occurring microorganism possesses an increased glutamate dehydrogenase activity as compared to the wild-type microorganism. In an additional and/or alternative embodiment, the non-naturally occurring microorganism has been genetically engineered to overexpress a glutamate dehydrogenase and/or contains at least one additional nucleotide sequence allowing the expression of a glutamate dehydrogenase or a functional variant thereof.

Glutamate dehydrogenase converts glutamate to α-ketoglutarate. The overexpression of glutamate dehydrogenase increases the formation of α-ketoglutarate, which in turn can be converted to glutamate by glutamate synthase, for example by glutamate synthase as encoded by *E. coli* gltD or a functional variant thereof. Glutamate can then be converted to glutamine by glutamine synthetase (GlnA) or a functional variant thereof.

In an additional and/or alternative embodiment, the additional nucleotide sequence allowing expression of a glutamate dehydrogenase or functional variant thereof includes the protein-coding region of the *E. coli* glutamate dehydrogenase GdhA (SEQ ID NO: 91). The nucleotide sequence encoding the glutamate dehydrogenase or functional variant thereof may be SEQ ID NO: 90 or a nucleotide sequence having a sequence identity of at least 80%, at least 85%, at least 90%, at least 95%, at least 98% or at least 99% to the *E. coli* gdhA gene (SEQ ID NO: 90). In an additional and/or alternative embodiment, the non-naturally-occurring microorganism unable to synthesize lipopolysaccharides (LPS) and/or colanic acid. In an additional and/or alternative embodiment, the non-naturally-occurring microorganism has been genetically engineered to abolish the synthesis of LPS and/or colonic acid.

In an embodiment, the non-naturally-occurring microorganism has been genetically engineered to delete the wzxC gene, to impair expression of the wzxC gene, or to abolish the activity of the WzxC enzyme by introducing on eor more mutations into the protein-coding region of the gene the polypeptide being encoded by said altered nucleotide sequence does not possess the enzymatic activity of WzxC. WzxC is required for LPS biosynthesis and encodes a putative export protein. The nucleotide sequence of *E. coli* wzxC is represented by SEQ ID NO: 92, and the deduced amino acid sequence by SEQ ID NO: 93.

In an additional and/or alternative embodiment the non-naturally-occurring microorganism does not possess UDP-glucose:undecaprenylphosphate glucose-1-phosphate transferase activity.

In an additional and/or alternative embodiment the non-naturally-occurring microorganism has been genetically engineered to abolis UDP-glucose:undecaprenylphosphate glucose-1-phosphate transferase activity, preferably by deleting the wcaJ gene or a functional variant thereof, by impairing expression of the wcaJ gene or a functional variant thereof, or by abolishing the activity of the WcaJ enzyme by introducing mutations into the protein-coding region of the such that the polypeptide encoded by the altered nucleotide sequence does not possess enzymatic activity of WcaJ. WcaJ encodes a UDP-glucose:undecaprenylphosphate glucose-1-phosphate transferase. Said UDP-glucose:undecaprenylphosphate glucose-1-phosphate transferase is the first enzyme in colanic acid biosynthesis. The nucleotide sequence of *E. coli* wcaJ is represented by SEQ ID NO: 94, and the deduced amino acid sequence by SEQ ID NO: 95.

In an additional and/or alternative embodiment, the non-naturally-occurring microorganism may not comprise a functional β-galactoside permease (LacY) and/or a functional β-galactosidase (LacZ) provided that the non-naturally-occurring microorganism can be cultivated on another sole carbon source than lactose, for example on sucrose or glucose as sole carbon source.

In an additional and/or alternative embodiment, the non-naturally-occurring microorganism has been genetically engineered in that the β-galactoside permease gene (lacY) and/or the β-galactosidase gene (lacZ) has been deleted, in that the expression of the β-galactoside permease gene and/or the β-galactosidase gene is impaired or in that the nucleotide sequence of the protein coding region of the β-galactoside permease gene and/or the β-galactosidase gene is amended such that the polypeptide being encoded by said altered nucleotide sequence(s) does not possess the enzymatic activity of the β-galactoside permease and/or the β-galactosidase.

In an additional and/or alternative embodiment, the non-naturally-occurring microorganism does not possess a functional YjhC. YjhC is an oxidoreductase encoded by the yjhC gene or a functional variant thereof.

In an additional and/or alternative embodiment the non-naturally-occurring microorganism has been genetically engineered to abolish YjhC oxidoreductase activity, preferably by deleting the yjhC gene, by impairing expression of the yjhC gene, or by introducing one or more mutations into the protein-coding region of the yjhC gene such that the polypeptide being encoded by the altered nucleotide sequence does not possess YjhC oxidoreductase activity.

The nucleotide sequence of *E. coli* yjhC is represented by SEQ ID NO: 96, and the deduced amino acid sequence by SEQ ID NO: 97.

In an additional and/or alternative embodiment, then non-naturally-occurring microorganism does not possess one or more of the following enzyme activities: fucose isomerase, fuculokinase and N-acetylglutamine aminoacylase. In an embodiment, the non-naturally-occurring microorganism has been genetically engineered to abolish the activity of one or more of these enzyme activities.

Fucose isomerase converts aldose L-fucose into the corresponding ketose L-fuculose. Fucose isomerase is the first enzyme in the subpathway that synthesizes L-lactaldehyde and glycerone phosphate from L-fucose. The *E. coli* fucose isomerase FucI (SEQ ID NO: 99) is encoded by the *E. coli* fucI gene (SEQ ID NO: 98).

In an additional and/or alternative embodiment the non-naturally-occurring microorganism has been genetically engineered to abolish fucose isomerase activity, preferably by the deletion the fucI gene, by impairing expression of the fucI gene, or by modifying the protein-coding region of the fucI gene such that the polypeptide being encoded by said altered nucleotide sequence does not possess fucose isomerase activity.

Fuculokinase catalyzes the phosphorylation of fucose. Fuculokinase is the second enzyme in the subpathway that synthesizes L-lactaldehyde and glycerone phosphate from L-fucose. The *E. coli* fuculokinase FucK (SEQ ID NO: 101) is encoded by the *E. coli* fucK gene (SEQ ID NO: 100). *E. coli* fuculokinase can also phosphorylate, with lower efficiency, D-ribulose, D-xylulose and D-fructose.

In an additional and/or alternative embodiment the non-naturally-occurring microorganism has been genetically engineered to abolish fucose isomerase activity, preferably by the deletion of the fucK gene or, by impairing expression of the fucK gene, or by introducing mutations into the protein-coding region of the fucK gene such that the polypeptide being encoded by said altered nucleotide sequence does not possess fucose isomerase activity.

N-acetylgalactosamine-6-phosphate deacetylase catalyzes the following reaction: N-acetyl-D-galactosamine 6-phosphate+$H_2O$→D-galactosamine 6-phosphate+acetate. N-acetylgalactosamine-6-phosphate deacetylase is encoded by the agaA gene. In contrast to *E. coli* strains C and EC3132, K-12 strains cannot grow on N-acetylgalactosamine and D-galactosamine, because they carry a deletion and thus lack an active PTS systems specific for these compounds. Therefore, in K-12 strains, AgaA is not involved in the degradation of these compounds. The *E. coli* AgaA (SEQ ID NO: 103) is encoded by the *E. coli* agaA gene (SEQ ID NO: 102).

In an additional and/or alternative embodiment the non-naturally-occurring microorganism has been genetically engineered to abolish N-acetylgalactosamine-6-phosphate deacetylase activity, preferably by deletion of the agaA gene, by impairing expression of the agaA gene, or by introducing mutations into the protein-coding region of the agaA gene such that the polypeptide being encoded by said altered nucleotide sequence does not possess N-acetylgalactosamine-6-phosphate deacetylase activity.

The non-naturally-occurring microorganism is selected from the group consisting of yeasts, fungi and bacteria. Preferably, the non-naturally-occurring microorganism is an organism that is generally recognized as safe (GRAS), for example as affirmed by the Federal Drug Administration (FDA) or determined independently by qualified experts, more preferably a prokaryotic microorganism, most preferably a bacterial microorganism. Bacteria suitable for the production of Neu5Ac may be selected from the following genera: *Bacillus, Lactobacillus, Lactococcus, Enterococcus, Bifidobacterium, Sporolactobacillus, Micromomospora, Micrococcus, Rhodococcus*, and *Pseudomonas*. Suitable bacterial species include *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, Bacillus circulans, Bifidobacterium longum, Bifidobacterium infantis, Bifidobacterium bifidum, Citrobacter freundii, Clostridium cellulolyticum, Clostridium lungdahlii,*

*Clostridium autoethanogenum, Clostridium acetobutylicum, Corynebacterium glutamicum, Enterococcus faecium, Enterococcus thermophiles, Escherichia coli, Erwinia herbicola (Pantoea agglomerans), Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Pantoea citrea, Pectobacterium carotovorum, Proprionibacterium freudenreichii, Pseudomonas fluorescens, Pseudomonas aeruginosa, Streptococcus thermophiles* and *Xanthomonas campestris*.

According to the second aspect, provided is the use of a non-naturally-occurring microorganism as described herein before for the production of Neu5Ac. The non-naturally-occurring microorganism is capable of producing Neu5Ac in an industrial scale. The terms "capable" and "able" with respect to the production of Neu5Ac as used herein refers to the ability of the non-naturally-occurring microorganism to synthesize Neu5Ac and to secrete said Neu5Ac into the fermentation broth, provided that the said non-naturally-occurring microorganism is cultivated under conditions permissive for the production of Neu5Ac. This includes the ability of the said non-naturally-occurring microorganism to proliferate to high cell densities and to be cultured in large volumes, e.g. volumes exceeding 1,000 L, preferably 10,000 L, more preferably 80,000 L and most preferably 200,000 L.

According to the third aspect, provided is a method for the production of Neu5Ac by microbial fermentation. The method comprises the steps of
  providing a non-naturally-occurring microorganism that is able to produce Neu5Ac, preferably a non-naturally-occurring microorganism as described herein before;
  cultivating the said non-naturally-occurring microorganism in a fermentation broth under permissive conditions for the production of Neu5Ac by said microorganism; and—optionally —
  recovering Neu5Ac from the fermentation broth.

The fermentation broth contains at least one carbon source for the non-naturally-occurring microorganism. This carbon source is preferably selected from the group consisting of glucose, xylose, fructose, sucrose, lactose, glycerol, syngas and combinations thereof.

In an additional and/or alternative embodiment, the non-naturally-occurring microorganism is cultivated in the absence of and/or without the addition of one or more selected from the group consisting of pyruvate, glucosamine, N-acetylglucosamine in the fermentation broth.

The method includes an optional step of recovering Neu5Ac produced by the non-naturally-occurring microorganism during its cultivation in the fermentation broth. The Neu5Ac can be recovered from the fermentation broth after the non-naturally-occurring microorganisms have been removed from the fermentation broth, for example by centrifugation. Subsequently, the Neu5Ac can be further purified from the thus clarified fermentation broth by suitable techniques such as microfiltration, ultrafiltration, diafiltration, simulated moving bed type chromatography, electrodialysis, reverse osmosis, gel filtration, anion exchange chromatography, cation exchange chromatography, and the like.

The method is suitable for the large-scale and economically sustainable production of Neu5Ac by microbial fermentation.

According to the fourth aspect, provided is Neu5Ac, produced by microbial fermentation as described herein.

According to the fifth aspect, provided is the use of Neu5Ac produced as described herein for the manufacture of a nutritional composition.

According to the sixth aspect, provided is a nutritional composition containing Neu5Ac which has been produced by the method of the third aspect.

In an additional and/or alternative embodiment, the nutritional composition further contains at least one human milk oligosaccharide (HMO), preferably at least one neutral HMO and/or at least one acidic HMO.

The neutral HMO(s) may be selected from the group consisting of 2'-fucosyllactose (2'-FL), 3-fucosyllactose (3-FL), lacto-N-tetraose (LNT), lacto-N-neotetraose (LNnT) and lacto-N-fucopentaose I (LNPFI).

The one acidic HMO(s) may be selected from the group consisting of sialylated HMOs, preferably from the group consisting of 3'-sialyllactose (3-SL), 6'-sialyllactose (6-SL), sialyllacto-N-tetraose a (LST-a), sialyllacto-N-tetraose b (LST-b), sialyllacto-N-tetraose c (LST-c) and disialyllacto-N-tetraose (DSLNT).

In an additional embodiment, the nutritional composition is selected from the group consisting of medicinal formulations, infant formula and dietary supplements.

The nutritional composition may be present in liquid form or in solid form including, but not limited to, powders, granules, flakes and pellets.

In an additional and/or alternative embodiment, the nutritional composition also includes microorganisms, preferably probiotic microorganisms. For infant food applications, preferred microorganisms are derived from or can be found in the microbiome of a healthy human. Preferably, the microorganisms are selected from the genera *Bifidobacterium, Lactobacillus, Enterococcus, Streptococcus, Staphylococcus, Peptostreptococcus, Leuconostoc, Clostridium, Eubacterium, Veilonella, Fusobacterium, Bacterioides, Prevotella, Escherichia, Propionibacterium* or *Saccharomyces*, but others may also be appropriate. In an additional and/or alternative embodiment, the microorganism is selected from the group consisting of *Bifidobacterium breve, Bifidobacterium longum, Bifidobacterium lactis, Bifidobacterium animalis, Bifidobacterium bifidum, Bifidobacterium infantis, Bifidobacterium aldolescentis, Lactobacillus acidophilus, Lactobacillus plantarum, Lactobacillus salivarius, Lactobacillus casei, Lactobacillus gasseri, Lactobacillus reuteri, Lactobacillus rhamnosus, Lactobacillus plantarum, Lactobacillus salivarius, Lactococcus lactis, Lactobacillus paracasei, Lactobacillus bulgaricus, Lactobacillus helveticus, Lactobacillus fermentum, Leuconostoc mesenteroides; Escherichia coli, Enterococcus faecium*, and *Streptococcus thermophilus* (VSL #3).

In addition to the combination of Neu5Ac with living organisms, Neu5Ac can be also be used in combination with killed cultures which are sometimes used in the field of probiotics (e.g. tyndalized bacteria). Such killed cultures may provide proteins, peptides, oligosaccharides, cell wall fragments, and natural products that cause a short therm stimulation of the immune system.

The combination of Neu5Ac and probiotic microorganisms in the nutritional composition is particularly advantageous to establish or re-establish an appropriate microbiome in the gut, and the health benefits associated therewith are facilitated.

Even more advantageous is the combination of sialic acid with established prebiotics such as galactooligosaccharides (GOS) and/or fructooligosaccharides (FOS) including inulin.

The present invention will be described with respect to particular embodiments and with reference to drawings, but the invention is not limited thereto but only by the claims. Furthermore, the terms first, second and the like in the description and in the claims, are used to distinguish between similar elements and not necessarily to describe a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noted that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to an "embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may refer to many and/or different embodiments. Furthermore, the particular features, structures or characteristics may be combined in any suitable manner, as would be apparent to one of ordinary skill in the art from this disclosure, in one or more embodiments.

Similarly it should be appreciated that in the description of representative embodiments of the invention, various features of the invention are sometimes grouped together in a single embodiment, figure, or description thereof for the purpose of streamlining the disclosure and facilitating the understanding of one or more of the various inventive aspects. This method of disclosure, however, is not to be interpreted as reflecting an intention that the claimed invention requires more features than are expressly stated in each claim. Rather, as the following claims reflect, inventive aspects lie in less than all of the features of a single foregoing disclosed embodiment. Thus, the claims following the detailed description are hereby expressly incorporated into this detailed description, with each claim standing on its own as a separate embodiment of this invention.

Furthermore, whereas some embodiments described herein include some but not other features included in other embodiments, combinations of features of different embodiments are meant to fall within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method.

Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order to simplify the description and facilitate understanding.

The invention will now be described by means of a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Examples

Example 1: Metabolic Engineering of an *E. coli* BL21(DE3) Strain Producing N-Acetylneuraminic Acid Metabolic engineering was achieved by the mutagenesis and deletions of specific endogenous genes and the genomic integration of heterologous genes. The genes lacZ and araA were inactivated by mutagenesis using mismatch-oligonucleotides as described by Ellis et al., (Proc. Natl. Acad. Sci. USA 98: 6742-6746 (2001)). Genomic deletions were generated according to the method of Datsenko and Wanner (Proc. Natl. Acad. Sci. USA 97:6640-6645 (2000)). To prevent the degradation of N-acetylglucosamine the following genes were deleted from the genome of *E. coli* strain BL21 (DE3): N-acetylglucosamine specific PTS enzyme II (nagE), N-acetylglucosamine-6-phosphate deacetylase (nagA), and glucosamine-6-phosphate deaminase (nagB). The whole N-acetylneuraminic acid catabolic gene cluster encoding N-acetylmannosamine kinase (nanK), N-acetylmannosamine-6-phosphate epimerase (nanE), N-acetylneuraminic acid aldolase (nanA) and the sialic acid permease (nanT) was also deleted. The genes manX, manY and manZ, encoding a phosphoenolpyruvate-dependent phosphotransferase system facilitating the import of glucosamine, were also deleted. The wzxC-wcaJ genes were also deleted. The wcaJ gene encodes an UDP-glucose: undecaprenyl phosphate glucose-1-phosphate transferase catalyzing the first step in colanic acid synthesis (Stevenson et al., J. Bacteriol. 1996, 178:4885-4893). In addition, the genes fucI and fucK and agaA were deleted, encoding L-fucose isomerase, L-fuculose kinase, and N-acetylgalactosamine-6-phosphate deacetylase, respectively.

The genomic integration of heterologous genes was achieved by transposition, using either the EZ-Tn5™ transposase (Epicentre, USA) or the hyperactive C9-mutant of the mariner transposase Himar1 (Proc. Natl. Acad. Sci. 1999, USA 96:11428-11433). To produce EZ-Tn5 transposomes the gene of interest together with a FRT-site flanked antibiotic resistance marker (alternatively the resistance marker gene was flanked by lox66-lox71 sites) was amplified. The resulting PCR-product carried at both termini the 19-bp Mosaic End recognition sites for the EZ-Tn5 transposase. For integration using Himar1 transposase expression constructs (operons) of interest were similarly cloned together with a FRT-site/lox66-lox71-site flanked by antibiotic resistance markers and transferred into the pEcomar vector, which encodes the hyperactive C9-mutant of the mariner transposase Himar1 under the control of the arabinose-inducible promoter $P_{araB}$. All genes were codon-optimized for expression in *E. coli* and prepared synthetically by GenScript Corp.

The expression fragment <$P_{tet}$-lacY-FRT-aadA-FRT> (SEQ ID NO: 1) was integrated by using the EZ-Tn5 transposase. After successful integration of the gene for the lactose importer LacY from *E. coli* K12 TG1 (GenBank: ABN72583) the resistance gene was eliminated from streptomycin resistant clones by the FLP recombinase encoded on plasmid pCP20 (Proc. Natl. Acad. Sci. 2000, USA 97:6640-6645). The csc-gene cluster (SEQ ID NO: 2) from *E. coli* W (GenBank: CP002185.1), comprising the genes for sucrose permease, fructokinase, sucrose hydrolase, and a transcriptional repressor (genes cscB, cscK, cscA, and cscR, respectively), enabling the strain to grow on sucrose as a sole carbon source, was also inserted in the genome. This cluster was integrated into the genome of the *E. coli* BL21 (DE3) strain by transposition using plasmid pEcomar-cscABKR.

The resulting strain was further modified for the production of Neu5Ac by the genomic integration of the following expression cassettes: <$P_{tet}$-slr1975-gna1-lox66-aacC1-lox71> (SEQ ID NO: 3), <$P_{tet}$-neuB-lox66-kanR-lox71> (SEQ ID NO: 4) <$P_{tet}$-slr1975-$P_{t5}$-neuB-FRT-dhfr-FRT> (SEQ ID NO: 5), <$P_{tet}$-glmS*-gna1-lox66-aacC1-lox71> (SEQ ID NO: 6) and <$P_{tet}$-ppsA-lox66-aacC1-lox71> (SEQ ID NO: 7). Except for the dhfr expression cassette of SEQ ID NO 5, all resistance marker genes were removed in a stepwise manner from the genome (before the next round of gene integration) by introducing plasmid pKD-Cre (SEQ ID NO: 8) followed by selection on 2YT agar plates containing 100 μg·mL$^{-1}$ ampicillin and 100 mM L-arabinose at 30° C. Resistant clones were subsequently transferred to 2YT agar plates lacking ampicillin as well as the selective antibiotic used for genomic integration. The plates were incubated at 42° C. to cure the cells of the plasmid. Clones that were sensitive to ampicillin and the selective antibiotic were used for further experiments and modifications.

The gene slr1975 (GenBank: BAL35720) encodes *Synechocystis* sp. PCC6803 N-acetylglucosamine 2-epimerase. The gene gna1 (GenBank: NP_116637) encodes a glucosamine-6-phosphate acetyltransferase from *Saccharomyces cerevisiae*. The gene neuB (GenBank: AF305571) encodes a sialic acid synthase from *Campylobacter jejuni*. The gene glmS* is a mutated version of the *E. coli* L-glutamine:D-fructose-6-phosphate aminotransferase gene (Metab Eng. 2005 May; 7(3):201-14). The gene ppsA (GenBank: ACT43527) encodes the phosphoenolpyruvate synthase of *E. coli* BL21(DE3).

For the generation of <$P_{tet}$-slr1975-gna1-lox66-aacC1-lox71>, the genes slr1975 and gna1 were subcloned as an operon behind the constitutive promotor $P_{tet}$ and fused to the gentamycin resistance gene (flanked by lox66/lox71 sites) and inserted into the pEcomar vector by blunt-end ligation. The resulting expression cassette was integrated into the genome using vector pEcomar-slr195-gna1-aacC1 and the hyperactive C9-mutant of the mariner transposase Himar1 under the control of the arabinose-inducible promoter $P_{araB}$.

For the generation of <$P_{tet}$-neuB-lox66-kanR-lox71>, neuB was cloned behind the constitutive promotor $P_{tet}$ and fused to the kanamycin resistance gene (flanked by lox66/lox71 sites). The resulting expression cassette was integrated into the genome using the EZ-Tn5 transposase. For the generation of <$P_{tet}$-slr1975-$P_{t5}$-neuB-FRT-dhfr-FRT>, the genes slr1975 and neuB were separately subcloned behind the constitutive promotors $P_{tet}$ and $P_{t5}$, respectively, and fused to the trimethoprim resistance gene (flanked by FRT sites). The resulting expression cassette was integrated into the genome by using the EZ-Tn5 transposase.

Expression cassette <$P_{tet}$-glmS*-gna1-lox66-aacC1-lox71> was generated by cloning glmS* and gna1 as an operon behind the constitutive promotor $P_{tet}$. This construct was further fused to the gentamycin resistance gene (flanked by lox66/lox71 sites). The resulting expression cassette was integrated into the genome by using the EZ-Tn5 transposase.

For the generation of <$P_{tet}$-ppsA-lox66-aacC1-lox71>, the ppsA gene was cloned behind the constitutive promoter Per and fused to the gentamycin resistance gene (flanked by lox66/lox71 sites). The resulting expression cassette was integrated into the genome by using the EZ-Tn5 transposase.

Altogether, the cumulative genome modifications gave rise to the Neu5Ac-producing strain *E. coli* #NANA1.

Example 2: Production of N-Acetylneuraminic Acid During a Fed-Batch Fermentation The *E. coli* BL21 (DE3) strain #NANA1 was cultivated at 30° C. in 3 L fermenters (New Brunswick, Edison, USA) starting with 1000 mL mineral salts medium containing 7 g·L$^{-1}$ NH$_4$H$_2$PO$_4$, 7 g·L$^{-1}$ K$_2$HPO$_4$, 2 g·L$^{-1}$ KOH, 0.3 g·L$^{-1}$ citric acid, 2 g·L$^{-1}$ MgSO$_4$×7·H$_2$O, 5 g·L$^{-1}$ NH$_4$Cl$_2$ and 0.015 g·L$^{-1}$ CaCl$_2$×6·H$_2$O, supplemented with 1 mL·L$^{-1}$ trace element solution (54.4 g·L$^{-1}$ ammonium ferric citrate, 9.8 g·L$^{-1}$ MnCl$_2$×4·H$_2$O, 1.6 g·L$^{-1}$ COCl$_2$×6·H$_2$O, 1 g·L$^{-1}$ CuCl$_2$×2·H$_2$O, 1.9 g·L$^{-1}$ H$_3$BO$_3$, 9 g·L$^{-1}$ ZnSO$_4$×7·H$_2$O, 1.1 g·L$^{-1}$ Na$_2$MoO$_4$×2·H$_2$O, 1.5 g·L$^{-1}$ Na$_2$SeO$_3$, 1.5 g·L$^{-1}$ NiSO$_4$×6·H$_2$O) and containing 2% (m/v) sucrose as carbon source as well as the antibiotic zeocin (10 μg·mL$^{-1}$). Cultivation was started with a 2.5% (v/v) inoculum from a pre-culture grown in the same sucrose-containing medium. The end of the batch phase was characterized by a rise in the dissolved oxygen level. A sucrose feed was applied immediately after leaving the batch phase. The 50% (m/v) sucrose feed was supplemented with 2 g·L$^{-1}$ MgSO$_4$×7·H$_2$O, 0.015 g·L$^{-1}$ CaCl$_2$×6·H$_2$O and 1 mL·L$^{-1}$ trace element solution. A feeding rate of 9.0 to 11.0 mL·L$^{-1}$ was applied, referring to the starting volume. Aeration was maintained at 3 L·min$^{-1}$. Dissolved oxygen was maintained at 20-30% saturation by controlling the rate of agitation. The pH was maintained at 7.0 by adding 25% ammonia solution.

High performance liquid chromatography (HPLC, Shimadzu) was used to detect Neu5Ac in the culture supernatant. The equipment comprised a UV-VIS detector at λ=210 nm (SPD-10A vp, Shimadzu) and a Rezex ROA-organic acid H+ analytical column (300×7.8 mm) with an appropriate guard cartridge. Isocratic elution was performed in 5 mM H$_2$SO$_4$ at 50° C. was carried out at a flow rate of 0.5 ml·min$^{-1}$. The culture supernatant was centrifuged, filter-sterilized and heated at 95° C. for 5 min. After a final centrifugation, 5 μL of the sample was applied to the column. The concentration of N-acetylneuraminic acid was calculated from a standard curve using a commercially available standard (Carbosynth, Compton, UK). After incubation for 88 h, the final Neu5Ac titer in the culture supernatant was of 68.6 g·L$^{-1}$.

Example 3: Generation and Cultivation of Single Knock-Out Mutants in *E. coli* Strain #NANA1 Revealing Improved Neu5Ac Production Capability The *E. coli* BL21 (DE3) strain #NANA1 was further modified creating deletion mutants that removed or disrupted the genes gltB, yjhC and ppC. Strains #NANA1, #NANA1ΔgltB, #NANA1ΔyjhC and #NANA1ΔppC were cultivated in 96-well plates. Therefore, single colonies of the strains were transferred from agar plates into microtiter plates containing 200 µL of the minimal medium described in Example 2 and were incubated for ~20 h at 30° C. with vigorous shaking. Subsequently, 50 µL of the culture broth was transferred to deepwell 96-well plates (2.0 mL) containing 400 µL of minimal medium per well.

After an incubation for another 48 hours, cultivation was stopped and the quantity pf N-acetylneuraminic acid in the supernatant was determined by mass spectrometry in multiple reaction monitoring (MRM) mode using an LC Triple-Quadrupole MS detection system. Precursor ions are selected and analyzed in quadrupole 1, fragmentation takes place in the collision cell using argon as the collision gas, and fragment ions are selected in quadrupole 3. A 1-µl sample of N-acetylneuraminic acid was injected into the HPLC instrument after diluting the culture supernatant 1:100 with LC/MS-grade water. The sample was separated on a XBridge Amide HPLC column (3.5 µm, 2.1×50 mm) (Waters, USA) with a XBridge Amide guard cartridge (3.5 µm, 2.1×10 mm) (Waters, USA) at 50° C. in acetonitrile: $H_2O$ with 10 mM ammonium acetate at a flow rate of 400 µl·min$^{-1}$. Each separation lasted 240 s. N-acetylneuraminic acid was analyzed by MRM in electrospray ionization (ESI) positive-ionization mode. The mass spectrometer was operated at unit resolution. N-acetylneuraminic acid forms an ion of m/z 309.2 [M+H]. The precursor ion of N-acetylneuraminic acid was fragmented further in the collision cell into the fragment ions m/z 292.20, m/z 274.15 and m/z 121.15. Collision energy, Q1 and Q3 Pre Bias were optimized for each analyte individually. The quantification method was established using a commercially available standard (Carbosynth, Compton, UK).

Figure 3:
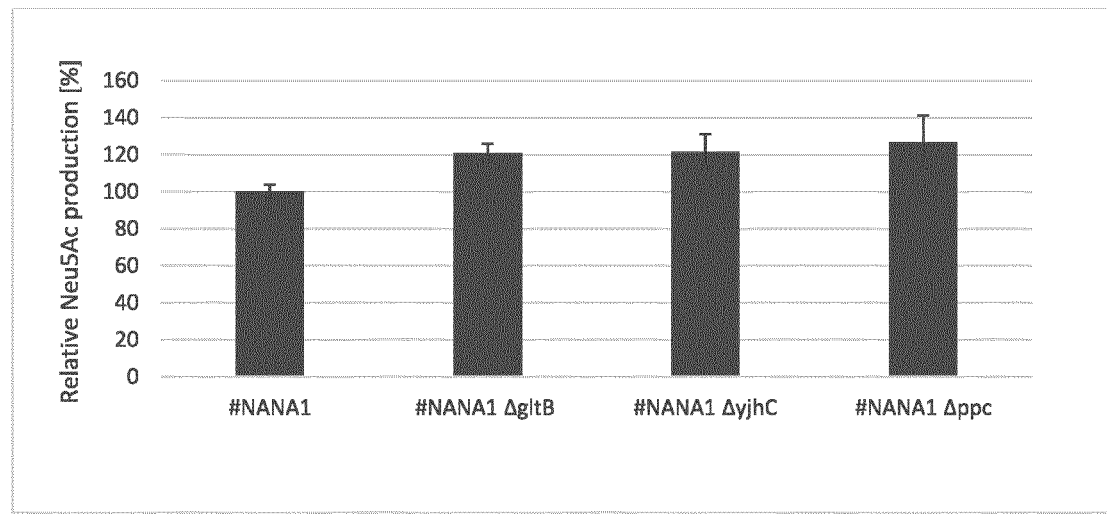
FIG. 3 displays a column graph illustrating the levels of Neu5Ac production by different non-naturally-occurring *E. coli* strains.

FIG. 3 shows the relative Neu5Ac yields of the cultivated strains. In comparison to the parental strain, the value for strain #NANA1 was set to 100%, and the single knock-out mutants produced 20% to 25% more N-acetylneuraminic acid.

Example 4: Purification of Neu5Ac from Fermentation Broth

After termination of the fermentation, the biomass was separated from the fermentation medium by ultrafiltration followed by using sequentially a winding module filter (0.05 µm cut-off) (CUT membrane technology, Erkrath, Germany), and a cross-flow filter (150 kDa cut-off) (Microdyn-Nadir, Wiesbaden, Germany). An approximately 1 m$^3$ cell-free fermentation medium was obtained containing more than 19 g·L$^{-1}$ sialic acid.

The cell-free liquid was then deionized by ion exchange chromatography. First, cationic contaminants were removed on a strong cationic exchanger in a volume of 200 L (Lewatit® S 2568 (Lanxess AG, Cologne, Germany) in H$^+$ form. Using NaOH the obtained solution with a pH of about 1.5 was neutralized to 7.0. In a second step, anionic ions and undesired colorants were removed from the solution using the strong anionic exchanger Lewatit® S 6368 A (Lanxess AG, Cologne, Germany) in the chloride form. The ion exchanger had a bed volume of 200 L. Using a second filtration step on the cross-flow filter (150 kDa cut-off) (Microdyn-Nadir GmbH, Wiesbaden, Germany), precipitates originating from acidifying the solution were removed. For concentration of the sugar, the solution was nanofiltrated on a Dow Filmtec® NF270-4040 (INAQUA Vertriebsgesellschaft mbH, Mönchengladbach, Germany) to about % of the Volume. The concentrated Neu5Ac solution was then further concentrated on a rotary evaporator to a concentration of about 400 g L$^{-1}$ or higher. Specific crystallization of the product was performed with a 10-fold excess of glacial acetic acid at 5° C. for 12-60 hours. The solid fraction was filtrated and washed with ethanol and dried at 40° C. The dry crystallized product was further purified. Therefore, the dry product was solved in 2 L $H_2O$ per kg, and treated with activated charcoal (CAS-No: 7440-44-0, Carl Roth GmbH & Co. KG, Karlsruhe, Germany). The clarified solution, after separation from the charcoal, was concentrated by evaporation at 50° C. until it solidified. The solid material was mixed with 99% ethanol and incubated at 4° C. at least for 16 h. Afterwards the solid fraction was filtrated and dried at 40° C. A crystalline, white product having a purity of more than 95% by means of area under curve of a chromatogram as determined by HPLC using a Rezex ROA-organic acid H$^+$ column (Phenomenex, Aschaffenburg, Germany) was obtained.

Example 5: An Alternative Pathway for N-Acetylneuraminic Acid Production

The *E. coli* BL21 (DE3) strain as described in example 1 (ΔlacZ, ΔaraA, ΔnagABE, ΔnanATEK, ΔmanXYZ, ΔwcaJ, ΔfuclK, ΔagaA, lacY$^+$, cscABKR$^+$) was further modified by integration of the expression cassette <P$_{tet}$-glmS*-gna1-lox66-aacC1-lox71>, giving rise to a strain being able to synthesize N-acetylglucosamine (strain A). The strain A was modified to generate a strain for the production of N-acetylneuraminic acid. To this end, the expression constructs <P$_{tet}$-slr1975-P$_{t5}$-neuB-FRT-dhfr-FRT> (SEQ ID NO: 5) or <P$_{tet}$-EcnanE-P$_{t5}$-neuB-FRT-dhfr-FRT> (SEQ ID NO: 9) were individually integrated into the genome of strain A resulting in strains B and C, respectively. The EcnanE gene (GenBank: YP_003614592) encodes an N-acylglucosamine-6-phosphate 2-epimerase from *Enterobacter cloacae* subsp. *cloacae* ATCC 13047. All expression cassettes were integrated into the genome using the EZ-Tn5 transposase.

Single colonies of these strains were transferred from agar plates into microtiter plates containing 200 µL of the minimal medium described in example 2 and were cultivated for ~20 h at 30° C. with vigorous shaking. Subsequently, 50 µL of the culture broth was transferred to deepwell 96-well plates (2.0 mL) containing 400 µL of minimal medium per well. After incubation of another 48 hours, cultivation was stopped and the N-acetylneuraminic acid level in the supernatants were determined by mass spectrometry.

Figure 4:
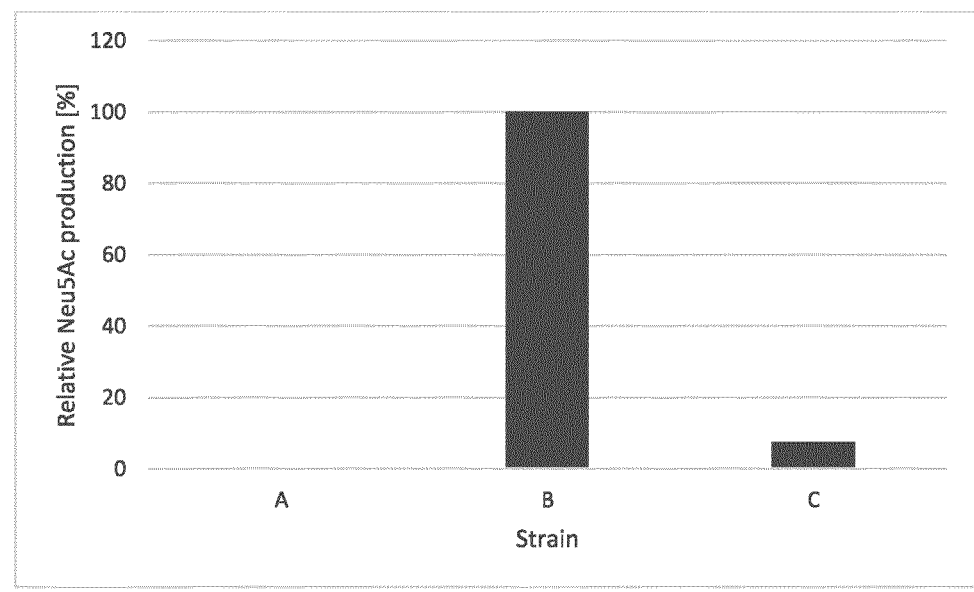
FIG. 4 displays a column graph illustrating the levels of Neu5Ac production by different non-naturally-occurring *E. coli* strains.

Neu5Ac production was only detectable in culture supernatants of strains B and C. In FIG. 4, the relative Neu5Ac production of the cultivated strains is shown. In comparison, the Neu5Ac production value of strain B was set to 100%. Strain C produced about 7.5% of Neu5Ac as compared to strain B.

Example 6: Composition of an Infant Formula Containing Neu5Ac

Infant formula: Skimmed milk
Vegetable oils (palm oil, rapeseed oil, sunflower oil)
Human milk oligosaccharides
L-Fucose
N-acetylneuraminic acid
Skimmed milk powder
Oil of *Mortierella alpine*

Fish oil
Calcium carbonate
Potassium chloride
Vitamin C
Sodium chloride
Vitamin E
Iron acetate
Zinc sulphate
Niacin
Calcium-D-panthothenate Copper sulphate
Vitamin A
Vitamin B1
Vitamin B6
Magnesium sulphate
Potassium iodate
Folic acid
Vitamin K
Sodium selenite
Vitamin D

The invention claimed is:

1. A method for producing N-acetylneuraminic acid (Neu5Ac) by fermentation using a non-naturally-occurring microorganism able to produce Neu5Ac, the method comprising:
   a) providing a non-naturally-occurring microorganism which is capable of producing Neu5Ac, wherein said non-naturally-occurring microorganism possesses a sialic acid biosynthesis pathway comprising at least one heterologous enzyme, wherein the naturally occurring sialic acid catabolic pathway of the microorganism has been disabled, wherein at least one phosphoenolpyruvate: sugar phosphotransferase system for the import of a saccharide that is not used as a carbon source during fermentative production of Neu5Ac has been disabled, and wherein the microorganism can utilize an exogenous carbon source present in a fermentation broth as a sole carbon source without using a phosphoenolpyruvate:sugar phosphotransferase system for the acquisition of said exogenous carbon source, and wherein the sialic acid biosynthesis pathway comprises the at least one heterologous enzyme selected from the group consisting of glutamine-fructose-6-phosphate aminotransferase, glucosamine-6-phosphate N-acetyltransferase, N-acetylglucosamine 2-epimerase, N-acetylneuraminic acid synthase, and a sugar phosphatase of the haloacid dehydrogenase (HAD)-like superfamily; and
   b) cultivating the non-naturally-occurring microorganism in the fermentation broth and under conditions permissive for the non-naturally-occurring microorganism to produce Neu5Ac.

2. The method of claim 1, wherein the fermentation broth contains a carbon source for growing the non-naturally-occurring microorganism.

3. The method of claim 1, wherein one or more of the genes encoding an enzyme which is involved in the sialic acid catabolic pathway is deleted from the genome of the non-naturally-occurring microorganism, in that the expression of one or more of the genes encoding an enzyme which is involved in the sialic acid catabolic pathway is impaired, or in that the nucleotide sequence of the protein coding region of at least one gene encoding an enzyme which is involved in the sialic acid catabolic pathway is altered such that the polypeptide being encoded by said altered protein-coding nucleotide sequence does not possess the enzymatic activity of the enzyme being encoded by the non-altered nucleotide sequence.

4. The method of claim 1, wherein the non-naturally-occurring microorganism has been genetically engineered to delete one or more of the genes selected from genes encoding N-acetylmannosamine kinase, N-acetylmannosamine-6-phosphate epimerase, N-acetylneuraminic acid aldolase and sialic acid permease, in that the expression of one or more of these genes is impaired, or in that the nucleotide sequence of the protein coding region of at least one of these genes is altered such that the polypeptide encoded by said altered nucleotide sequence does not possess the enzymatic activity of the enzyme encoded by the non-altered nucleotide sequence.

5. The method of claim 1, wherein the activities of one or more additional enzymes selected from N-acetylglucosamine-6-phosphate deacetylase and N-acetylglucosamine-6-phosphate deaminase have been abolished in the non-naturally-occurring microorganism.

6. The method of claim 1, wherein the non-naturally-occurring microorganism has been genetically engineered to abolish N-acetylglucosamine-6-phosphate deacetylase and/or N-acetylglucosamine-6-phosphate deaminase activity by deleting one or both genes encoding these enzymes, by impairing expression of one or both of these genes, or by altering the protein-coding region of one or both genes such that the polypeptide being encoded by each altered nucleotide sequence does not possess the enzymatic activity of the enzyme encoded by the non-altered nucleotide sequence.

7. The method of claim 1, wherein at least one phosphoenolpyruvate (PEP)-dependent, sugar transporting phosphotransferase system for the import of a carbohydrate by the non-naturally-occurring microorganism has been disabled.

8. The method of claim 1, wherein the non-naturally-occurring microorganism comprises a saccharide/H+symporter.

9. The method of claim 8, wherein the saccharide/H+-symporter is selected from a sucrose proton symporter, a lactose proton symporter, and a glucose proton symporter.

10. The method of claim 1, wherein the non-naturally-occurring microorganism possesses an enhanced PEP biosynthesis as compared to the wild-type microorganism due to the overexpression of PEP synthase.

11. The method of claim 1, wherein the non-naturally-occurring microorganism lacks one or more of a functional PEP carboxylase, a functional glutamate synthase, a functional WzxC protein, a functional UDP-glucose: undecaprenylphosphate glucose-1-phosphate transferase, a functional β-galactoside permease, a functional β-galactosidase, a functional YjhC protein, a functional fucose isomerase, a functional fuculokinase, and a functional N-acetylglutamine aminoacylase.

12. The method of claim 1, wherein the non-naturally-occurring microorganism possesses an enhanced glutamine synthesis as compared to the wild-type microorganism due to the overexpression of glutamine synthase.

13. The method of claim 1, wherein the method further comprises recovering the Neu5Ac from the fermentation broth.

14. The method of claim 2, wherein the carbon source is selected from glucose, xylose, sucrose, fructose, lactose, glycerol, syngas, and combinations thereof.

* * * * *

SEQUENCE LISTING

<160> NUMBER OF SEQ ID NOS: 103

<210> SEQ ID NO 1
<211> LENGTH: 2851
<212> TYPE: DNA
<213> ORGANISM: Artificial Sequence
<220> FEATURE:
<223> OTHER INFORMATION: Expression fragment

<400> SEQUENCE: 1

```
tggccagatg attaattcct aattttttgtt gacactctat cattgataga gttattttac      60
cactccctat cagtgataga gaaaagtgaa atgaatagtt cgacaaaaat ctagaaataa     120
ttttgtttaa ctttaagaag gagatataca aatgtactat ttaaaaaaca caaacttttg     180
gatgttcggt ttattctttt tcttttactt ttttatcatg ggagcctact tcccgttttt     240
cccgatttgg ctacatgaca tcaaccatat cagcaaaagt gatacgggta ttattttgc      300 cgctatttct ctgttctcgc tattattcca accgctgttt ggtctgcttt ctgacaaact     360
cgggctgcgc aaatacctgc tgtggattat taccggcatg ttagtgatgt ttgcgccgtt     420
ctttattttt atcttcgggc cactgttaca atacaacatt ttagtaggat cgattgttgg     480
tggtatttat ctaggctttt gttttaacgc cggtgcgcca gcagtagagg catttattga     540
gaaagtcagc cgtcgcagta atttcgaatt tggtcgcgcg cggatgtttg gctgtgttgg     600
ctgggcgctg tgtgcctcga ttgtcggcat catgttcacc atcaataatc agtttgtttt     660
ctggctgggc tctggctgtg cactcatcct cgccgtttta ctcttttttcg ccaaaacgga     720 tgcgccctct tctgccacgg ttgccaatgc ggtaggtgcc aaccattcgg catttagcct     780
taagctggca ctggaactgt tcagacagcc aaaactgtgg tttttgtcac tgtatgttat     840 tggcgttttcc tgcacctacg atgttttttga ccaacagttt gctaatttct ttacttcgtt     900
ctttgctacc ggtgaacagg gtacgcgggt atttggctac gtaacgacaa tgggcgaatt     960
acttaacgcc tcgattatgt tctttgcgcc actgatcatt aatcgcatcg gtgggaaaaa    1020
cgccctgctg ctggctggca ctattatgtc tgtacgtatt attggctcat cgttcgccac    1080
ctcagcgctg gaagtggtta ttctgaaaac gctgcatatg tttgaagtac cgttcctgct    1140
ggtgggctgc tttaaatata ttaccagcca gtttgaagtg cgttttttcag cgacgattta    1200 tctggtctgt ttctgcttct ttaagcaact ggcgatgatt tttatgtctg tactggcggg    1260
caatatgtat gaaagcatcg gtttccaggg cgcttatctg gtgctgggtc tggtggcgct    1320
gggcttcacc ttaatttccg tgttcacgct tagcggcccc ggcccgcttt ccctgctgcg    1380
tcgtcaggtg aatgaagtcg ctgggagcta agcggccgcg tcgacacgca aaaaggccat    1440
ccgtcaggat ggccttctgc ttaatttgat gcctggcagt ttatggcggg cgtcctgccc    1500
gccaccctcc gggccgttgc ttcgcaacgt tcaaatccgc tcccggcgga tttgtcctac    1560
tcaggagagc gttcaccgac aaacaacaga taaaacgaaa ggcccagtct ttcgactgag    1620
```

```
cctttcgttt tatttgatgc ctggcagttc cctactctcg catggggaga ccccacacta      1680
ccatcatgta tgaatatcct ccttagttcc tattccgaag ttcctattct ctagaaagta      1740
taggaacttc ggcgcgtcct acctgtgaca cgcgtgccgc agtctcacgc ccggagcgta      1800
gcgaccgagt gagctagcta tttgtttatt tttctaaata cattcaaata tgtatccgct      1860
catgagacaa taaccctgat aaatgcttca ataatattga aaaggaaga gtatgaggga       1920 agcggtgatc gccgaagtat cgactcaact atcagaggta gttggcgtca tcgagcgcca      1980
tctcgaaccg acgttgctgg ccgtacattt gtacggctcc gcagtggatg gcggcctgaa      2040
gccacacagt gatattgatt tgctggttac ggtgaccgta aggcttgatg aaacaacgcg      2100
gcgagctttg atcaacgacc ttttggaaac ttcggcttcc cctggagaga gcgagattct      2160
ccgcgctgta gaagtcacca ttgttgtgca cgacgacatc attccgtggc gttatccagc      2220
taagcgcgaa ctgcaatttg agaatggca gcgcaatgac attcttgcag gtatcttcga      2280
gccagccacg atcgacattg atctggctat cttgctgaca aaagcaagag aacatagcgt      2340
tgccttggta ggtccagcgg cggaggaact cttttgatccg gttcctgaac aggatctatt     2400
tgaggcgcta aatgaaacct taacgctatg gaactcgccg cccgactggg ctggcgatga     2460
gcgaaatgta gtgcttacgt tgtcccgcat ttggtacagc gcagtaaccg gcaaaatcgc     2520
gccgaaggat gtcgctgccg actgggcaat ggagcgcctg ccggcccagt atcagcccgt     2580
catacttgaa gctagacagg cttatcttgg acaagaagaa gatcgcttgg cctcgcgcgc     2640
agatcagttg gaagaatttg tccactacgt gaaaggcgag atcaccaagg tagtcggcaa     2700
ataatgtcta acaattcgtt caagccgagg ggccgcaaga tccggccacg atgacccggt     2760
cgtcgggtac cggcagggcg gggcgtaagg cgcgccattt aaatgaagtt cctattccga     2820
agttcctatt ctctagaaag tataggaact t                                    2851
```

<210> SEQ ID NO 2
<211> LENGTH: 5226
<212> TYPE: DNA
<213> ORGANISM: Artificial Sequence
<220> FEATURE:
<223> OTHER INFORMATION: E. coli W csc gene cluster comprising the genes
      for sucrose permease (cscB), fructokinase (cscK), sucrose
      hydrolase (cscA) and a transcriptional repressor (cscR)

<400> SEQUENCE: 2

```
acaggttggc tgataagtcc ccggtctggc agccgcgact gtaccagaac atgaatgagg       60
cgtttggatt aggcgattat tagcagggct aagcatttta ctattattat tttccggttg      120
agggatatag agctatcgac aacaaccgga aaaagtttac gtctatattg ctgaaggtac      180 aggcgttttcc ataactattt gctcgcgttt tttactcaag aagaaaatgc caaatagcaa     240
catcaggcag acaataccccg aaattgcgaa gaaaactgtc tggtagcctg cgtggtcaaa    300
gagtatccca gtcggcgttg aaagcagcac aatcccaagc gaactggcaa tttgaaaacc     360
aatcagaaag atcgtcgacg acaggcgctt atcaaagttt gccacgctgt atttgaagac     420
ggatatgaca caaagtggaa cctcaatggc atgtaacaac ttcactaatg aaataatcca     480
ggggttaacg aacagcgcgc aggaaaggat acgcaacgcc ataatcacaa ctccgataag     540
taatgcattt tttggcccta cccgattcac aaagaaagga ataatcgcca tgcacagcgc    600
ttcgagtacc acctggaatg agttgagata accatacagg cgcgttccta catcgtgtga    660
ttcgaataaa cctgaataaa agacaggaaa agttgttga tcaaaaatgt tatagaaaga      720
ccacgtcccc acaataaata tgacgaaaac ccagaagttt cgatccttga aaactgcgat     780
```

```
aaaatcctct tttttttaccc ctcccgcatc tgccgctacg cactggtgat ccttatcttt    840
aaaacgcatg ttgatcatca taaatacagc gccaaatagc gagaccaacc agaagttgat    900
atggggactg atactaaaaa atatgccggc aagaacgcg ccaatagcat agccaaaaga    960
tccccaggcg cgcgctgttc catattcgaa atgaaatttt cgcgccattt tttcggtgaa   1020
gctatcaagc aaaccgcatc ccgccagata ccccaagcca aaaatagcg ccccagaat    1080 tagacctaca gaaaaattgc tttgcagtaa cggttcataa acgtaaatca taaacggtcc   1140
ggtcaagacc aggatgaaac tcatacacca gatgagcggt ttcttcagac cgagtttatc   1200
ctgaacgatg ccgtagaaca tcataaatag aatgctggta aactggttga ccgaataaag   1260
tgtacctaat tccgtccctg tcaaccctag atgtcctttc agccaaatag cgtataacga   1320
ccaccacagc gaccaggaaa taaaaagag aaatgagtaa ctggatgcaa aacgatagta   1380
cgcatttctg aatggaatat tcagtgccat aattacctgc ctgtcgttaa aaaattcacg   1440
tcctatttag agataagagc gacttcgccg tttacttctc actattccag ttcttgtcga   1500
catggcagcg ctgtcattgc ccctttcgcc gttactgcaa gcgctccgca acgttgagcg   1560
agatcgataa ttcgtcgcat ttctctctca tctgtagata tcccgtaga ggacagacct    1620 gtgagtaacc cggcaacgaa cgcatctccc gccccgtgc tatcgacaca attcacagac   1680 attcagcaa aatggtgaac ttgtcctcga taacagacca ccacccctc tgcacccttta   1740 gtcaccaaca gcatggcgat ctcatactct tttgccaggg cgcatatatc ctgatcgttc   1800 tgtgttttttc cactgataag tcgccattct tcttccgaga gcttgacgac atccgccagt   1860
tgtagcgcct gccgcaaaca caagcggagc aaatgctcgt cttgccatag atcttcacga   1920
atattaggat cgaagctgac aaaacctccg gcatgccgga tcgccgtcat cgcagtaaat   1980
gcgctggtac gcgaaggctc ggcagacaac gcaattgaac agagatgtaa ccattcgcca   2040
tgtcgccagc agggcaagtc tgtcgtctct aaaaaaagat cggcactggg gcggaccata   2100
aacgtaaatg aacgttcccc ttgatcgttc agatcgacaa gcaccgtgga tgtccggtgc   2160
cattcatctt gcttcagata cgtgatatcg actccctcag ttagcagcgt tctttgcatt   2220
aacgcaccaa aaggatcatc ccccacccga cctataaacc cacttgttcc gcctaatctg   2280
gcgattccca ccgcaacgtt agctggcgcg ccgccaggac aaggcagtag gcgcccgtct   2340
gattctggca agagatctac gaccgcatcc cctaaaaccc atactttggc tgacattttt   2400
ttcccttaaa ttcatctgag ttacgcatag tgataaacct ctttttcgca aaatcgtcat   2460
ggatttacta aaacatgcat attcgatcac aaaacgtcat agttaacgtt aacatttgtg   2520
atattcatcg catttatgaa agtaagggac tttattttta taaagttaa cgttaacaat   2580 tcaccaaatt tgcttaacca ggatgattaa aatgacgcaa tctcgattgc atgcggcgca   2640
aaacgcccta gcaaaacttc atgagcaccg gggtaacact ttctatcccc attttcacct   2700
cgcgcctcct gccgggtgga tgaacgatcc aaacggcctg atctggttta acgatcgtta   2760
tcacgcgttt tatcaacatc atccgatgag cgaacactgg gggccaatgc actggggaca   2820
tgccaccagc gacgatatga tccactggca gcatgagcct attgcgctag cgccaggaga   2880
cgataatgac aaagacgggt gttttttcagg tagtgctgtc gatgacaatg gtgtcctctc   2940
acttatctac accggacacg tctggctcga tggtgcaggt aatgacgatg caattcgcga   3000
agtacaatgt ctggctacca gtcgggatgg tattcatttc gagaaacagg gtgtgatcct   3060
cactccacca gaaggaatca tgcacttccg cgatcctaaa gtgtggcgtg aagccgacac   3120
```

-continued

| | |
|---|---|
| atggtggatg gtagtcgggg cgaaagatcc aggcaacacg gggcagatcc tgctttatcg | 3180 |
| cggcagttcg ttgcgtgaat ggaccttcga tcgcgtactg gcccacgctg atgcgggtga | 3240 |
| aagctatatg tgggaatgtc cggacttttt cagccttggc gatcagcatt atctgatgtt | 3300 |
| ttccccgcag ggaatgaatg ccgagggata cagttaccga aatcgctttc aaagtggcgt | 3360 |
| aatacccgga atgtggtcgc caggacgact ttttgcacaa tccgggcatt ttactgaact | 3420 |
| tgataacggg catgactttt atgcaccaca aagcttttta gcgaaggatg gtcggcgtat | 3480 |
| tgttatcggc tggatggata tgtgggaatc gccaatgccc tcaaaacgtg aaggatgggc | 3540 |
| aggctgcatg acgctggcgc gcgagctatc agagagcaat ggcaaacttc tacaacgccc | 3600 |
| ggtacacgaa gctgagtcgt tacgccagca gcatcaatct gtctctcccc gcacaatcag | 3660 |
| caataaatat gttttgcagg aaaacgcgca agcagttgag attcagttgc agtgggcgct | 3720 |
| gaagaacagt gatgccgaac attacggatt acagctcggc actggaatgc ggctgtatat | 3780 |
| tgataaccaa tctgagcgac ttgttttgtg gcggtattac ccacacgaga atttagacgg | 3840 |
| ctaccgtagt attcccctcc cgcagcgtga cacgctcgcc taaggatat ttatcgatac | 3900 |
| atcatccgtg gaagtattta ttaacgacgg ggaagcggtg atgagtagtc gaatctatcc | 3960 |
| gcagccagaa gaacgggaac tgtcgcttta tgcctcccac ggagtggctg tgctgcaaca | 4020 |
| tggagcactc tggctactgg gttaacataa tatcaggtgg aacaacggat caacagcggg | 4080 |
| caagggatcc gcgtcactct tcccccttca cgaccttcaa taatatgcaa tgcagcttcc | 4140 |
| cgcccgataa tgtcatgtgg aagctgaatt gtggtcagcg gcggtaaaaa cagatgcccg | 4200 |
| acgccaacca gattatcaaa gcccattacg gcgacatcct gcgggattcg tacccccttc | 4260 |
| gccagaagaa cctgataagc cacaaaggct gcgcgatcgt taccacatat cagaacatca | 4320 |
| aaatctggtt tgcccggttt gaagtgggca ttgagtaaac ttgcgagatc ggtgtagtga | 4380 |
| tcatcacctg ttgccatgtg aaattgtttc acctcagcca gatctcgtcc agcatcacgc | 4440 |
| caggcctgct caaatccctg ccgacgtac cctgttgcca acgcactttc cggtagccag | 4500 |
| aagcataacg gttgacgata gcccgccgcg agcaaatgct gtgttgattc atattgtgca | 4560 |
| gtgtaatcat cagggatata actgggtaac gctgggtcat ccgccacaca gttcgccaat | 4620 |
| acaatatttt caccatacag agactcaggc agcgtgatat gtcgcagccc cattgtagta | 4680 |
| tagataatgc catccggacg gtgggcaagc agctgacgtg ccgcgcgggc agcgtcatct | 4740 |
| tcagaaaaaa tattgattaa aaaactattc cagccgaact cgctggcggt ttgctcaatg | 4800 |
| gcaagcagaa tatcaacaga gaaaggagtg gtagccgtgt cctgcgccag cacggcgaga | 4860 |
| gtcgacggct tacgtccttg agcgcgcatc ttacgggcgg aaagatcagg aacataattc | 4920 |
| agggtctgga ttgcctgcaa tacgcggtca cgcgttgcag gacgcacaga ttctgcatta | 4980 |
| tgcatcaccc gggagactgt catcatcgac actcccgcca ggcgtgcgac atcctttaat | 5040 |
| gaagccatac ccaagccgtt tgccgtaaaa cgggcactgt agcagaaaca gacgtcactg | 5100 |
| gcgagatcca acgccctatc acctgacaca gcaatacaat aaaaaataac aataattccc | 5160 |
| ggacaattgt ccccaattcc gcctctgttc tcgcattgta gaccggggac ttatcagcca | 5220 |
| acctgt | 5226 |

<210> SEQ ID NO 3
<211> LENGTH: 3123
<212> TYPE: DNA
<213> ORGANISM: Artificial Sequence
<220> FEATURE:
<223> OTHER INFORMATION: Expression cassette

<400> SEQUENCE: 3

```
ctgtctctta tacacatctc cggccagatg attaattcct aattttttgtt gacactctat      60
cattgataga gttattttac cactccctat cagtgataga gaaaagtgaa atgaatagtt      120
cgacaaaaat ctagaaataa ttttgtttaa ctttaagaag gagatataca aatgatcgct      180
caccgtcgtc aggaactggc tcaacagtat tatcaggctc tgcaccaaga tgtgctgccg      240
ttctgggaaa agtattcgct ggatcgtcaa ggcggtggct attttacctg cctggaccgc      300
aagggtcagg ttttgatac ggacaagttc atttggctgc aaaaccgtca agtgtggcaa      360
tttgcggttt tctacaatcg cctggaaccg aaaccgcagt ggctggaaat cgctcgtcat      420
ggtgcggatt ttctggcacg tcacggtcgt gatcaggacg gtaactggta tttcgccctg      480
gatcaggaag gcaaaccgct cgccaaccg tacaatgtgt tttccgactg tttcgcggcg      540
atggcgttta gccagtatgc actggcttct ggtgctcaag aagcgaaggc cattgcactg      600
caagcgtata caatgttct gcgtcgccag cataacccga aaggtcaata tgaaaagagt      660
tacccgggta cccgtccgct gaaatccctg gcagtgccga tgatcctggc taatctgacg      720
ctggaaatgg aatggctgct gccgccgacc acggtcgaag aagtgctggc ccagaccgtt      780
cgtgaagtca tgacggattt tctggacccg gaaattggcc tgatgcgcga agcagttacc      840
ccgacgggtg aatttgtcga ttcattcgaa ggccgcctgc tgaacccggg tcatggcatt      900
gaagcgatgt ggtttatgat ggatattgcc cagcgttcgg gtgaccgcca gctgcaagaa      960
caggctattg cggtggttct gaatacctg gaatatgcat gggatgaaga atttggtggc     1020
atcttttact tcctggaccg tcaaggtcac ccgccgcagc aactggaatg ggatcagaaa     1080
ctgtggtggg tccatctgga aaccctggtg gccctggcaa aaggtcacca ggcgacgggc     1140
caagaaaagt gctggcagtg gttttgaacgc gtgcatgatt atgcatggag ccactttgct     1200
gaccccggaat atggtgaatg gttccggctac ctgaaccgtc gcggtgaagt gctgctgaat     1260
ctgaaaggtg gcaaatggaa gggctgcttc cacgttccgc gtgcgctgtg gctgtgtgcc     1320
gaaaccctgc aactgccggt ctcttaataa tcgaaggaga tacaacatga gcttacccga     1380
tggattttat ataaggcgaa tggaagaggg ggatttggaa caggtcactg agacgctaaa     1440
ggttttgacc accgtgggca ctattacccc cgaatccttc agcaaactca taaaatactg     1500
gaatgaagcc acagtatgga atgataacga agataaaaaa ataatgcaat ataacccat      1560
ggtgattgtg gacaagcgca ccgagacggt tgccgctacg gggaatatca tcatcgaaag     1620
aaagatcatt catgaactgg ggctatgtgg ccacatcgag gacattgcag taaactccaa     1680
gtatcagggc caaggtttgg gcaagctctt gattgatcaa ttggtaacta tcggctttga     1740
ctacggttgt tataagatta ttttagattg cgatgagaaa aatgtcaaat tctatgaaaa     1800
atgtgggttt agcaacgcag gcgtggaaat gcaaattaga aaatagaata actagcataa     1860
accccctttgg ggcctctaaa cgggtcttga ggggtttttt gctgaaacca atttgcctgg     1920
cggcagtagc gcggtggtcc cacctgaccc catgccgaac tcagaagtga aacgccgtag     1980
cgccgatggt agtgtggggt ctccccatgc gagagtaggg aactgccagg catcaaataa     2040
aacgaaaggc tcagtcgaaa gactgggcct ttcgggatcc aggccggcct gttaagacgg     2100
ccagtgaatt cgagctcggt acctaccgtt cgtataatgt atgctatacg aagttatcga     2160
gctctagaga atgatcccct cattaggcca cacgttcaag tgcagcgcac accgtggaaa     2220
cggatgaagg cacgaaccca gttgacataa gcctgttcgg ttcgtaaact gtaatgcaag     2280
```

| | |
|---|---|
| tagcgtatgc gctcacgcaa ctggtccaga accttgaccg aacgcagcgg tggtaacggc | 2340 |
| gcagtggcgg ttttcatggc ttgttatgac tgttttttg tacagtctat gcctcgggca | 2400 |
| tccaagcagc aagcgcgtta cgccgtgggt cgatgtttga tgttatggag cagcaacgat | 2460 |
| gttacgcagc agcaacgatg ttacgcagca gggcagtcgc cctaaaacaa agttaggtgg | 2520 |
| ctcaagtatg gcatcattc gcacatgtag gctcggccct gaccaagtca atccatgcg | 2580 |
| ggctgctctt gatcttttcg gtcgtgagtt cggagacgta gccacctact cccaacatca | 2640 |
| gccggactcc gattacctcg ggaacttgct ccgtagtaag acattcatcg cgcttgctgc | 2700 |
| cttcgaccaa gaagcggttg ttggcgctct cgcggcttac gttctgccca ggtttgagca | 2760 |
| gccgcgtagt gagatctata tctatgatct cgcagtctcc ggcgagcacc ggaggcaggg | 2820 |
| cattgccacc gcgctcatca atctcctcaa gcatgaggcc aacgcgcttg gtgcttatgt | 2880 |
| gatctacgtg caagcagatt acggtgacga tcccgcagtg gctctctata caaagttggg | 2940 |
| catacgggaa gaagtgatgc actttgatat cgacccaagt accgccacct aacaattcgt | 3000 |
| tcaagccgag atcgtagaat tcgacgacc tgcagccaag cataacttcg tataatgtat | 3060 |
| gctatacgaa cggtaggatc ctctagagtc gacctgcagg catgagatgt gtataagaga | 3120 |
| cag | 3123 |

<210> SEQ ID NO 4
<211> LENGTH: 2965
<212> TYPE: DNA
<213> ORGANISM: Artificial Sequence
<220> FEATURE:
<223> OTHER INFORMATION: Expression cassette

<400> SEQUENCE: 4

| | |
|---|---|
| ctgtctctta tacacatctc cggccagatg attaattcct aattttttgtt gacactctat | 60 |
| cattgataga gttattttac cactccctat cagtgataga gaaaagtgaa atgaatagtt | 120 |
| cgacaaaaat ctagaaataa ttttgtttaa cttaagaag gagatataca atgaaagaa | 180 |
| atcaaaatcc agaacatcat catcagcgaa gaaaagcgc cgctggttgt gccggaaatc | 240 |
| ggcattaacc ataatggtag tctggaactg gcaaaaatca tggtggatgc ggcctttagc | 300 |
| gccggtgcaa aaatcattaa acatcagacc cacattgtgg aagatgaaat gtctaaagca | 360 |
| gcgaaaaaag ttatcccggg caacgcgaaa atcagtatct acgaaatcat gcagaaatgc | 420 |
| gcgctggatt acaaagatga actggccctg aaagaatata ccgaaaaact gggtctggtg | 480 |
| tacctgtcta ccccgtttag tcgtgcgggt gcaaaccgtc tggaagatat gggtgttagt | 540 |
| gcgttcaaaa tcggcagcgg tgaatgtaac aattatccgc tgatcaaaca tattgccgca | 600 |
| tttaaaaaac cgatgattgt tagcaccggc atgaatagca tcgaatctat taaaccgacg | 660 |
| gtgaaaatcc tgctggataa cgaaattccg tttgttctga tgcataccac gaatctgtac | 720 |
| ccgacccccg caaacctggt gcgtctgaat gccatgctgg aactgaaaaa agaattctct | 780 |
| tgcatggttg gtctgagtga tcacaccacg ataatctgg catgcctggg tgcagtggtt | 840 |
| ctgggtgcgt gtgtgctgga acgtcatttc accgatagca tgcaccgctc tggtccggat | 900 |
| attgtttgta gtatggatac gaaagcactg aaagaactga tcattcagag cgaacagatg | 960 |
| gcgatcattc gcggcaacaa tgaatctaaa aaagcggcca acaggaaca ggtgaccatc | 1020 |
| gattttgcat tcgcgagtgt ggttagcatc aaagatatca aaaaggcga agtgctgagc | 1080 |
| atggataata tttgggttaa acgtccgggt ctgggcggta tctctgcagc ggaatttgaa | 1140 |
| aacattctgg gcaaaaaagc actgcgcgat attgaaaatg atgcgcagct gtcttatgaa | 1200 |

```
gatttcgcct aataaatcga tactagcata accccttggg gcctctaaac gcgtcgacac    1260 gcaaaaggc catccgtcag gatggccttc tgcttaattt gatgcctggc agtttatggc    1320
gggcgtcctg cccgccaccc tccgggccgt tgcttcgcaa cgttcaaatc cgctcccggc    1380
ggatttgtcc tactcaggag agcgttcacc gacaaacaac agataaaacg aaaggcccag    1440
tctttcgact gagcctttcg ttttatttga tgcctggcag ttccctactc tcgcatgggg    1500
agaccccaca ctaccatccg gtatcgataa gcttgatggc gaaaggggga tgtgctgcaa    1560
ggcgattaag ttgggtaacg ccagggtttt cccagtcacg acgttgtaaa acgacggcca    1620
gtgaattcga gctcggtacc taccgttcgt ataatgtatg ctatacgaag ttatcgagct    1680
ctagagaatg atcccctccc tcacgctgcc gcaagcactc agggcgcaag ggctgctaaa    1740
ggaagcggaa cacgtagaaa gccagtccgc agaaacggtg ctgaccccgg atgaatgtca    1800
gctactgggc tatctggaca agggaaaacg caagcgcaaa gagaaagcag gtagcttgca    1860
gtgggcttac atggcgatag ctagactggg cggttttatg gacagcaagc gaaccggaat    1920
tgccagctgg ggcgccctct ggtaaggttg ggaagccctg caaagtaaac tggatggctt    1980
tcttgccgcc aaggatctga tggcgcaggg gatcaagatc tgatcaagag acaggatgag    2040
gatcgtttcg catgattgaa caagatggat tgcacgcagg ttctccggcc gcttgggtgg    2100
agaggctatt cggctatgac tgggcacaac agacaatcgg ctgctctgat gccgccgtgt    2160
tccggctgtc agcgcagggg cgcccggttc tttttgtcaa gaccgacctg tccggtgccc    2220
tgaatgaact gcaggacgag gcagcgcggc tatcgtggct ggccacgacg ggcgttcctt    2280
gcgcagctgt gctcgacgtt gtcactgaag cgggaaggga ctggctgcta ttgggcgaag    2340
tgccggggca ggatctcctg tcatctcacc ttgctcctgc cgagaaagta tccatcatgg    2400
ctgatgcaat gcggcggctg catacgcttg atccggctac ctgcccattc gaccaccaag    2460
cgaaacatcg catcgagcga gcacgtactc ggatggaagc cggtcttgtc gatcaggatg    2520
atctggacga agagcatcag gggctcgcgc cagccgaact gttcgccagg ctcaaggcgc    2580
gcatgcccga cggcgaggat ctcgtcgtga cccatggcga tgcctgcttg ccgaatatca    2640
tggtggaaaa tggccgcttt tctggattca tcgactgtgg ccggctgggt gtggcggacc    2700
gctatcagga catagcgttg gctacccgtg atattgctga agagcttggc ggcgaatggg    2760
ctgaccgctt cctcgtgctt tacggtatcg ccgctcccga ttcgcagcgc atcgccttct    2820
atcgccttct tgacgagttc ttctgagcgg gactctggga atttcgacga cctgcagcca    2880
agcataactt cgtataatgt atgctatacg aacggtagga tcctctagag tcgacctgca    2940
ggcatgagat gtgtataaga gacag                                         2965
```

<210> SEQ ID NO 5
<211> LENGTH: 3904
<212> TYPE: DNA
<213> ORGANISM: Artificial Sequence
<220> FEATURE:
<223> OTHER INFORMATION: Expression cassette

<400> SEQUENCE: 5

```
ctgtctctta tacacatctc cggccagatg attaattcct aattttttgtt gacactctat     60 cattgataga gttattttac cactccctat cagtgataga gaaaagtgaa atgaatagtt    120
cgacaaaaat ctagaaataa ttttgtttaa ctttaagaag gagatataca aatgatcgct    180
caccgtcgtc aggaactggc tcaacagtat tatcaggctc tgcaccaaga tgtgctgccg    240
```

```
ttctgggaaa agtattcgct ggatcgtcaa ggcggtggct attttacctg cctggaccgc      300
aagggtcagg tttttgatac ggacaagttc atttggctgc aaaaccgtca agtgtggcaa      360
tttgcggttt tctacaatcg cctggaaccg aaaccgcagt ggctggaaat cgctcgtcat      420
ggtgcggatt tctgcacg tcacggtcgt gatcaggacg gtaactggta tttcgccctg        480
gatcaggaag gcaaaccgct gcgccaaccg tacaatgtgt tttccgactg tttcgcggcg      540
atggcgttta gccagtatgc actggcttct ggtgctcaag aagcgaaggc cattgcactg      600
caagcgtata acaatgttct gcgtcgccag cataacccga aaggtcaata tgaaaagagt      660
tacccgggta cccgtccgct gaaatccctg gcagtgccga tgatcctggc taatctgacg      720
ctggaaatgg aatggctgct gccgccgacc acggtcgaag aagtgctggc ccagaccgtt      780
cgtgaagtca tgacggattt tctgaccccg gaaattggcc tgatgcgcga agcagttacc      840
ccgacgggtg aatttgtcga ttcattcgaa ggccgcctgc tgaacccggg tcatggcatt      900
gaagcgatgt ggtttatgat ggatattgcc cagcgttcgg gtgaccgcca gctgcaagaa      960
caggctattg cggtggttct gaatacectg gaatatgcat gggatgaaga atttggtggc     1020 atctttttact tcctggaccg tcaaggtcac ccgccgcagc aactggaatg ggatcagaaa     1080
ctgtggtggg tccatctgga aaccctggtg gccctggcaa aaggtcacca ggcgacgggc     1140
caagaaaagt gctggcagtg gttgaacgc gtgcatgatt atgcatggag ccactttgct     1200
gacccggaat atggtgaatg gttcggctac ctgaaccgtc gcggtgaagt gctgctgaat     1260
ctgaaaggtg gcaaatggaa gggctgcttc cacgttccgc gtgcgctgtg gctgtgtgcc     1320
gaaaccctgc aactgccggt ctcttaattt cgtcgacaca caggaaacat attaaaaatt     1380
aaaacctgca ggagtttaaa cgcggccgcg atatcgttgt aaaacgacgg ccagtgcaag     1440
aatcataaaa aatttatttg ctttcaggaa aattttctg tataatagat tcataaattt      1500
gagagaggag ttttgtgag cggataacaa ttccccatct tagtatatta gttaagtata      1560
aatacacaag gagatataca tatgaaagaa atcaaaatcc agaacatcat catcagcgaa      1620
gaaaaagcgc cgctggttgt gccggaaatc ggcattaacc ataatggtag tctggaactg      1680
gcaaaaatca tggtggatgc ggcctttagc gccggtgcaa aaatcattaa acatcagacc     1740
cacattgtgg aagatgaaat gtctaaagca gcgaaaaaag ttatcccggg caacgcgaaa     1800
atcagtatct acgaaatcat gcagaaatgc gcgctggatt acaaagatga actgaccctg     1860
aaagaatata ccgaaaaact gggtctggtg tacctgtcta ccccgtttag tcgtgcgggt     1920
gcaaaccgtc tggaagatat gggtgttagt gcgttcaaaa tcggcagcgg tgaatgtaac     1980
aattatccgc tgatcaaaca tattgccgca tttaaaaaac cgatgattgt tagcaccggc     2040
atgaatagca tcgaatctat taaaccgacg gtgaaaatcc tgctggataa cgaaattccg     2100
tttgttctga tgcataccac gaatctgtac ccgaccccgc acaacctggt gcgtctgaat     2160
gccatgctgg aactgaaaaa agaattctct tgcatggttg gtctgagtga tcacaccacg     2220
gataatctgg catgcctggg tgcagtggtt ctggtgcgt gtgtgctgga acgtcatttc       2280
accgatagca tgcaccgctc tggtccggat attgtttgta gtatggatac gaaagcactg     2340
aaagaactga tcattcagag cgaacagatg gcgatcattc gcggcaacaa tgaatctaaa     2400
aaagcggcca acaggaaca ggtgaccatc gattttgcat tcgcgagtgt ggttagcatc       2460
aaagatatca aaaaggcga agtgctgagc atggataata tttgggttaa acgtccgggt       2520
ctgggcggta tctctgcagc ggaatttgaa acattctgg gcaaaaaagc actgcgcgat       2580
attgaaaatg atgcgcagct gtcttatgaa gatttcgcct aaaataacta gcataacccc     2640
```

```
ttggggcctc taaacgggtc ttgaggggtt ttttgctgaa accaatttgc ctggcggcag      2700
tagcgcggtg gtcccacctg accccatgcc gaactcagaa gtgaaacgcc gtagcgccga      2760
tggtagtgtg gggtctcccc atgcgagagt agggaactgc caggcatcaa ataaaacgaa      2820
aggctcagtc gaaagactgg gcctttcggg atccaggccg gctgttaac gaattaatct       2880 tccgcggcgg tatcgataag cttgatatcg aattccgaag ttcctattct ctagaaagta      2940
taggaacttc aggtctgaag aggagtttac gtccagccaa gctagcttgg ctgcaggtcg      3000
tcgaaattct accgggtagg ggaggcgctt ttcccaaggc agtctggagc atgcgcttta      3060
gcagccccgc tgggcacttg gcgctacaca agtggcctct ggcctcgcac acattccaca      3120
tccaccggta ggcgccaacc ggctccgttc tttggtggcc cttcgcgcc accttctact       3180 cctcccctag tcaggaagtt cccccccgcc ccgcagctcg cgtcgtgcag gacgtgacaa      3240
atggaagtag cacgtctcac tagtctcgtg cagatggaca gcaccgctga gcaatggaag      3300
cgggtaggcc tttggggcag cggccaatag cagctttgct ccttcgcttt ctgggctcag      3360 ggcgggctc aggggggcggg gcgggcgccc gaaggtcctc cggaggcccg gcattctgca      3420
cgcttcaaaa gcgcacgtct gccgcgctgt tctcctcttc ctcatctccg gccttttcga      3480
cctgcagcct gttgacaatt aatcatcggc atagtatatc ggcatagtat aatacgacaa      3540
ggtgaggaac taaaccatgg gtcaaagtag cgatgaagcc aacgctcccg ttgcagggca      3600
gtttgcgctt cccctgagtg ccacctttgg cttaggggat cgcgtacgca agaaatctgg      3660
tgccgcttgg cagggtcaag tcgtcggttg gtattgcaca aaactcactc ctgaaggcta      3720
tgcggtcgag tccgaatccc acccaggctc agtgcaaatt tatcctgtgg ctgcacttga      3780
acgtgtggcc taatgagggg atcaattctc tagagctcgc tgatcagaag ttcctattct      3840
ctagaaagta taggaacttc gatggcgcct catccctgaa gccaaagatg tgtataagag      3900
acag                                                                  3904
```

<210> SEQ ID NO 6
<211> LENGTH: 3793
<212> TYPE: DNA
<213> ORGANISM: Artificial Sequence
<220> FEATURE:
<223> OTHER INFORMATION: expression cassette

<400> SEQUENCE: 6

```
ctgtctctta tacacatctc cggccagatg attaattcct aattttgtt gacactctat        60 cattgataga gttattttac cactccctat cagtgataga gaaagtgaa atgaatagtt       120 cgacaaaaat ctagaaataa ttttgtttgg cgtcgagaag gagatagaaa atgtgcggta      180
tcgttggtgc tatcgcacag cgtgatgtag cgaaaatcct cctggaaggt ctgcgtcgtc      240
tcgaataccg tggttacgac tctgccggtc tggcagtagt ggatgcagaa ggtcacatga      300
ctcgtctgcg tcgtctgggt aaagtgcaga tgctcgcgca ggcggcgaa gaacacccac        360 tccacggtgg tacgggtatc gcacacactc gttgggcaac ccacggtgaa ccgtctgagg      420
tcaacgcaca cccgcatgtt agcgagcaca tcgtagtcgt tcacaacggt atcatcgaga      480
accacgaacc actccgtgag gaactcaaag cccgtggtta caccttcgta agcgaaaccg      540
acacggaagt tatcgcccac ctcgttaact gggaactcaa acagggtggt actctgcgtg      600
aagcagttct gcgtgccatt ccacagctgc gtggtcata cggtaccgtg atcatggact       660
ctcgtcatcc ggatacccctg ctcgccgcac gttctggttc tccactcgtt atcggtctgg    720
```

-continued

```
gtatgggtga gaacttcatc gcctctgatc agctggccct gctcccagtt accgtcgct     780 tcatcttcct ggaagagggt gacatcgccg aaatcacccg tcgttccgtt aacatcttcg    840
acaaaacggg tgcggaagtt aaacgtcagg acatcgagtc taacctgcag tatgacgctg    900
gtgacaaagg catctaccgt cactacatgc agaaagagat ctacgaacag ccgaacgcga    960
tcaaaaacac cctgaccggt cgtatctctc acggtcaggt tgacctgtct gagctgggtc    1020
caaacgcgga cgaactcctg tccaaagtcg agcacatcca gatcctggct tgtggtacct    1080
cttacaactc cggtatggtt tctcgttact ggttcgaatc tctggcaggt atcccatgcg    1140
acgttgaaat cgcctccgaa ttccgttatc gtaaatctgc ggtacgtcgt aactccctca    1200
tgatcaccct gtctcagtct ggtgaaaccg ctgatactct ggcaggtctg cgtctcagca    1260
aagaactggg ttacctgggt tctctggcca tctgcaacgt tccgggttct agcctggttc    1320
gtgagtctgt gctggctctg atgaccaacg cgggtacgga gatcggtgtt gcctctacca    1380
aagcgttcac tacccagctc actgtcctgc tgatgctggt tgccaaactg tctcgtctca    1440
aaggcctcga cgctagcatc gaacacgaca tcgtacacgg tctgcaggcc ctcccatctc    1500
gtatcgagca gatgctgccg caggacaaac gtatcgaagc actggcagaa gacttcagcg    1560
acaaacacca cgcgctgttt ctgggtcgtg gtgaccagta cccaattgcg ctggaaggtg    1620
ccctgaaact gaaagagatc agctacatcc atgcagaggc atacgcagcg ggtgagctga    1680
aacatggtcc actggccctg atcgacgcag atatgccggt tattgtggtt gctccgaaca    1740
acggcctgct ggagaaactg aaatccaaca tcgaggaagt acgtgcgcgt ggtggtcagc    1800
tgtacgtgtt tgctgaccag gacgcgggtt tcgtttccag cgacaacatg cacatcatcg    1860
aaatgccgca tgttgaagag gtaatcgcgc aatcttcta caccgtaccg ctgcagctgc    1920
tggcgtacca tgtagccctg atcaaaggta cggacgttga ccagccgcgt aacctggcga    1980
aatccgtgac cgtggaataa cgaaggagat agaaccatga gcttaccga tggattttat    2040 ataaggcgaa tggaagaggg ggatttggaa caggtcactg agacgctaaa ggttttgacc    2100
accgtgggca ctattacccc cgaatccttc agcaaactca taaaatactg gaatgaagcc    2160
acagtatgga atgataacga agataaaaaa ataatgcaat ataaccccat ggtgattgtg    2220
gacaagcgca ccgagacggt tgccgctacg gggaatatca tcatcgaaag aaagatcatt    2280
catgaactgg ggctatgtgg ccacatcgag gacattgcag taaactccaa gtatcagggc    2340
caaggtttgg gcaagctctt gattgatcaa ttggtaacta tcggctttga ctacggttgt    2400
tataagatta ttttagattg cgatgagaaa aatgtcaaat tctatgaaaa atgtgggttt    2460
agcaacgcag gcgtggaaat gcaaattaga aaatagcatc cgtatcggaa acactagcat    2520
aaccccttgg ggcctctaaa cgggtcttga ggggttttt gctgaaacca atttgcctgg    2580
cggcagtagc gcggtggtcc cacctgaccc catgccgaac tcagaagtga aacgccgtag    2640
cgccgatggt agtgtggggt ctccccatgc gagagtaggg aactgccagg catcaaataa    2700
aacgaaaggc tcagtcgaaa gactgggcct ttcgcttcca caactttgta taataaagtt    2760
gtccccacgg ccagtgaatt cgagctcggt acctaccgtt cgtataatgt atgctatacg    2820
aagttatcga gctctagaga atgatcccct cattaggcca cacgttcaag tgcagcgcac    2880
accgtggaaa cggatgaagg cacgaaccca gttgacataa gcctgttcgg ttcgtaaact    2940
gtaatgcaag tagcgtatgc gctcacgcaa ctggtccaga accttgaccg aacgcagcgg    3000
tggtaacggc gcagtggcgg ttttcatggc ttgttatgac tgtttttttg tacagtctat    3060
gcctcgggca tccaagcagc aagcgcgtta cgccgtgggt cgatgtttga tgttatgag     3120
```

| | |
|---|---|
| cagcaacgat gttacgcagc agcaacgatg ttacgcagca gggcagtcgc cctaaaacaa | 3180 |
| agttaggtgg ctcaagtatg gcatcattc gcacatgtag gctcggccct gaccaagtca | 3240 |
| aatccatgcg ggctgctctt gatcttttcg gtcgtgagtt cggagacgta gccacctact | 3300 |
| cccaacatca gccggactcc gattacctcg ggaacttgct ccgtagtaag acattcatcg | 3360 |
| cgcttgctgc cttcgaccaa gaagcggttg ttggcgctct cgcggcttac gttctgccca | 3420 |
| ggtttgagca gccgcgtagt gagatctata tctatgatct cgcagtctcc ggcgagcacc | 3480 |
| ggaggcaggg cattgccacc gcgctcatca atctcctcaa gcatgaggcc aacgcgcttg | 3540 |
| gtgcttatgt gatctacgtg caagcagatt acggtgacga tcccgcagtg gctctctata | 3600 |
| caaagttggg catacgggaa gaagtgatgc actttgatat cgacccaagt accgccacct | 3660 |
| aacaattcgt tcaagccgag atcgtagaat ttcgacgacc tgcagccaag cataacttcg | 3720 |
| tataatgtat gctatacgaa cggtaggatc ctctagagtc gacctgcagg catgagatgt | 3780 |
| gtataagaga cag | 3793 |

<210> SEQ ID NO 7
<211> LENGTH: 3847
<212> TYPE: DNA
<213> ORGANISM: Artificial Sequence
<220> FEATURE:
<223> OTHER INFORMATION: Expression cassette

<400> SEQUENCE: 7

| | |
|---|---|
| ctgtctctta tacacatctc cggccagatg attaattcct aattttgtt gacactctat | 60 |
| cattgataga gttattttac cactccctat cagtgataga gaaaagtgaa atgaatagtt | 120 |
| cgacaaaaat ctagaaataa ttttgtttgg cgtcgagaag gagatagaac catgtccaac | 180 |
| aatggctcgt caccgctggt gctttggtat aaccaactcg gcatgaatga tgtagacagg | 240 |
| gttgggggca aaaatgcctc cctgggtgaa atgattacta acctttccgg aatgggtgtt | 300 |
| tccgttccga atggtttcgc cacaaccgcc gacgcgttta ccagtttct ggaccaaagc | 360 |
| ggcgtaaacc agcgcattta tgaactgctg gataaaacgg atattgacga tgttactcag | 420 |
| cttgcgaaag cgggcgcgca aatccgccag tggattatcg cactcccctt ccagcctgag | 480 |
| ctggaaaacg ccatcagcga agcctatgca cagctttctg ccgatgacga aaacgcctct | 540 |
| tttgcggtgc gctcctccgc caccgcagaa gatatgccgg acgcttcttt tgccggtcag | 600 |
| caggaaacct tcctcaacgt tcagggtttt gacgccgttc tcgtggcagt gaaacatgta | 660 |
| tttgcttctc tgtttaacga tcgcgccatc tcttatcgtg tgcaccaggg ttacgatcac | 720 |
| cgtggtgtgg cgctctccgc cggtgttcaa cggatggtgc gctctgacct cgcatcatct | 780 |
| ggcgtgatgt tctccattga taccgaatcc ggctttgacc aggtggtgtt tatcacttcc | 840 |
| gcatggggcc ttggtgagat ggtcgtgcag ggtgcggtta acccggatga gttttacgtg | 900 |
| cataaaccga cactggcggc gaatcgcccg gctatcgtgc gccgcaccat ggggtcgaaa | 960 |
| aaaatccgca tggtttacgc gccgacccag gagcacggca agcaggttaa atcgaagac | 1020 |
| gtaccgcagg aacagcgtga catcttctcg ctgaccaacg aagaagtgca ggaactggca | 1080 |
| aaacaggccg tacaaattga gaaacactac ggtcgcccga tggatattga gtgggcgaaa | 1140 |
| gatggccaca ccggtaaact gttcattgtg caggcgcgtc cggaaaccgt gcgctcacgc | 1200 |
| ggtcaggtca tggagcgtta tacgctgcat tcacagggta aagattatcg cgaaggccgt | 1260 |
| gctatcggtc atcgcatcgg tgcgggtccg gtgaaagtca tccatgatat cagcgaaatg | 1320 |

-continued

```
aaccgcatcg aacctggtga cgtgctggtc actgacatga ccgacccgga ctgggaaccg    1380
atcatgaaga aagcatctgc catcgtcacc aaccgtggcg gtcgtacctg tcacgcggcg    1440
atcatcgctc gtgaactggg cattccggcg gtagtgggct gtggtgatgc aacagaacgg    1500
atgaaagacg gtgagaacgt cactgtttct tgtgccgaag gtgataccgg ttacgtctat    1560
gcggagttgc tggaatttag cgtgaaaagc tccagcgtag aaacgatgcc ggatctgccg    1620
ttgaaagtga tgatgaacgt cggtaacccg gaccgagctt tcgacttcgc ctgtctgccg    1680
aacgaaggcg tgggacttgc gcgtctggaa tttatcatca accgtatgat tggcgtccac    1740
ccacgcgcac tgcttgagtt tgacgatcag gaaccgcagt tgcaaaacga aatccgcgag    1800
atgatgaaag gttttgattc tccgcgtgaa ttttacgttg gtcgtctgac tgaagggatc    1860
gcgacgctgg gtgccgcgtt ttatccgaag cgcgtcattg tccgtctctc tgattttaaa    1920
tcgaacgaat atgccaacct ggtcggtggt gagcgttacg agccagatga agagaacccg    1980
atgctcggct ccgtggcgc gggacgctat atttccgaca gcttccgcga ctgtttcgcg     2040
ctggagtgcg aagcagtgaa acgtgtgcgc aacgacatgg ggctgaccaa cgttgagatc    2100
atgatcccgt tcgtgcgaac cgtagatcag gcgaaagcgg tggttgagga actggcgcgt    2160
caggggctga acgtggtga gaacgggctg aaaatcatca tgatgtgtga aatcccgtcc     2220
aacgccttgc tggccgagca gttcctcgaa tatttcgacg gcttctcaat tggctcaaac    2280
gacatgacgc agctggcgct cggtctggat cgtgactccg gcgtggtgtc tgaactgttc    2340
gatgagcgca cgatgcggt gaaagcactg ctgtcgatgg cgattcgtgc cgcgaagaaa     2400
cagggcaaat atgtcgggat tgcggtcag ggtccgtccg accacgaaga ctttgccgca    2460
tggttgatgg aagaggggat cgatagcctg tctctgaacc cggacaccgt ggtgcaaacc    2520
tggttaagcc tggctgaact gaagaaataa catccgtatc ggaaacacta gcataacccc    2580
ttggggcctc taaacgggtc ttgagggtt ttttgctgaa accaatttgc ctggcggcag     2640
tagcgcggtg gtcccacctg accccatgcc gaactcagaa gtgaaacgcc gtagcgccga    2700
tggtagtgtg gggtctcccc atgcgagagt agggaactgc caggcatcaa ataaaacgaa    2760
aggctcagtc gaaagactgg gcctttcgct tccacaactt tgtataataa agttgtcccc    2820
acggccagtg aattcgagct cggtacctac cgttcgtata atgtatgcta tacgaagtta    2880
tcgagctcta gagaatgatc ccctcattag gccacgcgtt caagtgcagc gcacaccgtg    2940
gaaacggatg aaggcacgaa cccagttgac ataagcctgt tcggttcgta aactgtaatg    3000
caagtagcgt atgcgctcac gcaactggtc cagaaccttg accgaacgca gcggtggtaa    3060
cggcgcagtg gcggttttca tggcttgtta tgactgtttt tttgtacagt ctatgcctcg    3120
ggcatccaag cagcaagcgc gttacgccgt gggtcgatgt tgatgttat ggagcagcaa     3180 cgatgttacg cagcagcaac gatgttacgc agcagggcag tcgccctaaa acaaagttag    3240
gtggctcaag tatgggcatc attcgcacat gtaggctcgg ccctgaccaa gtcaaatcca    3300
tgcgggctgc tcttgatctt ttcggtcgtg agttcggaga cgtagccacc tactcccaac    3360
atcagccgga ctccgattac ctcgggaact gctccgtag taagacattc atcgcgcttg     3420
ctgccttcga ccaagaagcg gttgttggcg ctctcgcggc ttacgttctg ccaggtttg     3480 agcagccgcg tagtgagatc tatatctatg atctcgcagt ctccggcgag caccggaggc    3540
agggcattgc caccgcgctc atcaatctcc tcaagcatga ggccaacgcg cttggtgctt    3600
atgtgatcta cgtgcaagca gattacggtg acgatcccgc agtggctctc tatacaaagt    3660
tgggcatacg ggaagaagtg atgcactttg atatcgaccc aagtaccgcc acctaacaat    3720
```

-continued

| | |
|---|---|
| tcgttcaagc cgagatcgta gaatttcgac gacctgcagc caagcataac ttcgtatat | 3780 |
| gtatgctata cgaacggtag gatcctctag agtcgacctg caggcatgag atgtgtataa | 3840 |
| gagacag | 3847 |

<210> SEQ ID NO 8
<211> LENGTH: 5554
<212> TYPE: DNA
<213> ORGANISM: Artificial Sequence
<220> FEATURE:
<223> OTHER INFORMATION: Plasmid

<400> SEQUENCE: 8

| | |
|---|---|
| catcgattta ttatgacaac ttgacggcta catcattcac ttttttcttca caaccggcac | 60 |
| ggaactcgct cgggctggcc ccggtgcatt ttttaaatac ccgcgagaaa tagagttgat | 120 |
| cgtcaaaacc aacattgcga ccgacggtgg cgataggcat ccgggtggtg ctcaaaagca | 180 |
| gcttcgcctg gctgatacgt tggtcctcgc gccagcttaa gacgctaatc cctaactgct | 240 |
| ggcggaaaag atgtgacaga cgcgacggcg acaagcaaac atgctgtgcg acgctggcga | 300 |
| tatcaaaatt gctgtctgcc aggtgatcgc tgatgtactg acaagcctcg cgtacccgat | 360 |
| tatccatcgg tggatggagc gactcgttaa tcgcttccat gcgccgcagt aacaattgct | 420 |
| caagcagatt tatcgccagc agctccgaat agcgcccttc cccttgcccg gcgttaatga | 480 |
| tttgcccaaa caggtcgctg aaatgcggct ggtgcgcttc atccgggcga agaaccccg | 540 |
| tattggcaaa tattgacggc cagttaagcc attcatgcca gtaggcgcgc ggacgaaagt | 600 |
| aaacccactg gtgataccat tcgcgagcct ccggatgacg accgtagtga tgaatctctc | 660 |
| ctggcgggaa cagcaaaata tcacccggtc ggcaaacaaa ttctcgtccc tgatttttca | 720 |
| ccaccccctg accgcgaatg gtgagattga gaatataacc tttcattccc agcggtcggt | 780 |
| cgataaaaaa atcgagataa ccgttggcct caatcggcgt taaacccgcc accagatggg | 840 |
| cattaaacga gtatcccggc agcaggggat cattttgcgc ttcagccata cttttcatac | 900 |
| tcccgccatt cagagaagaa accaattgtc catattgcat cagacattgc cgtcactgcg | 960 |
| tcttttactg gctcttctcg ctaaccaaac cggtaacccc gcttattaaa agcattctgt | 1020 |
| aacaaagcgg gaccaaagcc atgacaaaaa cgcgtaacaa aagtgtctat aatcacggca | 1080 |
| gaaaagtcca cattgattat ttgcacggcg tcacactttg ctatgccata gcatttttat | 1140 |
| ccataagatt agcggatcct acctgacgct ttttatcgca actctctact gtttctccat | 1200 |
| acccgttttt tgggaattc gagctctaag gaggttataa aaaatgtcta atctgctgac | 1260 |
| ggtccaccaa aacctgccgg ctctgccggt cgatgctacc tctgatgaag ttcgcaaaaa | 1320 |
| cctgatggat atgtttcgtg atcgccaggc attcagcgaa catacctgga aaatgctgct | 1380 |
| gtccgtgtgc cgttcatggg cggcctggtg taaactgaac aatcgcaaat ggtttccggc | 1440 |
| ggaaccggaa gatgtccgtg actatctgct gtacctgcag gcccgcgtc tggcagttaa | 1500 |
| aacgatccag caacatctgg gccaactgaa tatgctgcac cgtcgctccg gtctgccgcg | 1560 |
| tccgagcgat tctaatgcgg tgtcactggt tatgcgtcgc attcgtaaag aaaacgtgga | 1620 |
| tgcaggcgaa cgcgctaaac aggcactggc ttttgaacgt accgatttcg accaagttcg | 1680 |
| ctcgctgatg gaaaacagcg atcgttgcca ggacatccgc aatctggcgt tcctgggtat | 1740 |
| tgcctataac accctgctgc gcattgcaga aatcgctcgt attcgcgtga agatatcag | 1800 |
| ccgtacggac ggcggtcgca tgctgattca catcggccgt accaaaacgc tggtctctac | 1860 |

```
cgcaggcgtg gaaaaagctc tgagtctggg tgtgacgaaa ctggttgaac gctggattag    1920
tgtctccggc gtggcggatg acccgaacaa ttacctgttt tgtcgtgttc gcaaaaatgg    1980
tgtcgcagct ccgtcagcca cctcgcagct gagcacgcgt gcactggaag gcatcttcga    2040
agctacccat cgcctgattt atggcgccaa agatgactcg ggtcaacgtt acctggcgtg    2100
gtctggtcac agtgcacgtg ttggtgccgc acgtgatatg gcccgtgccg gtgtttccat    2160
cccggaaatt atgcaggcag gcggttggac caacgttaat atcgtcatga actatattcg    2220
caatctggac tcggaaacgg gtgctatggt tcgcctgctg gaagacggtg actaatgagt    2280
gccggagttc atcgaaaaaa tggacgaggc actggctgaa attggttttg tatttgggga    2340
gcaatggcga tgacgcatcc tcacgataat atccgggtag gcgcaatcac tttcgtctac    2400
tccgttacaa agcgaggctg gtatttcccc ggcctttctg ttatccgaaa tccactgaaa    2460
gcacagcggc tggctgagga gataaataat aaacgagggg ctgtatgcac aaagcatctt    2520
ctgttgagtt aagaacgagt atcgagatgg cacatagcct tgctcaaatt ggaatcaggt    2580
ttgtgccaat accagtagaa acagacgaag aatccatggg tatggacagt tttccctttg    2640
atatgtaacg gtgaacagtt gttctacttt tgtttgttag tcttgatgct tcactgatag    2700
atacaagagc cataagaacc tcagatcctt ccgtatttag ccagtatgtt ctctagtgtg    2760
gttcgttgtt tttgcgtgag ccatgagaac gaaccattga gatcatactt actttgcatg    2820
tcactcaaaa attttgcctc aaaactggtg agctgaattt ttgcagttaa agcatcgtgt    2880
agtgtttttc ttagtccgtt acgtaggtag gaatctgatg taatggttgt tggtattttg    2940
tcaccattca tttttatctg gttgttctca agttcggtta cgagatccat ttgtctatct    3000
agttcaactt ggaaaatcaa cgtatcagtc gggcggcctc gcttatcaac caccaatttc    3060
atattgctgt aagtgtttaa atctttactt attggtttca aaaccattg gttaagcctt    3120 ttaaactcat ggtagttatt ttcaagcatt aacatgaact taaattcatc aaggctaatc    3180
tctatatttg ccttgtgagt tttcttttgt gttagttctt ttaataacca ctcataaatc    3240
ctcatagagt atttgttttc aaaagactta acatgttcca gattatattt tatgaatttt    3300
tttaactgga aaagataagg caatatctct tcactaaaaa ctaattctaa ttttttcgctt    3360 gagaacttgg catagtttgt ccactggaaa atctcaaagc ctttaaccaa aggattcctg    3420
atttccacag ttctcgtcat cagctctctg gttgctttag ctaatacacc ataagcattt    3480
tccctactga tgttcatcat ctgagcgtat tggttataag tgaacgatac cgtccgttct    3540
ttccttgtag ggttttcaat cgtggggttg agtagtgcca cacagcataa aattagcttg    3600
gtttcatgct ccgttaagtc atagcgacta atcgctagtt catttgcttt gaaaacaact    3660
aattcagaca tacatctcaa ttggtctagg tgattttaat cactatacca attgagatgg    3720
gctagtcaat gataattact agtccttttc ctttgagttg tgggtatctg taaattctgc    3780
tagacctttg ctggaaaact tgtaaattct gctagaccct ctgtaaattc cgctagacct    3840
ttgtgtgttt tttttgttta tattcaagtg gttataattt atagaataaa gaaagaataa    3900
aaaaagataa aagaataga tcccagccct gtgtataact cactactta gtcagttccg    3960 cagtattaca aaaggatgtc gcaaacgctg tttgctcctc tacaaaacag accttaaaac    4020
cctaaaggct taagtagcac cctcgcaagc tcggttgcgg ccgcaatcgg gcaaatcgct    4080
gaatattcct tttgtctccg accatcaggc acctgagtcg ctgtcttttt cgtgacattc    4140
agttcgctgc gctcacggct ctggcagtga atggggtaa atggcactac aggcgccttt    4200
tatggattca tgcaaggaaa ctacccataa tacaagaaaa gcccgtcacg ggcttctcag    4260
```

```
ggcgttttat ggcgggtctg ctatgtggtg ctatctgact ttttgctgtt cagcagttcc    4320
tgccctctga ttttccagtc tgaccacttc ggattatccc gtgacaggtc attcagactg    4380
gctaatgcac ccagtaaggc agcggtatca tcaacggggt ctgacgctca gtggaacgaa    4440
aactcacgtt aagggatttt ggtcatgaga ttatcaaaaa ggatcttcac ctagatcctt    4500
ttaaattaaa aatgaagttt taaatcaatc taaagtatat atgagtaaac ttggtctgac    4560
agttaccaat gcttaatcag tgaggcacct atctcagcga tctgtctatt tcgttcatcc    4620
atagttgcct gactccccgt cgtgtagata actacgatac gggagggctt accatctggc    4680
cccagtgctg caatgatacc gcgagaccca cgctcaccgg ctccagattt atcagcaata    4740
aaccagccag ccggaagggc cgagcgcaga agtggtcctg caactttatc cgcctccatc    4800
cagtctatta attgttgccg ggaagctaga gtaagtagtt cgccagttaa tagtttgcgc    4860
aacgttgttg ccattgctac aggcatcgtg gtgtcacgct cgtcgtttgg tatggcttca    4920
ttcagctccg gttcccaacg atcaaggcga gttacatgat cccccatgtt gtgcaaaaaa    4980
gcggttagct ccttcggtcc tccgatcgtt gtcagaagta agttggccgc agtgttatca    5040
ctcatggtta tggcagcact gcataattct cttactgtca tgccatccgt aagatgcttt    5100
tctgtgactg gtgagtactc aaccaagtca ttctgagaat agtgtatgcg gcgaccgagt    5160
tgctcttgcc cggcgtcaat acgggataat accgcgccac atagcagaac tttaaaagtg    5220
ctcatcattg gaaaacgttc ttcggggcga aaactctcaa ggatcttacc gctgttgaga    5280
tccagttcga tgtaacccac tcgtgcaccc aactgatctt cagcatcttt tactttcacc    5340
agcgtttctg ggtgagcaaa aacaggaagg caaaatgccg caaaaaaggg aataagggcg    5400
acacggaaat gttgaatact catactcttc ctttttcaat attattgaag catttatcag    5460
ggttattgtc tcatgagcgg atacatattt gaatgtattt agaaaaataa acaaataggg    5520
gttccgcgca catttccccg aaaagtgcca cctg                                5554

<210> SEQ ID NO 9
<211> LENGTH: 3436
<212> TYPE: DNA
<213> ORGANISM: Artificial Sequence
<220> FEATURE:
<223> OTHER INFORMATION: Expression cassette

<400> SEQUENCE: 9
ctgtctctta tacacatctc cggccagatg attaattcct aattttgtt gacactctat      60 cattgataga gttattttac cactccctat cagtgataga gaaaagtgaa atgaatagtt     120
cgacaaaaat ctagaaataa ttttgtttaa ctttaagaag gagatataca atgaagacc     180 gtgctggaca ccctgaaagg tcgcctggtt gtgagctgcc aagcgctgga aaatgagccg     240
ctgcatagcc cgtttattat gagccgtatg gcgctggcgg cgcgtcaggg tggtgcggcg     300
gcgatccgtg cgaacagcgt ggttgatatc gaggcgatta aggaacaagt taccctgccg     360
gtgatcggca tcattaagcg tgagtacccg gatagcgaag ttttcattac cgcgaccatg     420
aaagaggtgg acgaactgat gaccgtgagc ccggcgatca ttgcgctgga tgcgaccgac     480
cgtgcgcgtc cgggtggcga gagcctggcg atgctggtta cccgtatccg tacccgttat     540
ccgagcgtgc tgctgatggc ggatattgcg accgttgacg aagcggtgac cgcgcaggcg     600
ctgggtttcg attgcgttgg caccacccctg tacggttata ccgcgcagac cgtgggtcat     660
gcgctgccgg acgatgactg ccaatttctg aaagcggttc tggcggcggt taccgtgccg     720
```

```
gtggttgcgg aaggcaacgt ggacaccccg gaacgtgcgg cgcgttgcct ggcgctgggt        780
gcgcacatgg tggttgtggg tggcgcgatt acccgtccgc aacagattac cgaacgcttc        840
atggcggcga ttgatgcgca gagcaccgac cgtgcgtaat ttcgtcgaca cacaggaaac        900
atattaaaaa ttaaaacctg caggagttta acgcggccg cgatatcgtt gtaaaacgac        960
ggccagtgca agaatcataa aaaatttatt tgctttcagg aaaattttc tgtataatag       1020 attcataaat ttgagagagg agttttgtg agcggataac aattccccat cttagtatat       1080
tagttaagta taaatacaca aggagatata catatgaaag aaatcaaaat ccagaacatc       1140
atcatcagcg aagaaaaagc gccgctggtt gtgccgaaa tcggcattaa ccataatggt       1200
agtctggaac tggcaaaaat catggtggat gcggcctta gcgccggtgc aaaaatcatt       1260
aaacatcaga cccacattgt ggaagatgaa atgtctaaag cagcgaaaaa agttatcccg       1320
ggcaacgcga aaatcagtat ctacgaaatc atgcagaaat gcgcgctgga ttacaaagat       1380
gaactggccc tgaaagaata taccgaaaaa ctgggtctgg tgtacctgtc taccccgttt       1440
agtcgtgcgg gtgcaaaccg tctggaagat atgggtgtta gtgcgttcaa atcggcagc       1500 ggtgaatgta acaattatcc gctgatcaaa catattgccg catttaaaaa accgatgatt       1560
gttagcaccg gcatgaatag catcgaatct attaaaccga cggtgaaaat cctgctggat       1620
aacgaaattc cgtttgttct gatgcatacc acgaatctgt acccgacccc gcacaacctg       1680
gtgcgtctga atgccatgct ggaactgaaa aagaattct cttgcatggt tggtctgagt       1740
gatcacacca cggataatct ggcatgcctg ggtgcagtgg ttctgggtgc gtgtgtgctg       1800
gaacgtcatt tcaccgatag catgcaccgc tctggtccgg atattgtttg tagtatggat       1860
acgaaagcac tgaaagaact gatcattcag agcgaacaga tggcgatcat tcgcggcaac       1920
aatgaatcta aaaaagcggc caaacaggaa caggtgacca tcgattttgc attcgcgagt       1980
gtggttagca tcaaagatat caaaaaggc gaagtgctga gcatggataa tatttgggtt       2040
aaacgtccgg gtctgggcgg tatctctgca gcggaatttg aaaacattct gggcaaaaaa       2100
gcactgcgcg atattgaaaa tgatgcgcag ctgtcttatg aagatttcgc ctaaaataac       2160
tagcataacc ccttgggccc tctaaacggg tcttgagggg ttttttgctg aaaccaatt       2220 gcctggcggc agtagcgcgg tggtcccacc tgaccccatg ccgaactcag aagtgaaacg       2280
ccgtagcgcc gatggtagtg tggggtctcc ccatgcgaga gtagggaact gccaggcatc       2340
aaataaaacg aaaggctcag tcgaaagact gggcctttcg gatccaggc cggcctgtta       2400 acgaattaat cttccgcggc ggtatcgata agcttgatat cgaattccga agttcctatt       2460
ctctagaaag tataggaact tcaggtctga agaggagttt acgtccagcc aagctagctt       2520
ggctgcaggt cgtcgaaatt ctaccgggta ggggaggcgc ttttcccaag gcagtctgga       2580
gcatgcgctt tagcagcccc gctgggcact tggcgctaca caagtggcct ctggcctcgc       2640
acacattcca catccaccgg taggcgccaa ccggctccgt tctttggtgg ccccttcgcg       2700
ccaccttcta ctcctcccct agtcaggaag ttccccccg ccccgcagct cgcgtcgtgc       2760
aggacgtgac aaatggaagt agcacgtctc actagtctcg tgcagatgga cagcaccgct       2820
gagcaatgga agcgggtagg cctttgggc agcggccaat agcagctttg ctccttcgct       2880
ttctgggctc aggggcgggc tcaggggcg ggcgggcgc ccgaaggtcc tccggaggcc       2940
cggcattctg cacgcttcaa aagcgcacgt ctgccgcgct gttctcctct tcctcatctc       3000
cgggcctttc gacctgcagc ctgttgacaa ttaatcatcg gcatagtata tcggcatagt       3060
ataatacgac aaggtgagga actaaaccat gggtcaaagt agcgatgaag ccaacgctcc       3120
```

| | | |
|---|---|---|
| cgttgcaggg cagtttgcgc ttccctgag tgccacctt ggcttagggg atcgcgtacg | 3180 | |
| caagaaatct ggtgccgctt ggcagggtca agtcgtcggt tggtattgca caaaactcac | 3240 | |
| tcctgaaggc tatgcggtcg agtccgaatc ccacccaggc tcagtgcaaa tttatcctgt | 3300 | |
| ggctgcactt gaacgtgtgg cctaatgagg ggatcaattc tctagagctc gctgatcaga | 3360 | |
| agttcctatt ctctagaaag tataggaact tcgatggcgc ctcatccctg aagccaaaga | 3420 | |
| tgtgtataag agacag | 3436 | |

<210> SEQ ID NO 10
<211> LENGTH: 1830
<212> TYPE: DNA
<213> ORGANISM: Escherichia coli

<400> SEQUENCE: 10

| | | |
|---|---|---|
| atgtgtggaa ttgttggcgc gatcgcgcaa cgtgatgtag cagaaatcct tcttgaaggt | 60 | |
| ttacgtcgtc tggaataccg cggatatgac tctgccggtc tggccgttgt tgatgcagaa | 120 | |
| ggtcatatga cccgcctgcg tcgcctcggt aaagtccaga tgctggcaca ggcagcggaa | 180 | |
| gaacatcctc tgcatggcgg cactggtatt gctcacactc gctgggcgac ccacggtgaa | 240 | |
| ccttcagaag tgaatgcgca tccgcatgtt tctgaacaca ttgtggtggt gcataacggc | 300 | |
| atcatcgaaa accatgaacc gctgcgtgaa gagctaaaag cgcgtggcta taccttcgtt | 360 | |
| tctgaaaccg acaccgaagt gattgcccat ctggtgaact gggagctgaa acaaggcggg | 420 | |
| actctgcgtg aggccgttct gcgtgctatc ccgcagctgc gtggtgcgta cggtacagtg | 480 | |
| atcatggact cccgtcaccc ggataccctg ctggcggcac gttctggtag tccgctggtg | 540 | |
| attggcctgg ggatgggcga aaactttatc gcttctgacc agctggcgct gttgccggtg | 600 | |
| acccgtcgct ttatcttcct tgaagagggc gatattgcgg aaatcactcg ccgttcggta | 660 | |
| aacatcttcg ataaaactgg cgcggaagta aaacgtcagg atatcgaatc caatctgcaa | 720 | |
| tatgacgcgg gcgataaagg catttaccgt cactacatgc agaaagagat ctacgaacag | 780 | |
| ccgaacgcga tcaaaaacac ccttaccgga cgcatcagcc acggtcaggt tgatttaagc | 840 | |
| gagctgggac cgaacgccga cgaactgctg tcgaaggttg agcatattca gatcctcgcc | 900 | |
| tgtggtactt cttataactc cggtatggtt tcccgctact ggtttgaatc gctagcaggt | 960 | |
| attccgtgcg acgtcgaaat cgcctctgaa ttccgctatc gcaaatctgc cgtgcgtcgt | 1020 | |
| aacagcctga tgatcacctt gtcacagtct ggcgaaaccg cggatacct ggctggcctg | 1080 | |
| cgtctgtcga aagagctggg ttaccttggt tcactggcaa tctgtaacgt tccgggttct | 1140 | |
| tctctggtgc gcgaatccga tctggcgcta atgaccaacg cgggtacaga aatcggcgtg | 1200 | |
| gcatccacta aagcattcac cactcagtta actgtgctgt tgatgctggt ggcgaagctg | 1260 | |
| tctcgcctga aggtctgga tgcctccatt gaacatgaca tcgtgcatgg tctgcaggcg | 1320 | |
| ctgccgagcc gtattgagca gatgctgtct caggacaaac gcattgaagc gctggcagaa | 1380 | |
| gatttctctg acaaacatca cgcgctgttc ctgggccgtg gcgatcagta cccaatcgcg | 1440 | |
| ctggaaggcg cattgaagtt gaaagagatc tcttacattc acgctgaagc ctacgctgct | 1500 | |
| ggcgaactga aacacggtcc gctggcgcta attgatgccg atatgccggt tattgttgtt | 1560 | |
| gcaccgaaca cgaattgct ggaaaaactg aaatccaaca ttgaagaagt cgcgcgcgt | 1620 | |
| ggcggtcagt tgtatgtctt cgccgatcag gatgcgggtt ttgtaagtag cgataacatg | 1680 | |
| cacatcatcg agatgccgca tgtggaagag gtgattgcac cgatcttcta caccgttccg | 1740 | |

```
ctgcagctgc tggcttacca tgtcgcgctg atcaaaggca ccgacgttga ccagccgcgt    1800
aacctggcaa atcggttac ggttgagtaa                                      1830
```

<210> SEQ ID NO 11
<211> LENGTH: 609
<212> TYPE: PRT
<213> ORGANISM: Escherichia coli

<400> SEQUENCE: 11

| | | | | | | | | | | | | | | |
|---|---|---|---|---|---|---|---|---|---|---|---|---|---|---|
| Met | Cys | Gly | Ile | Val | Gly | Ala | Ile | Ala | Gln | Arg | Asp | Val | Ala | Glu | Ile |
| 1 | | | | 5 | | | | | 10 | | | | | 15 | |

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr

```
                355                 360                 365
Leu Gly Ser Leu Ala Ile Cys Asn Val Pro Gly Ser Ser Leu Val Arg
        370                 375                 380
Glu Ser Asp Leu Ala Leu Met Thr Asn Ala Gly Thr Glu Ile Gly Val
385                 390                 395                 400
Ala Ser Thr Lys Ala Phe Thr Thr Gln Leu Thr Val Leu Leu Met Leu
                405                 410                 415
Val Ala Lys Leu Ser Arg Leu Lys Gly Leu Asp Ala Ser Ile Glu His
            420                 425                 430
Asp Ile Val His Gly Leu Gln Ala Leu Pro Ser Arg Ile Glu Gln Met
            435                 440                 445
Leu Ser Gln Asp Lys Arg Ile Glu Ala Leu Ala Glu Asp Phe Ser Asp
    450                 455                 460
Lys His His Ala Leu Phe Leu Gly Arg Gly Asp Gln Tyr Pro Ile Ala
465                 470                 475                 480
Leu Glu Gly Ala Leu Lys Leu Lys Glu Ile Ser Tyr Ile His Ala Glu
                485                 490                 495
Ala Tyr Ala Ala Gly Glu Leu Lys His Gly Pro Leu Ala Leu Ile Asp
            500                 505                 510
Ala Asp Met Pro Val Ile Val Ala Pro Asn Asn Glu Leu Leu Glu
            515                 520                 525
Lys Leu Lys Ser Asn Ile Glu Glu Val Arg Ala Arg Gly Gly Gln Leu
    530                 535                 540
Tyr Val Phe Ala Asp Gln Asp Ala Gly Phe Val Ser Ser Asp Asn Met
545                 550                 555                 560
His Ile Ile Glu Met Pro His Val Glu Val Ile Ala Pro Ile Phe
                565                 570                 575
Tyr Thr Val Pro Leu Gln Leu Leu Ala Tyr His Val Ala Leu Ile Lys
            580                 585                 590
Gly Thr Asp Val Asp Gln Pro Arg Asn Leu Ala Lys Ser Val Thr Val
        595                 600                 605
Glu

<210> SEQ ID NO 12
<211> LENGTH: 1830
<212> TYPE: DNA
<213> ORGANISM: Escherichia coli

<400> SEQUENCE: 12
atgtgcggta tcgttggtgc tatcgcacag cgtgatgtag cgaaaatcct cctggaaggt      60
ctgcgtcgtc tcgaataccg tggttacgac tctgccggtc tggcagtagt ggatgcagaa     120
ggtcacatga ctcgtctgcg tcgtctgggt aaagtgcaga tgctcgcgca ggcggcggaa     180
gaacacccac tccacggtgg tacgggtatc gcacacactc gttgggcaac ccacggtgaa     240
ccgtctgagg tcaacgcaca cccgcatgtt agcgagcaca tcgtagtcgt tcacaacggt     300
atcatcgaga accacgaacc actccgtgag gaactcaaag cccgtggtta caccttcgta     360
agcgaaaccg acacggaagt tatcgcccac ctcgttaact gggaactcaa acagggtggt     420
actctgcgtg aagcagttct gcgtgccatt ccacagctgc gtggtgcata cggtaccgtg     480
atcatggact ctcgtcatcc ggatacgctg ctcgccgcac gttctggttc ccactcgtt     540 atcggtctgg gtatgggtga acttcatcg cctctgatc agctggccct gctcccagtt     600
acccgtcgct tcatcttcct ggaagagggt gacatcgccg aaatcacccg tcgttccgtt     660
```

```
aacatcttcg acaaaacggg tgcggaagtt aaacgtcagg acatcgagtc taacctgcag    720
tatgacgctg gtgacaaagg catctaccgt cactacatgc agaaagagat ctacgaacag    780
ccgaacgcga tcaaaaacac cctgaccggt cgtatctctc acggtcaggt tgacctgtct    840
gagctgggtc aaacgcgga cgaactcctg tccaaagtcg agcacatcca gatcctggct    900
tgtggtacct cttacaactc cggtatggtt tctcgttact ggttcgaatc tctggcaggt    960
atcccatgcg acgttgaaat cgcctccgaa ttccgttatc gtaaatctgc ggtacgtcgt   1020
aactccctca tgatcaccct gtctcagtct ggtgaaaccg ctgatactct ggcaggtctg   1080
cgtctcagca agaactgggt tacctgggt tctctggcca tctgcaacgt tccgggttct   1140
agcctggttc gtgagtctgt gctggctctg atgaccaacg cgggtacgga tcggtgtt    1200
gcctctacca agcgttcac tacccagctc actgtcctgc tgatgctggt tgccaaactg   1260
tctcgtctca aggcctcga cgctagcatc gaacacgaca tcgtacacgg tctgcaggcc   1320
ctcccatctc gtatcgagca gatgctgccg caggacaaac gtatcgaagc actggcagaa   1380
gacttcagcg acaaacacca cgcgctgttt ctgggtcgtg gtgaccagta cccaattgcg   1440
ctggaaggtg ccctgaaact gaaagagatc agctacatcc atgcagaggc atacgcagcg   1500
ggtgagctga acatggtcc actggccctg atcgacgcag atatgccggt tattgtggtt   1560
gctccgaaca acggcctgct ggagaaactg aaatccaaca tcgaggaagt acgtgcgcgt   1620
ggtggtcagc tgtacgtgtt tgctgaccag gacgcgggtt tcgtttccag cgacaacatg   1680
cacatcatcg aaatgccgca tgttgaagag gtaatcgcgc caatcttcta caccgtaccg   1740
ctgcagctgc tggcgtacca tgtagccctg atcaaaggta cggacgttga ccagccgcgt   1800
aacctggcga atccgtgac cgtggaataa                                      1830
```

<210> SEQ ID NO 13
<211> LENGTH: 609
<212> TYPE: PRT
<213> ORGANISM: Escherichia coli

<400> SEQUENCE: 13

```
Met Cys Gly Ile Val Gly Ala Ile Ala Gln Arg Asp Val Ala Lys Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
```

Ser Pro Leu Val Ile Gly Leu Gly Met Gly Glu Asn Phe Ile Ala Ser
165                 170                 175

Asp Gln Leu Ala Leu Leu Pro Val Thr Arg Arg Phe Ile Phe Leu Glu
180                 185                 190

Glu Gly Asp Ile Ala Glu Ile Thr Arg Arg Ser Val Asn Ile Phe Asp
195                 200                 205

Lys Thr Gly Ala Glu Val Lys Arg Gln Asp Ile Glu Ser Asn Leu Gln
210                 215                 220

Tyr Asp Ala Gly Asp Lys Gly Ile Tyr Arg His Tyr Met Gln Lys Glu
225                 230                 235                 240

Ile Tyr Glu Gln Pro Asn Ala Ile Lys Asn Thr Leu Thr Gly Arg Ile
    245                 250                 255

Ser His Gly Gln Val Asp Leu Ser Glu Leu Gly Pro Asn Ala Asp Glu
260                 265                 270

Leu Leu Ser Lys Val Glu His Ile Gln Ile Leu Ala Cys Gly Thr Ser
275                 280                 285

Tyr Asn Ser Gly Met Val Ser Arg Tyr Trp Phe Glu Ser Leu Ala Gly
290                 295                 300

Ile Pro Cys Asp Val Glu Ile Ala Ser Glu Phe Arg Tyr Arg Lys Ser
305                 310                 315                 320

Ala Val Arg Arg Asn Ser Leu Met Ile Thr Leu Ser Gln Ser Gly Glu
    325                 330                 335

Thr Ala Asp Thr Leu Ala Gly Leu Arg Leu Ser Lys Glu Leu Gly Tyr
340                 345                 350

Leu Gly Ser Leu Ala Ile Cys Asn Val Pro Gly Ser Ser Leu Val Arg
355                 360                 365

Glu Ser Val Leu Ala Leu Met Thr Asn Ala Gly Thr Glu Ile Gly Val
370                 375                 380

Ala Ser Thr Lys Ala Phe Thr Thr Gln Leu Thr Val Leu Leu Met Leu
385                 390                 395                 400

Val Ala Lys Leu Ser Arg Leu Lys Gly Leu Asp Ala Ser Ile Glu His
    405                 410                 415

Asp Ile Val His Gly Leu Gln Ala Leu Pro Ser Arg Ile Glu Gln Met
420                 425                 430

Leu Pro Gln Asp Lys Arg Ile Glu Ala Leu Ala Glu Asp Phe Ser Asp
435                 440                 445

Lys His His Ala Leu Phe Leu Gly Arg Gly Asp Gln Tyr Pro Ile Ala
450                 455                 460

Leu Glu Gly Ala Leu Lys Leu Lys Glu Ile Ser Tyr Ile His Ala Glu
465                 470                 475                 480

Ala Tyr Ala Ala Gly Glu Leu Lys His Gly Pro Leu Ala Leu Ile Asp
    485                 490                 495

Ala Asp Met Pro Val Ile Val Ala Pro Asn Asn Gly Leu Leu Glu
500                 505                 510

Lys Leu Lys Ser Asn Ile Glu Glu Val Arg Ala Arg Gly Gly Gln Leu
515                 520                 525

Tyr Val Phe Ala Asp Gln Asp Ala Gly Phe Val Ser Ser Asp Asn Met
530                 535                 540

His Ile Ile Glu Met Pro His Val Glu Val Ile Ala Pro Ile Phe
545                 550                 555                 560

Tyr Thr Val Pro Leu Gln Leu Leu Ala Tyr His Val Ala Leu Ile Lys
    565                 570                 575

580                 585                 590

Gly Thr Asp Val Asp Gln Pro Arg Asn Leu Ala Lys Ser Val Thr Val
        595                 600                 605

Glu

<210> SEQ ID NO 14
<211> LENGTH: 480
<212> TYPE: DNA
<213> ORGANISM: Saccharomyces cerevisiae

<400> SEQUENCE: 14
atgagcttac ccgatggatt ttatataagg cgaatggaag aggggganttt ggaacaggtc    60 actgagacgc taaaggtttt gaccaccgtg ggcactatta cccccgaatc cttcagcaaa   120
ctcataaaat actggaatga agccacagta tggaatgata cgaagataa aaaaataatg    180 caatataacc ccatggtgat tgtggacaag cgcaccgaga cggttgccgc tacggggaat   240
atcatcatcg aaagaaagat cattcatgaa ctggggctat gtggccacat cgaggacatt   300 gcagtaaaact ccaagtatca gggccaaggt ttgggcaagc tcttgattga tcaattggta   360
actatcggct ttgactacgg ttgttataag attatttag attgcgatga gaaaaatgtc    420
aaattctatg aaaaatgtgg gtttagcaac gcaggcgtgg aaatgcaaat tagaaaatag   480

<210> SEQ ID NO 15
<211> LENGTH: 159
<212> TYPE: PRT
<213> ORGANISM: Saccharomyces cerevisiae

<400> SEQUENCE: 15

Met Ser Leu Pro Asp Gly Phe Tyr Ile Arg Arg Met Glu Glu Gly Asp
1               5                   10                  15

Leu Glu Gln Val Thr Glu Thr Leu Lys Val Leu Thr Thr Val Gly Thr
            20                  25                  30

Ile Thr Pro Glu Ser Phe Ser Lys Leu Ile Lys Tyr Trp Asn Glu Ala
        35                  40                  45

Thr Val Trp Asn Asp Asn Glu Asp Lys Lys Ile Met Gln Tyr Asn Pro
    50                  55                  60

Met Val Ile Val Asp Lys Arg Thr Glu Thr Val Ala Ala Thr Gly Asn
65                  70                  75                  80

Ile Ile Ile Glu Arg Lys Ile Ile His Glu Leu Gly Leu Cys Gly His
                85                  90                  95

Ile Glu Asp Ile Ala Val Asn Ser Lys Tyr Gln Gly Gln Gly Leu Gly
            100                 105                 110

Lys Leu Leu Ile Asp Gln Leu Val Thr Ile Gly Phe Asp Tyr Gly Cys
        115                 120                 125

Tyr Lys Ile Ile Leu Asp Cys Asp Glu Lys Asn Val Lys Phe Tyr Glu
    130                 135                 140

Lys Cys Gly Phe Ser Asn Ala Gly Val Glu Met Gln Ile Arg Lys
145                 150                 155

<210> SEQ ID NO 16
<211> LENGTH: 567
<212> TYPE: DNA
<213> ORGANISM: Escherichia coli

<400> SEQUENCE: 16
atgtacgagc gttatgcagg tttaatttt gatatggatg cacaatcct ggatacggag    60 cctacgcacc gtaaagcgtg gcgcgaagta ttagggcact acggtcttca gtacgatatt   120

| | |
|---|---|
| caggcgatga ttgcgcttaa tggatcgccc acctggcgta ttgctcaggc aattattgag | 180 |
| ctgaatcagg ccgatctcga cccgcatgcg ttagcgcgtg aaaaaacaga agcagtaaga | 240 |
| agtatgctgc tggatagcgt cgaaccgctt cctcttgttg atgtggtgaa agttggcat | 300 |
| ggtcgtcgcc caatggctgt aggaacgggg agtgaaagcg ccatcgctga ggcattgctg | 360 |
| gcgcacctgg gattacgcca ttattttgac gccgtcgtcg ctgccgatca cgtcaaacac | 420 |
| cataaacccg cgccagacac attttttgttg tgcgcgcagc gtatgggcgt gcaaccgacg | 480 |
| cagtgtgtgg tctttgaaga tgccgatttc ggtattcagg cggcccgtgc agcaggcatg | 540 |
| gacgccgtgg atgttcgctt gctgtga | 567 |

<210> SEQ ID NO 17
<211> LENGTH: 188
<212> TYPE: PRT
<213> ORGANISM: Escherichia coli

<400> SEQUENCE: 17

Met Tyr Glu Arg Tyr Ala Gly Leu Ile Phe Asp Met Asp Gly Thr Ile
1               5                   10                  15
Leu Asp Thr Glu Pro Thr His Arg Lys Ala Trp Arg Glu Val Leu Gly
            20                  25                  30
His Tyr Gly Leu Gln Tyr Asp Ile Gln Ala Met Ile Ala Leu Asn Gly
        35                  40                  45
Ser Pro Thr Trp Arg Ile Ala Gln Ala Ile Ile Glu Leu Asn Gln Ala
    50                  55                  60
Asp Leu Asp Pro His Ala Leu Ala Arg Glu Lys Thr Glu Ala Val Arg
65                  70                  75                  80
Ser Met Leu Leu Asp Ser Val Glu Pro Leu Pro Leu Val Asp Val Val
                85                  90                  95
Lys Ser Trp His Gly Arg Arg Pro Met Ala Val Gly Thr Gly Ser Glu
            100                 105                 110
Ser Ala Ile Ala Glu Ala Leu Leu Ala His Leu Gly Leu Arg His Tyr
        115                 120                 125
Phe Asp Ala Val Val Ala Ala Asp His Val Lys His His Lys Pro Ala
    130                 135                 140
Pro Asp Thr Phe Leu Leu Cys Ala Gln Arg Met Gly Val Gln Pro Thr
145                 150                 155                 160
Gln Cys Val Val Phe Glu Asp Ala Asp Phe Gly Ile Gln Ala Ala Arg
                165                 170                 175
Ala Ala Gly Met Asp Ala Val Asp Val Arg Leu Leu
            180                 185

<210> SEQ ID NO 18
<211> LENGTH: 600
<212> TYPE: DNA
<213> ORGANISM: Escherichia coli

<400> SEQUENCE: 18

| | |
|---|---|
| atgctctata tctttgattt aggtaatgtg attgtcgata tcgactttaa ccgtgtgctg | 60 |
| ggagcctgga gcgatttaac gcgtattccg ctggcatcgc ttaagaagag ttttcatatg | 120 |
| ggggaggcgt tcatcagca tgagcgtggg gaaattagcg acgaagcgtt cgcagaggcg | 180 |
| ctgtgtcatg agatggctct accgctaagc tacgagcagt tctctcacgg ctggcaggcg | 240 |
| gtgtttgttg cgctgcgccc ggaagtgatc gccatcatgc ataaactgcg tgagcagggg | 300 |

```
catcgcgtgg tggtgctttc caataccaac cgcctgcata ccaccttctg gccggaagaa    360
tacccggaaa ttcgtgatgc tgctgaccat atctatctgt cgcaagatct ggggatgcgc    420
aaacctgaag cacgaattta ccagcatgtt ttgcaggcgg aaggttttc  acccagcgat    480 acggtctttt tcgacgataa cgccgataat atagaaggag ccaatcagct gggcattacc    540
agtattctgg tgaaagataa aaccaccatc ccggactatt tcgcgaaggt gttatgctaa    600
```

<210> SEQ ID NO 19
<211> LENGTH: 199
<212> TYPE: PRT
<213> ORGANISM: Escherichia coli

<400> SEQUENCE: 19

```
Met Leu Tyr Ile Phe Asp Leu Gly Asn Val Ile Val Asp Ile Asp Phe
1               5                   10                  15

Asn Arg Val Leu Gly Ala Trp Ser Asp Leu Thr Arg Ile Pro Leu Ala
            20                  25                  30

Ser Leu Lys Lys Ser Phe His Met Gly Glu Ala Phe His Gln His Glu
        35                  40                  45

Arg Gly Glu Ile Ser Asp Glu Ala Phe Ala Glu Ala Leu Cys His Glu
    50                  55                  60

Met Ala Leu Pro Leu Ser Tyr Glu Gln Phe Ser His Gly Trp Gln Ala
65                  70                  75                  80

Val Phe Val Ala Leu Arg Pro Glu Val Ile Ala Ile Met His Lys Leu
                85                  90                  95

Arg Glu Gln Gly His Arg Val Val Leu Ser Asn Thr Asn Arg Leu
            100                 105                 110

His Thr Thr Phe Trp Pro Glu Glu Tyr Pro Glu Ile Arg Asp Ala Ala
        115                 120                 125

Asp His Ile Tyr Leu Ser Gln Asp Leu Gly Met Arg Lys Pro Glu Ala
    130                 135                 140

Arg Ile Tyr Gln His Val Leu Gln Ala Glu Gly Phe Ser Pro Ser Asp
145                 150                 155                 160

Thr Val Phe Phe Asp Asp Asn Ala Asp Asn Ile Glu Gly Ala Asn Gln
                165                 170                 175

Leu Gly Ile Thr Ser Ile Leu Val Lys Asp Lys Thr Thr Ile Pro Asp
            180                 185                 190

Tyr Phe Ala Lys Val Leu Cys
        195
```

<210> SEQ ID NO 20
<211> LENGTH: 1266
<212> TYPE: DNA
<213> ORGANISM: Bacteroides ovatus

<400> SEQUENCE: 20

```
atggatagta agaataacat tggtcattca gcagacatct ctttaactgc tgaattaccc     60
ataccaatct ataatggaaa tacgattatg gatttcaaaa aactggcaag tctgtacaag    120
gatgagctcc tggacaacgt ccttcctttc tggcttgaac attcacaaga ccatgagtat    180
ggtggttact tcacctgtct ggaccgtgaa ggaaaagtat tcgatacgga taagtttatt    240
tggctgcaaa gtcgtgaggt atggatgttc tccatgcttt acaacaaagt ggagaaacgt    300
caggaatggc tagactgtgc cattcagggt ggcgaattt  taaaaaaata tggacatgac    360
ggcaattata actggtattt ttccctcgac cgttcgggta gaccattggt agaaccgtac    420
```

```
aatatattct cgtatacatt cgctaccatg gctttcggac agttgagcct tacaaccggt    480
aatcaggaat atgcggacat tgccaagaaa actttcgata taatcctttc caaagtggat    540
aatccgaaag ggagatggaa taagcttcat ccgggtaccc gtaatctgaa gaactttgcc    600
ttgccaatga tcctctgtaa cttggcactg gagatagagc atttattgga tgaaacgtat    660
ctgcgggaaa caatggatac ttgtatccat gaagtgatgg aagttttcta tcgtcctgaa    720
ctcggaggta tcattgttga aaacgtggac atagacggta atttggtcga ttgttttgaa    780
ggccgtcagg tgaccccggg acatgccatt gaagcgatgt ggtttatcat ggatctaggc    840
aagcgtctga atcgtccgga attgatagag aaagccaaag agactactct cacgatgctt    900
aattatggct gggacaagca atatggaggt atctactatt ttatggatcg taacggttgt    960
cctccccaac aattggagtg ggaccagaaa ctctggtggg tccatatcga aacgcttatt   1020
tccctgctga aaggctatca attgacggga gacaaaaaat gcttggaatg gtttgaaaag   1080
gtacatgact acacttggga gcatttcaag gataaagaat atcctgaatg gtatggctac   1140
ttgaaccgaa gaggcgaagt attgctacca ctcaaaggag gaaaatggaa aggatgcttc   1200
catgtgccaa gaggactgta tcagtgctgg aaaacattag aagaaataaa aaatatagta   1260
tcctaa                                                              1266

<210> SEQ ID NO 21
<211> LENGTH: 421
<212> TYPE: PRT
<213> ORGANISM: Bacteroides ovatus

<400> SEQUENCE: 21

Met Asp Ser Lys Asn Asn Ile Gly His Ser Ala Asp Ile Ser Leu Thr
1               5                   10                  15

Ala Glu Leu Pro Ile Pro Ile Tyr Asn Gly Asn Thr Ile Met Asp Phe
            20                  25                  30

Lys Lys Leu Ala Ser Leu Tyr Lys Asp Glu Leu Leu Asp Asn Val Leu
        35                  40                  45

Pro Phe Trp Leu Glu His Ser Gln Asp His Glu Tyr Gly Gly Tyr Phe
    50                  55                  60

Thr Cys Leu Asp Arg Glu Gly Lys Val Phe Asp Thr Asp Lys Phe Ile
65                  70                  75                  80

Trp Leu Gln Ser Arg Glu Val Trp Met Phe Ser Met Leu Tyr Asn Lys
                85                  90                  95

Val Glu Lys Arg Gln Glu Trp Leu Asp Cys Ala Ile Gln Gly Gly Glu
            100                 105                 110

Phe Leu Lys Lys Tyr Gly His Asp Gly Asn Tyr Asn Trp Tyr Phe Ser
        115                 120                 125

Leu Asp Arg Ser Gly Arg Pro Leu Val Glu Pro Tyr Asn Ile Phe Ser
    130                 135                 140

Tyr Thr Phe Ala Thr Met Ala Phe Gly Gln Leu Ser Leu Thr Thr Gly
145                 150                 155                 160

Asn Gln Glu Tyr Ala Asp Ile Ala Lys Lys Thr Phe Asp Ile Ile Leu
                165                 170                 175

Ser Lys Val Asp Asn Pro Lys Gly Arg Trp Asn Lys Leu His Pro Gly
            180                 185                 190

Thr Arg Asn Leu Lys Asn Phe Ala Leu Pro Met Ile Leu Cys Asn Leu
        195                 200                 205

Ala Leu Glu Ile Glu His Leu Leu Asp Glu Thr Tyr Leu Arg Glu Thr
    210                 215                 220
```

```
Met Asp Thr Cys Ile His Glu Val Met Glu Val Phe Tyr Arg Pro Glu
225                 230                 235                 240

Leu Gly Gly Ile Ile Val Glu Asn Val Asp Ile Asp Gly Asn Leu Val
            245                 250                 255

Asp Cys Phe Glu Gly Arg Gln Val Thr Pro Gly His Ala Ile Glu Ala
                260                 265                 270

Met Trp Phe Ile Met Asp Leu Gly Lys Arg Leu Asn Arg Pro Glu Leu
            275                 280                 285

Ile Glu Lys Ala Lys Glu Thr Thr Leu Thr Met Leu Asn Tyr Gly Trp
290                 295                 300

Asp Lys Gln Tyr Gly Gly Ile Tyr Tyr Phe Met Asp Arg Asn Gly Cys
305                 310                 315                 320

Pro Pro Gln Gln Leu Glu Trp Asp Gln Lys Leu Trp Trp Val His Ile
                325                 330                 335

Glu Thr Leu Ile Ser Leu Leu Lys Gly Tyr Gln Leu Thr Gly Asp Lys
            340                 345                 350

Lys Cys Leu Glu Trp Phe Glu Lys Val His Asp Tyr Thr Trp Glu His
                355                 360                 365

Phe Lys Asp Lys Glu Tyr Pro Glu Trp Tyr Gly Tyr Leu Asn Arg Arg
370                 375                 380

Gly Glu Val Leu Leu Pro Leu Lys Gly Gly Lys Trp Lys Gly Cys Phe
385                 390                 395                 400

His Val Pro Arg Gly Leu Tyr Gln Cys Trp Lys Thr Leu Glu Glu Ile
                405                 410                 415

Lys Asn Ile Val Ser
            420

<210> SEQ ID NO 22
<211> LENGTH: 1176
<212> TYPE: DNA
<213> ORGANISM: Synechocystis PCC6803

<400> SEQUENCE: 22
atgattgccc atcgccgtca ggagttagcc cagcaatatt accaggcttt acaccaggac      60
gtattgccct tttgggaaaa atattccctc gatcgccagg ggggcggtta ctttacctgc     120
ttagaccgta aaggccaggt ttttgacaca gataaattca tttggttaca aaaccgtcag     180
gtatggcagt ttgccgtttt ctacaaccgt ttggaaccaa accccaatg gttagaaatt      240 gcccgccatg gtgctgattt tttagctcgc acggccgag atcaagacgg taattggtat      300
tttgctttgg atcaggaagg caaacccctg cgtcaaccct ataacgtttt ttccgattgc     360
ttcgccgcca tggcctttag tcaatatgcc ttagccagtg gggcgcagga agctaaagcc     420
attgccctgc aggcctacaa taacgtccta cgccgtcagc acaatcccaa aggtcaatac     480
gagaagtcct atccaggtac tagacccctc aaatccctgg cggtgccgat gattttagcc     540
aacctcaccc tggagatgga atggttatta ccgcctacta ccgtgaaaga ggtgttggcc     600
caaaccgtca gagaagtgat gacggatttc ctcgacccag aaataggatt aatgcgggaa     660
gcggtgaccc ccacaggaga atttgttgat agttttgaag gcggttgct caacccagga      720 cacggcattg aagccatgtg gttcatgatg acattgccc aacgctccgg cgatcgccag      780
ttacaggagc aagccattgc agtggtgttg aacaccctgg aatatgcctg ggatgaagaa     840
tttggtggca tattttattt ccttgatcgc cagggccacc ctccccaaca actggaatgg     900
gaccaaaagc tctggtgggt acatttggaa accctggttg ccctagccaa gggccaccaa     960
```

-continued

```
gccactggcc aagaaaaatg ttggcaatgg tttgagcggg tccatgatta cgcctggagt      1020
catttcgccg atcctgagta tggggaatgg tttggctacc tgaatcgccg gggagaggtg      1080
ttactcaacc taaaaggggg gaaatggaaa gggtgcttcc acgtgccccg agctctgtgg      1140
ctctgtgcgg aaactctcca acttccggtt agttaa                                1176
```

<210> SEQ ID NO 23
<211> LENGTH: 391
<212> TYPE: PRT
<213> ORGANISM: Synechocystis PCC6803

<400> SEQUENCE: 23

```
Met Ile Ala His Arg Arg Gln Glu Leu Ala Gln Gln Tyr Tyr Gln Ala
1               5                   10                  15

Leu His Gln Asp Val Leu Pro Phe Trp Glu Lys Tyr Ser Leu Asp Arg
            20                  25                  30

Gln Gly Gly Gly Tyr Phe Thr Cys Leu Asp Arg Lys Gly Gln Val Phe
        35                  40                  45

Asp Thr Asp Lys Phe Ile Trp Leu Gln Asn Arg Gln Val Trp Gln Phe
    50                  55                  60

Ala Val Phe Tyr Asn Arg Leu Glu Pro Lys Pro Gln Trp Leu Glu Ile
65                  70                  75                  80

Ala Arg His Gly Ala Asp Phe Leu Ala Arg His Gly Arg Asp Gln Asp
                85                  90                  95

Gly Asn Trp Tyr Phe Ala Leu Asp Gln Glu Gly Lys Pro Leu Arg Gln
            100                 105                 110

Pro Tyr Asn Val Phe Ser Asp Cys Phe Ala Ala Met Ala Phe Ser Gln
        115                 120                 125

Tyr Ala Leu Ala Ser Gly Ala Gln Glu Ala Lys Ala Ile Ala Leu Gln
    130                 135                 140

Ala Tyr Asn Asn Val Leu Arg Arg Gln His Asn Pro Lys Gly Gln Tyr
145                 150                 155                 160

Glu Lys Ser Tyr Pro Gly Thr Arg Pro Leu Lys Ser Leu Ala Val Pro
                165                 170                 175

Met Ile Leu Ala Asn Leu Thr Leu Glu Met Glu Trp Leu Leu Pro Pro
            180                 185                 190

Thr Thr Val Glu Glu Val Leu Ala Gln Thr Val Arg Glu Val Met Thr
        195                 200                 205

Asp Phe Leu Asp Pro Glu Ile Gly Leu Met Arg Glu Ala Val Thr Pro
    210                 215                 220

Thr Gly Glu Phe Val Asp Ser Phe Glu Gly Arg Leu Leu Asn Pro Gly
225                 230                 235                 240

His Gly Ile Glu Ala Met Trp Phe Met Met Asp Ile Ala Gln Arg Ser
                245                 250                 255

Gly Asp Arg Gln Leu Gln Glu Gln Ala Ile Ala Val Val Leu Asn Thr
            260                 265                 270

Leu Glu Tyr Ala Trp Asp Glu Glu Phe Gly Gly Ile Phe Tyr Phe Leu
        275                 280                 285

Asp Arg Gln Gly His Pro Pro Gln Gln Leu Glu Trp Asp Gln Lys Leu
    290                 295                 300

Trp Trp Val His Leu Glu Thr Leu Val Ala Leu Ala Lys Gly His Gln
305                 310                 315                 320

Ala Thr Gly Gln Glu Lys Cys Trp Gln Trp Phe Glu Arg Val His Asp
                325                 330                 335
```

Tyr Ala Trp Ser His Phe Ala Asp Pro Glu Tyr Gly Glu Trp Phe Gly
                340                 345                 350

Tyr Leu Asn Arg Arg Gly Glu Val Leu Leu Asn Leu Lys Gly Gly Lys
            355                 360                 365

Trp Lys Gly Cys Phe His Val Pro Arg Ala Leu Trp Leu Cys Ala Glu
        370                 375                 380

Thr Leu Gln Leu Pro Val Ser
385                 390

<210> SEQ ID NO 24
<211> LENGTH: 708
<212> TYPE: DNA
<213> ORGANISM: Enterobacter cloacae

<400> SEQUENCE: 24
atgaaaactg tactggatac cctgaaggga agactggtcg tctcctgtca ggcgcttgag      60
aacgaaccgt tgcatagccc gtttattatg tcgcggatgg cgctggcggc gcgtcaggga     120
ggggctgcgg ccatccgtgc aacagcgtg gtggatattg aggcgatcaa agagcaggtt     180
acgctgccgg ttattggcat catcaagcgg gagtaccccg acagcgaggt gtttatcacc     240
gcaacgatga agaggtgga tgaactgatg accgtctccc cggcgatcat tgcgcttgat     300
gcgaccgaca gggcgcggcc tggcggggaa tctctggcaa tgctggttac gcgcattcgt     360
acccgttatc cctcggtgct gcttatggct gatatagcca ctgttgatga ggccgtcacg     420
gcgcaggcgc tggggtttga ttgtgtcggg accacgcttt acggctacac cgcgcagacc     480
gtcggccacg ccttacccga tgatgactgt cagtttctga aagcggtact ggcagccgtc     540
acggtaccgg tggtggccga aggtaacgtg gacaccccgg aacgcgccgc cagatgtctg     600
gcgttggggg cgcatatggt ggtggtgggc ggggcaatca cccgcccgca gcagattacg     660
gaacgcttta tggcggcaat tgacgcgcaa agcaccgatc gagcatga              708

<210> SEQ ID NO 25
<211> LENGTH: 235
<212> TYPE: PRT
<213> ORGANISM: Enterobacter cloacae

<400> SEQUENCE: 25

Met Lys Thr Val Leu Asp Thr Leu Lys Gly Arg Leu Val Val Ser Cys
1               5                   10                  15

Gln Ala Leu Glu Asn Glu Pro Leu His Ser Pro Phe Ile Met Ser Arg
            20                  25                  30

Met Ala Leu Ala Ala Arg Gln Gly Gly Ala Ala Ala Ile Arg Ala Asn
        35                  40                  45

Ser Val Val Asp Ile Glu Ala Ile Lys Glu Gln Val Thr Leu Pro Val
    50                  55                  60

Ile Gly Ile Ile Lys Arg Glu Tyr Pro Asp Ser Glu Val Phe Ile Thr
65                  70                  75                  80

Ala Thr Met Lys Glu Val Asp Glu Leu Met Thr Val Ser Pro Ala Ile
                85                  90                  95

Ile Ala Leu Asp Ala Thr Asp Arg Ala Arg Pro Gly Gly Glu Ser Leu
            100                 105                 110

Ala Met Leu Val Thr Arg Ile Arg Thr Arg Tyr Pro Ser Val Leu Leu
        115                 120                 125

Met Ala Asp Ile Ala Thr Val Asp Glu Ala Val Thr Ala Gln Ala Leu
    130                 135                 140

```
Gly Phe Asp Cys Val Gly Thr Thr Leu Tyr Gly Tyr Thr Ala Gln Thr
145                 150                 155                 160

Val Gly His Ala Leu Pro Asp Asp Cys Gln Phe Leu Lys Ala Val
            165                 170                 175

Leu Ala Ala Val Thr Val Pro Val Ala Glu Gly Asn Val Asp Thr
            180                 185                 190

Pro Glu Arg Ala Ala Arg Cys Leu Ala Leu Gly Ala His Met Val Val
        195                 200                 205

Val Gly Gly Ala Ile Thr Arg Pro Gln Gln Ile Thr Glu Arg Phe Met
210                 215                 220

Ala Ala Ile Asp Ala Gln Ser Thr Asp Arg Ala
225                 230                 235

<210> SEQ ID NO 26
<211> LENGTH: 2652
<212> TYPE: DNA
<213> ORGANISM: Escherichia coli

<400> SEQUENCE: 26
atgaacgaac aatattccgc attgcgtagt aatgtcagta tgctcggcaa agtgctggga      60
gaaaccatca aggatgcgtt gggagaacac attcttgaac gcgtagaaac tatccgtaag     120
ttgtcgaaat cttcacgcgc tggcaatgat gctaaccgcc aggagttgct caccaccttg     180
caaaatttgt cgaacgacga gctgctgccc gttgcgcgtg cgtttagtca gttcctgaac     240
ctggccaaca ccgccgagca ataccacagc atttcgccga aggcgaagc tgccagcaac     300 ccggaagtga tcgcccgcac cctgcgtaaa ctgaaaaacc agccggaact gagcgaagac     360
accatcaaaa aagcagtgga tcgctgtcg ctggaactgg tcctcacggc tcacccaacc     420
gaaattaccc gtcgtacact gatccacaaa atggtggaag tgaacgcctg tttaaaacag     480
ctcgataaca aagatatcgc tgactacgaa cacaaccagc tgatgcgtcg cctgcgccag     540
ttgatcgccc agtcatggca taccgatgaa atccgtaagc tgcgtccaag cccggtagat     600
gaagccaaat ggggctttgc cgtagtggaa acagcctgt ggcaaggcgt accaaattac     660
ctgcgcgaac tgaacgaaca actggaagag aacctcggct acaaactgcc cgtcgaattt     720
gttccggtcc gtttacttc gtggatgggc ggcgaccgcg acggcaaccc gaacgtcact     780
gccgatatca cccgccacgt cctgctactc agccgctgga agccaccga tttgttcctg     840 aaagatattc aggtgctggt ttctgaactg tcgatggttg aagcgacccc tgaactgctg     900
gcgctggttg cgaagaagg tgccgcagaa ccgtatcgct atctgatgaa aaacctgcgt     960
tctcgcctga tggcgacaca ggcatggctg aagcgcgcc tgaaaggcga agaactgcca    1020
aaaccagaag gcctgctgac acaaaacgaa gaactgtggg aaccgctcta cgcttgctac    1080
cagtcacttc aggcgtgtgg catgggtatt atcgccaacg gcgatctgct cgacaccctg    1140
cgccgcgtga atgtttcgg cgtaccgctg gtccgtattg atatccgtca ggagagcacg    1200
cgtcataccg aagcgctggg cgagctgacc cgctacctcg gtatcggcga ctacgaaagc    1260
tggtcagagg ccgacaaaca ggcgttcctg atccgcgaac tgaactccaa acgtccgctt    1320
ctgccgcgca actggcaacc aagcgccgaa acgcgcgaaa tgctcgatac ctgccaggtg    1380
attgccgaag caccgcaagg ctccattgcc gcctacgtga tctcgatggc gaaaacgccg    1440
tccgacgtac tggctgtcca cctgctgctg aaagaagcgg gtatcgggtt tgcgatgccg    1500
gttgctccgc tgtttgaaac cctcgatgat ctgaacaacg ccaacgatgt catgacccag    1560
```

-continued

```
ctgctcaata ttgactggta tcgtggcctg attcagggca aacagatggt gatgattggc    1620
tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc cagaaatcac cgtcagcagc ctgtcgcttt ataccggggc gattctggaa    1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaagg ccaggaaccg    2580 gatcctcgcg tcgaacaagc gttaatggtc actattgccg ggattgcggc aggtatgcgt    2640
aataccggct aa                                                        2652
```

<210> SEQ ID NO 27
<211> LENGTH: 883
<212> TYPE: PRT
<213> ORGANISM: Escherichia coli

<400> SEQUENCE: 27

```
Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175
```

```
Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
            275                 280                 285

Glu Leu Ser Met Val Glu Ala Thr Pro Glu Leu Leu Ala Leu Val Gly
        290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
```

Arg Val Thr Glu Gln Gly Glu Met Ile Arg Phe Lys Tyr Gly Leu Pro
595                 600                 605
                610                 615                 620

Glu Ile Thr Val Ser Ser Leu Ser Leu Tyr Thr Gly Ala Ile Leu Glu
625                 630                 635                 640

Ala Asn Leu Leu Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
                660                 665                 670

Arg Glu Asn Lys Asp Phe Val Pro Tyr Phe Arg Ser Ala Thr Pro Glu
                675                 680                 685

Gln Glu Leu Gly Lys Leu Pro Leu Gly Ser Arg Pro Ala Lys Arg Arg
                690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
                740                 745                 750

Met Cys Arg Asp Trp Pro Phe Phe Ser Thr Arg Leu Gly Met Leu Glu
                755                 760                 765

Met Val Phe Ala Lys Ala Asp Leu Trp Leu Ala Glu Tyr Tyr Asp Gln
770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
                820                 825                 830

Asn Ile Tyr Thr Asp Pro Leu Asn Val Leu Gln Ala Glu Leu Leu His
                835                 840                 845

Arg Ser Arg Gln Ala Glu Lys Glu Gly Gln Glu Pro Asp Pro Arg Val
                850                 855                 860

Glu Gln Ala Leu Met Val Thr Ile Ala Gly Ile Ala Ala Gly Met Arg
865                 870                 875                 880

Asn Thr Gly

<210> SEQ ID NO 28
<211> LENGTH: 1041
<212> TYPE: DNA
<213> ORGANISM: Campylobacter jejuni

<400> SEQUENCE: 28
atgaaagaaa taaaatacaa aaatataatc ataagtgaag aaaaagcacc cttagtcgtg    60
cctgaaatag gcattaatca taatggcagt ttagaactag ctaaaattat ggtagatgca   120
gcctttagcg caggtgctaa gattataaag catcaaaccc acatcgttga agatgagatg   180
agtaaggccg ctaaaaaagt aattcctggt aatgcaaaaa taagcattta tgagattatg   240 caaaatgtg ctttagatta taagatgag ctagcactta agaatacac agaaaaatta   300 ggtcttgttt atcttagcac accttttct cgtgcaggtg caaaccgctt agaagatatg   360
ggagttagtg ctttttaagat tggttcaggt gagtgtaata attattccgct tattaaacac   420 atagcagcct ttaaaaagcc tatgatagtt agcacaggaa tgaatagtat tgaaagtata   480

```
aaaccaactg taaaaatctt attagacaat gaaattccct ttgttttaat gcactcgacc     540
aatctttacc caaccccgca taatcttgta agattaaacg ctatgcttga attaaaaaaa     600
gaattttctt gcatggtagg cttaagcgac cacacaacag ataatcttgc gtgtttaggt     660
gcggttgcac ttggtgcttg tgtgcttgaa agacatttta ctgatagtat gcatagaagt     720
ggccctgata tagtttgttc tatggataca aaggctttaa aagagctaat tatccaaagt     780
gagcaaatgg ctataatgaa aggaaataat gaaagcaaaa aagcagctaa gcaagaacaa     840
gttacaattg attttgcctt tgcaagcgta gttagcatta agatattaa aaaaggcgaa      900 gttttatcta tggacaatat ctgggttaaa agacctggac ttggtggaat tagtgcggct     960
gaatttgaaa atattttagg caaaaaagca ttaagagata tagaaaatga tactcagtta    1020
agctatgagg attttgcgtg a                                              1041
```

<210> SEQ ID NO 29
<211> LENGTH: 346
<212> TYPE: PRT
<213> ORGANISM: Campylobacter jejuni

<400> SEQUENCE: 29

```
Met Lys Glu Ile Lys Ile Gln Asn Ile Ile Ile Ser Glu Glu Lys Ala
1               5                   10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Ala Gly Ala Lys Ile
        35                  40                  45

Ile Lys His Gln Thr His Ile Val Glu Asp Glu Met Ser Lys Ala Ala
    50                  55                  60

Lys Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
        115                 120                 125

Ser Gly Glu Cys Asn Asn Tyr Pro Leu Ile Lys His Ile Ala Ala Phe
    130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Ser Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Ala Leu
    210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Met Lys Gly Asn Asn Glu Ser
            260                 265                 270
```

```
Lys Lys Ala Ala Lys Gln Glu Gln Val Thr Ile Asp Phe Ala Phe Ala
            275                 280                 285

Ser Val Val Ser Ile Lys Asp Ile Lys Lys Gly Glu Val Leu Ser Met
            290                 295                 300

Asp Asn Ile Trp Val Lys Arg Pro Gly Leu Gly Gly Ile Ser Ala Ala
305                 310                 315                 320

Glu Phe Glu Asn Ile Leu Gly Lys Lys Ala Leu Arg Asp Ile Glu Asn
                325                 330                 335

Asp Thr Gln Leu Ser Tyr Glu Asp Phe Ala
            340                 345
```

<210> SEQ ID NO 30
<211> LENGTH: 876
<212> TYPE: DNA
<213> ORGANISM: Escherichia coli

<400> SEQUENCE: 30

```
atgaccacac tggcgattga tatcggcggt actaaacttg ccgccgcgct gattggcgct     60
gacgggcaga tccgcgatcg tcgtgaactt cctacgccag ccagccagac accagaagcc    120
ttgcgtgatg ccttatccgc attagtctct ccgttgcaag ctcatgcgca gcgggttgcc    180
atcgcttcga ccgggataat ccgtgacggc agcttgctgg cgcttaatcc gcataatctt    240
ggtggattgc tacactttcc gttagtcaaa acgctggaac aacttaccaa tttgccgacc    300
attgccatta cgacgcgcag gccgcagca tgggcggagt ttcaggcgct ggatggcgat    360
ataaccgata tggtctttat caccgtttcc accggcgttg cggcggtgt agtgagcggc    420
tgcaaactgc ttaccggccc tggcggtctg gcggggcata tcgggcatac gcttgccgat    480
ccacacggcc cagtctgcgg ctgtggacgc acaggttgcg tggaagcgat tgcttctggt    540
cgcggcattg cagcggcagc gcaggggag ttggctggcg cggatgcgaa aactattttc     600
acgcgcgccg gcagggtga cgagcaggcg cagcagctga ttcaccgctc cgcacgtacg     660
cttgcaaggc tgatcgctga tattaaagcc acaactgatt gccagtgcgt ggtggtcggt    720
ggcagcgttg gtctggcaga agggtatctg gcgctggtgg aaacgtatct ggcgcaggag    780
ccagcggcat tcatgttga tttactggcg gcgcattacc gccatgatgc aggtttactt     840
ggggctgcgc tgttggccca gggagaaaaa ttatga                              876
```

<210> SEQ ID NO 31
<211> LENGTH: 291
<212> TYPE: PRT
<213> ORGANISM: Escherichia coli

<400> SEQUENCE: 31

```
Met Thr Thr Leu Ala Ile Asp Ile Gly Gly Thr Lys Leu Ala Ala Ala
1               5                   10                  15

Leu Ile Gly Ala Asp Gly Gln Ile Arg Asp Arg Arg Glu Leu Pro Thr
            20                  25                  30

Pro Ala Ser Gln Thr Pro Glu Ala Leu Arg Asp Ala Leu Ser Ala Leu
        35                  40                  45

Val Ser Pro Leu Gln Ala His Ala Gln Arg Val Ala Ile Ala Ser Thr
    50                  55                  60

Gly Ile Ile Arg Asp Gly Ser Leu Leu Ala Leu Asn Pro His Asn Leu
65                  70                  75                  80

Gly Gly Leu Leu His Phe Pro Leu Val Lys Thr Leu Glu Gln Leu Thr
                85                  90                  95
```

```
Asn Leu Pro Thr Ile Ala Ile Asn Asp Ala Gln Ala Ala Trp Ala
            100                 105                 110
Glu Phe Gln Ala Leu Asp Gly Asp Ile Thr Asp Met Val Phe Ile Thr
    115                 120                 125
Val Ser Thr Gly Val Gly Gly Val Val Ser Gly Cys Lys Leu Leu
130                 135                 140
Thr Gly Pro Gly Gly Leu Ala Gly His Ile Gly His Thr Leu Ala Asp
145                 150                 155                 160
Pro His Gly Pro Val Cys Gly Cys Gly Arg Thr Gly Cys Val Glu Ala
                165                 170                 175
Ile Ala Ser Gly Arg Gly Ile Ala Ala Ala Gln Gly Glu Leu Ala
            180                 185                 190
Gly Ala Asp Ala Lys Thr Ile Phe Thr Arg Ala Gly Gln Gly Asp Glu
    195                 200                 205
Gln Ala Gln Gln Leu Ile His Arg Ser Ala Arg Thr Leu Ala Arg Leu
210                 215                 220
Ile Ala Asp Ile Lys Ala Thr Thr Asp Cys Gln Cys Val Val Gly
225                 230                 235                 240
Gly Ser Val Gly Leu Ala Glu Gly Tyr Leu Ala Leu Val Glu Thr Tyr
                245                 250                 255
Leu Ala Gln Glu Pro Ala Ala Phe His Val Asp Leu Leu Ala Ala His
            260                 265                 270
Tyr Arg His Asp Ala Gly Leu Leu Gly Ala Ala Leu Leu Ala Gln Gly
        275                 280                 285
Glu Lys Leu
    290
```

```
<210> SEQ ID NO 32
<211> LENGTH: 690
<212> TYPE: DNA
<213> ORGANISM: Escherichia coli

<400> SEQUENCE: 32
atgtcgttac ttgcacaact ggatcaaaaa atcgctgcta acggtggcct gattgtctcc      60
tgccagccgg ttccggacag cccgctcgat aaacccgaaa tcgtcgccgc catggcatta     120
gcggcagaac aggcgggcgc ggttgccatt cgcattgaag gtgtggcaaa tctgcaagcc     180
acgcgtgcgc tggtgagcgt gccgattatt ggaattgtga acgcgatctg gaggattct      240 ccggtacgca tcacggccta tattgaagat gttgatgcgc tggcgcaggc gggcgcggac     300
attatcgcca ttgacggcac cgaccgcccg cgtccggtgc ctgttgaaac gctgctggca     360
cgtattcacc atcacggttt actggcgatg accgactgct caacgccgga gacggcctg     420 gcatgccaaa agctgggagc cgaaattatt ggcactacgc tttctggcta taccacgcct     480
gaaacgccag aagagccgga tctggcgctg gtgaaaacgt tgagcgacgc cggatgtcgg     540
gtgattgccg aagggcgtta caacacgcct gctcaggcgg cggatgcgat cgccacggc     600 gcgtgggcgg tgacggtcgg ttctgcaatc acgcgtcttg agcacatttg tcagtggtac     660
aacacagcga tgaaaaaggc ggtgctatga                                       690
```

```
<210> SEQ ID NO 33
<211> LENGTH: 229
<212> TYPE: PRT
<213> ORGANISM: Escherichia coli

<400> SEQUENCE: 33
```

```
Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

Ala Gly Ala Asp Ile Ile Ala Ile Asp Gly Thr Asp Arg Pro Arg Pro
            100                 105                 110

Val Pro Val Glu Thr Leu Leu Ala Arg Ile His His Gly Leu Leu
            115                 120                 125

Ala Met Thr Asp Cys Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
            180                 185                 190

Ala Ala Asp Ala Met Arg His Gly Ala Trp Ala Val Thr Val Gly Ser
    195                 200                 205

Ala Ile Thr Arg Leu Glu His Ile Cys Gln Trp Tyr Asn Thr Ala Met
210                 215                 220

Lys Lys Ala Val Leu
225
```

<210> SEQ ID NO 34
<211> LENGTH: 894
<212> TYPE: DNA
<213> ORGANISM: Escherichia coli

<400> SEQUENCE: 34

```
atggcaacga atttacgtgg cgtaatggct gcactcctga ctccttttga ccaacaacaa      60
gcactggata aagcgagtct gcgtcgcctg gttcagttca atattcagca gggcatcgac     120
ggtttatacg tgggtggttc gaccggcgag gcctttgtac aaagcctttc cgagcgtgaa     180
caggtactgg aaatcgtcgc gaagaggcg aaaggtaaga ttaaactcat cgcccacgtc      240
ggttgcgtca gcaccgccga agccaacaa cttgcggcat cggctaaacg ttatggcttc      300
gatgccgtct ccgccgtcac gccgttctac tatcctttca gctttgaaga cactgcgat     360
cactatcggg caattattga ttcggcggat ggtttgccga tggtggtgta caacattcca     420
gccctgagtg gggtaaaact gaccctggat cagatcaaca cacttgttac attgcctggc     480
gtaggtgcgc tgaaacagac ctctggcgat ctctatcaga tggagcagat ccgtcgtgaa     540
catcctgatc ttgtgctcta taacggttac gacgaaatct tcgcctctgg tctgctggcg     600
ggcgctgatg gtggtatcgg cagtacctac aacatcatgg gctggcgcta tcagggatc      660
gttaaggcgc tgaaagaagg cgatatccag accgcgcaga aactgcaaac tgaatgcaat     720
aaagtcattg atttactgat caaaacgggc gtattccgcg gcctgaaaac tgtcctccat     780
```

```
tatatggatg tcgtttctgt gccgctgtgc cgcaaaccgt ttggaccggt agatgaaaaa    840
tatctgccag aactgaaggc gctggcccag cagttgatgc aagagcgcgg gtga          894
```

<210> SEQ ID NO 35
<211> LENGTH: 297
<212> TYPE: PRT
<213> ORGANISM: Escherichia coli

<400> SEQUENCE: 35

```
Met Ala Thr Asn Leu Arg Gly Val Met Ala Ala Leu Leu Thr Pro Phe
1               5                   10                  15

Asp Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
    50                  55                  60

Ile Val Ala Glu Glu Ala Lys Gly Lys Ile Lys Leu Ile Ala His Val
65                  70                  75                  80

Gly Cys Val Ser Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
    130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
    210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
    290                 295
```

<210> SEQ ID NO 36
<211> LENGTH: 1491
<212> TYPE: DNA
<213> ORGANISM: Escherichia coli

<400> SEQUENCE: 36

```
atgagtacta caacccagaa tatcccgtgg tatcgccatc tcaaccgtgc acaatggcgc    60
```

```
gcatttccg ctgcctggtt gggatatctg cttgacggtt ttgatttcgt tttaatcgcc      120
ctggtactca ccgaagtaca aggtgaattc gggctgacga cggtgcaggc ggcaagtctg      180
atctctgcag cctttatctc tcgctggttc ggcggcctga tgctcggcgc tatgggtgac      240
cgctacgggc gtcgtctggc aatggtcacc agcatcgttc tcttctcggc cgggacgctg      300
gcctgcggct ttgcgccagg ctacatcacc atgtttatcg ctcgtctggt catcggcatg      360
gggatggcgg gtgaatacgg ttccagcgcc acctatgtca ttgaaagctg gccaaaacat      420
ctgcgtaaca aagccagtgg tttttttgatt tcaggcttct ctgtggggggc cgtcgttgcc     480
gctcaggtct atagcctggt ggttccggtc tggggctggc gtgcgctgtt ctttatcggc      540
attttgccaa tcatctttgc tctctggctg cgtaaaaaca tcccggaagc ggaagactgg      600
aaagagaaac acgcaggtaa agcaccagta cgcacaatgg tggatattct ctaccgtggt      660
gaacatcgca ttgccaatat cgtaatgaca ctggcggcgg ctactgcgct gtggttctgc      720
ttcgccggta acctgcaaaa tgccgcgatc gtcgctgttc ttgggctgtt atgcgccgca      780
atctttatca gctttatggt gcagagtgca ggcaaacgct ggccaacggg cgtaatgctg      840
atggtggtcg tgttgtttgc tttcctctac tcatggccga ttcaggcgct gctgccaacg      900
tatctgaaaa ccgatctggc ttataacccg catactgtag ccaatgtgct gttctttagt      960
ggctttggcg cggcggtggg atgctgcgta ggtggcttcc tcggtgactg gctgggaacc     1020
cgcaaagcgt acgtttgtag cctgctggcc tcgcagctgc tgattattcc ggtatttgcg     1080
attggcggcg caaacgtctg ggtgctcggt ctgttactgt tcttccagca aatgcttgga     1140
caagggatcg ccgggatctt accaaaactg attggcggtt atttcgatac cgaccagcgt     1200
gcagcgggcc tgggctttac ctacaacgtt ggcgcattgg gcggtgcact ggccccaatc     1260
atcgcgcgcg tgatcgctca acgtctggat ctgggtactg cgctggcatc gctctcgttc     1320
agtctgacgt tcgtggtgat cctgctgatt gggctggata tgccttctcg cgttcagcgt     1380
tggttgcgcc cggaagcgtt gcgtactcat gacgctatcg acggtaaacc attcagcggt     1440
gccgtgccgt ttggcagcgc caaaaacgat ttagtcaaaa ccaaaagtta a               1491

<210> SEQ ID NO 37
<211> LENGTH: 496
<212> TYPE: PRT
<213> ORGANISM: Escherichia coli

<400> SEQUENCE: 37

Met Ser Thr Thr Thr Gln Asn Ile Pro Trp Tyr Arg His Leu Asn Arg
1               5                   10                  15

Ala Gln Trp Arg Ala Phe Ser Ala Ala Trp Leu Gly Tyr Leu Leu Asp
                20                  25                  30

Gly Phe Asp Phe Val Leu Ile Ala Leu Val Leu Thr Glu Val Gln Gly
            35                  40                  45

Glu Phe Gly Leu Thr Thr Val Gln Ala Ala Ser Leu Ile Ser Ala Ala
        50                  55                  60

Phe Ile Ser Arg Trp Phe Gly Gly Leu Met Leu Gly Ala Met Gly Asp
65                  70                  75                  80

Arg Tyr Gly Arg Arg Leu Ala Met Val Thr Ser Ile Val Leu Phe Ser
                85                  90                  95

Ala Gly Thr Leu Ala Cys Gly Phe Ala Pro Gly Tyr Ile Thr Met Phe
            100                 105                 110

Ile Ala Arg Leu Val Ile Gly Met Gly Met Ala Gly Glu Tyr Gly Ser
        115                 120                 125
```

```
Ser Ala Thr Tyr Val Ile Glu Ser Trp Pro Lys His Leu Arg Asn Lys
130                 135                 140

Ala Ser Gly Phe Leu Ile Ser Gly Phe Ser Val Gly Ala Val Val Ala
145                 150                 155                 160

Ala Gln Val Tyr Ser Leu Val Val Pro Val Trp Gly Trp Arg Ala Leu
                165                 170                 175

Phe Phe Ile Gly Ile Leu Pro Ile Ile Phe Ala Leu Trp Leu Arg Lys
                180                 185                 190

Asn Ile Pro Glu Ala Glu Asp Trp Lys Glu Lys His Ala Gly Lys Ala
            195                 200                 205

Pro Val Arg Thr Met Val Asp Ile Leu Tyr Arg Gly Glu His Arg Ile
210                 215                 220

Ala Asn Ile Val Met Thr Leu Ala Ala Ala Thr Ala Leu Trp Phe Cys
225                 230                 235                 240

Phe Ala Gly Asn Leu Gln Asn Ala Ala Ile Val Ala Val Leu Gly Leu
                245                 250                 255

Leu Cys Ala Ala Ile Phe Ile Ser Phe Met Val Gln Ser Ala Gly Lys
                260                 265                 270

Arg Trp Pro Thr Gly Val Met Leu Met Val Val Leu Phe Ala Phe
            275                 280                 285

Leu Tyr Ser Trp Pro Ile Gln Ala Leu Leu Pro Thr Tyr Leu Lys Thr
290                 295                 300

Asp Leu Ala Tyr Asn Pro His Thr Val Ala Asn Val Leu Phe Phe Ser
305                 310                 315                 320

Gly Phe Gly Ala Ala Val Gly Cys Cys Val Gly Phe Leu Gly Asp
                325                 330                 335

Trp Leu Gly Thr Arg Lys Ala Tyr Val Cys Ser Leu Leu Ala Ser Gln
                340                 345                 350

Leu Leu Ile Ile Pro Val Phe Ala Ile Gly Gly Ala Asn Val Trp Val
                355                 360                 365

Leu Gly Leu Leu Leu Phe Phe Gln Gln Met Leu Gly Gln Gly Ile Ala
370                 375                 380

Gly Ile Leu Pro Lys Leu Ile Gly Gly Tyr Phe Asp Thr Asp Gln Arg
385                 390                 395                 400

Ala Ala Gly Leu Gly Phe Thr Tyr Asn Val Gly Ala Leu Gly Gly Ala
                405                 410                 415

Leu Ala Pro Ile Ile Gly Ala Leu Ile Ala Gln Arg Leu Asp Leu Gly
                420                 425                 430

Thr Ala Leu Ala Ser Leu Ser Phe Ser Leu Thr Phe Val Val Ile Leu
435                 440                 445

Leu Ile Gly Leu Asp Met Pro Ser Arg Val Gln Arg Trp Leu Arg Pro
450                 455                 460

Glu Ala Leu Arg Thr His Asp Ala Ile Asp Gly Lys Pro Phe Ser Gly
465                 470                 475                 480

Ala Val Pro Phe Gly Ser Ala Lys Asn Asp Leu Val Lys Thr Lys Ser
                485                 490                 495

<210> SEQ ID NO 38
<211> LENGTH: 1149
<212> TYPE: DNA
<213> ORGANISM: Escherichia coli

<400> SEQUENCE: 38
atgtatgcat taacccaggg ccggatcttt accggccacg aatttcttga tgaccacgcg    60
```

```
gttgttatcg ctgatggcct gattaaaagc gtctgtccgg tagcggaact gccgccagag    120
atcgaacaac gttcactgaa cggggccatt ctctcccccg gttttatcga tgtgcagtta    180
aacggctgcg gcggcgtaca gtttaacgac accgctgaag cggtcagcgt ggaaacgctg    240
gaaatcatgc agaaagccaa tgagaaatca ggctgtacta actatctgcc gacgcttatc    300
accaccagcg atgagctgat gaaacagggc gtgcgcgtta tgcgcgagta cctggcaaaa    360
catccgaatc aggcgttagg tctgcatctg aaggtccgt ggctgaatct ggtaaaaaaa     420
ggcacccata tccgaatttt gtgcgtaag cctgatgccg cgctggtcga tttcctgtgt     480
gaaaacgccg acgtcattac caaagtgacc ctggcaccgg aaatggttcc tgcggaagtc    540
atcagcaaac tggcaaatgc cgggattgtg gtttctgccg gtcactccaa cgcgacgttg    600
aaagaagcaa aagccggttt ccgcgcgggg attacctttg ccacccatct gtacaacgcg    660
atgccgtata ttaccggtcg tgaacctggc ctggcgggcg cgatcctcga cgaagctgac    720
atttattgcg gtattattgc tgatggcctg catgttgatt acgccaacat tgcaacgct     780 aaacgtctga aggcgacaa actgtgtctg gttactgacg ccaccgcgcc agcaggtgcc    840
aacattgaac agttcatttt tgcgggtaaa acaatatact accgtaacgg actttgtgtg    900
gatgagaacg gtacgttaag cggttcatcc ttaaccatga ttgaaggcgt gcgtaatctg    960
gtcgaacatt gcggtatcgc actggatgaa gtgctacgta tggcgacgct ctatccggcg   1020
cgtgcgattg gcgttgagaa acgtctcggc acactcgccg caggtaaagt agccaacctg   1080
actgcattca cacctgattt taaaatcacc aagaccatcg ttaacggtaa cgaggtcgta   1140
actcaataa                                                           1149
```

<210> SEQ ID NO 39
<211> LENGTH: 382
<212> TYPE: PRT
<213> ORGANISM: Escherichia coli

<400> SEQUENCE: 39

```
Met Tyr Ala Leu Thr Gln Gly Arg Ile Phe Thr Gly His Glu Phe Leu
1               5                   10                  15

Asp Asp His Ala Val Val Ile Ala Asp Gly Leu Ile Lys Ser Val Cys
                20                  25                  30

Pro Val Ala Glu Leu Pro Pro Glu Ile Glu Gln Arg Ser Leu Asn Gly
            35                  40                  45

Ala Ile Leu Ser Pro Gly Phe Ile Asp Val Gln Leu Asn Gly Cys Gly
        50                  55                  60

Gly Val Gln Phe Asn Asp Thr Ala Glu Ala Val Ser Val Glu Thr Leu
65                  70                  75                  80

Glu Ile Met Gln Lys Ala Asn Glu Lys Ser Gly Cys Thr Asn Tyr Leu
                85                  90                  95

Pro Thr Leu Ile Thr Thr Ser Asp Glu Leu Met Lys Gln Gly Val Arg
            100                 105                 110

Val Met Arg Glu Tyr Leu Ala Lys His Pro Asn Gln Ala Leu Gly Leu
        115                 120                 125

His Leu Glu Gly Pro Trp Leu Asn Leu Val Lys Lys Gly Thr His Asn
    130                 135                 140

Pro Asn Phe Val Arg Lys Pro Asp Ala Ala Leu Val Asp Phe Leu Cys
145                 150                 155                 160

Glu Asn Ala Asp Val Ile Thr Lys Val Thr Leu Ala Pro Glu Met Val
                165                 170                 175
```

Pro Ala Glu Val Ile Ser Lys Leu Ala Asn Ala Gly Ile Val Val Ser
            180                 185                 190

Ala Gly His Ser Asn Ala Thr Leu Lys Glu Ala Lys Ala Gly Phe Arg
        195                 200                 205

Ala Gly Ile Thr Phe Ala Thr His Leu Tyr Asn Ala Met Pro Tyr Ile
    210                 215                 220

Thr Gly Arg Glu Pro Gly Leu Ala Gly Ala Ile Leu Asp Glu Ala Asp
225                 230                 235                 240

Ile Tyr Cys Gly Ile Ile Ala Asp Gly Leu His Val Asp Tyr Ala Asn
                245                 250                 255

Ile Arg Asn Ala Lys Arg Leu Lys Gly Asp Lys Leu Cys Leu Val Thr
            260                 265                 270

Asp Ala Thr Ala Pro Ala Gly Ala Asn Ile Glu Gln Phe Ile Phe Ala
        275                 280                 285

Gly Lys Thr Ile Tyr Tyr Arg Asn Gly Leu Cys Val Asp Glu Asn Gly
    290                 295                 300

Thr Leu Ser Gly Ser Ser Leu Thr Met Ile Glu Gly Val Arg Asn Leu
305                 310                 315                 320

Val Glu His Cys Gly Ile Ala Leu Asp Glu Val Leu Arg Met Ala Thr
                325                 330                 335

Leu Tyr Pro Ala Arg Ala Ile Gly Val Glu Lys Arg Leu Gly Thr Leu
            340                 345                 350

Ala Ala Gly Lys Val Ala Asn Leu Thr Ala Phe Thr Pro Asp Phe Lys
        355                 360                 365

Ile Thr Lys Thr Ile Val Asn Gly Asn Glu Val Val Thr Gln
    370                 375                 380

<210> SEQ ID NO 40
<211> LENGTH: 801
<212> TYPE: DNA
<213> ORGANISM: Escherichia coli

<400> SEQUENCE: 40
atgagactga tccccctgac taccgctgaa caggtcggca atgggctgc tcgccatatc    60 gtcaatcgta tcaatgcgtt caaaccgact gccgatcgtc cgtttgtact gggcctgccg   120
actggcggca cgccgatgac cacctataaa gcgttagtcg aaatgcataa agcaggccag   180
gtcagcttta agcacgttgt caccttcaac atggacgaat atgtcggtct gccgaaagag   240
catccggaaa gctactacag ctttatgcac cgtaatttct tcgatcacgt tgatattcca   300
gcagaaaaca tcaaccttct caacggcaac gccccggata tcgacgccga gtgccgccag   360
tatgaagaaa aaatccgttc ttacggaaaa attcatctgt ttatgggcgg tgtaggtaac   420
gacggtcata ttgcatttaa cgaaccggcg tcttctctgg cttctcgtac tcgtatcaaa   480
accctgactc atgacactcg cgtcgcaaac tctcgtttct tgataacga tgttaatcag   540 gtgccaaaat atgccctgac tgtcggtgtt ggtacactgc tggatgccga agaagtgatg   600
attctggtgc tgggtagcca gaaagcactg gcgctgcagg ccgccgttga aggttgcgtg   660
aaccatatgt ggaccatcag ctgtctgcaa ctgcatccga aagcgatcat ggtgtgcgat   720
gaaccttcca ccatggagct gaaagttaag actttaagat atttcaatga attagaagca   780
gaaaatatca aggtctgta a                                              801

<210> SEQ ID NO 41
<211> LENGTH: 266

<212> TYPE: PRT
<213> ORGANISM: Escherichia coli

<400> SEQUENCE: 41

Met Arg Leu Ile Pro Leu Thr Thr Ala Glu Gln Val Gly Lys Trp Ala
1               5                   10                  15

Ala Arg His Ile Val Asn Arg Ile Asn Ala Phe Lys Pro Thr Ala Asp
            20                  25                  30

Arg Pro Phe Val Leu Gly Leu Pro Thr Gly Gly Thr Pro Met Thr Thr
        35                  40                  45

Tyr Lys Ala Leu Val Glu Met His Lys Ala Gly Gln Val Ser Phe Lys
    50                  55                  60

His Val Val Thr Phe Asn Met Asp Glu Tyr Val Gly Leu Pro Lys Glu
65                  70                  75                  80

His Pro Glu Ser Tyr Tyr Ser Phe Met His Arg Asn Phe Phe Asp His
                85                  90                  95

Val Asp Ile Pro Ala Glu Asn Ile Asn Leu Leu Asn Gly Asn Ala Pro
            100                 105                 110

Asp Ile Asp Ala Glu Cys Arg Gln Tyr Glu Glu Lys Ile Arg Ser Tyr
        115                 120                 125

Gly Lys Ile His Leu Phe Met Gly Gly Val Gly Asn Asp Gly His Ile
    130                 135                 140

Ala Phe Asn Glu Pro Ala Ser Ser Leu Ala Ser Arg Thr Arg Ile Lys
145                 150                 155                 160

Thr Leu Thr His Asp Thr Arg Val Ala Asn Ser Arg Phe Phe Asp Asn
                165                 170                 175

Asp Val Asn Gln Val Pro Lys Tyr Ala Leu Thr Val Gly Val Gly Thr
            180                 185                 190

Leu Leu Asp Ala Glu Glu Val Met Ile Leu Val Leu Gly Ser Gln Lys
        195                 200                 205

Ala Leu Ala Leu Gln Ala Ala Val Glu Gly Cys Val Asn His Met Trp
    210                 215                 220

Thr Ile Ser Cys Leu Gln Leu His Pro Lys Ala Ile Met Val Cys Asp
225                 230                 235                 240

Glu Pro Ser Thr Met Glu Leu Lys Val Lys Thr Leu Arg Tyr Phe Asn
                245                 250                 255

Glu Leu Glu Ala Glu Asn Ile Lys Gly Leu
            260                 265

<210> SEQ ID NO 42
<211> LENGTH: 1947
<212> TYPE: DNA
<213> ORGANISM: Escherichia coli

<400> SEQUENCE: 42
atgaatattt taggtttttt ccagcgactc ggtagggcgt tacagctccc tatcgcggtg      60
ctgccggtgg cggcactgtt gctgcgattc ggtcagccag atttacttaa cgttgcgttt     120
attgcccagg cgggcggtgc gattttttgat aacctcgcat taatcttcgc catcggtgtg    180
gcatccagct ggtcgaaaga cagcgctggt gcggcggcgc tggcgggtgc ggtaggttac     240
tttgtgttaa ccaaagcgat ggtgaccatc aacccagaaa ttaacatggg tgtactggcg     300
ggtatcatta ccggtctggt tggtggcgca gcctataacc gttggtccga tattaaactg     360
ccggacttcc tgagcttctt cggcggcaaa cgctttgtgc cgattgccac cggattcttc     420
tgcctggtgc tggcggccat ttttggttac gtctggccgc cggtacagca cgctatccat     480

```
gcaggcggcg agtggatcgt ttctgcgggc gcgctgggtt ccggtatctt tggtttcatc    540
aaccgtctgc tgatcccaac cggtctgcat caggtactga acaccatcgc ctggttccag    600
attggtgaat tcaccaacgc ggcgggtacg gttttccacg gtgacattaa ccgcttctat    660
gccggtgacg caccgcggg gatgttcatg tccggcttct cccgatcat gatgttcggt     720 ctgccgggtg cggcgctggc gatgtacttc gcagcaccga agagcgtcg tccgatggtt    780 ggcggtatgc tgctttctgt tgctgttact gcgttcctga ccggtgtgac tgagccgctg    840
gaattcctgt tcatgttcct tgctccgctg ctgtacctcc tgcacgcact gctgaccggt    900
atcagcctgt tgtggcaac gctgctgggt atccacgcgg gcttctcttt ctctgcgggg    960
gctatcgact acgcgttgat gtataacctg ccggccgcca gccagaacgt ctggatgctg    1020
ctggtgatgg gcgttatctt cttcgctatc tacttcgtgg tgttcagttt ggttatccgc    1080
atgttcaacc tgaaaacgcc gggtcgtgaa gataaagaag acgagatcgt tactgaagaa    1140
gccaacagca acactgaaga aggtctgact caactggcaa ccaactatat tgctgcggtt    1200
ggcggcactg acaacctgaa agcgattgac gcctgtatca cccgtctgcg ccttacagtg    1260
gctgactctg cccgcgttaa cgatacgatg tgtaaacgtc tgggtgcttc tggggtagtg    1320
aaactgaaca acagactat tcaggtgatt gttggcgcga agcagaatc catcggcgat    1380 gcgatgaaga aagtcgttgc ccgtggtccg gtagccgctg cgtcagctga agcaactccg    1440
gcaactgccg cgcctgtagc aaaaccgcag gctgtaccaa acgcggtatc tatcgcggag    1500
ctggtatcgc cgattaccgg tgatgtcgtg gcactggatc aggttcctga cgaagcattc    1560
gccagcaaag cggtgggtga cggtgtggcg gtgaaaccga cagataaaat cgtcgtatca    1620
ccagccgcag ggacaatcgt gaaaatcttc aacaccaacc acgcgttctg cctggaaacc    1680
gaaaaaggcg cggagatcgt cgtccatatg gtatcgaca ccgtagcgct ggaaggtaaa     1740
ggctttaaac gtctggtgga agagggtgcg caggtaagcg cagggcaacc gattctggaa    1800
atggatctgg attacctgaa cgctaacgcc cgctcgatga ttagcccggt ggtttgcagc    1860
aatatcgacg atttcagtgg cttgatcatt aaagctcagg ccatattgt ggcgggtcaa     1920 acaccgctgt atgaaatcaa aaagtaa                                       1947
```

<210> SEQ ID NO 43
<211> LENGTH: 648
<212> TYPE: PRT
<213> ORGANISM: Escherichia coli

<400> SEQUENCE: 43

```
Met Asn Ile Leu Gly Phe Phe Gln Arg Leu Gly Arg Ala Leu Gln Leu
1               5                   10                  15

Pro Ile Ala Val Leu Pro Val Ala Ala Leu Leu Leu Arg Phe Gly Gln
            20                  25                  30

Pro Asp Leu Leu Asn Val Ala Phe Ile Ala Gln Ala Gly Gly Ala Ile
        35                  40                  45

Phe Asp Asn Leu Ala Leu Ile Phe Ala Ile Gly Val Ala Ser Ser Trp
    50                  55                  60

Ser Lys Asp Ser Ala Gly Ala Ala Ala Leu Ala Gly Ala Val Gly Tyr
65                  70                  75                  80

Phe Val Leu Thr Lys Ala Met Val Thr Ile Asn Pro Glu Ile Asn Met
                85                  90                  95

Gly Val Leu Ala Gly Ile Ile Thr Gly Leu Val Gly Gly Ala Ala Tyr
            100                 105                 110
```

-continued

```
Asn Arg Trp Ser Asp Ile Lys Leu Pro Asp Phe Leu Ser Phe Phe Gly
            115                 120                 125

Gly Lys Arg Phe Val Pro Ile Ala Thr Gly Phe Phe Cys Leu Val Leu
130                 135                 140

Ala Ala Ile Phe Gly Tyr Val Trp Pro Val Gln His Ala Ile His
145                 150                 155                 160

Ala Gly Gly Glu Trp Ile Val Ser Ala Gly Leu Gly Ser Gly Ile
                165                 170                 175

Phe Gly Phe Ile Asn Arg Leu Leu Ile Pro Thr Gly Leu His Gln Val
            180                 185                 190

Leu Asn Thr Ile Ala Trp Phe Gln Ile Gly Glu Phe Thr Asn Ala Ala
            195                 200                 205

Gly Thr Val Phe His Gly Asp Ile Asn Arg Phe Tyr Ala Gly Asp Gly
210                 215                 220

Thr Ala Gly Met Phe Met Ser Gly Phe Phe Pro Ile Met Met Phe Gly
225                 230                 235                 240

Leu Pro Gly Ala Ala Leu Ala Met Tyr Phe Ala Ala Pro Lys Glu Arg
                245                 250                 255

Arg Pro Met Val Gly Gly Met Leu Leu Ser Val Ala Val Thr Ala Phe
            260                 265                 270

Leu Thr Gly Val Thr Glu Pro Leu Glu Phe Leu Phe Met Phe Leu Ala
            275                 280                 285

Pro Leu Leu Tyr Leu Leu His Ala Leu Leu Thr Gly Ile Ser Leu Phe
            290                 295                 300

Val Ala Thr Leu Leu Gly Ile His Ala Gly Phe Ser Phe Ser Ala Gly
305                 310                 315                 320

Ala Ile Asp Tyr Ala Leu Met Tyr Asn Leu Pro Ala Ala Ser Gln Asn
                325                 330                 335

Val Trp Met Leu Leu Val Met Gly Val Ile Phe Phe Ala Ile Tyr Phe
            340                 345                 350

Val Val Phe Ser Leu Val Ile Arg Met Phe Asn Leu Lys Thr Pro Gly
            355                 360                 365

Arg Glu Asp Lys Glu Asp Glu Ile Val Thr Glu Glu Ala Asn Ser Asn
            370                 375                 380

Thr Glu Glu Gly Leu Thr Gln Leu Ala Thr Asn Tyr Ile Ala Ala Val
385                 390                 395                 400

Gly Gly Thr Asp Asn Leu Lys Ala Ile Asp Ala Cys Ile Thr Arg Leu
                405                 410                 415

Arg Leu Thr Val Ala Asp Ser Ala Arg Val Asn Asp Thr Met Cys Lys
            420                 425                 430

Arg Leu Gly Ala Ser Gly Val Val Lys Leu Asn Lys Gln Thr Ile Gln
            435                 440                 445

Val Ile Val Gly Ala Lys Ala Glu Ser Ile Gly Asp Ala Met Lys Lys
450                 455                 460

Val Val Ala Arg Gly Pro Val Ala Ala Ala Ser Ala Glu Ala Thr Pro
465                 470                 475                 480

Ala Thr Ala Ala Pro Val Ala Lys Pro Gln Ala Val Pro Asn Ala Val
                485                 490                 495

Ser Ile Ala Glu Leu Val Ser Pro Ile Thr Gly Asp Val Val Ala Leu
            500                 505                 510

Asp Gln Val Pro Asp Glu Ala Phe Ala Ser Lys Ala Val Gly Asp Gly
            515                 520                 525
```

Val Ala Val Lys Pro Thr Asp Lys Ile Val Val Ser Pro Ala Ala Gly
            530                 535                 540

Thr Ile Val Lys Ile Phe Asn Thr Asn His Ala Phe Cys Leu Glu Thr
545                 550                 555                 560

Glu Lys Gly Ala Glu Ile Val Val His Met Gly Ile Asp Thr Val Ala
                565                 570                 575

Leu Glu Gly Lys Gly Phe Lys Arg Leu Val Glu Gly Ala Gln Val
            580                 585                 590

Ser Ala Gly Gln Pro Ile Leu Glu Met Asp Leu Asp Tyr Leu Asn Ala
            595                 600                 605

Asn Ala Arg Ser Met Ile Ser Pro Val Val Cys Ser Asn Ile Asp Asp
        610                 615                 620

Phe Ser Gly Leu Ile Ile Lys Ala Gln Gly His Ile Val Ala Gly Gln
625                 630                 635                 640

Thr Pro Leu Tyr Glu Ile Lys Lys
            645

<210> SEQ ID NO 44
<211> LENGTH: 972
<212> TYPE: DNA
<213> ORGANISM: Escherichia coli

<400> SEQUENCE: 44

| | | |
|---|---|---|
| atgaccattg ctattgttat aggcacacat ggttgggctg cagagcagtt gcttaaaacg | 60 |
| gcagaaatgc tgttaggcga gcaggaaaac gtcggctgga tcgatttcgt tccaggtgaa | 120 |
| aatgccgaaa cgctgattga aaagtacaac gctcagttgg caaaactcga caccactaaa | 180 |
| ggcgtgctgt ttctcgttga tacatgggga ggcagcccgt tcaatgctgc agccgcatt | 240 |
| gtcgtcgaca agagcatta tgaagtcatt gcaggcgtta acattccaat gctcgtggaa | 300 |
| acgttaatgg cccgtgatga tgacccaagc tttgatgaac tggtggcact ggcagtagaa | 360 |
| acaggccgtg aaggcgtgaa agcactgaaa gccaaaccgg ttgaaaaagc gcgccagca | 420 |
| cccgctgccg cagcaccaaa agcggctcca actccggcaa aaccaatggg gccaaacgac | 480 |
| tacatggtta ttggccttgc gcgtatcgac accgtctga ttcacggtca ggtcgccacc | 540 |
| cgctggacca agaaaccaa tgtctcccgt attattgttg ttagtgatga agtggctgcg | 600 |
| gataccgttc gtaagacact gctcacccag gttgcacctc cgggcgtaac agcacacgta | 660 |
| gttgatgttg ccaaaatgat tcgcgtctac aacaacccga aatatgctgg cgaacgcgta | 720 |
| atgctgttat ttaccaaccc aacagatgta gagcgtctcg ttgaaggcgg cgtgaaaatc | 780 |
| acctctgtta acgtcggtgg tatggcattc cgtcagggta aaacccaggt gaataacgcg | 840 |
| gtttcggttg atgaaaaaga tatcgaggcg ttcaagaaac tgaatgcgcg cggtattgag | 900 |
| ctggaagtcc gtaaggtttc caccgatccg aaactgaaaa tgatggatct gatcagcaaa | 960 |
| atcgataagt aa | 972 |

<210> SEQ ID NO 45
<211> LENGTH: 323
<212> TYPE: PRT
<213> ORGANISM: Escherichia coli

<400> SEQUENCE: 45

Met Thr Ile Ala Ile Val Ile Gly Thr His Gly Trp Ala Ala Glu Gln
1               5                   10                  15

Leu Leu Lys Thr Ala Glu Met Leu Leu Gly Glu Gln Glu Asn Val Gly
            20                  25                  30

Trp Ile Asp Phe Val Pro Gly Glu Asn Ala Glu Thr Leu Ile Glu Lys
                35                  40                  45

Tyr Asn Ala Gln Leu Ala Lys Leu Asp Thr Thr Lys Gly Val Leu Phe
 50                  55                  60

Leu Val Asp Thr Trp Gly Gly Ser Pro Phe Asn Ala Ala Ser Arg Ile
 65                  70                  75                  80

Val Val Asp Lys Glu His Tyr Glu Val Ile Ala Gly Val Asn Ile Pro
                 85                  90                  95

Met Leu Val Glu Thr Leu Met Ala Arg Asp Asp Pro Ser Phe Asp
                100                 105                 110

Glu Leu Val Ala Leu Ala Val Glu Thr Gly Arg Glu Gly Val Lys Ala
                115                 120                 125

Leu Lys Ala Lys Pro Val Glu Lys Ala Ala Pro Ala Pro Ala Ala Ala
    130                 135                 140

Ala Pro Lys Ala Ala Pro Thr Pro Ala Lys Pro Met Gly Pro Asn Asp
145                 150                 155                 160

Tyr Met Val Ile Gly Leu Ala Arg Ile Asp Asp Arg Leu Ile His Gly
                165                 170                 175

Gln Val Ala Thr Arg Trp Thr Lys Glu Thr Asn Val Ser Arg Ile Ile
                180                 185                 190

Val Val Ser Asp Glu Val Ala Ala Asp Thr Val Arg Lys Thr Leu Leu
                195                 200                 205

Thr Gln Val Ala Pro Pro Gly Val Thr Ala His Val Val Asp Val Ala
    210                 215                 220

Lys Met Ile Arg Val Tyr Asn Asn Pro Lys Tyr Ala Gly Glu Arg Val
225                 230                 235                 240

Met Leu Leu Phe Thr Asn Pro Thr Asp Val Glu Arg Leu Val Glu Gly
                245                 250                 255

Gly Val Lys Ile Thr Ser Val Asn Val Gly Gly Met Ala Phe Arg Gln
                260                 265                 270

Gly Lys Thr Gln Val Asn Asn Ala Val Ser Val Asp Glu Lys Asp Ile
    275                 280                 285

Glu Ala Phe Lys Lys Leu Asn Ala Arg Gly Ile Glu Leu Glu Val Arg
    290                 295                 300

Lys Val Ser Thr Asp Pro Lys Leu Lys Met Met Asp Leu Ile Ser Lys
305                 310                 315                 320

Ile Asp Lys

<210> SEQ ID NO 46
<211> LENGTH: 801
<212> TYPE: DNA
<213> ORGANISM: Escherichia coli

<400> SEQUENCE: 46
atggagatta ccactcttca aattgtgctg gtatttatcg tagcctgtat cgcaggtatg      60
ggatcaatcc tcgatgaatt tcagtttcac cgtccgctaa tcgcgtgtac cctggtgggt     120
atcgttcttg gggatatgaa aaccggtatt attatcggtg gtacgctgga aatgatcgcg     180
ctgggctgga tgaacatcgg tgctgcagtt gcgcctgacg ccgctctggc ttctatcatt     240
tctaccattc tggttatcgc aggtcatcag agcattggtg caggtatcgc actggcaatc     300
cctctggccg ctgcgggcca ggtactgacc atcatcgttc gtactattac cgttgctttc     360
cagcacgctg cggataaggc tgctgataac ggcaacctga cagcgatttc ctggatccac     420

```
gtttcttctc tgttcctgca agcaatgcgt gtggctattc cggccgtcat cgttgcgctg    480
tctgttggta ccagcgaagt acagaacatg ctgaatgcga ttccggaagt ggtgaccaat    540
ggtctgaata tcgccggtgg catgatcgtg gtggttggtt atgcgatggt tatcaacatg    600
atgcgtgctg gctacctgat gccgttcttc tacctcggct tcgtaaccgc agcattcacc    660
aactttaacc tggttgctct gggtgtgatt ggtactgtta tggcagtgct ctacatccaa    720
cttagcccga aatacaaccg cgtagccggt gcgcctgctc aggcagctgg taacaacgat    780
ctcgataacg aactggacta a                                              801
```

<210> SEQ ID NO 47
<211> LENGTH: 266
<212> TYPE: PRT
<213> ORGANISM: Escherichia coli

<400> SEQUENCE: 47

```
Met Glu Ile Thr Thr Leu Gln Ile Val Leu Val Phe Ile Val Ala Cys
 1               5                  10                  15

Ile Ala Gly Met Gly Ser Ile Leu Asp Glu Phe Gln Phe His Arg Pro
                20                  25                  30

Leu Ile Ala Cys Thr Leu Val Gly Ile Val Leu Gly Asp Met Lys Thr
            35                  40                  45

Gly Ile Ile Ile Gly Gly Thr Leu Glu Met Ile Ala Leu Gly Trp Met
        50                  55                  60

Asn Ile Gly Ala Ala Val Ala Pro Asp Ala Ala Leu Ala Ser Ile Ile
 65                  70                  75                  80

Ser Thr Ile Leu Val Ile Ala Gly His Gln Ser Ile Gly Ala Gly Ile
                85                  90                  95

Ala Leu Ala Ile Pro Leu Ala Ala Ala Gly Gln Val Leu Thr Ile Ile
            100                 105                 110

Val Arg Thr Ile Thr Val Ala Phe Gln His Ala Ala Asp Lys Ala Ala
        115                 120                 125

Asp Asn Gly Asn Leu Thr Ala Ile Ser Trp Ile His Val Ser Ser Leu
130                 135                 140

Phe Leu Gln Ala Met Arg Val Ala Ile Pro Ala Val Ile Val Ala Leu
145                 150                 155                 160

Ser Val Gly Thr Ser Glu Val Gln Asn Met Leu Asn Ala Ile Pro Glu
                165                 170                 175

Val Val Thr Asn Gly Leu Asn Ile Ala Gly Gly Met Ile Val Val Val
            180                 185                 190

Gly Tyr Ala Met Val Ile Asn Met Met Arg Ala Gly Tyr Leu Met Pro
        195                 200                 205

Phe Phe Tyr Leu Gly Phe Val Thr Ala Ala Phe Thr Asn Phe Asn Leu
    210                 215                 220

Val Ala Leu Gly Val Ile Gly Thr Val Met Ala Val Leu Tyr Ile Gln
225                 230                 235                 240

Leu Ser Pro Lys Tyr Asn Arg Val Ala Gly Ala Pro Ala Gln Ala Ala
                245                 250                 255

Gly Asn Asn Asp Leu Asp Asn Glu Leu Asp
            260                 265
```

<210> SEQ ID NO 48
<211> LENGTH: 852
<212> TYPE: DNA
<213> ORGANISM: Escherichia coli

<400> SEQUENCE: 48

```
atggttgata caactcaaac taccaccgag aaaaaactca ctcaaagtga tattcgtggc    60
gtcttcctgc gttctaacct cttccagggt tcatggaact tcgaacgtat gcaggcactg   120
ggtttctgct tctctatggt accggcaatt cgtcgcctct accctgagaa caacgaagct   180
cgtaaacaag ctattcgccg tcacctggag ttctttaaca cccagccgtt cgtggctgcg   240
ccgattctcg gcgtaaccct ggcgctggaa gaacagcgtg ctaatggcgc agagatcgac   300
gacggtgcta tcaacggtat caaagtcggt ttgatggggc cactggctgg tgtaggcgac   360
ccgatcttct ggggaaccgt acgtccggta tttgcagcac tgggtgccgg tatcgcgatg   420
agcggcagcc tgttaggtcc gctgctgttc ttcatcctgt ttaacctggt gcgtctggca   480
acccgttact acggcgtagc gtatggttac tccaaaggta tcgatatcgt taaagatatg   540
ggtggtggct tcctgcaaaa actgacggaa ggggcgtcta cctcggcct gtttgtcatg   600
ggggcattgg ttaacaagtg gacacatgtc aacatcccgc tggttgtctc tcgcattact   660
gaccagacgg gcaaagaaca cgttactact gtccagacta ttctggacca gttaatgcca   720
ggcctggtac cactgctgct gacctttgct tgtatgtggc tactgcgcaa aaaagttaac   780
ccgctgtgga tcatcgttgg cttcttcgtc atcggtatcg ctggttacgc ttgcggcctg   840
ctgggactgt aa                                                       852
```

<210> SEQ ID NO 49
<211> LENGTH: 283
<212> TYPE: PRT
<213> ORGANISM: Escherichia coli

<400> SEQUENCE: 49

```
Met Val Asp Thr Thr Gln Thr Thr Thr Glu Lys Lys Leu Thr Gln Ser
1               5                   10                  15

Asp Ile Arg Gly Val Phe Leu Arg Ser Asn Leu Phe Gln Gly Ser Trp
            20                  25                  30

Asn Phe Glu Arg Met Gln Ala Leu Gly Phe Cys Phe Ser Met Val Pro
        35                  40                  45

Ala Ile Arg Arg Leu Tyr Pro Glu Asn Asn Glu Ala Arg Lys Gln Ala
    50                  55                  60

Ile Arg Arg His Leu Glu Phe Phe Asn Thr Gln Pro Phe Val Ala Ala
65                  70                  75                  80

Pro Ile Leu Gly Val Thr Leu Ala Leu Glu Glu Gln Arg Ala Asn Gly
                85                  90                  95

Ala Glu Ile Asp Asp Gly Ala Ile Asn Gly Ile Lys Val Gly Leu Met
            100                 105                 110

Gly Pro Leu Ala Gly Val Gly Asp Pro Ile Phe Trp Gly Thr Val Arg
        115                 120                 125

Pro Val Phe Ala Ala Leu Gly Ala Gly Ile Ala Met Ser Gly Ser Leu
    130                 135                 140

Leu Gly Pro Leu Leu Phe Phe Ile Leu Phe Asn Leu Val Arg Leu Ala
145                 150                 155                 160

Thr Arg Tyr Tyr Gly Val Ala Tyr Gly Tyr Ser Lys Gly Ile Asp Ile
                165                 170                 175

Val Lys Asp Met Gly Gly Gly Phe Leu Gln Lys Leu Thr Glu Gly Ala
            180                 185                 190

Ser Ile Leu Gly Leu Phe Val Met Gly Ala Leu Val Asn Lys Trp Thr
        195                 200                 205
```

```
        His Val Asn Ile Pro Leu Val Val Ser Arg Ile Thr Asp Gln Thr Gly
            210                 215                 220

Lys Glu His Val Thr Thr Val Gln Thr Ile Leu Asp Gln Leu Met Pro
        225                 230                 235                 240

Gly Leu Val Pro Leu Leu Leu Thr Phe Ala Cys Met Trp Leu Leu Arg
                        245                 250                 255

Lys Lys Val Asn Pro Leu Trp Ile Ile Val Gly Phe Phe Val Ile Gly
                    260                 265                 270

Ile Ala Gly Tyr Ala Cys Gly Leu Leu Gly Leu
                    275                 280

<210> SEQ ID NO 50
<211> LENGTH: 1434
<212> TYPE: DNA
<213> ORGANISM: Escherichia coli

<400> SEQUENCE: 50
atgtttaaga atgcatttgc taacctgcaa aaggtcggta atcgctgat gctgccggta      60 tccgtactgc ctatcgcagg tattctgctg ggcgtcggtt ccgcgaattt cagctggctg    120
cccgccgttg tatcgcatgt tatggcagaa gcaggcggtt ccgtctttgc aaacatgcca    180 ctgattttg cgatcggtgt cgccctcggc tttaccaata cgatggcgt atccgcgctg      240 gccgcagttg ttgcctatgg catcatggtt aaaaccatgg ccgtggttgc gccactggta    300
ctgcatttac ctgctgaaga atcgcctct aaacacctgg cggatactgg cgtactcgga    360
gggattatct ccggtgcgat cgcagcgtac atgtttaacc gtttctaccg tattaagctg    420
cctgagtatc ttggcttctt tgccggtaaa cgctttgtgc cgatcatttc tggcctggct    480 gccatctta ctggcgttgt gctgtccttc atttggccgc cgattggttc tgcaatccag    540
accttctctc agtgggctgc ttaccagaac ccggtagttg cgtttggcat ttacggtttc    600
atcgaacgtt gcctggtacc gtttggtctg caccacatct ggaacgtacc tttccagatg    660
cagattggtg aatacaccaa cgcagcaggt caggttttcc acggcgacat tccgcgttat    720
atggcgggtg acccgactgc gggtaaactg tcctgttcaa aatgtacggt                780
ctgccagctg ccgcaattgc tatctggcac tctgctaaac cagaaaaccg cgcgaaagtg    840
ggcggtatta tgatctccgc ggcgctgacc tcgttcctga ccggtatcac cgagccgatc    900
gagttctcct tcatgttcgt tgcgccgatc ctgtacatca tccacgcgat tctggcaggc    960
ctggcattcc caatctgtat tcttctgggg atgcgtgacg gtacgtcgtt ctcgcacggt   1020
ctgatcgact tcatcgttct gtctggtaac agcagcaaac tgtggctgtt cccgatcgtc   1080
ggtatcggtt atgcgattgt ttactacacc atcttccgcg tgctgattaa agcactggat   1140
ctgaaaacgc cgggtcgtga agacgcgact gaagatgcaa aagcgacagg taccagcgaa   1200
atggcaccgg ctctggttgc tgcatttggt ggtaaagaaa acattactaa cctcgacgca   1260
tgtattaccc gtctgcgcgt cagcgttgct gatgtgtcta aagtggatca ggccggcctg   1320
aagaaactgg gcgcagcggg cgtagtggtt gctggttctg gtgttcaggc gatttcggt    1380 actaaatccg ataacctgaa aaccgagatg gatgagtaca tccgtaacca ctaa         1434

<210> SEQ ID NO 51
<211> LENGTH: 477
<212> TYPE: PRT
<213> ORGANISM: Escherichia coli

<400> SEQUENCE: 51
```

```
Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
                20                  25                  30

Gly Ser Ala Asn Phe Ser Trp Leu Pro Ala Val Val Ser His Val Met
            35                  40                  45

Ala Glu Ala Gly Gly Ser Val Phe Ala Asn Met Pro Leu Ile Phe Ala
50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
                100                 105                 110

Leu Ala Asp Thr Gly Val Leu Gly Gly Ile Ile Ser Gly Ala Ile Ala
                115                 120                 125

Ala Tyr Met Phe Asn Arg Phe Tyr Arg Ile Lys Leu Pro Glu Tyr Leu
130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
                180                 185                 190

Val Ala Phe Gly Ile Tyr Gly Phe Ile Glu Arg Cys Leu Val Pro Phe
                195                 200                 205

Gly Leu His His Ile Trp Asn Val Pro Phe Gln Met Gln Ile Gly Glu
                210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
                260                 265                 270

Lys Pro Glu Asn Arg Ala Lys Val Gly Gly Ile Met Ile Ser Ala Ala
                275                 280                 285

Leu Thr Ser Phe Leu Thr Gly Ile Thr Glu Pro Ile Glu Phe Ser Phe
                290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
                340                 345                 350

Lys Leu Trp Leu Phe Pro Ile Val Gly Ile Gly Tyr Ala Ile Val Tyr
                355                 360                 365

Tyr Thr Ile Phe Arg Val Leu Ile Lys Ala Leu Asp Leu Lys Thr Pro
                370                 375                 380

Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
```

```
                420             425             430
Ser Lys Val Asp Gln Ala Gly Leu Lys Lys Leu Gly Ala Ala Gly Val
            435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn His
465                 470                 475

<210> SEQ ID NO 52
<211> LENGTH: 510
<212> TYPE: DNA
<213> ORGANISM: Escherichia coli

<400> SEQUENCE: 52
atgggtttgt tcgataaact gaaatctctg gtttccgacg acaagaagga taccggaact      60
attgagatca ttgctccgct ctctggcgag atcgtcaata tcgaagacgt gccggatgtc    120 gttttttgcgg aaaaaatcgt tggtgatggt attgctatca aaccaacggg taacaaaatg    180
gtcgcgccag tagacggcac cattggtaaa atctttgaaa ccaaccacgc attctctatc    240
gaatctgata gcggcgttga actgttcgtc cacttcggta tcgacaccgt tgaactgaaa    300
ggcgaaggct tcaagcgtat tgctgaagaa ggtcagcgcg tgaaagttgg cgatactgtc    360
attgaatttg atctgccgct gctggaagag aaagccaagt ctaccctgac tccggttgtt    420
atctccaaca tggacgaaat caaagaactg atcaaactgt ccggtagcgt aaccgtgggt    480
gaaaccccgg ttatccgcat caagaagtaa                                     510

<210> SEQ ID NO 53
<211> LENGTH: 169
<212> TYPE: PRT
<213> ORGANISM: Escherichia coli

<400> SEQUENCE: 53

Met Gly Leu Phe Asp Lys Leu Lys Ser Leu Val Ser Asp Asp Lys Lys
1               5                   10                  15

Asp Thr Gly Thr Ile Glu Ile Ile Ala Pro Leu Ser Gly Glu Ile Val
            20                  25                  30

Asn Ile Glu Asp Val Pro Asp Val Val Phe Ala Glu Lys Ile Val Gly
        35                  40                  45

Asp Gly Ile Ala Ile Lys Pro Thr Gly Asn Lys Met Val Ala Pro Val
    50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Glu Gly Phe Lys Arg Ile Ala Glu Glu Gly Gln
            100                 105                 110

Arg Val Lys Val Gly Asp Thr Val Ile Glu Phe Asp Leu Pro Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Ile Lys Leu Ser Gly Ser Val Thr Val Gly
145                 150                 155                 160

Glu Thr Pro Val Ile Arg Ile Lys Lys
                165
```

```
<210> SEQ ID NO 54
<211> LENGTH: 1248
<212> TYPE: DNA
<213> ORGANISM: Escherichia coli

<400> SEQUENCE: 54
atggcactga atattccatt cagaaatgcg tactatcgtt ttgcatccag ttactcattt      60 ctcttttta tttcctggtc gctgtggtgg tcgttatacg ctatttggct gaaaggacat     120
ctaggattaa cagggacgga attaggtaca ctttattcgg tcaaccagtt taccagcatt     180
ctatttatga tgttctacgg catcgttcag gataaactcg gtctgaagaa accgctcatc     240
tggtgtatga gtttcattct ggtcttgacc ggaccgttta tgatttacgt ttatgaaccg     300
ttactgcaaa gcaatttttc tgtaggtcta attctggggg cgctcttttt tggcctgggg     360
tatctggcgg gatgcggttt gcttgacagc ttcaccgaaa aaatggcgcg aaattttcat     420
ttcgaatatg aacagcgcg cgcctgggga tcttttggct atgctattgg cgcgttcttt     480
gccggtatat tttttagtat cagtccccat atcaacttct ggttggtctc gctatttggc     540
gctgtattta tgatgatcaa catgcgtttt aaagataagg atcaccagtg catagcggcg     600
gatgcgggag gggtaaaaaa agaggatttt atcgcagttt tcaaggatcg aaacttctgg     660
gttttcgtca tatttattgt ggggacgtgg tctttctata acatttttga tcaacaactc     720 ttcctgtct tttatgcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggtg ttgtgattat ggcgttgcgt     900
atcctttcct gcgcgttgtt cgttaacccc tggattattt cattagtgaa gctgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cctgagtaaa    1200
aaacgcgagc aaatagttat ggaaacgcct gtaccttcag caatatag                 1248

<210> SEQ ID NO 55
<211> LENGTH: 415
<212> TYPE: PRT
<213> ORGANISM: Escherichia coli

<400> SEQUENCE: 55

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
```

```
            115                 120                 125
Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Ile Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ala Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 56
<211> LENGTH: 924
<212> TYPE: DNA
<213> ORGANISM: Escherichia coli

<400> SEQUENCE: 56
atgtcagcca aagtatgggt tttaggggat gcggtcgtag atctcttgcc agaatcagac      60
gggcggctac tgccttgtcc tggcggcgcg ccagctaacg ttgcggtggg aatcgccaga     120
ttaggcggaa caagtgggtt tataggtcgg gtcggtgatg atccttttgg tgcgttaatg     180
caaagaacgc tgctaactga gggtgtcgat atcacgtatc tgaagcaaga tgaatggcac     240
cggacatcca cggtgcttgt cgatctgaac gatcaaggag aacgttcatt tacgtttatg     300
gtccgcccca gtgccgatct tttttagag acgacagact tgccctgctg gcgacatggc     360
gaatggttac atctctgttc aattgcgttg tctgccgagc cttcgcgtac cagcgcattt     420
actgcgatga cggcgatccg gcatgccgga ggttttgtca gcttcgatcc caatattcgt     480
```

-continued

```
gaagatctat ggcaagacga gcatttgctc cgcttgtgtt tgcggcaggc gctacaactg    540
gcggatgtcg tcaagctctc ggaagaagaa tggcgactta tcagtggaaa aacacagaac    600
gatcgggata tatgcgccct ggcaaaagag tatgagatcg ccatgctgtt ggtgactaaa    660
ggtgcagaag gggtggtggt ctgttatcga ggacaagtcc accattttgc tggaatgtct    720
gtgaattgtg tcgatagcac tggggcggga gatgcgttcg ttgccgggtt actcacaggt    780
ctgtcctcta cgggattatc tacagatgag agagaaatgc gacgaattat cgatctcgct    840
caacgttgcg gagcgcttgc agtaacagcg aaggggcaa tgacagcgct gccatgtcga    900
caagaactgg aaagtgagaa gtaa                                             924
```

<210> SEQ ID NO 57
<211> LENGTH: 307
<212> TYPE: PRT
<213> ORGANISM: Escherichia coli

<400> SEQUENCE: 57

```
Met Ser Ala Lys Val Trp Val Leu Gly Asp Ala Val Asp Leu Leu
1               5                   10                  15

Pro Glu Ser Asp Gly Arg Leu Leu Pro Cys Pro Gly Gly Ala Pro Ala
                20                  25                  30

Asn Val Ala Val Gly Ile Ala Arg Leu Gly Gly Thr Ser Gly Phe Ile
            35                  40                  45

Gly Arg Val Gly Asp Asp Pro Phe Gly Ala Leu Met Gln Arg Thr Leu
        50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
                100                 105                 110

Asp Leu Pro Cys Trp Arg His Gly Glu Trp Leu His Leu Cys Ser Ile
            115                 120                 125

Ala Leu Ser Ala Glu Pro Ser Arg Thr Ser Ala Phe Thr Ala Met Thr
        130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Arg Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285
```

```
Thr Ala Lys Gly Ala Met Thr Ala Leu Pro Cys Arg Gln Glu Leu Glu
    290                 295                 300

Ser Glu Lys
305
```

<210> SEQ ID NO 58
<211> LENGTH: 1434
<212> TYPE: DNA
<213> ORGANISM: Escherichia coli

<400> SEQUENCE: 58

| | | | | | |
|---|---|---|---|---|---|
| atgacgcaat | ctcgattgca | tgcggcgcaa | aacgccctag | caaaacttca | tgagcaccgg | 60 |
| ggtaacactt | tctatcccca | ttttcacctc | gcgcctcctg | ccgggtggat | gaacgatcca | 120 |
| aacggcctga | tctggtttaa | cgatcgttat | cacgcgtttt | atcaacatca | tccgatgagc | 180 |
| gaacactggg | ggccaatgca | ctggggacat | gccaccagcg | acgatatgat | ccactggcag | 240 |
| catgagccta | ttgcgctagc | gccaggagac | gataatgaca | agacgggtg | ttttcaggt | 300 |
| agtgctgtcg | atgacaatgg | tgtcctctca | cttatctaca | ccgacacgt | ctggctcgat | 360 |
| ggtgcaggta | atgacgatgc | aattcgcgaa | gtacaatgtc | tggctaccag | tcgggatggt | 420 |
| attcatttcg | agaaacaggg | tgtgatcctc | actccaccag | aaggaatcat | gcacttccgc | 480 |
| gatcctaaag | tgtggcgtga | agccgacaca | tggtggatgg | tagtcgggc | gaaagatcca | 540 |
| ggcaacacgg | ggcagatcct | gctttatcgc | ggcagttcat | tgcgtgaatg | gaccttcgat | 600 |
| cgcgtactgg | cccacgctga | tgcgggtgaa | agctatatgt | gggaatgtcc | ggactttttc | 660 |
| agccttggcg | atcagcatta | tctgatgttt | tccccgcagg | gaatgaatgc | cgagggatac | 720 |
| agttaccgaa | atcgctttca | aagtggcgta | ataccccggaa | tgtggtcgcc | aggacgactt | 780 |
| tttgcacaat | ccgggcattt | tactgaactt | gataacgggc | atgactttta | tgcaccacaa | 840 |
| agctttttag | cgaaggatgg | tcggcgtatt | gttatcggat | ggatggatat | gtgggaatcg | 900 |
| ccaatgccct | caaacgtga | aggctgggca | ggctgcatga | cgctggcgcg | cgagctatca | 960 |
| gagagcaatg | gcaaacttct | acaacgcccg | gttcacgaag | ctgagtcgtt | acgccagcag | 1020 |
| catcaatctg | tctctccccg | cacaatcagc | aataaatatg | ttttgcagga | aaacgcgcaa | 1080 |
| gcagttgaga | ttcagttgca | gtgggcgctg | aagaacagtg | atgccgaaca | ttacggatta | 1140 |
| cagctcggca | ctggaatgcg | gctgtatatt | gataaccaat | ctgagcgact | tgttttgtgg | 1200 |
| cggtattacc | cacacgagaa | tttagacggc | taccgtagta | ttcccctccc | gcagcgtgac | 1260 |
| acgctcgccc | taaggatatt | tatcgataca | tcatccgtgg | aagtatttat | taacgacggg | 1320 |
| gaagcggtga | tgagtagtcg | aatctatccg | cagccagaag | aacgggaact | gtcgctttat | 1380 |
| gcctcccacg | gagtggctgt | gctgcaacat | ggagcactct | ggctactggg | ttaa | 1434 |

<210> SEQ ID NO 59
<211> LENGTH: 480
<212> TYPE: PRT
<213> ORGANISM: Escherichia coli

<400> SEQUENCE: 59

```
Met Ile Lys Met Thr Gln Ser Arg Leu His Ala Ala Gln Asn Ala Leu
1               5                   10                  15

Ala Lys Leu His Glu His Arg Gly Asn Thr Phe Tyr Pro His Phe His
                20                  25                  30

Leu Ala Pro Pro Ala Gly Trp Met Asn Asp Pro Asn Gly Leu Ile Trp
            35                  40                  45
```

```
Phe Asn Asp Arg Tyr His Ala Phe Tyr Gln His His Pro Met Ser Glu
 50                  55                  60
His Trp Gly Pro Met His Trp Gly His Ala Thr Ser Asp Asp Met Ile
 65                  70                  75                  80
His Trp Gln His Glu Pro Ile Ala Leu Ala Pro Gly Asp Asp Asn Asp
                 85                  90                  95
Lys Asp Gly Cys Phe Ser Gly Ser Ala Val Asp Asp Asn Gly Val Leu
                100                 105                 110
Ser Leu Ile Tyr Thr Gly His Val Trp Leu Asp Gly Ala Gly Asn Asp
            115                 120                 125
Asp Ala Ile Arg Glu Val Gln Cys Leu Ala Thr Ser Arg Asp Gly Ile
130                 135                 140
His Phe Glu Lys Gln Gly Val Ile Leu Thr Pro Pro Glu Gly Ile Met
145                 150                 155                 160
His Phe Arg Asp Pro Lys Val Trp Arg Glu Ala Asp Thr Trp Trp Met
                165                 170                 175
Val Val Gly Ala Lys Asp Pro Gly Asn Thr Gly Gln Ile Leu Leu Tyr
            180                 185                 190
Arg Gly Ser Ser Leu Arg Glu Trp Thr Phe Asp Arg Val Leu Ala His
            195                 200                 205
Ala Asp Ala Gly Glu Ser Tyr Met Trp Glu Cys Pro Asp Phe Phe Ser
210                 215                 220
Leu Gly Asp Gln His Tyr Leu Met Phe Ser Pro Gln Gly Met Asn Ala
225                 230                 235                 240
Glu Gly Tyr Ser Tyr Arg Asn Arg Phe Gln Ser Gly Val Ile Pro Gly
                245                 250                 255
Met Trp Ser Pro Gly Arg Leu Phe Ala Gln Ser Gly His Phe Thr Glu
            260                 265                 270
Leu Asp Asn Gly His Asp Phe Tyr Ala Pro Gln Ser Phe Leu Ala Lys
            275                 280                 285
Asp Gly Arg Arg Ile Val Ile Gly Trp Met Asp Met Trp Glu Ser Pro
290                 295                 300
Met Pro Ser Lys Arg Glu Gly Trp Ala Gly Cys Met Thr Leu Ala Arg
305                 310                 315                 320
Glu Leu Ser Glu Ser Asn Gly Lys Leu Leu Gln Arg Pro Val His Glu
                325                 330                 335
Ala Glu Ser Leu Arg Gln Gln His Gln Ser Val Ser Pro Arg Thr Ile
            340                 345                 350
Ser Asn Lys Tyr Val Leu Gln Glu Asn Ala Gln Ala Val Glu Ile Gln
            355                 360                 365
Leu Gln Trp Ala Leu Lys Asn Ser Asp Ala Glu His Tyr Gly Leu Gln
370                 375                 380
Leu Gly Thr Gly Met Arg Leu Tyr Ile Asp Asn Gln Ser Glu Arg Leu
385                 390                 395                 400
Val Leu Trp Arg Tyr Tyr Pro His Glu Asn Leu Asp Gly Tyr Arg Ser
                405                 410                 415
Ile Pro Leu Pro Gln Arg Asp Thr Leu Ala Leu Arg Ile Phe Ile Asp
            420                 425                 430
Thr Ser Ser Val Glu Val Phe Ile Asn Asp Gly Glu Ala Val Met Ser
            435                 440                 445
Ser Arg Ile Tyr Pro Gln Pro Glu Glu Arg Glu Leu Ser Leu Tyr Ala
450                 455                 460
Ser His Gly Val Ala Val Leu Gln His Gly Ala Leu Trp Leu Leu Gly
```

<210> SEQ ID NO 60
<211> LENGTH: 954
<212> TYPE: DNA
<213> ORGANISM: Escherichia coli

<400> SEQUENCE: 60

```
atgatgacag tctcccgggt gatgcataat gcagaatctg tgcgtcctgc aacgcgtgac    60
cgcgtattgc aggcaatcca gaccctgaat tatgttcctg atctttccgc ccgtaagatg   120
cgcgctcaag gacgtaagcc gtcgactctc gccgtgctgg cgcaggacac ggctaccact   180
cctttctctg ttgatattct gcttgccatt gagcaaaccg ccagcgagtt cggctggaat   240
agttttttaa tcaatatttt ttctgaagat gacgctgccc gtgctgcacg tcagctgctt   300
gcccaccgtc cggatggcat tatctatact acaatggggc tgcgacatat cacgctgcct   360
gagtctctgt atggtgaaaa tattgtattg gcgaactgtg tggcggatga cccagcgtta   420
cccagttata tccctgatga ttacactgca caatatgaat caacacagca tttgctcgcg   480
gcgggctatc gtcaaccgtt atgcttctgg ctaccggaaa gtgcgttggc aacagggtat   540
cgtcggcagg gatttgagca ggcctggcgt gatgctggac gagatctggc tgaggtgaaa   600
caatttcaca tggcaacagg tgatgatcac tacaccgatc tcgcaagttt actcaatgcc   660
cacttcaaat cgggcaaacc agattttgat gttctgatat gtggtaacga tcgcgcagct   720
tttgtggctt atcaggttct tttggcgaag ggggtacgta tcccgcagga tgtcgccgta   780
atgggctttg ataatctggt tggcgtcggg catctgtttt taccgccgct gaccacaatt   840
cagcttccac atgacattat cgggcgggaa gctgcattgc atattattga aggtcgtgaa   900
ggggaagag tgacccggat cccttgcccg ctgttgatcc gttgttccac ctga          954
```

<210> SEQ ID NO 61
<211> LENGTH: 317
<212> TYPE: PRT
<213> ORGANISM: Escherichia coli

<400> SEQUENCE: 61

Met Met Thr Val Ser Arg Val Met His Asn Ala Glu Ser Val Arg Pro
1               5                   10                  15

Ala Thr Arg Asp Arg Val Leu Gln Ala Ile Gln Thr Leu Asn Tyr Val
            20                  25                  30

Pro Asp Leu Ser Ala Arg Lys Met Arg Ala Gln Gly Arg Lys Pro Ser
        35                  40                  45

Thr Leu Ala Val Leu Ala Gln Asp Thr Ala Thr Thr Pro Phe Ser Val
    50                  55                  60

Asp Ile Leu Leu Ala Ile Glu Gln Thr Ala Ser Glu Phe Gly Trp Asn
65                  70                  75                  80

Ser Phe Leu Ile Asn Ile Phe Ser Glu Asp Asp Ala Ala Arg Ala Ala
                85                  90                  95

Arg Gln Leu Leu Ala His Arg Pro Asp Gly Ile Ile Tyr Thr Thr Met
            100                 105                 110

Gly Leu Arg His Ile Thr Leu Pro Glu Ser Leu Tyr Gly Glu Asn Ile
        115                 120                 125

Val Leu Ala Asn Cys Val Ala Asp Asp Pro Ala Leu Pro Ser Tyr Ile
    130                 135                 140

Pro Asp Asp Tyr Thr Ala Gln Tyr Glu Ser Thr Gln His Leu Leu Ala
145                 150                 155                 160

```
Ala Gly Tyr Arg Gln Pro Leu Cys Phe Trp Leu Pro Glu Ser Ala Leu
            165                 170                 175

Ala Thr Gly Tyr Arg Arg Gln Gly Phe Glu Gln Ala Trp Arg Asp Ala
        180                 185                 190

Gly Arg Asp Leu Ala Glu Val Lys Gln Phe His Met Ala Thr Gly Asp
    195                 200                 205

Asp His Tyr Thr Asp Leu Ala Ser Leu Leu Asn Ala His Phe Lys Ser
210                 215                 220

Gly Lys Pro Asp Phe Asp Val Leu Ile Cys Gly Asn Asp Arg Ala Ala
225                 230                 235                 240

Phe Val Ala Tyr Gln Val Leu Leu Ala Lys Gly Val Arg Ile Pro Gln
            245                 250                 255

Asp Val Ala Val Met Gly Phe Asp Asn Leu Val Gly Val Gly His Leu
        260                 265                 270

Phe Leu Pro Pro Leu Thr Thr Ile Gln Leu Pro His Asp Ile Ile Gly
    275                 280                 285

Arg Glu Ala Ala Leu His Ile Ile Glu Gly Arg Glu Gly Gly Arg Val
    290                 295                 300

Thr Arg Ile Pro Cys Pro Leu Leu Ile Arg Cys Ser Thr
305                 310                 315

<210> SEQ ID NO 62
<211> LENGTH: 1254
<212> TYPE: DNA
<213> ORGANISM: Escherichia coli

<400> SEQUENCE: 62
atgtactatt taaaaaacac aaactttggg atgttcggtt tattcttttt cttttacttt      60
tttatcatgg gagcctactt cccgttttc  ccgatttggc tacatgacat caaccatatc     120
agcaaaagtg atacgggtat tattttttgcc gctatttctc tgttctcgct attattccaa    180
ccgctgtttg gtctgctttc tgacaaactc gggctgcgca ataccgtct gtggattatt      240 accggcatgt tagtgatgtt tgcgccgttc tttatttta tcttcgggcc actgttacaa      300
tacaacattt tagtaggatc gattgttggt ggtatttatc taggcttttg ttttaacgcc    360
ggtgcgccag cagtagaggc atttattgag aaagtcagcc gtcgcagtaa tttcgaattt    420
ggtcgcgcgc ggatgtttgg ctgtgttggc tgggcgctgt gtgcctcgat tgtcggcatc    480
atgttcacca tcaataatca gtttgttttc tggctgggct ctggctgtgc actcatcctc    540
gccgttttac tcttttcgc caaaacggat gcgccctctt ctgccacggt tgccaatgcg    600
gtaggtgcca accattcggc atttagcctt aagctggcac tggaactgtt cagacagcca    660
aaactgtggt ttttgtcact gtatgttatt ggcgtttcct gcacctacga tgttttgac     720 caacagtttg ctaatttctt tacttcgttc tttgctaccg gtgaacaggg tacgcgggta    780
tttggctacg taacgacaat gggcgaatta cttaacgcct cgattatgtt ctttgcgcca    840
ctgatcatta atcgcatcgg tgggaaaaac gccctgctgc tggctggcac tattatgtct    900
gtacgtatta ttggctcatc gttcgccacc tcagcgctgg aagtggttat tctgaaaacg    960
ctgcatatgt ttgaagtacc gttcctgctg gtgggctgct taaatatat taccagccag    1020 tttgaagtgc gttttcagc gacgatttat ctggtctgtt tctgcttctt taagcaactg    1080
gcgatgattt ttatgtctgt actggcgggc aatatgtatg aaagcatcgg tttccagggc    1140
gcttatctgg tgctgggtct ggtggcgctg ggcttcacct taatttccgt gttcacgctt    1200
```

```
agcggccccg gcccgctttc cctgctgcgt cgtcaggtga atgaagtcgc ttaa         1254
```

<210> SEQ ID NO 63
<211> LENGTH: 417
<212> TYPE: PRT
<213> ORGANISM: Escherichia coli
<400> SEQUENCE: 63

```
Met Tyr Tyr Leu Lys Asn Thr Asn Phe Trp Met Phe Gly Leu Phe Phe
1               5                   10                  15

Phe Phe Tyr Phe Ile Met Gly Ala Tyr Phe Pro Phe Pro Ile
            20                  25                  30

Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Ile Phe Ile Phe Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
    210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
        275                 280                 285

Lys Asn Ala Leu Leu Leu Ala Gly Thr Ile Met Ser Val Arg Ile Ile
    290                 295                 300

Gly Ser Ser Phe Ala Thr Ser Ala Leu Glu Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Val Leu
        355                 360                 365
```

```
Ala Gly Asn Met Tyr Glu Ser Ile Gly Phe Gln Gly Ala Tyr Leu Val
    370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala

<210> SEQ ID NO 64
<211> LENGTH: 3075
<212> TYPE: DNA
<213> ORGANISM: Escherichia coli

<400> SEQUENCE: 64
```

| | | | | | |
|---|---|---|---|---|---|
| atgaccatga | ttacggattc | actggccgtc | gttttacaac | gtcgtgactg | ggaaaaccct    60 |
| ggcgttaccc | aacttaatcg | ccttgcagca | catcccccttt | tcgccagctg | gcgtaatagc   120 |
| gaagaggccc | gcaccgatcg | cccttcccaa | cagttgcgca | gcctgaatgg | cgaatggcgc   180 |
| tttgcctggt | tccggcacc | agaagcggtg | ccggaaagct | ggctggagtg | cgatcttcct   240 |
| gaggccgata | ctgtcgtcgt | ccccctcaaac | tggcagatgc | acggttacga | tgcgcccatc   300 |
| tacaccaacg | tgacctatcc | cattacggtc | aatccgccgt | tgttcccac | ggagaatccg   360 |
| acgggttgtt | actcgctcac | atttaatgtt | gatgaaagct | ggctacagga | aggccagacg   420 |
| cgaattattt | ttgatggcgt | taactcggcg | tttcatctgt | ggtgcaacgg | cgctgggtc   480 |
| ggttacggcc | aggacagtcg | tttgccgtct | gaatttgacc | tgagcgcatt | tttacgcgcc   540 |
| ggagaaaacc | gcctcgcggt | gatggtgctg | cgctggagtg | acggcagtta | tctggaagat   600 |
| caggatatgt | ggcggatgag | cggcattttc | cgtgacgtct | cgttgctgca | taaaccgact   660 |
| acacaaatca | gcgatttcca | tgttgccact | cgctttaatg | atgatttcag | ccgcgctgta   720 |
| ctggaggctg | aagttcagat | gtgcggcgag | ttgcgtgact | acctacgggt | aacagtttct   780 |
| ttatggcagg | gtgaaacgca | ggtcgccagc | ggcaccgcgc | ctttcggcgg | tgaaattatc   840 |
| gatgagcgtg | tggttatgc | cgatcgcgtc | acactacgtc | tgaacgtcga | aaacccgaaa   900 |
| ctgtggagcg | ccgaaatccc | gaatctctat | cgtgcggtgg | ttgaactgca | caccgccgac   960 |
| ggcacgctga | ttgaagcaga | agcctgcgat | gtcggtttcc | gcgaggtgcg | gattgaaaat  1020 |
| ggtctgctgc | tgctgaacgg | caagccgttg | ctgattcgag | gcgttaaccg | tcacgagcat  1080 |
| catcctctgc | atggtcaggt | catggatgag | cagacgatgg | tgcaggatat | cctgctgatg  1140 |
| aagcagaaca | actttaacgc | cgtgcgctgt | tcgcattatc | cgaaccatcc | gctgtggtac  1200 |
| acgctgtgcg | accgctacgg | cctgtatgtg | gtggatgaag | ccaatattga | aacccacggc  1260 |
| atggtgccaa | tgaatcgtct | gaccgatgat | ccgcgctggc | taccggcgat | gagcgaacgc  1320 |
| gtaacgcgaa | tggtgcagcg | cgatcgtaat | cacccgagtg | tgatcatctg | gtcgctgggg  1380 |
| aatgaatcag | gccacggcgc | taatcacgac | gcgctgtatc | gctggatcaa | atctgtcgat  1440 |
| ccttcccgcc | cggtgcagta | tgaaggcggc | ggagccgaca | ccacggccac | cgatattatt  1500 |
| tgcccgatgt | acgcgcgcgt | ggatgaagac | cagcccttcc | cggctgtgcc | gaaatggtcc  1560 |
| atcaaaaaat | ggcttttcgct | acctggagag | acgcgcccgc | tgatcctttg | cgaatacgcc  1620 |
| cacgcgatgg | gtaacagtct | tggcggtttc | gctaaatact | ggcaggcgtt | tcgtcagtat  1680 |
| ccccgtttac | agggcggctt | cgtctgggac | tgggtggatc | agtcgctgat | taaatatgat  1740 |
| gaaaacggca | acccgtggtc | ggcttacggc | ggtgattttg | gcgatacgcc | gaacgatcgc  1800 |

-continued

```
cagttctgta tgaacggtct ggtctttgcc gaccgcacgc cgcatccagc gctgacggaa    1860
gcaaaacacc agcagcagtt tttccagttc cgtttatccg ggcaaaccat cgaagtgacc    1920
agcgaatacc tgttccgtca tagcgataac gagctcctgc actggatggt ggcgctggat    1980
ggtaagccgc tggcaagcgg tgaagtgcct ctggatgtcg ctccacaagg taaacagttg    2040
attgaactgc tgaactacc gcagccggag agcgccgggc aactctggct cacagtacgc    2100
gtagtgcaac cgaacgcgac cgcatggtca gaagccgggc acatcagcgc ctggcagcag    2160
tggcgtctgg cggaaaacct cagtgtgacg ctccccgccg cgtcccacgc catcccgcat    2220
ctgaccacca gcgaaatgga ttttgcatc gagctgggta ataagcgttg gcaatttaac    2280
cgccagtcag gctttctttc acagatgtgg attggcgata aaaacaact gctgacgccg    2340 ctgcgcgatc agttcacccg tgcaccgctg gataacgaca ttggcgtaag tgaagcgacc    2400
cgcattgacc ctaacgcctg ggtcgaacgc tggaaggcgg cgggccatta ccaggccgaa    2460
gcagcgttgt tgcagtgcac ggcagataca cttgctgatg cggtgctgat tacgaccgct    2520
cacgcgtggc agcatcaggg gaaaaaccta tttatcagcc ggaaaaccta ccggattgat    2580
ggtagtggtc aaatggcgat taccgttgat gttgaagtgg cgagcgatac accgcatccg    2640
gcgcggattg gcctgaactg ccagctggcg caggtagcag agcgggtaaa ctggctcgga    2700
ttagggccgc aagaaaacta tcccgaccgc cttactgccg cctgttttga ccgctgggat    2760
ctgccattgt cagacatgta tacccgtac gtcttcccga gcgaaaacgg tctgcgctgc    2820
gggacgcgcg aattgaatta tggcccacac cagtggcgcg gcgacttcca gttcaacatc    2880
agccgctaca gtcaacagca actgatgaaa accagccatc gccatctgct gcacgcggaa    2940
gaaggcacat ggctgaatat cgacggtttc catatgggga ttggtggcga cgactcctgg    3000
agcccgtcag tatcggcgga attccagctg agcgccggtc gctaccatta ccagttggtc    3060
tggtgtcaaa aataa                                                     3075
```

<210> SEQ ID NO 65
<211> LENGTH: 1024
<212> TYPE: PRT
<213> ORGANISM: Escherichia coli

<400> SEQUENCE: 65

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140
```

```
Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
        165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
            405                 410                 415

Glu Thr His Gly Met Val Pro Met Asn Arg Leu Thr Asp Asp Pro Arg
        420                 425                 430

Trp Leu Pro Ala Met Ser Glu Arg Val Thr Arg Met Val Gln Arg Asp
    435                 440                 445

Arg Asn His Pro Ser Val Ile Ile Trp Ser Leu Gly Asn Glu Ser Gly
450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Ala Asp Thr Thr Ala
            485                 490                 495

Thr Asp Ile Ile Cys Pro Met Tyr Ala Arg Val Asp Glu Asp Gln Pro
        500                 505                 510

Phe Pro Ala Val Pro Lys Trp Ser Ile Lys Lys Trp Leu Ser Leu Pro
    515                 520                 525

Gly Glu Thr Arg Pro Leu Ile Leu Cys Glu Tyr Ala His Ala Met Gly
        530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
```

```
                565                 570                 575
Ile Lys Tyr Asp Glu Asn Gly Asn Pro Trp Ser Ala Tyr Gly Gly Asp
            580                 585                 590
Phe Gly Asp Thr Pro Asn Asp Arg Gln Phe Cys Met Asn Gly Leu Val
            595                 600                 605
Phe Ala Asp Arg Thr Pro His Pro Ala Leu Thr Glu Ala Lys His Gln
            610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
                660                 665                 670
Val Ala Pro Gln Gly Lys Gln Leu Ile Glu Leu Pro Glu Leu Pro Gln
                675                 680                 685
Pro Glu Ser Ala Gly Gln Leu Trp Leu Thr Val Arg Val Val Gln Pro
            690                 695                 700
Asn Ala Thr Ala Trp Ser Glu Ala Gly His Ile Ser Ala Trp Gln Gln
705                 710                 715                 720
Trp Arg Leu Ala Glu Asn Leu Ser Val Thr Leu Pro Ala Ala Ser His
                725                 730                 735
Ala Ile Pro His Leu Thr Thr Ser Glu Met Asp Phe Cys Ile Glu Leu
                740                 745                 750
Gly Asn Lys Arg Trp Gln Phe Asn Arg Gln Ser Gly Phe Leu Ser Gln
                755                 760                 765
Met Trp Ile Gly Asp Lys Lys Gln Leu Leu Thr Pro Leu Arg Asp Gln
            770                 775                 780
Phe Thr Arg Ala Pro Leu Asp Asn Asp Ile Gly Val Ser Glu Ala Thr
785                 790                 795                 800
Arg Ile Asp Pro Asn Ala Trp Val Glu Arg Trp Lys Ala Ala Gly His
                805                 810                 815
Tyr Gln Ala Glu Ala Ala Leu Leu Gln Cys Thr Ala Asp Thr Leu Ala
            820                 825                 830
Asp Ala Val Leu Ile Thr Thr Ala His Ala Trp Gln His Gln Gly Lys
            835                 840                 845
Thr Leu Phe Ile Ser Arg Lys Thr Tyr Arg Ile Asp Gly Ser Gly Gln
            850                 855                 860
Met Ala Ile Thr Val Asp Val Glu Val Ala Ser Asp Thr Pro His Pro
865                 870                 875                 880
Ala Arg Ile Gly Leu Asn Cys Gln Leu Ala Gln Val Ala Glu Arg Val
                885                 890                 895
Asn Trp Leu Gly Leu Gly Pro Gln Glu Asn Tyr Pro Asp Arg Leu Thr
            900                 905                 910
Ala Ala Cys Phe Asp Arg Trp Asp Leu Pro Leu Ser Asp Met Tyr Thr
            915                 920                 925
Pro Tyr Val Phe Pro Ser Glu Asn Gly Leu Arg Cys Gly Thr Arg Glu
            930                 935                 940
Leu Asn Tyr Gly Pro His Gln Trp Arg Gly Asp Phe Gln Phe Asn Ile
945                 950                 955                 960
Ser Arg Tyr Ser Gln Gln Gln Leu Met Glu Thr Ser His Arg His Leu
                965                 970                 975
Leu His Ala Glu Glu Gly Thr Trp Leu Asn Ile Asp Gly Phe His Met
            980                 985                 990
```

-continued

Gly Ile Gly Gly Asp Asp Ser Trp Ser Pro Ser Val Ser Ala Glu Phe
            995                 1000                1005

Gln Leu Ser Ala Gly Arg Tyr His Tyr Gln Leu Val Trp Cys Gln
    1010                1015                1020

Lys

<210> SEQ ID NO 66
<211> LENGTH: 1119
<212> TYPE: DNA
<213> ORGANISM: Staphylococcus epidermidis

<400> SEQUENCE: 66

| | |
|---|---|
| atgactaaac tccatatctt ttactttct ttaatgtact ttcttattgg catgatacac | 60 |
| acttttgtcg gttcatttaa tcaattctta aaaatagaac ttaatatgaa tcaatcagat | 120 |
| gtatcaaatc taattagtat tcagttcata acatttatga ttggagtatt ttattctacc | 180 |
| ttcttagtta ataaagacat aaagaatttt ttaaaaataa tacatttatt tattctatta | 240 |
| attactacta cttttattat atttgaacat tacttaataa tatatctgat tgtagctata | 300 |
| ttaggttttt gcgctggatt tattgaatca tctatcgcat catatatttt taatagtaag | 360 |
| tttgagtccg ctaaaacttt tggatatata gaatcatttt ttgcagtagg gtcatttttg | 420 |
| ctccctgtaa ttgtgaaagt gtttgaatac cattcagata caaaacacgc tattatcttt | 480 |
| atacttataa taaatataat cttatttta attatctatt cattagagtt tgaagtaagt | 540 |
| agcagcgata gaaataaaat acccatactg tcttttaata aaaagtcaat gctagttatg | 600 |
| attattttta catggtgttt cttttatatt agtatagaaa caaatttttc aaatttacta | 660 |
| ccatatatca acttagtttc tgaaaaatat agctatatta ctgtaagtat attttgggtt | 720 |
| ggaataatta taggaaggtt tttatatacg ctaatattga cgttaattag attcaggcta | 780 |
| gaatcattac tattaacata tacagtgaca tctttttttc tatatattat tttaatatat | 840 |
| ttgaatactc aagatgaagt caaattaata attttgtttt acttactct attcttagca | 900 |
| cctatgttcc ctttaggtgt tagtatcatt aatcaacata gtagtaataa gaacttacta | 960 |
| actagtattt ttattgctgt agctggatgt ggtggtgcag ttggtgcagt aattataaaa | 1020 |
| tcagctttat acattcatat tcccgtacat ttatctattt tattaatatt aatgacttgc | 1080 |
| ttattttaa gtactgtgat tttaaaaata aagctttaa | 1119 |

<210> SEQ ID NO 67
<211> LENGTH: 372
<212> TYPE: PRT
<213> ORGANISM: Staphylococcus epidermidis

<400> SEQUENCE: 67

Met Thr Lys Leu His Ile Phe Tyr Phe Ser Leu Met Tyr Phe Leu Ile
1               5                   10                  15

Gly Met Ile His Thr Phe Val Gly Ser Phe Asn Gln Phe Leu Lys Ile
            20                  25                  30

Glu Leu Asn Met Asn Gln Ser Asp Val Ser Asn Leu Ile Ser Ile Gln
        35                  40                  45

Phe Ile Thr Phe Met Ile Gly Val Phe Tyr Ser Thr Phe Leu Val Asn
    50                  55                  60

Lys Asp Ile Lys Asn Phe Leu Lys Ile Ile His Leu Phe Ile Leu Leu
65                  70                  75                  80

Ile Thr Thr Thr Phe Ile Ile Phe Glu His Tyr Leu Ile Ile Tyr Leu

```
            85                  90                  95
Ile Val Ala Ile Leu Gly Phe Cys Ala Gly Phe Ile Glu Ser Ser Ile
            100                 105                 110
Ala Ser Tyr Ile Phe Asn Ser Lys Phe Glu Ser Ala Lys Thr Phe Gly
            115                 120                 125
Tyr Ile Glu Ser Phe Phe Ala Val Gly Ser Phe Leu Leu Pro Val Ile
            130                 135                 140
Val Lys Val Phe Glu Tyr His Ser Asp Thr Lys His Ala Ile Ile Phe
145                 150                 155                 160
Ile Leu Ile Ile Asn Ile Ile Leu Phe Leu Ile Ile Tyr Ser Leu Glu
            165                 170                 175
Phe Glu Val Ser Ser Ser Asp Arg Asn Lys Ile Pro Ile Leu Ser Phe
            180                 185                 190
Asn Lys Lys Ser Met Leu Val Met Ile Ile Phe Thr Trp Cys Phe Phe
            195                 200                 205
Tyr Ile Ser Ile Glu Thr Asn Phe Ser Asn Leu Leu Pro Tyr Ile Asn
            210                 215                 220
Leu Val Ser Glu Lys Tyr Ser Tyr Ile Thr Val Ser Ile Phe Trp Val
225                 230                 235                 240
Gly Ile Ile Ile Gly Arg Phe Leu Tyr Thr Leu Ile Leu Thr Leu Ile
            245                 250                 255
Arg Phe Arg Leu Glu Ser Leu Leu Leu Thr Tyr Thr Val Thr Ser Phe
            260                 265                 270
Phe Leu Tyr Ile Ile Leu Ile Tyr Leu Asn Thr Gln Asp Glu Val Lys
            275                 280                 285
Leu Ile Ile Leu Phe Leu Leu Thr Leu Phe Leu Ala Pro Met Phe Pro
290                 295                 300
Leu Gly Val Ser Ile Ile Asn Gln His Ser Ser Asn Lys Asn Leu Leu
305                 310                 315                 320
Thr Ser Ile Phe Ile Ala Val Ala Gly Cys Gly Gly Ala Val Gly Ala
            325                 330                 335
Val Ile Ile Lys Ser Ala Leu Tyr Ile His Ile Pro Val His Leu Ser
            340                 345                 350
Ile Leu Leu Ile Leu Met Thr Cys Leu Phe Leu Ser Thr Val Ile Leu
            355                 360                 365
Lys Ile Lys Leu
    370

<210> SEQ ID NO 68
<211> LENGTH: 1350
<212> TYPE: DNA
<213> ORGANISM: Lactobacillus brevis

<400> SEQUENCE: 68
atgcaagcaa ctgaaaccaa gcacggctgg acccaattag cggacggcta cctcagcaaa        60
acgccattat ttcaatttat tttagtttca ttgatttttc cactgtgggg aactgcggca       120
agtttaaatg atattttgat tacgcagttc aagacagtct ttcaacttaa cgatgccgcg       180
acggcctttg ttcaaagtgc cttctatggt gggtatttct taattgccat tccggcatcc       240
ctgattatta agaagaacag ttataaattt gccatcatga ccgggttgat ctttatatc       300 atcgggtgtg gctgtttttt cccggcctca catctcgcaa cttacagtat gttcctggtg       360
gccatctttg ccattgccat tggtctgagc ttcttggaaa catcatgtga tacgtatagt       420
tcaatgctgg gaccgaagca acacgccacg atgcgcttga acttttccca gacattaatt       480
```

```
ccgttaggcg acatcatggg aattgtttta gggaagtact taattttttgg ttctgtaggt    540 aatttatctg aaaagatgag ccatatgcac ggcgcagcac gcattgctta cggcgaacag    600
atgttacaat tgacgttacg gccttacaaa tatatcttaa tcgtgttact cgtgatgctg    660
attatctttg ccgtaacgcc tatgccacgg gctaaggcga cgaaggaaat tggtggggaa    720
caacaagaag aacgtcctag tcttggggaa actctgaagt atctatcaca caacaagcac    780
tatattaaag gggtagtaac ccagttcttt tatgcgggtc tgcaaacaac cgtctggtcc    840
tttacgattc gtttggtatt aaacttgaac catcaaatta ccgacagcgg tgcatcaacc    900
tttatgattt atagttatgt ggcgtggttc gttggtaagc tggttgccaa tacctttatg    960
agtcgcttct caattacgaa ggtgctgacg tggtactcct tattggggac attagcatta   1020
gttgtgacct ttacggttcc gaatatgatt gcggtctacg cagccatctt aacgagtttc   1080
ttctttggtc cagaatggcc aacaatttat gcgcacacgt tggatgccgt tacggagaag   1140
aaatacactg aaacggctgg ggcaattatc gtgatggccc tgatcggtgg tgcagtcatt   1200
ccagccattc aaggcctggt ttctgatgcg accggttcaa tgcagttctc attcgttgta   1260
ccaatgctct gctacgcttt aattacaggg tacttttttct tcgaacatcg ttttgagaaa   1320 gctcaccctta acgaagttca agaacattaa                                    1350
```

<210> SEQ ID NO 69
<211> LENGTH: 449
<212> TYPE: PRT
<213> ORGANISM: Lactobacillus brevis

<400> SEQUENCE: 69

```
Met Gln Ala Thr Glu Thr Lys His Gly Trp Thr Gln Leu Ala Asp Gly
1               5                   10                  15

Tyr Leu Ser Lys Thr Pro Leu Phe Gln Phe Ile Leu Val Ser Leu Ile
            20                  25                  30

Phe Pro Leu Trp Gly Thr Ala Ala Ser Leu Asn Asp Ile Leu Ile Thr
        35                  40                  45

Gln Phe Lys Thr Val Phe Gln Leu Asn Asp Ala Ala Thr Ala Phe Val
    50                  55                  60

Gln Ser Ala Phe Tyr Gly Gly Tyr Phe Leu Ile Ala Ile Pro Ala Ser
65                  70                  75                  80

Leu Ile Ile Lys Lys Asn Ser Tyr Lys Phe Ala Ile Met Thr Gly Leu
                85                  90                  95

Ile Phe Tyr Ile Ile Gly Cys Gly Leu Phe Pro Ala Ser His Leu
            100                 105                 110

Ala Thr Tyr Ser Met Phe Leu Val Ala Ile Phe Ala Ile Ala Ile Gly
        115                 120                 125

Leu Ser Phe Leu Glu Thr Ser Cys Asp Thr Tyr Ser Ser Met Leu Gly
    130                 135                 140

Pro Lys Gln His Ala Thr Met Arg Leu Asn Phe Ser Gln Thr Leu Ile
145                 150                 155                 160

Pro Leu Gly Asp Ile Met Gly Ile Val Leu Gly Lys Tyr Leu Ile Phe
                165                 170                 175

Gly Ser Val Gly Asn Leu Ser Glu Lys Met Ser His Met His Gly Ala
            180                 185                 190

Ala Arg Ile Ala Tyr Gly Glu Gln Met Leu Gln Leu Thr Leu Arg Pro
        195                 200                 205

Tyr Lys Tyr Ile Leu Ile Val Leu Leu Val Met Leu Ile Ile Phe Ala
```

```
                210                 215                 220
Val Thr Pro Met Pro Arg Ala Lys Ala Thr Lys Glu Ile Gly Gly Glu
225                 230                 235                 240

Gln Gln Glu Glu Arg Pro Ser Leu Gly Glu Thr Leu Lys Tyr Leu Ser
                245                 250                 255

His Asn Lys His Tyr Ile Lys Gly Val Val Thr Gln Phe Phe Tyr Ala
            260                 265                 270

Gly Leu Gln Thr Thr Val Trp Ser Phe Thr Ile Arg Leu Val Leu Asn
        275                 280                 285

Leu Asn His Gln Ile Thr Asp Ser Gly Ala Ser Thr Phe Met Ile Tyr
    290                 295                 300

Ser Tyr Val Ala Trp Phe Val Gly Lys Leu Val Ala Asn Thr Phe Met
305                 310                 315                 320

Ser Arg Phe Ser Ile Thr Lys Val Leu Thr Trp Tyr Ser Leu Leu Gly
                325                 330                 335

Thr Leu Ala Leu Val Val Thr Phe Thr Val Pro Asn Met Ile Ala Val
            340                 345                 350

Tyr Ala Ala Ile Leu Thr Ser Phe Phe Gly Pro Glu Trp Pro Thr
        355                 360                 365

Ile Tyr Ala His Thr Leu Asp Ala Val Thr Glu Lys Lys Tyr Thr Glu
    370                 375                 380

Thr Ala Gly Ala Ile Ile Val Met Ala Leu Ile Gly Gly Ala Val Ile
385                 390                 395                 400

Pro Ala Ile Gln Gly Leu Val Ser Asp Ala Thr Gly Ser Met Gln Phe
                405                 410                 415

Ser Phe Val Val Pro Met Leu Cys Tyr Ala Leu Ile Thr Gly Tyr Phe
            420                 425                 430

Phe Phe Glu His Arg Phe Glu Lys Ala His Pro Asn Glu Val Gln Glu
        435                 440                 445

His

<210> SEQ ID NO 70
<211> LENGTH: 2379
<212> TYPE: DNA
<213> ORGANISM: Escherichia coli

<400> SEQUENCE: 70
atgtccaaca atggctcgtc accgctggtg ctttggtata accaactcgg catgaatgat     60
gtagacaggg ttgggggcaa aaatgcctcc ctgggtgaaa tgattactaa tctttccgga    120
atgggtgttt ccgttccgaa tggtttcgcc acaaccgccg acgcgtttaa ccagtttctg    180
gaccaaagcg gcgtaaacca gcgcatttat gaactgctgg ataaaacgga tattgacgat    240
gttactcagc ttgcgaaagc gggcgcgcaa atccgccagt ggattatcga cactcccttc    300
cagcctgagc tggaaaacgc catccgcgaa gcctatgcac agctttccgc cgatgacgaa    360
aacgcctctt ttgcggtgcg ctcctccgcc accgcagaag atatgccgga cgcttctttt    420
gccggtcagc aggaaaacctt cctcaacgtt cagggttttg acgccgttct cgtggcagtg    480
aaacatgtat ttgcttctct gtttaacgat cgcgccatct cttatcgtgt gcaccagggt    540
tacgatcacc gtggtgtggc gctctccgcc ggtgttcaac ggatggtgcg ctctgacctc    600
gcatcatctg gcgtgatgtt ctccattgat accgaatccg gctttgacca ggtggtgttt    660
atcacttccg catgggggcct tggtgagatg gtcgtgcagg gtgcggttaa cccggatgag    720
ttttacgtgc ataaaccgac actggcggcg aatcgcccgg ctatcgtgcg ccgcaccatg    780
```

```
gggtcgaaaa aaatccgcat ggtttacgcg ccgacccagg agcacggcaa gcaggttaaa    840
atcgaagacg taccgcagga acagcgtgac atcttctcgc tgaccaacga agaagtgcag    900
gaactggcaa acaggccgt acaaattgag aaacactacg gtcgcccgat ggatattgag    960
tgggcgaaag atggccacac cggtaaactg ttcattgtgc aggcgcgtcc ggaaaccgtg   1020
cgctcacgcg gtcaggtcat ggagcgttat acgctgcatt cacagggtaa gattatcgcc   1080
gaaggccgtg ctatcggtca tcgcatcggt gcgggtccgg tgaaagtcat ccatgacatc   1140
agcgaaatga accgcatcga acctggcgac gtgctggtta ctgacatgac cgacccggac   1200
tgggaaccga tcatgaagaa agcatctgcc atcgtcacca accgtggcgg tcgtacctgt   1260
cacgcggcga tcatcgctcg tgaactgggc attccggcgg tagtgggctg tggagatgca   1320
acagaacgga tgaaagacgg tgagaacgtc actgtttctt gtgccgaagg tgataccggt   1380
tacgtctatg cggagttgct ggaatttagc gtgaaaagct ccagcgtaga acgatgccg   1440 gatctgccgt tgaaagtgat gatgaacgtc ggtaacccgg accgtgcttt cgacttcgcc   1500
tgcctaccga acgaaggcgt gggccttgcg cgtctggaat ttatcatcaa ccgtatgatt   1560
ggcgtccacc cacgcgcact gcttgagttt gacgatcagg aaccgcagtt gcaaaacgaa   1620
atccgcgaga tgatgaaagg ttttgattct ccgcgtgaat tttacgttgg tcgtctgact   1680
gaagggatcg cgacgctggg tgccgcgttt tatccgaagc gcgtcattgt ccgtctctct   1740 gatttaaat cgaacgaata tgccaacctg gtcggtggtg agcgttacga gccagatgaa   1800
gagaacccga tgctcggctt ccgtggcgcg ggccgctatg tttccgacag cttccgcgac   1860
tgtttcgcgc tggagtgtga agcagtgaaa cgtgtgcgca acgacatggg actgaccaac   1920
gttgagatca tgatcccgtt cgtgcgtacc gtagatcagg cgaaagcggt ggttgaagaa   1980
ctggcgcgtc aggggctgaa acgtggcgag aacgggctga aaatcatcat gatgtgtgaa   2040
atcccgtcca acgccttgct ggccgagcag ttcctcgaat atttcgacgg cttctcaatt   2100
ggctcaaacg atatgacgca gctggcgctc ggtctggacc gtgactccgg cgtggtgtct   2160
gaattgttcg atgagcgcaa cgatgcggtg aaagcactgc tgtcgatggc tatccgtgcc   2220
gcgaagaaac agggcaaata tgtcgggatt tgcggtcagg gtccgtccga ccacgaagac   2280
tttgccgcat ggttgatgga agaggggatc gatagcctgt ctctgaaccc ggacaccgtg   2340
gtgcaaacct ggttaagcct ggctgaactg aagaaataa                         2379
```

<210> SEQ ID NO 71
<211> LENGTH: 792
<212> TYPE: PRT
<213> ORGANISM: Escherichia coli

<400> SEQUENCE: 71

```
Met Ser Asn Asn Gly Ser Ser Pro Leu Val Leu Trp Tyr Asn Gln Leu
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80

Val Thr Gln Leu Ala Lys Ala Gly Ala Gln Ile Arg Gln Trp Ile Ile
```

```
                    85                  90                  95
Asp Thr Pro Phe Gln Pro Glu Leu Glu Asn Ala Ile Arg Glu Ala Tyr
                100                 105                 110

Ala Gln Leu Ser Ala Asp Asp Glu Asn Ala Ser Phe Ala Val Arg Ser
            115                 120                 125

Ser Ala Thr Ala Glu Asp Met Pro Asp Ala Ser Phe Ala Gly Gln Gln
        130                 135                 140

Glu Thr Phe Leu Asn Val Gln Gly Phe Asp Ala Val Leu Val Ala Val
145                 150                 155                 160

Lys His Val Phe Ala Ser Leu Phe Asn Asp Arg Ala Ile Ser Tyr Arg
                165                 170                 175

Val His Gln Gly Tyr Asp His Arg Gly Val Ala Leu Ser Ala Gly Val
                180                 185                 190

Gln Arg Met Val Arg Ser Asp Leu Ala Ser Ser Gly Val Met Phe Ser
            195                 200                 205

Ile Asp Thr Glu Ser Gly Phe Asp Gln Val Val Phe Ile Thr Ser Ala
        210                 215                 220

Trp Gly Leu Gly Glu Met Val Gln Gly Ala Val Asn Pro Asp Glu
225                 230                 235                 240

Phe Tyr Val His Lys Pro Thr Leu Ala Ala Asn Arg Pro Ala Ile Val
                245                 250                 255

Arg Arg Thr Met Gly Ser Lys Lys Ile Arg Met Val Tyr Ala Pro Thr
            260                 265                 270

Gln Glu His Gly Lys Gln Val Lys Ile Glu Asp Val Pro Gln Glu Gln
        275                 280                 285

Arg Asp Ile Phe Ser Leu Thr Asn Glu Glu Val Gln Glu Leu Ala Lys
    290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                325                 330                 335

Pro Glu Thr Val Arg Ser Arg Gly Gln Val Met Glu Arg Tyr Thr Leu
            340                 345                 350

His Ser Gln Gly Lys Ile Ile Ala Glu Gly Arg Ala Ile Gly His Arg
        355                 360                 365

Ile Gly Ala Gly Pro Val Lys Val Ile His Asp Ile Ser Glu Met Asn
    370                 375                 380

Arg Ile Glu Pro Gly Asp Val Leu Val Thr Asp Met Thr Asp Pro Asp
385                 390                 395                 400

Trp Glu Pro Ile Met Lys Lys Ala Ser Ala Ile Val Thr Asn Arg Gly
                405                 410                 415

Gly Arg Thr Cys His Ala Ala Ile Ile Ala Arg Glu Leu Gly Ile Pro
            420                 425                 430

Ala Val Val Gly Cys Gly Asp Ala Thr Glu Arg Met Lys Asp Gly Glu
        435                 440                 445

Asn Val Thr Val Ser Cys Ala Glu Gly Asp Thr Gly Tyr Val Tyr Ala
    450                 455                 460

Glu Leu Leu Glu Phe Ser Val Lys Ser Ser Val Glu Thr Met Pro
465                 470                 475                 480

Asp Leu Pro Leu Lys Val Met Met Asn Val Gly Asn Pro Asp Arg Ala
                485                 490                 495

Phe Asp Phe Ala Cys Leu Pro Asn Glu Gly Val Gly Leu Ala Arg Leu
            500                 505                 510
```

Glu Phe Ile Ile Asn Arg Met Ile Gly Val His Pro Arg Ala Leu Leu
            515                 520                 525

Glu Phe Asp Asp Gln Glu Pro Gln Leu Gln Asn Glu Ile Arg Glu Met
        530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Pro Lys Arg Val Ile
                565                 570                 575

Val Arg Leu Ser Asp Phe Lys Ser Asn Glu Tyr Ala Asn Leu Val Gly
            580                 585                 590

Gly Glu Arg Tyr Glu Pro Asp Glu Asn Pro Met Leu Gly Phe Arg
        595                 600                 605

Gly Ala Gly Arg Tyr Val Ser Asp Ser Phe Arg Asp Cys Phe Ala Leu
        610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
        675                 680                 685

Glu Gln Phe Leu Glu Tyr Phe Asp Gly Phe Ser Ile Gly Ser Asn Asp
        690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
        755                 760                 765

Gly Ile Asp Ser Leu Ser Leu Asn Pro Asp Thr Val Val Gln Thr Trp
        770                 775                 780

Leu Ser Leu Ala Glu Leu Lys Lys
785                 790

<210> SEQ ID NO 72
<211> LENGTH: 1623
<212> TYPE: DNA
<213> ORGANISM: Escherichia coli

<400> SEQUENCE: 72
atgcgcgtta acaatggttt gaccccgcaa gaactcgagg cttatggtat cagtgacgta      60
catgatatcg tttacaaccc aagctacgac ctgctgtatc aggaagagct cgatccgagc     120
ctgacaggtt atgagcgcgg ggtgttaact aatctgggtg ccgttgccgt cgataccggg     180
atcttcaccg tcgttcacc aaaagataag tatatcgtcc gtgacgatac cactcgcgat     240
actttctggt gggcagacaa aggcaaaggt aagaacgaca caaacctct ctctccggaa     300 acctggcagc atctgaaagg cctggtgacc aggcagcttt ccggcaaacg tctgttcgtt     360
gtcgacgctt ctgtggtgc gaaccccggat actcgtcttt ccgtccgttt catcaccgaa     420
gtggcctggc aggcgcattt tgtcaaaaac atgtttattc gcccgagcga tgaagaactg     480

```
gcaggtttca aaccagactt tatcgttatg aacggcgcga agtgcactaa cccgcagtgg    540
aaagaacagg gtctcaactc cgaaaacttc gtggcgttta acctgaccga gcgcatgcag    600
ctgattggcg gcacctggta cggcggcgaa atgaagaaag gatgttctc gatgatgaac     660 tacctgctgc cgctgaaagg tatcgcttct atgcactgct ccgccaacgt tggtgagaaa    720
ggcgatgttg cggtgttctt cggcctttcc ggcaccggta aaaccaccct ttccaccgac    780
ccgaaacgtc gcctgattgg cgatgacgaa cacggctggg acgatgacgg cgtgtttaac    840
ttcgaaggcg gctgctacgc aaaaactatc aagctgtcga agaagcgga acctgaaatc     900 tacaacgcta tccgtcgtga tgcgttgctg gaaaacgtca ccgtgcgtga agatggcact    960
atcgactttg atgatggttc aaaaaccgag aacacccgcg tttcttatcc gatctatcac    1020
atcgataaca ttgttaagcc ggtttccaaa gcgggccacg cgactaaggt tatcttcctg    1080
actgctgatg ctttcggcgt gttgccgccg gtttctcgcc tgactgccga tcaaacccag    1140
tatcacttcc tctctggctt caccgccaaa ctggccggta ctgagcgtgg catcaccgaa    1200
ccgacgccaa ccttctccgc ttgcttcggc gcggcattcc tgtcgctgca cccgactcag    1260
tacgcagaag tgctggtgaa acgtatgcag gcggcgggcg cgcaggctta tctggttaac    1320
actggctgga acggcactgg caaacgtatc tcgattaaag ataccccgcgc cattatcgac    1380 gccatcctca acggttcgct ggataatgca gaaaccttca ctctgccgat gtttaacctg    1440
gcgatcccaa ccgaactgcc gggcgtagac acgaagattc tcgatccgcg taacacctac    1500
gcttctccgg aacagtggca ggaaaaagcc gaaaccctgg cgaaactgtt tatcgacaac    1560
ttcgataaat acaccgacac ccctgcgggt gccgcgctgg tagcggctgg tccgaaactg    1620
taa                                                                  1623
```

<210> SEQ ID NO 73
<211> LENGTH: 540
<212> TYPE: PRT
<213> ORGANISM: Escherichia coli

<400> SEQUENCE: 73

Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr

```
                165                 170                 175
Asn Pro Gln Trp Lys Glu Gln Gly Leu Asn Ser Glu Asn Phe Val Ala
        180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
        210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
    530                 535                 540

<210> SEQ ID NO 74
<211> LENGTH: 1443
<212> TYPE: DNA
<213> ORGANISM: Escherichia coli

<400> SEQUENCE: 74
```

| | |
|---|---|
| atgtccagaa ggcttcgcag aacaaaaatc gttaccacgt taggcccagc aacagatcgc | 60 |
| gataataatc ttgaaaaagt tatcgcggcg ggtgccaacg ttgtacgtat gaacttttct | 120 |
| cacggctcgc ctgaagatca caaatgcgc gcggataaag ttcgtgagat tgccgcaaaa | 180 |
| ctggggcgtc atgtggctat tctgggtgac ctccagggc ccaaaatccg tgtatccacc | 240 |
| tttaagaag gcaaagtttt cctcaatatt ggggataaat tcctgctcga cgccaacctg | 300 |
| ggtaaaggtg aaggcgacaa agaaaaagtc ggtatcgact acaaaggcct gcctgctgac | 360 |
| gtcgtgcctg gtgacatcct gctgctggac gatggtcgcg tccagttaaa agtactggaa | 420 |
| gttcagggca tgaaagtgtt caccgaagtc accgtcggtg gtcccctctc aacaataaa | 480 |
| ggtatcaaca aacttggcgg cggtttgtcg gctgaagcgc tgaccgaaaa agacaaagca | 540 |
| gacattaaga ctgcggcgtt gattggcgta gattacctgg ctgtctcctt cccacgctgt | 600 |
| ggcgaagatc tgaactatgc ccgtcgcctg gcacgcgatg caggatgtga tgcgaaaatt | 660 |
| gttgccaagg ttaacgtgc ggaagccgtt tgcagccagg atgcaatgga tgacatcatc | 720 |
| ctcgcctctg acgtggtaat ggttcacgt ggcgacctcg tgtggaaat tggcgacccg | 780 |
| gaactggtcg gcattcagaa agcgttgatc cgtcgtgcgc gtcagctaaa ccgagcggta | 840 |
| atcacggcga cccagatgat ggagtcaatg attactaacc cgatgccgac gcgtgcagaa | 900 |
| gtcatggacg tagcaaacgc cgttctggat ggtactgacg ctgtgatgct gtctgcagaa | 960 |
| actgccgctg gcagtatcc gtcagaaacc gttgcagcca tggcgcgcgt ttgcctgggt | 1020 |
| gcggaaaaaa tcccgagcat caacgtttct aaacaccgtc tggacgttca gttcgacaat | 1080 |
| gtggaagaag ctattgccat gtcagcaatg tacgcagcta accacctgaa aggcgttacg | 1140 |
| gcgatcatca ccatgaccga atcgggtcgt accgcgctga tgacctcccg tatcagctct | 1200 |
| ggtctgccaa ttttcgccat gtcgcgccat gaacgtacgc tgaacctgac tgctctctat | 1260 |
| cgtggcgtta cgccggtgca ctttgatagc gctaatgacg gcgtagcagc tgccagcgaa | 1320 |
| gcggttaatc tgctgcgcga taaaggttac ttgatgtctg gtgacctggt gattgtcacc | 1380 |
| cagggcgacg tgatgagtac cgtgggttct actaatacca cgcgtatttt aacggtagag | 1440 |
| taa | 1443 |

<210> SEQ ID NO 75
<211> LENGTH: 480
<212> TYPE: PRT
<213> ORGANISM: Escherichia coli

<400> SEQUENCE: 75

```
Met Ser Arg Arg Leu Arg Arg Thr Lys Ile Val Thr Thr Leu Gly Pro
1               5                   10                  15

Ala Thr Asp Arg Asp Asn Asn Leu Glu Lys Val Ile Ala Ala Gly Ala
            20                  25                  30

Asn Val Val Arg Met Asn Phe Ser His Gly Ser Pro Glu Asp His Lys
        35                  40                  45

Met Arg Ala Asp Lys Val Arg Glu Ile Ala Ala Lys Leu Gly Arg His
    50                  55                  60

Val Ala Ile Leu Gly Asp Leu Gln Gly Pro Lys Ile Arg Val Ser Thr
65                  70                  75                  80

Phe Lys Glu Gly Lys Val Phe Leu Asn Ile Gly Asp Lys Phe Leu Leu
                85                  90                  95

Asp Ala Asn Leu Gly Lys Gly Glu Gly Asp Lys Glu Lys Val Gly Ile
            100                 105                 110
```

```
Asp Tyr Lys Gly Leu Pro Ala Asp Val Val Pro Gly Asp Ile Leu Leu
            115                 120                 125

Leu Asp Asp Gly Arg Val Gln Leu Lys Val Leu Glu Val Gln Gly Met
130                 135                 140

Lys Val Phe Thr Glu Val Thr Val Gly Gly Pro Leu Ser Asn Asn Lys
145                 150                 155                 160

Gly Ile Asn Lys Leu Gly Gly Leu Ser Ala Glu Ala Leu Thr Glu
                165                 170                 175

Lys Asp Lys Ala Asp Ile Lys Thr Ala Leu Ile Gly Val Asp Tyr
            180                 185                 190

Leu Ala Val Ser Phe Pro Arg Cys Gly Glu Asp Leu Asn Tyr Ala Arg
            195                 200                 205

Arg Leu Ala Arg Asp Ala Gly Cys Asp Ala Lys Ile Val Ala Lys Val
210                 215                 220

Glu Arg Ala Glu Ala Val Cys Ser Gln Asp Ala Met Asp Asp Ile Ile
225                 230                 235                 240

Leu Ala Ser Asp Val Val Met Val Ala Arg Gly Asp Leu Gly Val Glu
                245                 250                 255

Ile Gly Asp Pro Glu Leu Val Gly Ile Gln Lys Ala Leu Ile Arg Arg
            260                 265                 270

Ala Arg Gln Leu Asn Arg Ala Val Ile Thr Ala Thr Gln Met Met Glu
            275                 280                 285

Ser Met Ile Thr Asn Pro Met Pro Thr Arg Ala Glu Val Met Asp Val
290                 295                 300

Ala Asn Ala Val Leu Asp Gly Thr Asp Ala Val Met Leu Ser Ala Glu
305                 310                 315                 320

Thr Ala Ala Gly Gln Tyr Pro Ser Glu Thr Val Ala Ala Met Ala Arg
                325                 330                 335

Val Cys Leu Gly Ala Glu Lys Ile Pro Ser Ile Asn Val Ser Lys His
            340                 345                 350

Arg Leu Asp Val Gln Phe Asp Asn Val Glu Glu Ala Ile Ala Met Ser
            355                 360                 365

Ala Met Tyr Ala Ala Asn His Leu Lys Gly Val Thr Ala Ile Ile Thr
370                 375                 380

Met Thr Glu Ser Gly Arg Thr Ala Leu Met Thr Ser Arg Ile Ser Ser
385                 390                 395                 400

Gly Leu Pro Ile Phe Ala Met Ser Arg His Glu Arg Thr Leu Asn Leu
                405                 410                 415

Thr Ala Leu Tyr Arg Gly Val Thr Pro Val His Phe Asp Ser Ala Asn
            420                 425                 430

Asp Gly Val Ala Ala Ser Glu Ala Val Asn Leu Leu Arg Asp Lys
            435                 440                 445

Gly Tyr Leu Met Ser Gly Asp Leu Val Ile Val Thr Gln Gly Asp Val
450                 455                 460

Met Ser Thr Val Gly Ser Thr Asn Thr Thr Arg Ile Leu Thr Val Glu
465                 470                 475                 480

<210> SEQ ID NO 76
<211> LENGTH: 1413
<212> TYPE: DNA
<213> ORGANISM: Escherichia coli

<400> SEQUENCE: 76
atgaaaaaga ccaaaattgt ttgcaccatc ggaccgaaaa ccgaatctga agagatgtta     60
```

```
gctaaaatgc tggacgctgg catgaacgtt atgcgtctga acttctctca tggtgactat    120
gcagaacacg gtcagcgcat tcagaatctg cgcaacgtga tgagcaaaac tggtaaaacc    180
gccgctatcc tgcttgatac caaaggtccg gaaatccgca ccatgaaact ggaaggcggt    240
aacgacgttt ctctgaaagc tggtcagacc tttactttca ccactgataa atctgttatc    300
ggcaacagcg aaatggttgc ggtaacgtat gaaggtttca ctactgacct gtctgttggc    360
aacaccgtac tggttgacga tggtctgatc ggtatggaag ttaccgccat gaaggtaac     420
aaagttatct gtaaagtgct gaacaacggt gacctgggcg aaaacaaagg tgtgaacctg    480
cctggcgttt ccattgctct gccagcactg gctgaaaaag acaaacagga cctgatcttt    540
ggttgcgaac aaggcgtaga ctttgttgct gcttccttta ttcgtaagcg ttctgacgtt    600
atcgaaatcc gtgagcacct gaaagcgcac ggcggcgaaa acatccacat catctccaaa    660
atcgaaaacc aggaaggcct caacaacttc gacgaaatcc tcgaagcctc tgacggcatc    720
atggttgcgc gtggcgacct gggtgtgaaa atcccggtag aagaagttat cttcgcccag    780
aagatgatga tcgaaaaatg tatccgtgca cgtaaagtcg ttatcactgc gacccagatg    840
ctggattcca tgatcaaaaa cccacgcccg actcgcgcag aagccggtga cgttgcaaac    900
gccatcctcg acggtactga cgcagtgatg ctgtctggtg aatccgcaaa aggtaaatac    960
ccgctggaag cggtttctat catggcgacc atctgcgaac gtaccgaccg cgtgatgaac   1020
agccgtctcg agttcaacaa tgacaaccgt aaactgcgca ttaccgaagc ggtatgccgt   1080
ggtgccgttg aaactgctga aaaactggat gctccgctga tcgtggttgc tactcagggc   1140
ggtaaatctg ctcgcgcagt acgtaaatac ttcccggatg ccaccatcct ggcactgacc   1200
accaacgaaa aacggctca tcagttggta ctgagcaaag gcgttgtgcc gcagcttgtt   1260
aaagagatca cttctactga tgatttctac cgtctgggta agaactggc tctgcagagc   1320
ggtctggcac acaaaggtga cgttgtagtt atggtttctg gtgcactggt accgagcggc   1380
actactaaca ccgcatctgt tcacgtcctg taa                                 1413
```

<210> SEQ ID NO 77
<211> LENGTH: 470
<212> TYPE: PRT
<213> ORGANISM: Escherichia coli

<400> SEQUENCE: 77

```
Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
```

```
            130                 135                 140
Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
        195                 200                 205

Ala His Gly Gly Glu Asn Ile His Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
        355                 360                 365

Leu Asp Ala Pro Leu Ile Val Val Ala Thr Gln Gly Gly Lys Ser Ala
    370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
            420                 425                 430

Gly Lys Glu Leu Ala Leu Gln Ser Gly Leu Ala His Lys Gly Asp Val
        435                 440                 445

Val Val Met Val Ser Gly Ala Leu Val Pro Ser Gly Thr Thr Asn Thr
    450                 455                 460

Ala Ser Val His Val Leu
465                 470

<210> SEQ ID NO 78
<211> LENGTH: 1410
<212> TYPE: DNA
<213> ORGANISM: Escherichia coli

<400> SEQUENCE: 78
atgtccgctg aacacgtact gacgatgctg aacgagcacg aagtgaagtt tgttgatttg      60
cgcttcaccg atactaaagg taaagaacag cacgtcacta tccctgctca tcaggtgaat     120
gctgaattct tcgaagaagg caaaatgttt gacggctcct cgattggcgg ctggaaaggc     180
```

```
attaacgagt ccgacatggt gctgatgcca gacgcatcca ccgcagtgat tgacccgttc    240
ttcgccgact ccaccctgat tatccgttgc gacatccttg aacctggcac cctgcaaggc    300
tatgaccgtg acccgcgctc cattgcgaag cgcgccgaag attacctgcg ttccactggc    360
attgccgaca ccgtactgtt cgggccagaa cctgaattct tcctgttcga tgacatccgt    420
ttcggatcat ctatctccgg ttcccacgtt gctatcgacg atatcgaagg cgcatggaac    480
tcctccaccc aatacgaagg tggtaacaaa ggtcaccgtc cggcagtgaa aggcggttac    540
ttcccggttc caccggtaga ctcggctcag gatattcgtt ctgaaatgtg tctggtgatg    600
gaacagatgg gtctggtggt tgaagcccat caccacgaag tagcgactgc tggtcagaac    660
gaagtggcta cccgcttcaa taccatgacc aaaaaagctg acgaaattca gatctacaaa    720
tatgttgtgc acaacgtagc gcaccgcttc ggtaaaaccg cgacctttat gccaaaaccg    780
atgttcggtg ataacggctc cggtatgcac tgccacatgt ctctgtctaa aaacggcgtt    840
aacctgttcg caggcgacaa atacgcaggt ctgtctgagc aggcgctgta ctacattggc    900
ggcgtaatca aacacgctaa agcgattaac gccctggcaa acccgaccac caactcttat    960
aagcgtctgg tcccgggcta tgaagcaccg gtaatgctgg cttactctgc gcgtaaccgt    1020
tctgcgtcta tccgtattcc ggtggtttct tctccgaaag cacgtcgtat cgaagtacgt    1080
ttcccggatc cggcagctaa cccgtacctg tgctttgctg ccctgctgat ggccggtctt    1140
gatggtatca agaacaagat ccatccgggc gaagccatgg acaaaaacct gtatgacctg    1200
ccgccagaag aagcgaaaga gatcccacag gttgcaggct ctctggaaga agcactgaac    1260
gaactggatc tggaccgcga gttcctgaaa gccggtggcg tgttcactga cgaagcaatt    1320
gatgcgtaca tcgctctgcg tcgcgaagaa gatgaccgcg tgcgtatgac tccgcatccg    1380
gtagagtttg agctgtacta cagcgtctaa                                     1410
```

<210> SEQ ID NO 79  
<211> LENGTH: 469  
<212> TYPE: PRT  
<213> ORGANISM: Escherichia coli

<400> SEQUENCE: 79

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Val Ile Asp Pro Phe
65                  70                  75                  80

Phe Ala Asp Ser Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
            100                 105                 110

Glu Asp Tyr Leu Arg Ser Thr Gly Ile Ala Asp Thr Val Leu Phe Gly
        115                 120                 125

Pro Glu Pro Glu Phe Phe Leu Phe Asp Asp Ile Arg Phe Gly Ser Ser
    130                 135                 140

Ile Ser Gly Ser His Val Ala Ile Asp Asp Ile Glu Gly Ala Trp Asn
145                 150                 155                 160
```

Ser Ser Thr Gln Tyr Glu Gly Gly Asn Lys Gly His Arg Pro Ala Val
             165                 170                 175

Lys Gly Gly Tyr Phe Pro Val Pro Val Asp Ser Ala Gln Asp Ile
             180                 185                 190

Arg Ser Glu Met Cys Leu Val Met Glu Gln Met Gly Leu Val Val Glu
             195                 200                 205

Ala His His His Glu Val Ala Thr Ala Gly Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
             245                 250                 255

Met Pro Lys Pro Met Phe Gly Asp Asn Gly Ser Gly Met His Cys His
             260                 265                 270

Met Ser Leu Ser Lys Asn Gly Val Asn Leu Phe Ala Gly Asp Lys Tyr
             275                 280                 285

Ala Gly Leu Ser Glu Gln Ala Leu Tyr Tyr Ile Gly Gly Val Ile Lys
             290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
             325                 330                 335

Ala Arg Asn Arg Ser Ala Ser Ile Arg Ile Pro Val Val Ser Ser Pro
             340                 345                 350

Lys Ala Arg Arg Ile Glu Val Arg Phe Pro Asp Pro Ala Ala Asn Pro
             355                 360                 365

Tyr Leu Cys Phe Ala Ala Leu Leu Met Ala Gly Leu Asp Gly Ile Lys
             370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
             405                 410                 415

Glu Ala Leu Asn Glu Leu Asp Leu Asp Arg Gly Phe Leu Lys Ala Gly
             420                 425                 430

Gly Val Phe Thr Asp Glu Ala Ile Asp Ala Tyr Ile Ala Leu Arg Arg
             435                 440                 445

Glu Glu Asp Asp Arg Val Arg Met Thr Pro His Pro Val Glu Phe Glu
450                 455                 460

Leu Tyr Tyr Ser Val
465

<210> SEQ ID NO 80
<211> LENGTH: 4461
<212> TYPE: DNA
<213> ORGANISM: Escherichia coli

<400> SEQUENCE: 80
atgttgtacg ataaatccct tgagagggat aactgtggtt tcggcctgat cgcccacata      60
gaaggcgaac ctagccacaa ggtagtgcgt actgcaatac acgcactggc ccgcatgcag     120
caccgtggcg cgattctcgc cgatggtaaa accggcgacg gttgcggctt gctgttacaa     180
aaaccggatc gcttttttcg catcgttgcg caggagcgcg gctggcgttt agcaaaaaac     240
tacgctgtcg ggatgctctt cctgaataaa gatcctgaac tcgccgctgc cgcacgccgc     300

```
atcgttgaag aagaactgca acgcgaaacc ttgtcgattg tgggctggcg tgatgtcccc    360
actaacgaag gcgtgctggg tgaaatcgcc ctctcctctc tgccacgcat tgagcaaatt    420
tttgtgaacg ccccggcagg ctggcgtcca cgcgatatgg agcgccgtct gtttatcgcc    480
cgccgccgca ttgaaaagcg tctcgaagcc gacaaagact tctacgtctg tagcctgtcg    540
aatctggtga acatctataa aggtctgtgt atgccgacgg atctgccgcg cttttatctg    600
gatcttgcgg acctgcgtct ggaatcggcc atttgcctgt tccaccagcg cttctccact    660
aacaccgtac cgcgctggcc gctggcgcaa ccgttccgct atctggcgca taacggtgaa    720
atcaacacca tcaccggtaa ccgccaatgg gcgcgtgcgc gtacttataa attccagaca    780
ccgcttatcc ctgacctgca cgacgccgca ccgttcgtca cgaaaccgg ctctgactcc    840 agttcgatgg ataacatgct ggaactgctg ctggcaggcg ggatggatat catccgcgcc    900
atgcgtctat tagtaccacc cgcctggcag aacaacccgg atatggaccc ggaactgcgt    960
gccttctttg actttaactc catgcatatg gagccgtggg atggcccggc gggcatcgtg   1020
atgtccgacg gtcgttttgc cgcctgtaac ctcgaccgta acggtctgcg tccggcgcgc   1080
tacgtcatca ccaaagataa gctcatcacc tgcgcctctg aagtcggtat ctgggattac   1140
cagcctgacg aagtggtcga aaaaggccgc gtcgggccag cgaactgat ggttatcgac    1200 acccgcagtg ggcgtattct gcactcggca gaaaccgatg acgatctgaa agccgccat   1260 ccatataaag agtggatgga gaaaaacgtc cgccgactgg taccgtttga agatctgccc   1320
gatgaagaag tgggtagccg cgaactggac gacgacacgc ttgccagcta ccagaaacag   1380
tttaactaca cgcgcggaaga gctggactcc gtaattcgcg tactgggcga aaacggtcag   1440
gaagcggtcg gttcgatggg cgatgatacc ccattcgccg tgctctccag tcagccgcgc   1500
attatttacg actacttccg ccagcagttt gcccaggtga ctaacccgcc aatcgacccg   1560
ctgcgtgaag cgcatgttat gtcgctcgcc accagtatcg gtcgtgaaat gaacgtcttt   1620
tgcgaagcag agggccaggc gcaccgttta agctttaaat cgccgattct gctctactcc   1680
gatttcaaac agctcacgac gatgaaagag gagcactacc gcgcagatac gctggatatc   1740
acctttgacg tcactaaaac cacgctcgaa gcgacagtca aagagctgtg cgacaaagcc   1800
gaaaaaatgg tacgtagcgg caccgtgctg ctggtgctct ccgaccggaa tatcgctaaa   1860
gatcgcctgc cggttccagc cccgatggcg gttggcgcga tccagacccg tctggtcgat   1920
caaagcctgc gttgcgatgc caacatcatc gtcgaaaccg ccagcgcccg cgatccgcac   1980
cacttcgccg tgttgctggg cttcggcgcg acggctattt atccatacct tgcctatgaa   2040
acgctgggcc gcctggtaga cacccatgcg attgccaaag attatcgtac cgtgatgctc   2100
aactaccgta acggcatcaa caaaggcttg tacaaaatca tgtccaaaat gggcatctcc   2160
accatcgcct cttaccgctg ctcgaaactg tttgaagcgg tcggtctaca cgatgatgta   2220
gtgggcctgt gcttccaggg ggcggtcagc cgcattggtg gagcaagctt tgaagacttc   2280
cagcaggatc tgctgaatct gtcgaaacgt gcctggctgg cgcgtaagcc catcagccag   2340
ggcggtctgc tgaaatacgt ccacggcggc gaataccacg cctacaaccc ggacgtggtg   2400
cgcacgctgc aacaagcggt acaaagcggc gagtacagcg actatcagga atacgcgaag   2460
ctggttaatg agcgtccggc aaccacgctg cgcgatctgc tggcaattac gccgggtgaa   2520
aacgcggtca acattgctga tgttgaaccg gcaagcgaac tgtttaaacg ctttgatacc   2580
gccgcgatgt ctatcggcgc gttaagcccg gaagcccacg aggcgctggc ggaagcgatg   2640
aacagcatcg gcggtaattc gaactccggt gaaggcggcg aagacccggc gcgctacggc   2700
```

-continued

```
accaacaaag tgtcgcgcat caagcaggtg gcttccggtc gctttggggt tactccggcg    2760
tatctggtca atgccgacgt cattcagatt aaagtcgccc agggcgcgaa gccaggcgaa    2820
ggcggtcagt tgccgggtga taaagtcacg ccttacatcg ccaaactgcg ctattcggtg    2880
cccggagtga cgctgatctc cccgccgccg caccacgata tctactctat cgaggactta    2940
gcgcagctca ttttcgacct caagcaggtt aacccgaaag cgatgatctc cgtgaagctg    3000
gtttccgaac cggagtagg caccatcgcg actggcgtgg caaaagctta tgcggacttg    3060
atcaccatcg caggctatga cggcggcacc ggcgcaagtc cgctttcatc ggtgaaatac    3120
gcaggctgtc cgtgggagct ggggcttgtt gaaacccagc aggcgctggt tgctaacggc    3180
ttgcgtcaca agatccgttt gcaggtcgat ggcggcctga aaacgggtgt cgatatcatc    3240
aaggcggcga ttctcggcgc agaaaagctt ggcttcggca ctggcccgat ggtggcgctc    3300
ggctgtaaat atctacgtat ttgccatctg aacaactgcg caacgggtgt agcaactcag    3360
gatgacaaac tgcgtaagaa ccactatcac ggcctgccat tcaaggtgac gaattacttt    3420
gagtttatcg cccgtgaaac ccgcgagctg atggcacagc ttggcgtaac acgtctggtg    3480
gatctgattg tcgcaccgga cctgctgaaa gagctggacg gtttcaccgc caaacagcag    3540
aagctggcgc tgtcgaagct gctggagact gccgaaccgc atccaggtaa ggcactctac    3600
tgcaccgaaa acaacccgcc gtttgataac ggcctgctga acgcgcagtt gctgaacag    3660 gcgaaaccgt ttgtcgatga gcgccagagc aaaaccttct ggttcgatat cgcaacacc    3720 gaccgttctg tcggcgcgtc gctttcaggc tatatcgccc agacgcacgg cgatcagggg    3780
ctggcagccg atcctatcaa agcgtacttc aacggcaccg caggccagag cttcggcgtg    3840
tggaacgcgg gcggcgtgga actgtacctg accggtgatg ccaacgacta tgtcggtaaa    3900
ggcatggcgg gcggcttaat cgccattcgt cctccggttg gttccgcctt ccgcagccat    3960
gaagcaagca ttatcggcaa cacctgcctg tatggcgcga ccggtggtcg tctgtatgcc    4020
gcaggccgcg cgggtgaacg tttcggcgtg cgtaactccg gtgctatcac cgtggtagaa    4080
ggcattggcg acaacggttg tgaatatatg acgggtggta tcgtctgcat tctgggtaaa    4140
accggcgtta acttcggtgc gggcatgacc ggcggtttcg cttacgttct cgatgaaagc    4200
ggcgatttcc gcaaacgcgt taacccggaa ctggtcgagg tcttaagcgt tgacgctctg    4260
gcgatccatg aagagcatct gcgtggtctt atcaccgagc atgtgcagca taccggctct    4320
cagcgcggtg aagagattct ggcgaactgg tcaaccttcg ccactaaatt tgcgctggtt    4380
aaaccgaagt ccagtgatgt aaaagcactg ctgggtcacc gtagtcgtag cgcagctgag    4440
ttgcgcgtgc aggcgcagta a                                              4461
```

<210> SEQ ID NO 81
<211> LENGTH: 1486
<212> TYPE: PRT
<213> ORGANISM: Escherichia coli

<400> SEQUENCE: 81

```
Met Leu Tyr Asp Lys Ser Leu Glu Arg Asp Asn Cys Gly Phe Gly Leu
1               5                   10                  15

Ile Ala His Ile Glu Gly Glu Pro Ser His Lys Val Val Arg Thr Ala
            20                  25                  30

Ile His Ala Leu Ala Arg Met Gln His Arg Gly Ala Ile Leu Ala Asp
        35                  40                  45

Gly Lys Thr Gly Asp Gly Cys Gly Leu Leu Leu Gln Lys Pro Asp Arg
```

```
            50                  55                  60
Phe Phe Arg Ile Val Ala Gln Glu Arg Gly Trp Arg Leu Ala Lys Asn
 65                  70                  75                  80

Tyr Ala Val Gly Met Leu Phe Leu Asn Lys Asp Pro Glu Leu Ala Ala
                     85                  90                  95

Ala Ala Arg Arg Ile Val Glu Glu Glu Leu Gln Arg Glu Thr Leu Ser
                    100                 105                 110

Ile Val Gly Trp Arg Asp Val Pro Thr Asn Glu Gly Val Leu Gly Glu
                115                 120                 125

Ile Ala Leu Ser Ser Leu Pro Arg Ile Glu Gln Ile Phe Val Asn Ala
            130                 135                 140

Pro Ala Gly Trp Arg Pro Arg Asp Met Glu Arg Arg Leu Phe Ile Ala
145                 150                 155                 160

Arg Arg Arg Ile Glu Lys Arg Leu Glu Ala Asp Lys Asp Phe Tyr Val
                    165                 170                 175

Cys Ser Leu Ser Asn Leu Val Asn Ile Tyr Lys Gly Leu Cys Met Pro
                180                 185                 190

Thr Asp Leu Pro Arg Phe Tyr Leu Asp Leu Ala Asp Leu Arg Leu Glu
            195                 200                 205

Ser Ala Ile Cys Leu Phe His Gln Arg Phe Ser Thr Asn Thr Val Pro
            210                 215                 220

Arg Trp Pro Leu Ala Gln Pro Phe Arg Tyr Leu Ala His Asn Gly Glu
225                 230                 235                 240

Ile Asn Thr Ile Thr Gly Asn Arg Gln Trp Ala Arg Ala Arg Thr Tyr
                245                 250                 255

Lys Phe Gln Thr Pro Leu Ile Pro Asp Leu His Asp Ala Ala Pro Phe
                260                 265                 270

Val Asn Glu Thr Gly Ser Asp Ser Ser Met Asp Asn Met Leu Glu
                275                 280                 285

Leu Leu Leu Ala Gly Gly Met Asp Ile Ile Arg Ala Met Arg Leu Leu
            290                 295                 300

Val Pro Pro Ala Trp Gln Asn Asn Pro Asp Met Asp Pro Glu Leu Arg
305                 310                 315                 320

Ala Phe Phe Asp Phe Asn Ser Met His Met Glu Pro Trp Asp Gly Pro
                325                 330                 335

Ala Gly Ile Val Met Ser Asp Gly Arg Phe Ala Ala Cys Asn Leu Asp
                340                 345                 350

Arg Asn Gly Leu Arg Pro Ala Arg Tyr Val Ile Thr Lys Asp Lys Leu
            355                 360                 365

Ile Thr Cys Ala Ser Glu Val Gly Ile Trp Asp Tyr Gln Pro Asp Glu
            370                 375                 380

Val Val Glu Lys Gly Arg Val Gly Pro Gly Glu Leu Met Val Ile Asp
385                 390                 395                 400

Thr Arg Ser Gly Arg Ile Leu His Ser Ala Glu Thr Asp Asp Asp Leu
                405                 410                 415

Lys Ser Arg His Pro Tyr Lys Glu Trp Met Glu Lys Asn Val Arg Arg
                420                 425                 430

Leu Val Pro Phe Glu Asp Leu Pro Asp Glu Val Gly Ser Arg Glu
                435                 440                 445

Leu Asp Asp Asp Thr Leu Ala Ser Tyr Gln Lys Gln Phe Asn Tyr Ser
450                 455                 460

Ala Glu Glu Leu Asp Ser Val Ile Arg Val Leu Gly Glu Asn Gly Gln
465                 470                 475                 480
```

```
Glu Ala Val Gly Ser Met Gly Asp Asp Thr Pro Phe Ala Val Leu Ser
                485             490                 495

Ser Gln Pro Arg Ile Ile Tyr Asp Tyr Phe Arg Gln Gln Phe Ala Gln
                500             505                 510

Val Thr Asn Pro Pro Ile Asp Pro Leu Arg Glu Ala His Val Met Ser
            515             520                 525

Leu Ala Thr Ser Ile Gly Arg Glu Met Asn Val Phe Cys Glu Ala Glu
        530             535                 540

Gly Gln Ala His Arg Leu Ser Phe Lys Ser Pro Ile Leu Leu Tyr Ser
545             550             555                 560

Asp Phe Lys Gln Leu Thr Thr Met Lys Glu Glu His Tyr Arg Ala Asp
                565             570                 575

Thr Leu Asp Ile Thr Phe Asp Val Thr Lys Thr Thr Leu Glu Ala Thr
                580             585                 590

Val Lys Glu Leu Cys Asp Lys Ala Glu Lys Met Val Arg Ser Gly Thr
            595             600                 605

Val Leu Leu Val Leu Ser Asp Arg Asn Ile Ala Lys Asp Arg Leu Pro
        610             615                 620

Val Pro Ala Pro Met Ala Val Gly Ala Ile Gln Thr Arg Leu Val Asp
625             630             635                 640

Gln Ser Leu Arg Cys Asp Ala Asn Ile Ile Val Glu Thr Ala Ser Ala
                645             650                 655

Arg Asp Pro His His Phe Ala Val Leu Leu Gly Phe Gly Ala Thr Ala
                660             665                 670

Ile Tyr Pro Tyr Leu Ala Tyr Glu Thr Leu Gly Arg Leu Val Asp Thr
            675             680                 685

His Ala Ile Ala Lys Asp Tyr Arg Thr Val Met Leu Asn Tyr Arg Asn
        690             695                 700

Gly Ile Asn Lys Gly Leu Tyr Lys Ile Met Ser Lys Met Gly Ile Ser
705             710             715                 720

Thr Ile Ala Ser Tyr Arg Cys Ser Lys Leu Phe Glu Ala Val Gly Leu
                725             730                 735

His Asp Asp Val Val Gly Leu Cys Phe Gln Gly Ala Val Ser Arg Ile
                740             745                 750

Gly Gly Ala Ser Phe Glu Asp Phe Gln Gln Asp Leu Leu Asn Leu Ser
            755             760                 765

Lys Arg Ala Trp Leu Ala Arg Lys Pro Ile Ser Gln Gly Gly Leu Leu
        770             775             780

Lys Tyr Val His Gly Gly Glu Tyr His Ala Tyr Asn Pro Asp Val Val
785             790             795                 800

Arg Thr Leu Gln Gln Ala Val Gln Ser Gly Glu Tyr Ser Asp Tyr Gln
                805             810                 815

Glu Tyr Ala Lys Leu Val Asn Glu Arg Pro Ala Thr Thr Leu Arg Asp
            820             825                 830

Leu Leu Ala Ile Thr Pro Gly Glu Asn Ala Val Asn Ile Ala Asp Val
        835             840                 845

Glu Pro Ala Ser Glu Leu Phe Lys Arg Phe Asp Thr Ala Ala Met Ser
850             855             860

Ile Gly Ala Leu Ser Pro Glu Ala His Glu Ala Leu Ala Glu Ala Met
865             870             875                 880

Asn Ser Ile Gly Gly Asn Ser Asn Ser Gly Glu Gly Gly Glu Asp Pro
                885             890                 895
```

-continued

```
Ala Arg Tyr Gly Thr Asn Lys Val Ser Arg Ile Lys Gln Val Ala Ser
                900                 905                 910

Gly Arg Phe Gly Val Thr Pro Ala Tyr Leu Val Asn Ala Asp Val Ile
            915                 920                 925

Gln Ile Lys Val Ala Gln Gly Ala Lys Pro Gly Glu Gly Gly Gln Leu
        930                 935                 940

Pro Gly Asp Lys Val Thr Pro Tyr Ile Ala Lys Leu Arg Tyr Ser Val
945                 950                 955                 960

Pro Gly Val Thr Leu Ile Ser Pro Pro His His Asp Ile Tyr Ser
                965                 970                 975

Ile Glu Asp Leu Ala Gln Leu Ile Phe Asp Leu Lys Gln Val Asn Pro
            980                 985                 990

Lys Ala Met Ile Ser Val Lys Leu Val Ser Glu Pro Gly Val Gly Thr
        995                 1000                1005

Ile Ala Thr Gly Val Ala Lys Ala Tyr Ala Asp Leu Ile Thr Ile
        1010                1015                1020

Ala Gly Tyr Asp Gly Gly Thr Gly Ala Ser Pro Leu Ser Ser Val
        1025                1030                1035

Lys Tyr Ala Gly Cys Pro Trp Glu Leu Gly Leu Val Glu Thr Gln
        1040                1045                1050

Gln Ala Leu Val Ala Asn Gly Leu Arg His Lys Ile Arg Leu Gln
        1055                1060                1065

Val Asp Gly Gly Leu Lys Thr Gly Val Asp Ile Ile Lys Ala Ala
        1070                1075                1080

Ile Leu Gly Ala Glu Ser Phe Gly Phe Gly Thr Gly Pro Met Val
        1085                1090                1095

Ala Leu Gly Cys Lys Tyr Leu Arg Ile Cys His Leu Asn Asn Cys
        1100                1105                1110

Ala Thr Gly Val Ala Thr Gln Asp Asp Lys Leu Arg Lys Asn His
        1115                1120                1125

Tyr His Gly Leu Pro Phe Lys Val Thr Asn Tyr Phe Glu Phe Ile
        1130                1135                1140

Ala Arg Glu Thr Arg Glu Leu Met Ala Gln Leu Gly Val Thr Arg
        1145                1150                1155

Leu Val Asp Leu Ile Gly Arg Thr Asp Leu Leu Lys Glu Leu Asp
        1160                1165                1170

Gly Phe Thr Ala Lys Gln Gln Lys Leu Ala Leu Ser Lys Leu Leu
        1175                1180                1185

Glu Thr Ala Glu Pro His Pro Gly Lys Ala Leu Tyr Cys Thr Glu
        1190                1195                1200

Asn Asn Pro Pro Phe Asp Asn Gly Leu Leu Asn Ala Gln Leu Leu
        1205                1210                1215

Gln Gln Ala Lys Pro Phe Val Asp Glu Arg Gln Ser Lys Thr Phe
        1220                1225                1230

Trp Phe Asp Ile Arg Asn Thr Asp Arg Ser Val Gly Ala Ser Leu
        1235                1240                1245

Ser Gly Tyr Ile Ala Gln Thr His Gly Asp Gln Gly Leu Ala Ala
        1250                1255                1260

Asp Pro Ile Lys Ala Tyr Phe Asn Gly Thr Ala Gly Gln Ser Phe
        1265                1270                1275

Gly Val Trp Asn Ala Gly Gly Val Glu Leu Tyr Leu Thr Gly Asp
        1280                1285                1290

Ala Asn Asp Tyr Val Gly Lys Gly Met Ala Gly Gly Leu Ile Ala
```

```
              1295                1300                1305
Ile Arg Pro Pro Val Gly Ser Ala Phe Arg Ser His Glu Ala Ser
       1310                1315                1320
Ile Ile Gly Asn Thr Cys Leu Tyr Gly Ala Thr Gly Gly Arg Leu
       1325                1330                1335
Tyr Ala Ala Gly Arg Ala Gly Glu Arg Phe Gly Val Arg Asn Ser
       1340                1345                1350
Gly Ala Ile Thr Val Val Glu Gly Ile Gly Asp Asn Gly Cys Glu
       1355                1360                1365
Tyr Met Thr Gly Gly Ile Val Cys Ile Leu Gly Lys Thr Gly Val
       1370                1375                1380
Asn Phe Gly Ala Gly Met Thr Gly Gly Phe Ala Tyr Val Leu Asp
       1385                1390                1395
Glu Ser Gly Asp Phe Arg Lys Arg Val Asn Pro Glu Leu Val Glu
       1400                1405                1410
Val Leu Ser Val Asp Ala Leu Ala Ile His Glu Glu His Leu Arg
       1415                1420                1425
Gly Leu Ile Thr Glu His Val Gln His Thr Gly Ser Gln Arg Gly
       1430                1435                1440
Glu Glu Ile Leu Ala Asn Trp Ser Thr Phe Ala Thr Lys Phe Ala
       1445                1450                1455
Leu Val Lys Pro Lys Ser Ser Asp Val Lys Ala Leu Leu Gly His
       1460                1465                1470
Arg Ser Arg Ser Ala Ala Glu Leu Arg Val Gln Ala Gln
       1475                1480                1485

<210> SEQ ID NO 82
<211> LENGTH: 1419
<212> TYPE: DNA
<213> ORGANISM: Escherichia coli

<400> SEQUENCE: 82
atgagtcaga atgtttatca atttatcgac ctgcagcgcg ttgatccgcc aaagaaaccg      60
ctgaagatcc gcaaaattga gtttgttgaa atttacgagc cgttttccga aggccaggcc     120
aaagcgcagg ctgaccgctg cctgtcgtgc ggcaacccat actgcgagtg gaaatgcccg     180
gtacacaact acatcccgaa ctggctgaag ctcgccaacg aggggcgtat ttttgaagcg     240
gcggaactgt cgcaccagac caacaccctg ccggaagttt gcggacgagt ctgcccgcaa     300
gaccgtctgt gcgaaggttc ctgcactctg aacgatgagt ttggcgcggt gaccatcggc     360
aacattgagc gctatatcaa cgataaagcg ttcgagatgg gctggcgtcc ggatatgtct     420
ggtgtgaaac agaccggtaa aaaagtggcg attatcggcg caggcccggc aggtctggcg     480
tgtgcggatg tcctgacgcg taacggcgta aaagccgttg tcttcgaccg tcatccagaa     540
attggcgggc tgctgacctt cggtattccg gccttcaagc tggaaaaaga ggtaatgacg     600
cgtcgccgtg aaatcttcac cggcatgggt attgaattca actcaatac cgaagtgggc     660 cgcgacgtac agctggacga tctgctgagt gattacgatg ccgtgttcct ggcgtcggg      720 acttatcagt caatgcgcgg cgggctgaaa acgaagacg ccgatggcgt gtacgcagcg     780
ctgccgttcc tcatcgccaa caccaaacag ttaatgggct ttggtgaaac ccgcgacgaa     840
ccgttcgtca gcatggaagg caaacgcgtg gtggtccttg cggtggcga cactgcgatg     900 gactgcgtgc gtacgtccgt gcgccaggga gcgaagcacg ttacctgtgc ctatcgtcgt     960
gatgaagaga acatgccggg ttcccgccgc gaagtgaaaa acgcgcggga agaaggcgta    1020
```

```
gagttcaaat tcaacgtcca gccgctgggt attgaagtga acggtaacgg caaagtcagc    1080
ggcgtaaaaa tggtgcgtac cgaaatgggc gaaccggacg ccaaaggccg tcgccgcgcg    1140
gagatcgttg caggttccga acatatcgtt ccggcagatg cggtgatcat ggcgtttggt    1200
ttccgtccac acaacatgga atggctggca aacacagcg tcgagctgga ttcacaaggc     1260
cgcatcatcg ccccggaagg cagcgacaac gccttccaga ccagcaaccc gaaaatcttt    1320
gctggcggcg atatcgtccg tggttccgat ctggtggtga ccgctattgc cgaaggtcgt    1380
aaggcggcag acgtattat gaactggctg gaagtttaa                            1419
```

<210> SEQ ID NO 83
<211> LENGTH: 472
<212> TYPE: PRT
<213> ORGANISM: Escherichia coli

<400> SEQUENCE: 83

```
Met Ser Gln Asn Val Tyr Gln Phe Ile Asp Leu Gln Arg Val Asp Pro
1               5                   10                  15

Pro Lys Lys Pro Leu Lys Ile Arg Lys Ile Glu Phe Val Glu Ile Tyr
            20                  25                  30

Glu Pro Phe Ser Glu Gly Gln Ala Lys Ala Gln Ala Asp Arg Cys Leu
        35                  40                  45

Ser Cys Gly Asn Pro Tyr Cys Glu Trp Lys Cys Pro Val His Asn Tyr
    50                  55                  60

Ile Pro Asn Trp Leu Lys Leu Ala Asn Glu Gly Arg Ile Phe Glu Ala
65                  70                  75                  80

Ala Glu Leu Ser His Gln Thr Asn Thr Leu Pro Glu Val Cys Gly Arg
                85                  90                  95

Val Cys Pro Gln Asp Arg Leu Cys Glu Gly Ser Cys Thr Leu Asn Asp
            100                 105                 110

Glu Phe Gly Ala Val Thr Ile Gly Asn Ile Glu Arg Tyr Ile Asn Asp
        115                 120                 125

Lys Ala Phe Glu Met Gly Trp Arg Pro Asp Met Ser Gly Val Lys Gln
    130                 135                 140

Thr Gly Lys Lys Val Ala Ile Ile Gly Ala Gly Pro Ala Gly Leu Ala
145                 150                 155                 160

Cys Ala Asp Val Leu Thr Arg Asn Gly Val Lys Ala Val Val Phe Asp
                165                 170                 175

Arg His Pro Glu Ile Gly Gly Leu Leu Thr Phe Gly Ile Pro Ala Phe
            180                 185                 190

Lys Leu Glu Lys Glu Val Met Thr Arg Arg Arg Glu Ile Phe Thr Gly
        195                 200                 205

Met Gly Ile Glu Phe Lys Leu Asn Thr Glu Val Gly Arg Asp Val Gln
    210                 215                 220

Leu Asp Asp Leu Leu Ser Asp Tyr Asp Ala Val Phe Leu Gly Val Gly
225                 230                 235                 240

Thr Tyr Gln Ser Met Arg Gly Gly Leu Glu Asn Glu Asp Ala Asp Gly
                245                 250                 255

Val Tyr Ala Ala Leu Pro Phe Leu Ile Ala Asn Thr Lys Gln Leu Met
            260                 265                 270

Gly Phe Gly Glu Thr Arg Asp Glu Pro Phe Val Ser Met Glu Gly Lys
        275                 280                 285

Arg Val Val Val Leu Gly Gly Gly Asp Thr Ala Met Asp Cys Val Arg
    290                 295                 300
```

Thr Ser Val Arg Gln Gly Ala Lys His Val Thr Cys Ala Tyr Arg Arg
305                 310                 315                 320

Asp Glu Glu Asn Met Pro Gly Ser Arg Arg Glu Val Lys Asn Ala Arg
            325                 330                 335

Glu Glu Gly Val Glu Phe Lys Phe Asn Val Gln Pro Leu Gly Ile Glu
        340                 345                 350

Val Asn Gly Asn Gly Lys Val Ser Gly Val Lys Met Val Arg Thr Glu
    355                 360                 365

Met Gly Glu Pro Asp Ala Lys Gly Arg Arg Arg Ala Glu Ile Val Ala
370                 375                 380

Gly Ser Glu His Ile Val Pro Ala Asp Ala Val Ile Met Ala Phe Gly
385                 390                 395                 400

Phe Arg Pro His Asn Met Glu Trp Leu Ala Lys His Ser Val Glu Leu
            405                 410                 415

Asp Ser Gln Gly Arg Ile Ile Ala Pro Glu Gly Ser Asp Asn Ala Phe
        420                 425                 430

Gln Thr Ser Asn Pro Lys Ile Phe Ala Gly Gly Asp Ile Val Arg Gly
    435                 440                 445

Ser Asp Leu Val Val Thr Ala Ile Ala Glu Gly Arg Lys Ala Ala Asp
    450                 455                 460

Gly Ile Met Asn Trp Leu Glu Val
465                 470

<210> SEQ ID NO 84
<211> LENGTH: 1665
<212> TYPE: DNA
<213> ORGANISM: Escherichia coli

<400> SEQUENCE: 84
atgtgttcaa tttttggcgt attcgatatc aaaacagacg cagttgagct gcgtaagaaa      60
gccctcgagc tgtcacgcct gatgcgtcat cgtggcccgg actggtccgg tatttatgcc     120
agcgataacg ccattctcgc ccacgaacgt ctgtcaattg ttgacgttaa cgcgggggcg     180
caacctctct acaaccaaca aaaaacccac gtactggcgg taaacggtga atctacaac     240 caccaggcat gcgcgccga atatggcgat cgttaccagt tccagaccgg gtctgactgt     300
gaagtgatcc tcgcgctgta tcaggaaaaa gggccgaat ttctcgacga cttgcagggc     360
atgtttgcct ttgcactgta cgacagcgaa aaagatgcct acctgattgg tcgcgaccat     420
ctggggatca tcccactgta tatggggtat gacgaacacg gtcagctgta tgtggcctca     480
gaaatgaaag cgctggtgcc agtttgccgc acgattaaag agttcccggc ggggagctat     540
ttgtggagcc aggacggcga aatccgttct tactatcatc gcgactggtt cgactacgat     600
gcggtgaaag ataacgtgac cgacaaaaac gagctgcgtc aggcactgga agattcagtt     660
aaaagccatc tgatgtctga tgtgccttac ggtgtgctgc tttctggtgg tctggattcc     720
tcaattattt ccgctatcac caagaaatac gcagcccgtc gcgtggaaga tcaggaacgc     780
tctgaagcct ggtggccgca gttacactcc tttgctgtag gtctgccggg ttcaccggat     840
ctgaaagcag cccaggaagt ggcaaaccat ctgggcacgg tgcatcacga aattcacttc     900
actgtacagg aaggtctgga tgccatccgc gacgtgattt accacatcga aacttatgat     960
gtgaccacta ttcgcgcttc aacaccgatg tatttaatgt cgcgtaagat caaggcgatg     1020
ggcattaaaa tggtgctgtc cggtgaaggt tctgatgaag tgttcggcgg ttatctttac    1080
ttccacaaag caccgaatgc caaagaactg catgaagaga cggtgcgtaa actgctggcc    1140

```
ctgcatatgt atgactgcgc gcgtgccaac aaagcgatgt cagcctgggg cgtggaagca    1200
cgcgttccgt tcctcgacaa aaaattcctt gatgtggcga tgcgtattaa cccacaggat    1260
aaaatgtgcg gtaacggcaa aatggaaaaa cacatcctgc gtgaatgttt tgaagcgtat    1320
ctgcctgcaa gcgtggcctg gcggcagaaa gagcagttct ccgatggcgt cggttacagt    1380
tggatcgaca ccctgaaaga agtggctgcg cagcaggttt ctgatcagca actggaaact    1440
gcccgcttcc gcttcccgta caacacgcca acctctaaag aagcgtactt gtatcgggag    1500
atctttgaag aactattccc gcttccgagc gccgctgagt gcgtgccggg cggtccttcc    1560
gtcgcttgtt cttccgctaa agcgatcgaa tgggatgaag cgttcaagaa aatggacgat    1620
ccgtctggtc gcgcggttgg tgttcaccag tcggcgtata agtaa                   1665
```

<210> SEQ ID NO 85  
<211> LENGTH: 554  
<212> TYPE: PRT  
<213> ORGANISM: Escherichia coli

<400> SEQUENCE: 85

```
Met Cys Ser Ile Phe Gly Val Phe Asp Ile Lys Thr Asp Ala Val Glu
1               5                   10                  15

Leu Arg Lys Lys Ala Leu Glu Leu Ser Arg Leu Met Arg His Arg Gly
            20                  25                  30

Pro Asp Trp Ser Gly Ile Tyr Ala Ser Asp Asn Ala Ile Leu Ala His
        35                  40                  45

Glu Arg Leu Ser Ile Val Asp Val Asn Ala Gly Ala Gln Pro Leu Tyr
    50                  55                  60

Asn Gln Gln Lys Thr His Val Leu Ala Val Asn Gly Glu Ile Tyr Asn
65                  70                  75                  80

His Gln Ala Leu Arg Ala Glu Tyr Gly Asp Arg Tyr Gln Phe Gln Thr
                85                  90                  95

Gly Ser Asp Cys Glu Val Ile Leu Ala Leu Tyr Gln Glu Lys Gly Pro
            100                 105                 110

Glu Phe Leu Asp Asp Leu Gln Gly Met Phe Ala Phe Ala Leu Tyr Asp
        115                 120                 125

Ser Glu Lys Asp Ala Tyr Leu Ile Gly Arg Asp His Leu Gly Ile Ile
    130                 135                 140

Pro Leu Tyr Met Gly Tyr Asp Glu His Gly Gln Leu Tyr Val Ala Ser
145                 150                 155                 160

Glu Met Lys Ala Leu Val Pro Val Cys Arg Thr Ile Lys Glu Phe Pro
                165                 170                 175

Ala Gly Ser Tyr Leu Trp Ser Gln Asp Gly Glu Ile Arg Ser Tyr Tyr
            180                 185                 190

His Arg Asp Trp Phe Asp Tyr Asp Ala Val Lys Asp Asn Val Thr Asp
        195                 200                 205

Lys Asn Glu Leu Arg Gln Ala Leu Glu Asp Ser Val Lys Ser His Leu
    210                 215                 220

Met Ser Asp Val Pro Tyr Gly Val Leu Leu Ser Gly Gly Leu Asp Ser
225                 230                 235                 240

Ser Ile Ile Ser Ala Ile Thr Lys Lys Tyr Ala Ala Arg Arg Val Glu
                245                 250                 255

Asp Gln Glu Arg Ser Glu Ala Trp Trp Pro Gln Leu His Ser Phe Ala
            260                 265                 270

Val Gly Leu Pro Gly Ser Pro Asp Leu Lys Ala Ala Gln Glu Val Ala
```

| | | | | | | | | | | | | |
|---|---|---|---|---|---|---|---|---|---|---|---|---|
| | | 275 | | | 280 | | | 285 | | | | |
| Asn | His | Leu | Gly | Thr | Val | His | His | Glu | Ile | His | Phe | Thr | Val | Gln | Glu |
| | 290 | | | | | 295 | | | | | 300 | | | | |
| Gly | Leu | Asp | Ala | Ile | Arg | Asp | Val | Ile | Tyr | His | Ile | Glu | Thr | Tyr | Asp |
| 305 | | | | | 310 | | | | | 315 | | | | | 320 |
| Val | Thr | Thr | Ile | Arg | Ala | Ser | Thr | Pro | Met | Tyr | Leu | Met | Ser | Arg | Lys |
| | | | | 325 | | | | | 330 | | | | | 335 | |
| Ile | Lys | Ala | Met | Gly | Ile | Lys | Met | Val | Leu | Ser | Gly | Glu | Gly | Ser | Asp |
| | | | 340 | | | | | 345 | | | | | 350 | | |
| Glu | Val | Phe | Gly | Gly | Tyr | Leu | Tyr | Phe | His | Lys | Ala | Pro | Asn | Ala | Lys |
| | | 355 | | | | | 360 | | | | | 365 | | | |
| Glu | Leu | His | Glu | Glu | Thr | Val | Arg | Lys | Leu | Leu | Ala | Leu | His | Met | Tyr |
| | 370 | | | | | 375 | | | | | 380 | | | | |
| Asp | Cys | Ala | Arg | Ala | Asn | Lys | Ala | Met | Ser | Ala | Trp | Gly | Val | Glu | Ala |
| 385 | | | | | 390 | | | | | 395 | | | | | 400 |
| Arg | Val | Pro | Phe | Leu | Asp | Lys | Lys | Phe | Leu | Asp | Val | Ala | Met | Arg | Ile |
| | | | | 405 | | | | | 410 | | | | | 415 | |
| Asn | Pro | Gln | Asp | Lys | Met | Cys | Gly | Asn | Gly | Lys | Met | Glu | Lys | His | Ile |
| | | | 420 | | | | | 425 | | | | | 430 | | |
| Leu | Arg | Glu | Cys | Phe | Glu | Ala | Tyr | Leu | Pro | Ala | Ser | Val | Ala | Trp | Arg |
| | | 435 | | | | | 440 | | | | | 445 | | | |
| Gln | Lys | Glu | Gln | Phe | Ser | Asp | Gly | Val | Gly | Tyr | Ser | Trp | Ile | Asp | Thr |
| | 450 | | | | | 455 | | | | | 460 | | | | |
| Leu | Lys | Glu | Val | Ala | Ala | Gln | Val | Ser | Asp | Gln | Gln | Leu | Glu | Thr | |
| 465 | | | | | 470 | | | | | 475 | | | | | 480 |
| Ala | Arg | Phe | Arg | Phe | Pro | Tyr | Asn | Thr | Pro | Thr | Ser | Lys | Glu | Ala | Tyr |
| | | | | 485 | | | | | 490 | | | | | 495 | |
| Leu | Tyr | Arg | Glu | Ile | Phe | Glu | Glu | Leu | Phe | Pro | Leu | Pro | Ser | Ala | Ala |
| | | | 500 | | | | | 505 | | | | | 510 | | |
| Glu | Cys | Val | Pro | Gly | Gly | Pro | Ser | Val | Ala | Cys | Ser | Ser | Ala | Lys | Ala |
| | | 515 | | | | | 520 | | | | | 525 | | | |
| Ile | Glu | Trp | Asp | Glu | Ala | Phe | Lys | Lys | Met | Asp | Asp | Pro | Ser | Gly | Arg |
| | 530 | | | | | 535 | | | | | 540 | | | | |
| Ala | Val | Gly | Val | His | Gln | Ser | Ala | Tyr | Lys | | | | | | |
| 545 | | | | 550 | | | | | | | | | | | |

<210> SEQ ID NO 86
<211> LENGTH: 933
<212> TYPE: DNA
<213> ORGANISM: Escherichia coli

<400> SEQUENCE: 86

| | |
|---|---|
| atgttagatg caaacaaatt acagcaggca gtggatcagg cttacaccca atttcactca | 60 |
| cttaacggcg acaaaatgc cgattacatt cccttctgg cgaatgtacc aggtcaactg | 120 |
| gcggcagtgg ctatcgtgac ctgcgatggc aacgtctata gtgcgggtga cagtgattac | 180 |
| cgctttgcac tggaatccat ctcgaaagtc tgtacgttag cccttgcgtt agaagatgtc | 240 |
| ggcccgcagg cggtacagga caaaattggc gctgacccga ccggattgcc ctttaactca | 300 |
| gttatcgcct tagagttgca tggcggcaaa ccgctttcgc cactggtaaa tgctggcgct | 360 |
| attgccacca ccagcctgat taacgctgaa atgttgaac aacgctggca gcgaattta | 420 |
| catatccaac agcaactggc tggcgagcag gtagcgctct ctgacgaagt caaccagtcg | 480 |
| gaacaaacaa ccaacttcca taaccgggcc atagcctggc tgctgtactc cgccggatat | 540 |

```
ctctattgtg atgcaatgga agcctgtgac gtgtataccc gtcagtgctc cacgctcctc      600
aatactattg aactggcaac gcttggcgcg acgctggcgg caggtggtgt gaatccgttg      660
acgcataaac gcgttcttca ggccgacaac gtgccgtaca ttctggccga atgatgatg      720 gaagggctgt atggtcgctc cggtgactgg gcgtatcgtg ttggtttacc gggcaaaagc      780
ggtgtaggtg gcggtattct ggcggtcgtc cctggagtga tgggaattgc cgcgttctca      840
ccaccgctgg acgaagatgg caacagtgtt cgcggtcaaa aaatggtggc atcggtcgct      900
aagcaactcg gctataacgt gtttaagggc tga                                    933
```

<210> SEQ ID NO 87
<211> LENGTH: 310
<212> TYPE: PRT
<213> ORGANISM: Escherichia coli

<400> SEQUENCE: 87

```
Met Leu Asp Ala Asn Lys Leu Gln Gln Ala Val Asp Gln Ala Tyr Thr
 1               5                  10                  15

Gln Phe His Ser Leu Asn Gly Gly Gln Asn Ala Asp Tyr Ile Pro Phe
                20                  25                  30

Leu Ala Asn Val Pro Gly Gln Leu Ala Ala Val Ala Ile Val Thr Cys
            35                  40                  45

Asp Gly Asn Val Tyr Ser Ala Gly Asp Ser Asp Tyr Arg Phe Ala Leu
        50                  55                  60

Glu Ser Ile Ser Lys Val Cys Thr Leu Ala Leu Ala Leu Glu Asp Val
65                  70                  75                  80

Gly Pro Gln Ala Val Gln Asp Lys Ile Gly Ala Asp Pro Thr Gly Leu
                85                  90                  95

Pro Phe Asn Ser Val Ile Ala Leu Glu Leu His Gly Gly Lys Pro Leu
            100                 105                 110

Ser Pro Leu Val Asn Ala Gly Ala Ile Ala Thr Thr Ser Leu Ile Asn
        115                 120                 125

Ala Glu Asn Val Glu Gln Arg Trp Gln Arg Ile Leu His Ile Gln Gln
130                 135                 140

Gln Leu Ala Gly Glu Val Ala Leu Ser Asp Glu Val Asn Gln Ser
                145                 150                 155                 160

Glu Gln Thr Thr Asn Phe His Asn Arg Ala Ile Ala Trp Leu Leu Tyr
            165                 170                 175

Ser Ala Gly Tyr Leu Tyr Cys Asp Ala Met Glu Ala Cys Asp Val Tyr
        180                 185                 190

Thr Arg Gln Cys Ser Thr Leu Leu Asn Thr Ile Glu Leu Ala Thr Leu
    195                 200                 205

Gly Ala Thr Leu Ala Ala Gly Val Asn Pro Leu Thr His Lys Arg
210                 215                 220

Val Leu Gln Ala Asp Asn Val Pro Tyr Ile Leu Ala Glu Met Met Met
225                 230                 235                 240

Glu Gly Leu Tyr Gly Arg Ser Gly Asp Trp Ala Tyr Arg Val Gly Leu
                245                 250                 255

Pro Gly Lys Ser Gly Val Gly Gly Ile Leu Ala Val Val Pro Gly
            260                 265                 270

Val Met Gly Ile Ala Ala Phe Ser Pro Pro Leu Asp Glu Asp Gly Asn
        275                 280                 285

Ser Val Arg Gly Gln Lys Met Val Ala Ser Val Ala Lys Gln Leu Gly
    290                 295                 300
```

Tyr Asn Val Phe Lys Gly
305              310

<210> SEQ ID NO 88
<211> LENGTH: 927
<212> TYPE: DNA
<213> ORGANISM: Escherichia coli

<400> SEQUENCE: 88

| | | | | | |
|---|---|---|---|---|---|
| atggcagtcg | ccatggataa | tgcaatttta | gaaaacatct | tgcggcaagt | gcggccgctc | 60 |
| attggtcagg | gtaaagtcgc | ggattatatt | ccggcgctgg | ctacagtaga | cggttcccga | 120 |
| ttggggattg | ctatctgtac | cgttgacgga | cagcttttc | aggccggaga | gcgcaagaa | 180 |
| cgttttccca | ttcagtctat | ttccaaagtg | ctgagtctcg | ttgtcgccat | gcgtcattac | 240 |
| tccgaagagg | aaatctggca | acgcgtcggc | aaagatccgt | ctggatcacc | gttcaattcc | 300 |
| ttagtgcaac | tggaaatgga | gcagggtata | ccgcgtaatc | cgttcattaa | tgccggtgcg | 360 |
| ctggtggtct | gcgatatgtt | gcaagggcga | ttaagcgcac | cacggcaacg | tatgctggaa | 420 |
| gtcgtgcgcg | gcttaagcgg | tgtgtctgat | atttcctacg | atacggtggt | agcgcgttcc | 480 |
| gaatttgaac | attccgcgcg | aaatgcggct | atcgcctggc | tgatgaagtc | gtttggcaat | 540 |
| ttccatcatg | acgtgacaac | cgttctgcaa | aactactttc | attactgcgc | tctgaaaatg | 600 |
| agctgtgtag | agctggcccg | gacgtttgtc | tttctggcta | atcagggaa | agctattcat | 660 |
| attgatgaac | cagtggtgac | gccaatgcag | gcgcggcaaa | ttaacgcgct | gatggcgacc | 720 |
| agtggtatgt | accagaacgc | gggggagttt | gcctggcggg | tggggctacc | ggcgaaatct | 780 |
| ggcgttggtg | gcggtattgt | ggcgattgtt | ccgcatgaaa | tggccatcgc | tgtctggagt | 840 |
| ccggaactgg | atgatgcagg | taactcgctt | gcgggtattg | ccgttcttga | acaattgacg | 900 |
| aaacagttag | ggcgttcggt | ttattaa | | | | 927 |

<210> SEQ ID NO 89
<211> LENGTH: 927
<212> TYPE: PRT
<213> ORGANISM: Escherichia coli

<400> SEQUENCE: 89

Gly Thr Gly Gly Cys Ala Gly Thr Cys Gly Cys Ala Thr Gly Gly
1               5                   10                  15

Ala Thr Ala Ala Thr Gly Cys Ala Ala Thr Thr Thr Ala Gly Ala
                20                  25                  30

Ala Ala Ala Cys Ala Thr Cys Thr Thr Gly Cys Gly Gly Cys Ala Ala
            35                  40                  45

Gly Thr Gly Cys Gly Gly Cys Cys Gly Cys Thr Cys Ala Thr Thr Gly
        50                  55                  60

Gly Thr Cys Ala Gly Gly Gly Thr Ala Ala Ala Gly Thr Cys Gly Cys
65                  70                  75                  80

Gly Gly Ala Thr Thr Ala Thr Ala Thr Thr Cys Cys Gly Gly Cys Gly
                85                  90                  95

Cys Thr Gly Gly Cys Thr Ala Cys Ala Gly Thr Ala Gly Ala Cys Gly
            100                 105                 110

Gly Thr Thr Cys Cys Cys Gly Ala Thr Thr Gly Gly Gly Ala Thr
                115                 120                 125

Thr Gly Cys Thr Ala Thr Cys Thr Gly Thr Ala Cys Cys Gly Thr Thr
            130                 135                 140

Gly Ala Cys Gly Gly Ala Cys Ala Gly Cys Thr Thr Thr Thr Thr Cys

-continued

```
        145                 150                 155                 160
Ala Gly Gly Cys Cys Gly Ala Gly Ala Cys Gly Cys Gly Cys Ala
                    165                 170                 175
Ala Gly Ala Ala Cys Gly Thr Thr Thr Thr Cys Cys Ala Thr Thr
                    180                 185                 190
Cys Ala Gly Thr Cys Thr Ala Thr Thr Thr Cys Cys Ala Ala Gly
                    195                 200                 205
Thr Gly Cys Thr Gly Ala Gly Thr Cys Thr Cys Gly Thr Gly Thr
        210                 215                 220
Cys Gly Cys Cys Ala Thr Gly Cys Gly Thr Cys Ala Thr Ala Cys
225                 230                 235                 240
Thr Cys Cys Gly Ala Ala Gly Ala Gly Ala Ala Ala Thr Cys Thr
                    245                 250                 255
Gly Gly Cys Ala Ala Cys Gly Cys Gly Thr Cys Gly Gly Cys Ala Ala
                    260                 265                 270
Ala Gly Ala Thr Cys Cys Gly Thr Cys Thr Gly Gly Ala Thr Cys Ala
                    275                 280                 285
Cys Cys Gly Thr Thr Cys Ala Ala Thr Thr Cys Cys Thr Thr Ala Gly
                    290                 295                 300
Thr Gly Cys Ala Ala Cys Thr Gly Gly Ala Ala Ala Thr Gly Gly Ala
305                 310                 315                 320
Gly Cys Ala Gly Gly Gly Thr Ala Thr Ala Cys Cys Gly Cys Gly Thr
                    325                 330                 335
Ala Ala Thr Cys Cys Gly Thr Thr Cys Ala Thr Thr Ala Ala Thr Gly
                    340                 345                 350
Cys Cys Gly Gly Thr Gly Cys Gly Cys Thr Gly Gly Thr Gly Gly Thr
                    355                 360                 365
Cys Thr Gly Cys Gly Ala Thr Ala Thr Gly Thr Thr Gly Cys Ala Ala
                    370                 375                 380
Gly Gly Gly Cys Gly Ala Thr Thr Ala Ala Gly Cys Gly Cys Ala Cys
385                 390                 395                 400
Cys Ala Cys Gly Gly Cys Ala Ala Cys Gly Thr Ala Thr Gly Cys Thr
                    405                 410                 415
Gly Gly Ala Ala Gly Thr Cys Gly Thr Gly Cys Gly Gly Cys
                    420                 425                 430
Thr Thr Ala Ala Gly Cys Gly Thr Gly Thr Gly Thr Cys Thr Gly
                    435                 440                 445
Ala Thr Ala Thr Thr Thr Cys Cys Thr Ala Cys Gly Ala Thr Ala Cys
        450                 455                 460
Gly Gly Thr Gly Gly Thr Ala Gly Cys Gly Cys Gly Thr Thr Cys Cys
465                 470                 475                 480
Gly Ala Ala Thr Thr Gly Ala Ala Cys Ala Thr Thr Cys Cys Gly
                    485                 490                 495
Cys Gly Cys Gly Ala Ala Ala Thr Gly Cys Gly Gly Cys Thr Ala Thr
                    500                 505                 510
Cys Gly Cys Cys Thr Gly Gly Cys Thr Gly Ala Thr Gly Ala Ala Gly
                    515                 520                 525
Thr Cys Gly Thr Thr Gly Gly Cys Ala Ala Thr Thr Cys Cys
                    530                 535                 540
Ala Thr Cys Ala Thr Gly Ala Cys Gly Thr Gly Ala Cys Ala Ala Cys
545                 550                 555                 560
Cys Gly Thr Thr Cys Thr Gly Cys Ala Ala Ala Ala Cys Thr Ala Cys
                    565                 570                 575
```

```
Thr Thr Thr Cys Ala Thr Ala Cys Thr Gly Cys Gly Cys Thr Cys
                580                 585                 590

Thr Gly Ala Ala Ala Thr Gly Ala Gly Cys Thr Gly Thr Gly Thr
        595                 600                 605

Ala Gly Ala Gly Cys Thr Gly Gly Cys Cys Gly Gly Ala Cys Gly
        610                 615                 620

Thr Thr Thr Gly Thr Cys Thr Thr Thr Cys Thr Gly Gly Cys Thr Ala
625                 630                 635                 640

Ala Thr Cys Ala Gly Gly Gly Ala Ala Ala Gly Cys Thr Ala Thr
                645                 650                 655

Thr Cys Ala Thr Ala Thr Thr Gly Ala Thr Gly Ala Ala Cys Ala
                660                 665                 670

Gly Thr Gly Gly Thr Gly Ala Cys Gly Cys Ala Ala Thr Gly Cys
                675                 680                 685

Ala Gly Gly Cys Gly Cys Gly Gly Cys Ala Ala Ala Thr Ala Ala
                690                 695                 700

Cys Gly Cys Gly Cys Thr Gly Ala Thr Gly Gly Cys Gly Ala Cys Cys
705                 710                 715                 720

Ala Gly Thr Gly Gly Thr Ala Thr Gly Thr Ala Cys Cys Ala Gly Ala
                725                 730                 735

Ala Cys Gly Cys Gly Gly Gly Gly Ala Gly Thr Thr Thr Gly Cys
                740                 745                 750

Cys Thr Gly Gly Cys Gly Gly Gly Thr Gly Gly Gly Cys Thr Ala
            755                 760                 765

Cys Cys Gly Gly Cys Gly Ala Ala Thr Cys Thr Gly Gly Cys Gly Gly
                770                 775                 780

Thr Thr Gly Gly Thr Gly Gly Cys Gly Gly Thr Ala Thr Thr Gly Thr
785                 790                 795                 800

Gly Gly Cys Gly Ala Thr Thr Gly Thr Thr Cys Cys Gly Cys Ala Thr
                805                 810                 815

Gly Ala Ala Ala Thr Gly Gly Cys Cys Ala Thr Cys Gly Cys Thr Gly
                820                 825                 830

Thr Cys Thr Gly Gly Ala Gly Thr Gly Cys Cys Gly Gly Ala Ala Cys Thr
                835                 840                 845

Gly Gly Ala Thr Gly Ala Thr Gly Cys Ala Gly Gly Thr Ala Ala Cys
        850                 855                 860

Thr Cys Gly Cys Thr Thr Gly Cys Gly Gly Gly Thr Ala Thr Thr Gly
865                 870                 875                 880

Cys Cys Gly Thr Thr Cys Thr Thr Gly Ala Ala Cys Ala Ala Thr Thr
                885                 890                 895

Gly Ala Cys Gly Ala Ala Ala Cys Ala Gly Thr Thr Ala Gly Gly Gly
                900                 905                 910

Cys Gly Thr Thr Cys Gly Gly Thr Thr Thr Ala Thr Thr Ala Ala
            915                 920                 925

<210> SEQ ID NO 90
<211> LENGTH: 1344
<212> TYPE: DNA
<213> ORGANISM: Escherichia coli

<400> SEQUENCE: 90
atggatcaga catattctct ggagtcattc ctcaaccatg tccaaaagcg cgacccgaat    60
caaaccgagt tcgcgcaagc cgttcgtgaa gtaatgacca cactctggcc ttttcttgaa    120
```

```
caaaatccaa aatatcgcca gatgtcatta ctggagcgtc tggttgaacc ggagcgcgtg    180
atccagtttc gcgtggtatg ggttgatgat cgcaaccaga tacaggtcaa ccgtgcatgg    240
cgtgtgcagt tcagctctgc catcggcccg tacaaaggcg gtatgcgctt ccatccgtca    300
gttaaccttt ccattctcaa attcctcggc tttgaacaaa ccttcaaaaa tgccctgact    360
actctgccga tgggcggtgg taaaggcggc agcgatttcg atccgaaagg aaaaagcgaa    420
ggtgaagtga tgcgttttg ccaggcgctg atgactgaac tgtatcgcca cctgggcgcg    480
gataccgacg ttccggcagg tgatatcggg gttggtggtc gtgaagtcgg ctttatggcg    540
gggatgatga aaaagctctc caacaatacc gcctgcgtct tcaccggtaa ggcctttca    600 tttggcggca gtcttattcg cccggaagct accggctacg gtctggttta tttcacagaa    660
gcaatgctaa aacgccacgg tatgggtttt gaagggatgc gcgtttccgt ttctggctcc    720
ggcaacgtcg cccagtacgc tatcgaaaaa gcgatggaat tggtgctcg tgtgatcact    780 gcgtcagact ccagcggcac tgtagttgat gaaagcggat tcacgaaaga gaaactggca    840
cgtcttatcg aaatcaaagc cagccgcgat ggtcgagtgg cagattacgc caaagaattt    900
ggtctggtct atctcgaagg ccaacagccg tggtctctac cggttgatat cgccctgcct    960
tgcgccaccc agaatgaact ggatgttgac gccgcgcatc agcttatcgc taatggcgtt   1020
aaagccgtcg ccgaagggc aaatatgccg accaccatcg aagcgactga actgttccag   1080
caggcaggcg tactatttgc accgggtaaa gcggctaatg ctggtggcgt cgctacatcg   1140
ggcctggaaa tggcacaaaa cgctgcgcgc ctgggctgga agccgagaa agttgacgca   1200 cgtttgcatc acatcatgct ggatatccac catgcctgtg ttgagcatgg tggtgaaggt   1260
gagcaaacca actacgtgca gggcgcgaac attgccggtt ttgtgaaggt tgccgatgcg   1320
atgctggcgc agggtgtgat ttaa                                          1344
```

<210> SEQ ID NO 91
<211> LENGTH: 447
<212> TYPE: PRT
<213> ORGANISM: Escherichia coli

<400> SEQUENCE: 91

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160
```

```
Asp Thr Asp Val Pro Ala Gly Asp Ile Gly Val Gly Arg Glu Val
            165                 170                 175

Gly Phe Met Ala Gly Met Met Lys Lys Leu Ser Asn Asn Thr Ala Cys
        180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 92
<211> LENGTH: 1479
<212> TYPE: DNA
<213> ORGANISM: Escherichia coli

<400> SEQUENCE: 92
atgagcttac gtgaaaaaac catcagcggc gcgaagtggt cggcgattgc cacggtgatc      60
atcatcggcc tcgggctggt gcagatgacc gtgctggcgc ggattatcga caaccaccag     120
ttcggcctgc ttaccgtgtc gctggtgatt atcgcgctgg cagatacgct ttctgacttc     180
ggtatcgcta actcgattat tcagcgaaaa gaaatcagtc accttgaact caccacgttg     240
tactggctga acgtcgggct ggggatcgtg gtgtgcgtgg cggtgttttt gttgagtgat     300
ctcatcggcg acgtgctgaa taacccggac ctggcaccgt tgattaaaac attatcgctg     360
gcgtttgtgg taatccccca cgggcaacag ttccgcgcgt tgatgcaaaa agagctggag     420
ttcaacaaaa tcggcatgat cgaaaccagc gcggtgctgg cgggcttcac ttgtacggtg     480
```

-continued

| | |
|---|---|
| gttagcgccc atttctggcc gctggcgatg accgcgatcc tcggttatct ggtcaatagt | 540 |
| gcggtgagaa cgctgctgtt tggctacttt ggccgcaaaa tttatcgccc cggtctgcat | 600 |
| ttctcgctgg cgtcggtggc accgaactta cgctttggtg cctggctgac ggcggacagc | 660 |
| atcatcaact atctcaatac caacctttca acgctcgtgc tggcgcgtat tctcggcgcg | 720 |
| ggcgtggcag ggggatacaa cctggcgtac aacgtggccg ttgtgccacc gatgaagctg | 780 |
| aacccaatca tcacccgcgt gttgtttccg gcattcgcca aaattcagga cgataccgaa | 840 |
| aagctgcgtg ttaacttcta caagctgctg tcggtagtgg ggattatcaa ctttccggcg | 900 |
| ctgctcgggc taatggtggt gtcgaataac tttgtaccgc tggtctttgg tgagaagtgg | 960 |
| aacagcatta ttccggtgct gcaattgctg tgtgtggtgg gtctgctgcg ctccgtaggt | 1020 |
| aacccgattg ttcgctgct gatggcgaaa gcgcgggtcg atatcagctt taaattcaac | 1080 |
| gtattcaaaa catttctgtt tattccggcg attgttatag gtgggcagat ggcgggcgcg | 1140 |
| atcggcgtca cgcttggctt cctgctggtg caaattatca acaccattct gagttacttc | 1200 |
| gtgatgatta aaccggttct tggttccagt tatcgccagt acatcctgag tttatggctg | 1260 |
| ccgttttatc tctcgctgcc gacgctggtg gtcagttatg cgctgggcat tgtgctgaaa | 1320 |
| gggcaactgg cgctggggat gctgctggcg gtgcaaatag ccacggggt gctggcgttt | 1380 |
| gtggtgatga ttgtgctgtc gcgccatccg ctggtggtgg aagtgaagcg tcagttttgt | 1440 |
| cgcagcgaaa aaatgaaaat gctttacgg gcggggtga | 1479 |

<210> SEQ ID NO 93
<211> LENGTH: 492
<212> TYPE: PRT
<213> ORGANISM: Escherichia coli

<400> SEQUENCE: 93

Met Ser Leu Arg Glu Lys Thr Ile Ser Gly Ala Lys Trp Ser Ala Ile
1               5                   10                  15

Ala Thr Val Ile Ile Gly Leu Gly Leu Val Gln Met Thr Val Leu
            20                  25                  30

Ala Arg Ile Ile Asp Asn His Gln Phe Gly Leu Leu Thr Val Ser Leu
        35                  40                  45

Val Ile Ile Ala Leu Ala Asp Thr Leu Ser Asp Phe Gly Ile Ala Asn
    50                  55                  60

Ser Ile Ile Gln Arg Lys Glu Ile Ser His Leu Glu Leu Thr Thr Leu
65                  70                  75                  80

Tyr Trp Leu Asn Val Gly Leu Gly Ile Val Cys Val Ala Val Phe
                85                  90                  95

Leu Leu Ser Asp Leu Ile Gly Asp Val Leu Asn Asn Pro Asp Leu Ala
            100                 105                 110

Pro Leu Ile Lys Thr Leu Ser Leu Ala Phe Val Val Ile Pro His Gly
        115                 120                 125

Gln Gln Phe Arg Ala Leu Met Gln Lys Glu Leu Glu Phe Asn Lys Ile
    130                 135                 140

Gly Met Ile Glu Thr Ser Ala Val Leu Ala Gly Phe Thr Cys Thr Val
145                 150                 155                 160

Val Ser Ala His Phe Trp Pro Leu Ala Met Thr Ala Ile Leu Gly Tyr
                165                 170                 175

Leu Val Asn Ser Ala Val Arg Thr Leu Leu Phe Gly Tyr Phe Gly Arg
            180                 185                 190

Lys Ile Tyr Arg Pro Gly Leu His Phe Ser Leu Ala Ser Val Ala Pro

```
                195                 200                 205
Asn Leu Arg Phe Gly Ala Trp Leu Thr Ala Asp Ser Ile Ile Asn Tyr
    210                 215                 220

Leu Asn Thr Asn Leu Ser Thr Leu Val Leu Ala Arg Ile Leu Gly Ala
225                 230                 235                 240

Gly Val Ala Gly Gly Tyr Asn Leu Ala Tyr Asn Val Ala Val Val Pro
                245                 250                 255

Pro Met Lys Leu Asn Pro Ile Ile Thr Arg Val Leu Phe Pro Ala Phe
            260                 265                 270

Ala Lys Ile Gln Asp Asp Thr Glu Lys Leu Arg Val Asn Phe Tyr Lys
        275                 280                 285

Leu Leu Ser Val Val Gly Ile Ile Asn Phe Pro Ala Leu Leu Gly Leu
    290                 295                 300

Met Val Val Ser Asn Asn Phe Val Pro Leu Val Phe Gly Glu Lys Trp
305                 310                 315                 320

Asn Ser Ile Ile Pro Val Leu Gln Leu Leu Cys Val Val Gly Leu Leu
                325                 330                 335

Arg Ser Val Gly Asn Pro Ile Gly Ser Leu Leu Met Ala Lys Ala Arg
            340                 345                 350

Val Asp Ile Ser Phe Lys Phe Asn Val Phe Lys Thr Phe Leu Phe Ile
        355                 360                 365

Pro Ala Ile Val Ile Gly Gly Gln Met Ala Gly Ala Ile Gly Val Thr
    370                 375                 380

Leu Gly Phe Leu Leu Val Gln Ile Ile Asn Thr Ile Leu Ser Tyr Phe
385                 390                 395                 400

Val Met Ile Lys Pro Val Leu Gly Ser Ser Tyr Arg Gln Tyr Ile Leu
                405                 410                 415

Ser Leu Trp Leu Pro Phe Tyr Leu Ser Leu Pro Thr Leu Val Val Ser
            420                 425                 430

Tyr Ala Leu Gly Ile Val Leu Lys Gly Gln Leu Ala Leu Gly Met Leu
        435                 440                 445

Leu Ala Val Gln Ile Ala Thr Gly Val Leu Ala Phe Val Val Met Ile
    450                 455                 460

Val Leu Ser Arg His Pro Leu Val Val Glu Val Lys Arg Gln Phe Cys
465                 470                 475                 480

Arg Ser Glu Lys Met Lys Met Leu Leu Arg Ala Gly
                485                 490

<210> SEQ ID NO 94
<211> LENGTH: 1395
<212> TYPE: DNA
<213> ORGANISM: Escherichia coli

<400> SEQUENCE: 94
atgacaaatc taaaaaagcg cgagcgagcg aaaaccaatg catcgttaat ctctatggtg      60
caacgctttt cagatatcac catcatgttt gccggactat ggctggtttg cgaagtcagc     120
ggactgtcat tcctctacat gcacctgttg gtggcgctga ttacgctggt ggtgttccag     180
atgctgggcg gcatcaccga tttttatcgc tcatggcgcg gtgttcgggc agcgacagaa     240
tttgccctgt tgctacaaaa ctggacctta agcgtgattt tcagcgccgg actggtggcg     300
ttcaacaatg atttcgacac gcaactgaaa atctggctgg cgtggtatgc gctgaccagc     360
atcggactgt ggtttgccg ttcgtgtatt cgcattgggg cgggctggct gcgtaatcat     420
ggctataaca agcgcatggt cgcggtggcg ggggatttag ccgccgggca aatgctgatg     480
```

```
gagagcttcc gtaaccagcc gtggttaggg tttgaagtgg tgggcgttta ccacgacccg    540
aaaccgggcg gcgtttctaa cgactgggcg ggtaacctgc aacagctggt cgaggacgcg    600
aaagcgggca agattcataa cgtctatatc gcgatgcaaa tgtgcgacgg cgcgcgagtg    660
aaaaaactgg tccatcaact ggcggacacc acctgttcgg tgctgctgat ccccgacgtc    720
tttaccttca acattctcca ttcacgcctc gaagagatga acggcgtacc ggtggtgccg    780
ctttacgaca cgccgctttc cggggttaac cgcctgctca acgtgcggaa agacattgtg    840
ctggcgacgc ttattctgct gctgatctcc ccggtgctgt gctgtattgc gctggcggtg    900
aaactcagtt caccagggcc ggttattttc cgccagactc gctacggcat ggatggcaag    960
ccgatcaaag tgtggaagtt ccgttccatg aaagtgatgg agaacgacaa agtggtgacc   1020
caggcgacgc agaacgatcc gcgcgtcacc aaagtgggga ctttctgcg ccgtacctcg    1080 ctggatgaat tgccgcagtt tatcaatgtg ctgaccgggg ggatgtcgat tgtcggtcca   1140
cgtccgcacg cagtagcgca taacgaacag tatcgacagc tcattgaagg ctacatgctg   1200
cgccataagg tgaaaccggg cattaccggc tgggcgcaga ttaacggctg gcgcggcgaa   1260
accgacacgc tggagaaaat ggaaaaacgc gtcgagttcg accttgagta catccgcgaa   1320
tggagcgtct ggttcgatat caaaatcgtt ttcctgacgg tgttcaaagg tttcgttaac   1380
aaagcggcat attga                                                    1395
```

<210> SEQ ID NO 95
<211> LENGTH: 464
<212> TYPE: PRT
<213> ORGANISM: Escherichia coli

<400> SEQUENCE: 95

Met Thr Asn Leu Lys Lys Arg Glu Arg Ala Lys Thr Asn Ala Ser Leu
1               5                   10                  15

Ile Ser Met Val Gln Arg Phe Ser Asp Ile Thr Ile Met Phe Ala Gly
            20                  25                  30

Leu Trp Leu Val Cys Glu Val Ser Gly Leu Ser Phe Leu Tyr Met His
        35                  40                  45

Leu Leu Val Ala Leu Ile Thr Leu Val Val Phe Gln Met Leu Gly Gly
    50                  55                  60

Ile Thr Asp Phe Tyr Arg Ser Trp Arg Gly Val Arg Ala Ala Thr Glu
65                  70                  75                  80

Phe Ala Leu Leu Leu Gln Asn Trp Thr Leu Ser Val Ile Phe Ser Ala
                85                  90                  95

Gly Leu Val Ala Phe Asn Asn Asp Phe Asp Thr Gln Leu Lys Ile Trp
            100                 105                 110

Leu Ala Trp Tyr Ala Leu Thr Ser Ile Gly Leu Val Val Cys Arg Ser
        115                 120                 125

Cys Ile Arg Ile Gly Ala Gly Trp Leu Arg Asn His Gly Tyr Asn Lys
    130                 135                 140

Arg Met Val Ala Val Ala Gly Asp Leu Ala Ala Gly Gln Met Leu Met
145                 150                 155                 160

Glu Ser Phe Arg Asn Gln Pro Trp Leu Gly Phe Glu Val Gly Val
                165                 170                 175

Tyr His Asp Pro Lys Pro Gly Gly Val Ser Asn Asp Trp Ala Gly Asn
            180                 185                 190

Leu Gln Gln Leu Val Glu Asp Ala Lys Ala Gly Lys Ile His Asn Val
        195                 200                 205

| Tyr | Ile | Ala | Met | Gln | Met | Cys | Asp | Gly | Ala | Arg | Val | Lys | Lys | Leu | Val |
| | 210 | | | | 215 | | | | 220 | | | | | | |

His Gln Leu Ala Asp Thr Thr Cys Ser Val Leu Ile Pro Asp Val
225 230 235 240

Phe Thr Phe Asn Ile Leu His Ser Arg Leu Glu Glu Met Asn Gly Val
245 250 255

Pro Val Val Pro Leu Tyr Asp Thr Pro Leu Ser Gly Val Asn Arg Leu
260 265 270

Leu Lys Arg Ala Glu Asp Ile Val Leu Ala Thr Leu Ile Leu Leu Leu
275 280 285

Ile Ser Pro Val Leu Cys Cys Ile Ala Leu Ala Val Lys Leu Ser Ser
290 295 300

Pro Gly Pro Val Ile Phe Arg Gln Thr Arg Tyr Gly Met Asp Gly Lys
305 310 315 320

Pro Ile Lys Val Trp Lys Phe Arg Ser Met Lys Val Met Glu Asn Asp
325 330 335

Lys Val Val Thr Gln Ala Thr Gln Asn Asp Pro Arg Val Thr Lys Val
340 345 350

Gly Asn Phe Leu Arg Arg Thr Ser Leu Asp Glu Leu Pro Gln Phe Ile
355 360 365

Asn Val Leu Thr Gly Gly Met Ser Ile Val Gly Pro Arg Pro His Ala
370 375 380

Val Ala His Asn Glu Gln Tyr Arg Gln Leu Ile Glu Gly Tyr Met Leu
385 390 395 400

Arg His Lys Val Lys Pro Gly Ile Thr Gly Trp Ala Gln Ile Asn Gly
405 410 415

Trp Arg Gly Glu Thr Asp Thr Leu Glu Lys Met Glu Lys Arg Val Glu
420 425 430

Phe Asp Leu Glu Tyr Ile Arg Glu Trp Ser Val Trp Phe Asp Ile Lys
435 440 445

Ile Val Phe Leu Thr Val Phe Lys Gly Phe Val Asn Lys Ala Ala Tyr
450 455 460

<210> SEQ ID NO 96
<211> LENGTH: 1119
<212> TYPE: DNA
<213> ORGANISM: Escherichia coli

<400> SEQUENCE: 96

```
atgattaatt atggcgttgt tggtgttgga tactttggcg ctgaattagc tcgttttatg      60
aatatgcatg ataatgcaaa aattacatgt gtatacgatc ctgaaaatgg agaaatatt     120 gcccgtgaat tgcagtgtat caatatgtca agcttggatg ctttagtctc aagtaaatta    180
gtcgattgcg tgatcgtagc caccccaaat tatctgcata agaaccagt aattaaagca     240 gcaaagaata gaagcatgt ttttttgtgaa aaaccaattg cattaagtta tgaagattgt    300
gtggatatgg tcaaagcgtg taagaagct ggtgtgacct ttatggccgg gcatattatg     360 aatttttca atggggttca atatgcacgg aagttaatta agaaggtgt tatcggcgaa      420 atattatcat gtcatactaa gagaaatggc tgggaaaaca acaagagag actttcctgg     480 aaaaagatga agaacaatc tggtggacat ctatatcatc atatacatga gttagattgt     540
gttcagcatt tacttggaga ataccagag acgttacta tgattggtgg aaatttggcc     600
cattctggtc caggatttgg caatgaagat gatatgttat ttatgacctt ggaattcccg   660
```

```
tcaggaaaac tagcaacctt agagtggggg agtgcattta actggccgga acattatgtc      720
atcatcaatg gaactaaagg ctctattaaa attgatatgc aagaaacagc agggtcactt      780
aggattggcg gtcagacaaa gcattttttg gtccatgaaa cacaagaaga agatgatgat      840
cgtcggaaag gcaatatgac ctcagaaatg gatggcgcta tagcatatgg tcatccagga      900
aaaaaaacac cattatggct tgccagttta ataagaaagg agacgttatt cctccataat      960
atcctctgtg gtgcaaaacc tgaagaagat tatattgacc ttctcaatgg tgaggcggcc     1020
atgtcggcga ttgctactgc tgatgctgcc actctttcaa gatcgcagga caggaaagtg     1080
aaaatcagtg agatcattaa acatacatca gtaatgtaa                            1119
```

<210> SEQ ID NO 97
<211> LENGTH: 372
<212> TYPE: PRT
<213> ORGANISM: Escherichia coli

<400> SEQUENCE: 97

```
Met Ile Asn Tyr Gly Val Val Gly Tyr Phe Gly Ala Glu Leu
1               5                   10                  15

Ala Arg Phe Met Asn Met His Asp Asn Ala Lys Ile Thr Cys Val Tyr
                20                  25                  30

Asp Pro Glu Asn Gly Glu Asn Ile Ala Arg Glu Leu Gln Cys Ile Asn
            35                  40                  45

Met Ser Ser Leu Asp Ala Leu Val Ser Ser Lys Leu Val Asp Cys Val
        50                  55                  60

Ile Val Ala Thr Pro Asn Tyr Leu His Lys Glu Pro Val Ile Lys Ala
65                  70                  75                  80

Ala Lys Asn Lys Lys His Val Phe Cys Glu Lys Pro Ile Ala Leu Ser
                85                  90                  95

Tyr Glu Asp Cys Val Asp Met Val Lys Ala Cys Lys Glu Ala Gly Val
            100                 105                 110

Thr Phe Met Ala Gly His Ile Met Asn Phe Phe Asn Gly Val Gln Tyr
        115                 120                 125

Ala Arg Lys Leu Ile Lys Glu Gly Val Ile Gly Glu Ile Leu Ser Cys
    130                 135                 140

His Thr Lys Arg Asn Gly Trp Glu Asn Lys Gln Glu Arg Leu Ser Trp
145                 150                 155                 160

Lys Lys Met Lys Glu Gln Ser Gly Gly His Leu Tyr His His Ile His
                165                 170                 175

Glu Leu Asp Cys Val Gln His Leu Leu Gly Glu Ile Pro Glu Thr Val
            180                 185                 190

Thr Met Ile Gly Gly Asn Leu Ala His Ser Gly Pro Gly Phe Gly Asn
        195                 200                 205

Glu Asp Asp Met Leu Phe Met Thr Leu Glu Phe Pro Ser Gly Lys Leu
    210                 215                 220

Ala Thr Leu Glu Trp Gly Ser Ala Phe Asn Trp Pro Glu His Tyr Val
225                 230                 235                 240

Ile Ile Asn Gly Thr Lys Gly Ser Ile Lys Ile Asp Met Gln Glu Thr
                245                 250                 255

Ala Gly Ser Leu Arg Ile Gly Gly Gln Thr Lys His Phe Leu Val His
            260                 265                 270

Glu Thr Gln Glu Glu Asp Asp Arg Arg Lys Gly Asn Met Thr Ser
        275                 280                 285

Glu Met Asp Gly Ala Ile Ala Tyr Gly His Pro Gly Lys Lys Thr Pro
```

```
                  290                 295                 300
Leu Trp Leu Ala Ser Leu Ile Arg Lys Glu Thr Leu Phe Leu His Asn
305                 310                 315                 320

Ile Leu Cys Gly Ala Lys Pro Glu Glu Asp Tyr Ile Asp Leu Leu Asn
                325                 330                 335

Gly Glu Ala Ala Met Ser Ala Ile Ala Thr Ala Asp Ala Ala Thr Leu
                340                 345                 350

Ser Arg Ser Gln Asp Arg Lys Val Lys Ile Ser Glu Ile Ile Lys His
            355                 360                 365

Thr Ser Val Met
    370

<210> SEQ ID NO 98
<211> LENGTH: 1776
<212> TYPE: DNA
<213> ORGANISM: Escherichia coli

<400> SEQUENCE: 98
```

| | | |
|---|---|---|
| atgaaaaaaa tcagcttacc gaaaattggt atccgcccgg ttattgacgg tcgtcgcatg | | 60 |
| ggtgttcgtg agtcgcttga agaacaaaca atgaatatgg cgaaagctac ggccgcactg | | 120 |
| ctgaccgaga aactgcgcca tgcctgcgga gctgccgtcg agtgtgtcat ttccgatacc | | 180 |
| tgtatcgcgg gtatggctga agccgctgct tgcgaagaaa aattcagcag tcagaatgta | | 240 |
| ggcctcacca ttacggtaac gccttgctgg tgctatggca gtgaaaccat cgacatggat | | 300 |
| ccaacccgcc cgaaggccat tggggctttt aacggcactg aacgccccgg cgctgtttac | | 360 |
| ctggcagcgg ctctggcagc tcacagccag aaaggcatcc agcattctc catttacggt | | 420 |
| catgacgttc aggatgccga tgacacatcg attcctgccg atgttgaaga aaaactgctg | | 480 |
| cgctttgccc gcgccggttt ggccgtcgcc agcatgaaag gtaaaagcta tctgtcgctg | | 540 |
| ggcggcgttt cgatgggtat cgccggttcc attgttgatc acaacttctt tgaatcctgg | | 600 |
| ctgggaatga agtccaggc ggtggatatg accgaactgc gtcgccgtat cgatcagaag | | 660 |
| atttacgacg aagccgaatt ggaaatggca ctggcctggg ctgataaaaa cttccgctat | | 720 |
| ggcgaagatg aaaataacaa acagtatcaa cgtaatgccg agcaaagccg cgcagttctg | | 780 |
| cgcgaaagtt tactgatggc gatgtgtatc cgcgacatga tgcaaggcaa cagcaaactg | | 840 |
| gccgatattg tcgcgtgga agaatcactt ggctacaacg ccatcgctgc gggcttccag | | 900 |
| gggcaacgtc actggaccga tcaatatccc aatggtgaca ccgccgaagc gatcctcaac | | 960 |
| agttcatttg actggaatgg cgtgcgcgaa ccctttgtcg tggcgaccga aaacgacagt | | 1020 |
| cttaacggcg tggcaatgct aatgggtcac cagctcaccg gcaccgctca ggtatttgcc | | 1080 |
| gatgtgcgta cctactggtc accagaagca attgagcgtg taacgggca taaactggat | | 1140 |
| ggactggcag aacacggcat catccatttg atcaactccg ttctgctgc gctggacggt | | 1200 |
| tcctgtaaac aacgcgacag cgaaggtaac ccgacgatga gccacactg gaaatctct | | 1260 |
| cagcaagagg ctgacgcttg cctcgccgct accgaatggt gccggcgat ccacgaatac | | 1320 |
| ttccgtggcg gcggttactc ttcccgcttc cttaccgaag cggcgtccc gttcaccatg | | 1380 |
| actcgtgtca acatcatcaa aggcctggga ccggtactgc aaatcgcgga aggctggagc | | 1440 |
| gtggaattgc cgaaggatgt gcatgacatc ctcaacaaac gcaccaactc aacctggcca | | 1500 |
| accacctggt tgcaccgcg cctcaccggt aaagggccgt ttacgatgt gtactcggta | | 1560 |
| atggcgaact ggggcgctaa ccatggggt ctgaccatcg ccacgttgg cgcagacttt | | 1620 |

```
atcactctcg cctccatgct gcgtatcccg gtatgtatgc acaacgttga agagaccaaa    1680
gtgtatcgtc cttctgcctg ggctgcgcac ggcatggata ttgaaggcca ggattaccgc    1740
gcttgccaga actacggtcc gttgtacaag cgttaa                              1776

<210> SEQ ID NO 99
<211> LENGTH: 591
<212> TYPE: PRT
<213> ORGANISM: Escherichia coli

<400> SEQUENCE: 99
```

| Met | Lys | Lys | Ile | Ser | Leu | Pro | Lys | Ile | Gly | Ile | Arg | Pro | Val | Ile | Asp |
|---|---|---|---|---|---|---|---|---|---|---|---|---|---|---|---|
| 1 | | | | 5 | | | | | 10 | | | | | 15 | |

| Gly | Arg | Arg | Met | Gly | Val | Arg | Glu | Ser | Leu | Glu | Glu | Gln | Thr | Met | Asn |
|---|---|---|---|---|---|---|---|---|---|---|---|---|---|---|---|
| | | | 20 | | | | | 25 | | | | | 30 | | |

| Met | Ala | Lys | Ala | Thr | Ala | Ala | Leu | Leu | Thr | Glu | Lys | Leu | Arg | His | Ala |
|---|---|---|---|---|---|---|---|---|---|---|---|---|---|---|---|
| | | 35 | | | | | 40 | | | | | 45 | | | |

| Cys | Gly | Ala | Ala | Val | Glu | Cys | Val | Ile | Ser | Asp | Thr | Cys | Ile | Ala | Gly |
|---|---|---|---|---|---|---|---|---|---|---|---|---|---|---|---|
| | 50 | | | | | 55 | | | | | 60 | | | | |

| Met | Ala | Glu | Ala | Ala | Ala | Cys | Glu | Glu | Lys | Phe | Ser | Ser | Gln | Asn | Val |
|---|---|---|---|---|---|---|---|---|---|---|---|---|---|---|---|
| 65 | | | | | 70 | | | | | 75 | | | | | 80 |

| Gly | Leu | Thr | Ile | Thr | Val | Thr | Pro | Cys | Trp | Cys | Tyr | Gly | Ser | Glu | Thr |
|---|---|---|---|---|---|---|---|---|---|---|---|---|---|---|---|
| | | | | 85 | | | | | 90 | | | | | 95 | |

| Ile | Asp | Met | Asp | Pro | Thr | Arg | Pro | Lys | Ala | Ile | Trp | Gly | Phe | Asn | Gly |
|---|---|---|---|---|---|---|---|---|---|---|---|---|---|---|---|
| | | | 100 | | | | | 105 | | | | | 110 | | |

| Thr | Glu | Arg | Pro | Gly | Ala | Val | Tyr | Leu | Ala | Ala | Leu | Ala | Ala | His |
|---|---|---|---|---|---|---|---|---|---|---|---|---|---|---|
| | | 115 | | | | | 120 | | | | | 125 | | |

| Ser | Gln | Lys | Gly | Ile | Pro | Ala | Phe | Ser | Ile | Tyr | Gly | His | Asp | Val | Gln |
|---|---|---|---|---|---|---|---|---|---|---|---|---|---|---|---|
| | 130 | | | | | 135 | | | | | 140 | | | | |

| Asp | Ala | Asp | Thr | Ser | Ile | Pro | Ala | Asp | Val | Glu | Glu | Lys | Leu | Leu |
|---|---|---|---|---|---|---|---|---|---|---|---|---|---|---|
| 145 | | | | | 150 | | | | | 155 | | | | | 160 |

| Arg | Phe | Ala | Arg | Ala | Gly | Leu | Ala | Val | Ala | Ser | Met | Lys | Gly | Lys | Ser |
|---|---|---|---|---|---|---|---|---|---|---|---|---|---|---|---|
| | | | | 165 | | | | | 170 | | | | | 175 | |

| Tyr | Leu | Ser | Leu | Gly | Gly | Val | Ser | Met | Gly | Ile | Ala | Gly | Ser | Ile | Val |
|---|---|---|---|---|---|---|---|---|---|---|---|---|---|---|---|
| | | | 180 | | | | | 185 | | | | | 190 | | |

| Asp | His | Asn | Phe | Phe | Glu | Ser | Trp | Leu | Gly | Met | Lys | Val | Gln | Ala | Val |
|---|---|---|---|---|---|---|---|---|---|---|---|---|---|---|---|
| | | 195 | | | | | 200 | | | | | 205 | | | |

| Asp | Met | Thr | Glu | Leu | Arg | Arg | Arg | Ile | Asp | Gln | Lys | Ile | Tyr | Asp | Glu |
|---|---|---|---|---|---|---|---|---|---|---|---|---|---|---|---|
| | 210 | | | | | 215 | | | | | 220 | | | | |

| Ala | Glu | Leu | Glu | Met | Ala | Leu | Ala | Trp | Ala | Asp | Lys | Asn | Phe | Arg | Tyr |
|---|---|---|---|---|---|---|---|---|---|---|---|---|---|---|---|
| 225 | | | | | 230 | | | | | 235 | | | | | 240 |

| Gly | Glu | Asp | Glu | Asn | Asn | Lys | Gln | Tyr | Gln | Arg | Asn | Ala | Glu | Gln | Ser |
|---|---|---|---|---|---|---|---|---|---|---|---|---|---|---|---|
| | | | | 245 | | | | | 250 | | | | | 255 | |

| Arg | Ala | Val | Leu | Arg | Glu | Ser | Leu | Leu | Met | Ala | Met | Cys | Ile | Arg | Asp |
|---|---|---|---|---|---|---|---|---|---|---|---|---|---|---|---|
| | | | 260 | | | | | 265 | | | | | 270 | | |

| Met | Met | Gln | Gly | Asn | Ser | Lys | Leu | Ala | Asp | Ile | Gly | Arg | Val | Glu | Glu |
|---|---|---|---|---|---|---|---|---|---|---|---|---|---|---|---|
| | | 275 | | | | | 280 | | | | | 285 | | | |

| Ser | Leu | Gly | Tyr | Asn | Ala | Ile | Ala | Ala | Gly | Phe | Gln | Gly | Gln | Arg | His |
|---|---|---|---|---|---|---|---|---|---|---|---|---|---|---|---|
| | 290 | | | | | 295 | | | | | 300 | | | | |

| Trp | Thr | Asp | Gln | Tyr | Pro | Asn | Gly | Asp | Thr | Ala | Glu | Ala | Ile | Leu | Asn |
|---|---|---|---|---|---|---|---|---|---|---|---|---|---|---|---|
| 305 | | | | | 310 | | | | | 315 | | | | | 320 |

| Ser | Ser | Phe | Asp | Trp | Asn | Gly | Val | Arg | Glu | Pro | Phe | Val | Val | Ala | Thr |
|---|---|---|---|---|---|---|---|---|---|---|---|---|---|---|---|
| | | | | 325 | | | | | 330 | | | | | 335 | |

| Glu | Asn | Asp | Ser | Leu | Asn | Gly | Val | Ala | Met | Leu | Met | Gly | His | Gln | Leu |
|---|---|---|---|---|---|---|---|---|---|---|---|---|---|---|---|
| | | | 340 | | | | | 345 | | | | | 350 | | |

```
Thr Gly Thr Ala Gln Val Phe Ala Asp Val Arg Thr Tyr Trp Ser Pro
        355                 360                 365

Glu Ala Ile Glu Arg Val Thr Gly His Lys Leu Asp Gly Leu Ala Glu
        370                 375                 380

His Gly Ile Ile His Leu Ile Asn Ser Gly Ala Ala Leu Asp Gly
385                 390                 395                 400

Ser Cys Lys Gln Arg Asp Ser Glu Gly Asn Pro Thr Met Lys Pro His
                405                 410                 415

Trp Glu Ile Ser Gln Gln Glu Ala Asp Ala Cys Leu Ala Ala Thr Glu
                420                 425                 430

Trp Cys Pro Ala Ile His Glu Tyr Phe Arg Gly Gly Tyr Ser Ser
        435                 440                 445

Arg Phe Leu Thr Glu Gly Gly Val Pro Phe Thr Met Thr Arg Val Asn
        450                 455                 460

Ile Ile Lys Gly Leu Gly Pro Val Leu Gln Ile Ala Glu Gly Trp Ser
465                 470                 475                 480

Val Glu Leu Pro Lys Asp Val His Asp Ile Leu Asn Lys Arg Thr Asn
                485                 490                 495

Ser Thr Trp Pro Thr Thr Trp Phe Ala Pro Arg Leu Thr Gly Lys Gly
        500                 505                 510

Pro Phe Thr Asp Val Tyr Ser Val Met Ala Asn Trp Gly Ala Asn His
        515                 520                 525

Gly Val Leu Thr Ile Gly His Val Gly Ala Asp Phe Ile Thr Leu Ala
        530                 535                 540

Ser Met Leu Arg Ile Pro Val Cys Met His Asn Val Glu Glu Thr Lys
545                 550                 555                 560

Val Tyr Arg Pro Ser Ala Trp Ala Ala His Gly Met Asp Ile Glu Gly
                565                 570                 575

Gln Asp Tyr Arg Ala Cys Gln Asn Tyr Gly Pro Leu Tyr Lys Arg
                580                 585                 590

<210> SEQ ID NO 100
<211> LENGTH: 1419
<212> TYPE: DNA
<213> ORGANISM: Escherichia coli

<400> SEQUENCE: 100
atgaaacaag aagttatcct ggtactcgac tgtggcgcga ccaatgtcag ggccatcgcg      60
gttaatcggc agggcaaaat tgttgcccgc gcctcaacgc taatgccag cgatatcgcg     120 atggaaaaca cacctggca ccagtggtct ttagacgcca ttttgcaacg ctttgctgat     180
tgctgtcggc aaatcaatag tgaactgact gaatgccaca tccgcggtat cgccgtcacc     240
acctttggtg tggatggcgc tctggtagat aagcaaggca atctgctcta tccgattatt     300
agctggaaat gtccgcgaac agcagcggtt atggacaata ttgaacggtt aatctccgca     360
cagcggttgc aggctatttc tggcgtcgga gcctttagtt tcaatacgtt atataagttg     420
gtgtggttga agaaaatca tccacaactg ctggaacgcg cgcacgcctg gctctttatt     480
tcgtcgctga ttaaccaccg tttaaccggc gaattcacta ctgatatcac gatgccgga     540 accagccaga tgctggatat ccagcaacgc gatttcagtc cgcaaatttt acaagccacc     600
ggtattccac gccgactctt ccctcgtctg gtggaagcgg tgaacagat tggtacgcta     660 cagaacagcg ccgcagcaat gctcggctta cccgttggca taccggtgat ttccgcaggt     720
cacgataccc agttcgccct ttttggcgct ggtgctgaac aaaatgaacc cgtgctctct     780
```

-continued

```
tccggtacat gggaaatttt aatggttcgc agcgcccagg ttgatacttc gctgttaagt    840
cagtacgccg gttccacctg cgaactggat agccaggcag ggttgtataa cccaggtatg    900
caatggctgg catccggcgt gctggaatgg gtgagaaaac tgttctggac ggctgaaaca    960
ccctggcaaa tgttgattga agaagctcgt ctgatcgcgc tggcgcgga tggcgtaaaa    1020 atgcagtgtg atttattgtc gtgtcagaac gctggctggc aaggagtgac gcttaatacc    1080
acgcgggggc atttctatcg cgcggcgctg aagggttaa ctgcgcaatt acagcgcaat    1140
ctacagatgc tggaaaaaat cgggcacttt aaggcctctg aattattgtt agtcggtgga    1200
ggaagtcgca acacattgtg gaatcagatt aaagccaata tgcttgatat tccggtaaaa    1260
gttctcgacg acgccgaaac gaccgtcgca ggagctgcgc tgttcggttg gtatggcgta    1320
ggggaattta acagcccgga agaagcccgc gcacagattc attatcagta ccgttatttc    1380
tacccgcaaa ctgaacctga atttatagag gaagtgtga                          1419
```

<210> SEQ ID NO 101
<211> LENGTH: 472
<212> TYPE: PRT
<213> ORGANISM: Escherichia coli

<400> SEQUENCE: 101

```
Met Lys Gln Glu Val Ile Leu Val Leu Asp Cys Gly Ala Thr Asn Val
1               5                   10                  15

Arg Ala Ile Ala Val Asn Arg Gln Gly Lys Ile Val Ala Arg Ala Ser
                20                  25                  30

Thr Pro Asn Ala Ser Asp Ile Ala Met Glu Asn Asn Thr Trp His Gln
            35                  40                  45

Trp Ser Leu Asp Ala Ile Leu Gln Arg Phe Ala Asp Cys Cys Arg Gln
        50                  55                  60

Ile Asn Ser Glu Leu Thr Glu Cys His Ile Arg Gly Ile Ala Val Thr
65                  70                  75                  80

Thr Phe Gly Val Asp Gly Ala Leu Val Asp Lys Gln Gly Asn Leu Leu
                85                  90                  95

Tyr Pro Ile Ile Ser Trp Lys Cys Pro Arg Thr Ala Ala Val Met Asp
            100                 105                 110

Asn Ile Glu Arg Leu Ile Ser Ala Gln Arg Leu Gln Ala Ile Ser Gly
        115                 120                 125

Val Gly Ala Phe Ser Phe Asn Thr Leu Tyr Lys Leu Val Trp Leu Lys
    130                 135                 140

Glu Asn His Pro Gln Leu Leu Glu Arg Ala His Ala Trp Leu Phe Ile
145                 150                 155                 160

Ser Ser Leu Ile Asn His Arg Leu Thr Gly Glu Phe Thr Thr Asp Ile
                165                 170                 175

Thr Met Ala Gly Thr Ser Gln Met Leu Asp Ile Gln Gln Arg Asp Phe
            180                 185                 190

Ser Pro Gln Ile Leu Gln Ala Thr Gly Ile Pro Arg Arg Leu Phe Pro
        195                 200                 205

Arg Leu Val Glu Ala Gly Glu Gln Ile Gly Thr Leu Gln Asn Ser Ala
    210                 215                 220

Ala Ala Met Leu Gly Leu Pro Val Gly Ile Pro Val Ile Ser Ala Gly
225                 230                 235                 240

His Asp Thr Gln Phe Ala Leu Phe Gly Ala Gly Ala Glu Gln Asn Glu
                245                 250                 255
```

```
Pro Val Leu Ser Ser Gly Thr Trp Glu Ile Leu Met Val Arg Ser Ala
            260                 265                 270

Gln Val Asp Thr Ser Leu Leu Ser Gln Tyr Ala Gly Ser Thr Cys Glu
        275                 280                 285

Leu Asp Ser Gln Ala Gly Leu Tyr Asn Pro Gly Met Gln Trp Leu Ala
    290                 295                 300

Ser Gly Val Leu Glu Trp Val Arg Lys Leu Phe Trp Thr Ala Glu Thr
305                 310                 315                 320

Pro Trp Gln Met Leu Ile Glu Glu Ala Arg Leu Ile Ala Pro Gly Ala
                325                 330                 335

Asp Gly Val Lys Met Gln Cys Asp Leu Leu Ser Cys Gln Asn Ala Gly
            340                 345                 350

Trp Gln Gly Val Thr Leu Asn Thr Thr Arg Gly His Phe Tyr Arg Ala
        355                 360                 365

Ala Leu Glu Gly Leu Thr Ala Gln Leu Gln Arg Asn Leu Gln Met Leu
    370                 375                 380

Glu Lys Ile Gly His Phe Lys Ala Ser Glu Leu Leu Val Gly Gly
385                 390                 395                 400

Gly Ser Arg Asn Thr Leu Trp Asn Gln Ile Lys Ala Asn Met Leu Asp
                405                 410                 415

Ile Pro Val Lys Val Leu Asp Asp Ala Glu Thr Thr Val Ala Gly Ala
            420                 425                 430

Ala Leu Phe Gly Trp Tyr Gly Val Gly Glu Phe Asn Ser Pro Glu Glu
        435                 440                 445

Ala Arg Ala Gln Ile His Tyr Gln Tyr Arg Tyr Phe Tyr Pro Gln Thr
    450                 455                 460

Glu Pro Glu Phe Ile Glu Glu Val
465                 470

<210> SEQ ID NO 102
<211> LENGTH: 492
<212> TYPE: DNA
<213> ORGANISM: Escherichia coli

<400> SEQUENCE: 102
atgcattgct ataacgggat gacaggttta catcaccgcg aaccgggaat ggttggcgcg      60
ggattaacgg acaagcgcgc ctggctggaa ctgatagccg atggtcatca tgtgcatccg     120
gcggcaatgt cgctgtgttg ttgctgtgcg aaagagagaa tcgtactgat caccgacgcg     180
atgcaggcag ctgggatgcc ggatggtcgc tatacgttat gtggtgaaga agtgcagatg     240
cacggtggcg ttgtccgtac cgcgtctggt gggctggcgg gcagtacgct gtctgttgat     300
gcggcagtgc gcaatatggt cgagttgacg ggcgtaacgc tgcggaagcc atccatatgg     360
cgtcgctgca tccggcgcga atgctgggtg ttgatggtgt tctgggatcg cttaaaccgg     420
gcaaacgcgc cagagtcgtt gcgctggata gcgggctaca tgtgcaacaa atctggattc     480
agggtcaatt ag                                                        492

<210> SEQ ID NO 103
<211> LENGTH: 167
<212> TYPE: PRT
<213> ORGANISM: Escherichia coli

<400> SEQUENCE: 103

Met His Cys Tyr Asn Gly Met Thr Gly Leu His His Arg Glu Pro Gly
1               5                   10                  15
```

-continued

```
Met Val Gly Ala Gly Leu Thr Asp Lys Arg Ala Trp Leu Glu Leu Ile
            20                  25                  30

Ala Asp Gly His His Val His Pro Ala Ala Met Ser Leu Cys Cys Cys
            35              40                  45

Cys Ala Lys Glu Arg Ile Val Leu Ile Thr Asp Ala Met Gln Ala Ala
        50                  55                  60

Gly Met Pro Asp Gly Arg Tyr Thr Leu Cys Gly Glu Glu Val Gln Met
65                      70                  75                  80

His Gly Gly Val Val Arg Thr Ala Ser Gly Gly Leu Ala Gly Ser Thr
                85                  90                  95

Leu Ser Val Asp Ala Ala Val Arg Asn Met Val Glu Leu Thr Gly Val
                100                 105                 110

Thr Pro Ala Glu Ala Ile His Met Ala Ser Leu His Pro Ala Arg Met
            115                 120                 125

Leu Gly Val Asp Gly Val Leu Gly Ser Leu Lys Pro Gly Lys Arg Ala
        130                 135             140

Ser Val Val Ala Leu Asp Ser Gly Leu His Val Gln Gln Ile Trp Ile
145                 150                 155                 160

Gln Gly Gln Leu Ala Ser Phe
                165
```